(12) United States Patent
Hasvold et al.

(10) Patent No.: US 9,050,346 B2
(45) Date of Patent: Jun. 9, 2015

(54) BROMODOMAIN INHIBITORS

(71) Applicant: AbbVie Inc., North Chicago, IL (US)

(72) Inventors: Lisa A. Hasvold, Grayslake, IL (US); Dachun Liu, Vernon Hills, WI (US); Keith F. McDaniel, Wauconda, IL (US); John Pratt, Kenosha, WI (US); George S. Sheppard, Wilmette, IL (US); Carol K Wada, Evanston, IL (US); Kevin R. Woller, Antioch, IL (US)

(73) Assignee: AbbVie Inc., North Chicago, IL (US)

( * ) Notice: Subject to any disclaimer, the term of this patent is extended or adjusted under 35 U.S.C. 154(b) by 0 days.

(21) Appl. No.: 14/203,641

(22) Filed: Mar. 11, 2014

(65) Prior Publication Data

US 2014/0256705 A1    Sep. 11, 2014

Related U.S. Application Data

(60) Provisional application No. 61/776,530, filed on Mar. 11, 2013.

(51) Int. Cl.
| | |
|---|---|
| *C07D 401/02* | (2006.01) |
| *C07D 401/10* | (2006.01) |
| *A61K 31/437* | (2006.01) |
| *A61K 31/4353* | (2006.01) |
| *A61K 31/5377* | (2006.01) |
| *C07D 471/04* | (2006.01) |
| *A61K 31/496* | (2006.01) |
| *A61K 31/497* | (2006.01) |
| *C07D 487/04* | (2006.01) |
| *A61K 31/501* | (2006.01) |
| *A61K 31/519* | (2006.01) |

(52) U.S. Cl.
CPC .......... *A61K 31/5377* (2013.01); *C07D 471/04* (2013.01); *A61K 31/437* (2013.01); *A61K 31/496* (2013.01); *A61K 31/497* (2013.01); *C07D 487/04* (2013.01); *A61K 31/501* (2013.01); *A61K 31/519* (2013.01)

(58) Field of Classification Search
CPC .. C07D 401/02; C07D 401/10; A61K 31/437; A61K 31/4353
USPC .......................................... 546/113; 514/300
See application file for complete search history.

(56) References Cited

U.S. PATENT DOCUMENTS

| | | | |
|---|---|---|---|
| 4,010,159 | A | 3/1977 | Tarzia et al. |
| 2008/0011457 | A1 | 1/2008 | Mirolli et al. |

FOREIGN PATENT DOCUMENTS

| | | |
|---|---|---|
| WO | 0204453 A2 | 1/2002 |
| WO | 2006129623 A1 | 12/2006 |
| WO | 2011054553 A1 | 5/2011 |
| WO | 2011161031 A1 | 12/2011 |
| WO | 2012075456 A1 | 6/2012 |
| WO | 2012143415 A1 | 10/2012 |
| WO | 2012143416 A2 | 10/2012 |
| WO | 2012150234 A1 | 11/2012 |
| WO | 2012151512 A2 | 11/2012 |
| WO | 2012174487 A2 | 12/2012 |
| WO | 2013024104 A1 | 2/2013 |
| WO | 2013027168 A1 | 2/2013 |

OTHER PUBLICATIONS

Banerjee C., et al., "BET Bromodomain Inhibition as a Novel Strategy for Reactivation of HIV-1," Journal of Leukocyte Biology, 2012, vol. 92 (6), pp. 1147-1154.
Barraja P., et al., "Synthesis of the New Ring System 6,8-dihydro-5H-pyrrolo[3,4-h]Quinazoline," Tetrahedron Letters, 2009, vol. 50 (38), pp. 5389-5391.
Berge, S. M. et al., "Pharmaceutical Salts," Journal of Pharmaceutical Sciences, 1977, vol. 66 (1), pp. 1-19.
Bew S.P., et al., "Stereoselective Synthesis of N-alkylaziridines from N-chloroamines," Chemical Communications, 2006, vol. 4 (41), pp. 4338-4340.
Dattolo G., et al., "Polycondensed Nitrogen Heterocycles. Part 22. Pyrrolo[3,4-d]-1,2,3-triazines: A New Ring System as Potential Antineoplastic Agent," Journal of Heterocyclic Chemistry, 1989, vol. 26 (6), pp. 1747-1749.
Dawson M.A., et al., "Inhibition of BET Recruitment to Chromatin as an Effective Treatment for MLL-fusion Leukaemia," Nature, 2011, vol. 478 (7370), pp. 529-533.
Delmore J.E., et al., "BET Bromodomain Inhibition as a Therapeutic Strategy to Target c-Myc," Cell, 2011, vol. 146 (6), pp. 904-917.
Denis G.V., "Bromodomain Coactivators in Cancer, Obesity, type 2 Diabetes, and Inflammation," Discovery Medicine, 2010, vol. 10 (55), pp. 489-499.
Eastwood B.J., et al., "The Minimum Significant Ratio: A Statistical Parameter to Characterize the Reproducibility of Potency Estimates from Concentration-Response Assays and Estimation by Replicate-Experiment Studies," Journal of Biomolecular Screening, 2006, vol. 11 (3), pp. 253-261.

(Continued)

*Primary Examiner* — Niloofar Rahmani
(74) *Attorney, Agent, or Firm* — Glen J. Gesicki

(57) ABSTRACT

The present invention provides for compounds of formula (I)

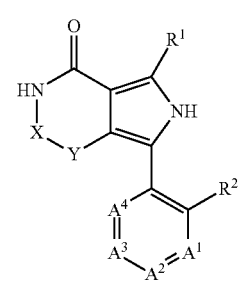

wherein $R^1$, $R^2$, $A^1$, $A^2$, $A^3$, $A^4$, X, and Y have any of the values defined in the specification, and pharmaceutically acceptable salts thereof, that are useful as agents in the treatment of diseases and conditions, including inflammatory diseases, cancer, and AIDS. Also provided are pharmaceutical compositions comprising one or more compounds of formula (I).

20 Claims, No Drawings

(56) References Cited

OTHER PUBLICATIONS

Green, et al., "Protecting Groups in Organic Synthesis" in: Antibodies, 3rd Edition, John Wiley & Sons, NY, 1999, pp. 20.

Huang B., et al., "Brd4 Coactivates Transcriptional Activation of NF-kappaB Via Specific Binding to Acetylated ReIA," Molecular and Cellular Biology, 2009, vol. 29 (5), pp. 1375-1387.

International Search Report and Written Opinion for Application No. PCT/US2014/023437, mailed on Jul. 11, 2014, 14 pages.

International Search Report and Written Opinion for Application No. PCT/US2014/023463, mailed on Jul. 2, 2014, 7 pages.

Jang M.K., et al., "The Bromodomain Protein Brd4 is a Positive Regulatory Component of P-TEFb and Stimulates RNA Polymerase II-dependent Transcription," Molecular Cell, 2005, vol. 19 (4), pp. 523-534.

Leroy G., et al., "The Double Bromodomain Proteins Brd2 and Brd3 Couple Histone Acetylation to Transcription," Molecular Cell, 2008, vol. 30 (1), pp. 51-60.

Matzuk M.M., et al., "Small-molecule Inhibition of BRDT for Male Contraception," Cell, 2012, vol. 150 (4), pp. 673-684.

Mertz J.A., et al., "Targeting MYC Dependence in Cancer by Inhibiting BET Bromodomains," Proceedings of the National Academy of Sciences, 2011, vol. 108 (40), pp. 16669-16674.

Miyaura N., et al., "Palladium-Catalyzed Cross-Coupling Reactions of Organoboron Compounds," Chemical Reviews, 1995, vol. 95 (7), pp. 2457-2483.

Nicodeme E., et al., "Suppression of Inflammation by a Synthetic Histone Mimic," Nature, 2010, vol. 468 (7327), pp. 1119-1123.

Prescott, Ed., Methods in Cell Biology, vol. XIV, Academic Press, New York, 1976, pp. 33.

Sutton, V.R. et al., "Bcl-2 Prevents Apoptosis Induced by Perforin and Granzyme B, But Not That Mediated by Whole Cytotoxic Lymphocytes," Journal of Immunology, 1997, vol. 158 (12), pp. 5783-5790.

Suzuki A, "Recent Advances in the Cross-Coupling Reactions of Organoboron Derivatives with Organic Electrophiles," Journal of Organometallic Chemistry, 1999, vol. 576, pp. 147-168.

Yang Z., et al., "Brd4 Recruits P-TEFb to Chromosomes at Late Mitosis to Promote G1 Gene Expression and Cell Cycle Progression," Molecular and Cellular Biology, 2008, vol. 28 (3), pp. 967-976.

Zhang G., et al., "Down-regulation of NF-κB Transcriptional Activity in HIV-associated Kidney Disease by BRD4 Inhibition," Journal of Biological Chemistry, 2012, vol. 287 (34), pp. 28840-28851.

Zuber J., et al., "RNAi Screen Identifies Brd4 as a Therapeutic Target in Acute Myeloid Leukaemia," Nature, 2011, vol. 478 (7370), pp. 524-528.

BROMODOMAIN INHIBITORS

BACKGROUND

Bromodomains refer to conserved protein structural folds which bind to N-acetylated lysine residues that are found in some proteins. The BET family of bromodomain containing proteins is comprised of four members (BRD2, BRD3, BRD4 and BRDt). Each member of the BET family employs two bromodomains to recognize N-acetylated lysine residues found primarily, but not exclusively, on the amino-terminal tails of histone proteins. These interactions modulate gene expression by recruiting transcription factors to specific genome locations within chromatin. For example, histone-bound BRD4 recruits the transcription factor P-TEFb to promoters, resulting in the expression of a subset of genes involved in cell cycle progression (Yang et al., Mol. Cell. Biol. 28: 967-976 (2008)). BRD2 and BRD3 also function as transcriptional regulators of growth promoting genes (LeRoy et al., Mol. Cell 30: 51-60 (2008)). BET family members were recently established as being important for the maintenance of several cancer types (Zuber et al., Nature 478: 524-528 (2011); Mertz et al; Proc. Nat'l. Acad. Sci. 108: 16669-16674 (2011); Delmore et al., Cell 146: 1-14, (2011); Dawson et al., Nature 478: 529-533 (2011)). BET family members have also been implicated in mediating acute inflammatory responses through the canonical NF-KB pathway (Huang et al., Mol. Cell. Biol. 29: 1375-1387 (2009)) resulting in the upregulation of genes associated with the production of cytokines (Nicodeme et al., Nature 468: 1119-1123, (2010)). Suppression of cytokine induction by BET bromodomain inhibitors has been shown to be an effective approach to treat inflammation-mediated kidney disease in an animal model (Zhang, et al., J. Biol. Chem. 287: 28840-28851 (2012)). BRD2 function has been linked to predisposition for dyslipidemia or improper regulation of adipogenesis, elevated inflammatory profiles and increased susceptibility to autoimmune diseases (Denis, Discovery Medicine 10: 489-499 (2010)). The human immunodeficiency virus utilizes BRD4 to initiate transcription of viral RNA from stably integrated viral DNA (Jang et al., Mol. Cell, 19: 523-534 (2005)). BET bromodomain inhibitors have also been shown to reactivate HIV transcription in models of latent T cell infection and latent monocyte infection (Banerjee, et al, J. Leukocyte Biol. doi:10.1189/jlb.0312165). BRDt has an important role in spermatogenesis that is blocked by BET bromodomain inhibitors (Matzuk, et al., Cell 150: 673-684 (2012)). Thus, compounds that inhibit the binding of BET family bromodomains to their cognate acetylated lysine proteins are being pursued for the treatment of cancer, inflammatory diseases, kidney diseases, diseases involving metabolism or fat accumulation, and some viral infections, as well as for providing a method for male contraception. Accordingly, there is an ongoing medical need to develop new drugs to treat these indications.

SUMMARY

In one aspect the present invention provides for compounds of formula (I) or a pharmaceutically acceptable salt thereof,

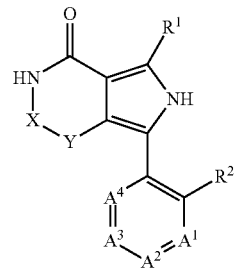

(I)

wherein $R^1$ is $C_1$-$C_3$ alkyl or $C_1$-$C_3$ haloalkyl;

X—Y is —CR$^3$=CH—, —N=CR$^4$—, —CR$^5$=N—, or —CR$^6$R$^7$—CR$^8$R$^9$—; wherein the left ends of the moieties are attached to the NH group in the ring;

$A^1$, $A^2$, $A^3$, and $A^4$ are CR$^x$; or one or two of $A^1$, $A^2$, $A^3$, and $A^4$ are N, and the others are CR$^x$;

$R^2$ is $R^{xa}$ when X—Y is —CR$^3$=CH—, —N=CR$^4$—, or —CR$^6$R$^7$—CR$^8$R$^9$—; or $R^2$ is -L-G when X—Y is —CR$^5$=N—, wherein L is O, N(R$^y$), O—$C_1$-$C_6$ alkylenyl, or N(R$^y$)—$C_1$-$C_6$ alkyenyl, wherein R$^y$ is hydrogen or $C_1$-$C_4$ alkyl;

$R^x$ and $R^{xa}$, at each occurrence, are each independently hydrogen, $C_1$-$C_6$ alkyl, $C_2$-$C_6$ alkenyl, $C_2$-$C_6$ alkynyl, halogen, $C_1$-$C_6$ haloalkyl, —CN, NO$_2$, G, —OR$^{x1}$, —OC(O)R$^{x2}$, —OC(O)NR$^{x3}$R$^{x4}$, —SR$^{x1}$, —S(O)$_2$R$^{x1}$, —S(O)$_2$NR$^{x3}$R$^{x4}$, —C(O)R$^{x1}$, —C(O)OR$^{x1}$, —C(O)NR$^{x3}$R$^{x4}$, —NR$^{x3}$R$^{x4}$, —N(R$^{x5}$)C(O)R$^{x2}$, —N(R$^{x5}$)S(O)$_2$R$^{x2}$, N(R$^{x5}$)C(O)O(R$^{x2}$), —N(R$^{x5}$)C(O)NR$^{x3}$R$^{x4}$, —N(R$^{x5}$)S(O)$_2$NR$^{x3}$R$^{x4}$, —($C_1$-$C_6$ alkylenyl)-G, —($C_1$-$C_6$ alkylenyl)-OR$^{x1}$, —($C_1$-$C_6$ alkylenyl)-OC(O)R$^{x2}$, —($C_1$-$C_6$ alkylenyl)-OC(O)NR$^{x3}$R$^{x4}$, —($C_1$-$C_6$ alkylenyl)-S(O)$_2$R$^{x1}$, —($C_1$-$C_6$ alkylenyl)-S(O)$_2$NR$^{x3}$R$^{x4}$, —($C_1$-$C_6$ alkylenyl)-C(O)R$^{x1}$, —($C_1$-$C_6$ alkylenyl)-C(O)OR$^{x1}$, —($C_1$-$C_6$ alkylenyl)-C(O)NR$^{x3}$R$^{x4}$, —($C_1$-$C_6$ alkylenyl)-NR$^{x3}$R$^{x4}$, —($C_1$-$C_6$ alkylenyl)-N(R$^{x5}$)C(O)R$^{x2}$, —($C_1$-$C_6$ alkylenyl)-N(R$^{x5}$)S(O)$_2$R$^{x2}$, —($C_1$-$C_6$ alkylenyl)-N(R$^{x5}$)C(O)O(R$^{x2}$), —($C_1$-$C_6$ alkylenyl)-N(R$^{x5}$)C(O)NR$^{x3}$R$^{x4}$, —($C_1$-$C_6$ alkylenyl)-N(R$^{x5}$)S(O)$_2$NR$^{x3}$R$^{x4}$, and —($C_1$-$C_6$ alkylenyl)-CN;

$R^{x1}$, $R^{x3}$, $R^{x4}$, and $R^{x5}$, at each occurrence, are each independently H, $C_1$-$C_6$ alkyl, $C_2$-$C_6$ alkenyl, $C_2$-$C_6$ alkynyl, $C_1$-$C_6$ haloalkyl, G, or —$C_1$-$C_6$ alkylenyl-G;

$R^{x2}$, at each occurrence, is independently $C_1$-$C_6$ alkyl, $C_2$-$C_6$ alkenyl, $C_2$-$C_6$ alkynyl, $C_1$-$C_6$ haloalkyl, G, or —$C_1$-$C_6$ alkylenyl-G;

G, at each occurrence, are each independently aryl, heteroaryl, $C_3$-$C_7$ heterocycle, $C_3$-$C_8$ cycloalkyl, or $C_5$-$C_8$ cycloalkenyl; and each G group is optionally substituted with 1, 2, 3, 4, or 5 R$^g$ groups;

$R^3$ is H, —CN, $C_1$-$C_6$ alkyl, $C_2$-$C_6$ alkenyl, $C_2$-$C_6$ alkynyl, halogen, $C_1$-$C_6$ haloalkyl, —C(O)R$^{3a}$, —C(O)OR$^{3a}$, —C(O)NR$^{3b}$R$^{3c}$, —C(O)N(R$^{3b}$)NR$^{3b}$R$^{3c}$, —S(O)R$^{3d}$, —S(O)$_2$R$^{3a}$, —S(O)$_2$NR$^{3b}$R$^{3c}$ or G$^1$; wherein the $C_1$-$C_6$ alkyl, $C_2$-$C_6$ alkenyl, and $C_2$-$C_6$ alkynyl are each independently unsubstituted or substituted with 1 or 2 substituents independently selected from the group consisting of G$^1$, —C(O)R$^{3a}$, —C(O)OR$^{3a}$, —C(O)NR$^{3b}$R$^{3c}$, —C(O)N(R$^{3b}$)NR$^{3b}$R$^{3c}$, —S(O)R$^{3d}$, —S(O)$_2$R$^{3a}$, —S(O)$_2$NR$^{3b}$R$^{3c}$, —OR$^{3a}$, —OC(O)R$^{3d}$, —NR$^{3b}$R$^{3c}$, $N(R^{3b})C(O)R^{3d}$, $N(R^{3b})SO_2R^{3d}$, $N(R^{3b})C(O)OR^{3d}$, $N(R^{3b})C(O)NR^{3b}R^{3c}$, and $N(R^{3b})SO_2NR^{3b}R^{3c}$;

$R^4$ is H, —CN, $C_1$-$C_6$ alkyl, $C_2$-$C_6$ alkenyl, $C_2$-$C_6$ alkynyl, halogen, or $C_1$-$C_6$ haloalkyl;

$R^5$ is H, —CN, $C_1$-$C_6$ alkyl, $C_2$-$C_6$ alkenyl, $C_2$-$C_6$ alkynyl, halogen, $C_1$-$C_6$ haloalkyl, —C(O)OR$^{5a}$, —C(O)NR$^{5b}$R$^{5c}$, or G$^1$;

$R^6$ is H, —CN, $C_1$-$C_6$ alkyl, $C_2$-$C_6$ alkenyl, $C_2$-$C_6$ alkynyl, halogen, or $C_1$-$C_6$ haloalkyl;

$R^8$ and $R^9$, are each independently H, $C_1$-$C_6$ alkyl, $C_2$-$C_6$ alkenyl, $C_2$-$C_6$ alkynyl, halogen, or $C_1$-$C_6$ haloalkyl;

$R^7$ is H, $C_1$-$C_6$ alkyl, $C_2$-$C_6$ alkenyl, $C_2$-$C_6$ alkynyl, halogen, $C_1$-$C_6$ haloalkyl, —C(O)R$^{7a}$, —C(O)OR$^{7a}$, —C(O)NR$^{7b}$R$^{7c}$, —S(O)R$^{7d}$, —S(O)$_2$R$^{7a}$, —S(O)$_2$NR$^{7b}$R$^{7c}$, or G$^1$; wherein the $C_1$-$C_6$ alkyl, $C_2$-$C_6$ alkenyl, and $C_2$-$C_6$ alkynyl are each independently unsubstituted or substituted with 1 or 2 substituents independently selected from the group consisting of G$^1$, —C(O)R$^{7a}$, —C(O)OR$^{7a}$, —C(O)NR$^{7b}$R$^{7c}$, —C(O)N(R$^{7b}$)NR$^{7b}$R$^{7c}$, —S(O)R$^{7d}$, —S(O)$_2$R$^{7a}$, —S(O)$_2$NR$^{7b}$R$^{7c}$, —OR$^{7a}$, —OC(O)R$^{7d}$, —NR$^{z3}$R$^{z4}$, N(R$^{7b}$)C(O)R$^{7d}$, N(R$^{7b}$)SO$_2$R$^{7d}$, N(R$^{7b}$)C(O)OR$^{7d}$, N(R$^{7b}$)C(O)NR$^{7b}$R$^{7c}$, and N(R$^{7b}$)SO$_2$NR$^{2b}$R$^{2c}$;

$R^{3a}$, $R^{3b}$, $R^{3c}$, $R^{5a}$, $R^{5b}$, $R^{5c}$, $R^{7a}$, $R^{7b}$, and $R^{7c}$, at each occurrence, are each independently H, $C_1$-$C_6$ alkyl, $C_1$-$C_6$ haloalkyl, G$^1$, —($C_1$-$C_6$ alkylenyl)-G$^1$, —($C_1$-$C_6$ alkylenyl)-OR$^a$, or —($C_1$-$C_6$ alkylenyl)-CN;

$R^{3d}$ and $R^{7d}$, at each occurrence, are each independently $C_1$-$C_6$ alkyl, $C_1$-$C_6$ haloalkyl, G$^1$, —($C_1$-$C_6$ alkylenyl)-G$^1$, —($C_1$-$C_6$ alkylenyl)-OR$^a$, or —($C_1$-$C_6$ alkylenyl)-CN;

G$^1$, at each occurrence, is independently aryl, heteroaryl, $C_3$-$C_7$ heterocycle, $C_3$-$C_8$ cycloalkyl, or $C_5$-$C_8$ cycloalkenyl; and each G$^1$ is optionally substituted with 1, 2, 3, 4, or 5 R$^{1g}$ groups;

$R^g$ and $R^{1g}$, at each occurrence, are each independently selected from the group consisting of oxo, $C_1$-$C_6$ alkyl, $C_2$-$C_6$ alkenyl, $C_2$-$C_6$ alkynyl, halogen, $C_1$-$C_6$ haloalkyl, —CN, NO$_2$, G$^{2a}$, —OR$^a$, —OC(O)R$^b$, —OC(O)NR$^c$R$^d$, —SR$^a$, —S(O)$_2$R$^a$, —S(O)$_2$NR$^c$R$^d$, —C(O)R$^a$, —C(O)OR$^a$, —C(O)NR$^c$R$^d$, —NR$^c$R$^d$, —N(R$^e$)C(O)R$^b$, —N(R$^e$)S(O)$_2$R$^b$, —N(R$^e$)C(O)O(R$^b$), —N(R$^e$)C(O)NR$^c$R$^d$, —N(R$^e$)S(O)$_2$NR$^c$R$^d$, —($C_1$-$C_6$ alkylenyl)-CN, —($C_1$-$C_6$ alkylenyl)-G$^{2a}$, —($C_1$-$C_6$ alkylenyl)-OR$^a$, —($C_1$-$C_6$ alkylenyl)-OC(O)R$^b$, —($C_1$-$C_6$ alkylenyl)-OC(O)NR$^c$R$^d$, —($C_1$-$C_6$ alkylenyl)-S(O)$_2$R$^a$, —($C_1$-$C_6$ alkylenyl)-S(O)$_2$NR$^c$R$^d$, —($C_1$-$C_6$ alkylenyl)-C(O)R$^a$, —($C_1$-$C_6$ alkylenyl)-C(O)OR$^a$, —($C_1$-$C_6$ alkylenyl)-C(O)NR$^c$R$^d$, —($C_1$-$C_6$ alkylenyl)-NR$^c$R$^d$, —($C_1$-$C_6$ alkylenyl)-N(R$^e$)C(O)R$^b$, —($C_1$-$C_6$ alkylenyl)-N(R$^e$)S(O)$_2$R$^b$, —($C_1$-$C_6$ alkylenyl)-N(R$^e$)C(O)O(R$^b$), —($C_1$-$C_6$ alkylenyl)-N(R$^e$)C(O)NR$^c$R$^d$, —($C_1$-$C_6$ alkylenyl)-N(R$^e$)S(O)$_2$NR$^c$R$^d$, or —($C_1$-$C_6$ alkylenyl)-CN;

$R^a$, $R^c$, $R^d$, and $R^e$, at each occurrence, are each independently H, $C_1$-$C_6$ alkyl, $C_2$-$C_6$ alkenyl, $C_2$-$C_6$ alkynyl, $C_1$-$C_6$ haloalkyl, G$^{2a}$, or —($C_1$-$C_6$ alkylenyl)-G$^{2a}$;

$R^b$, at each occurrence, is independently $C_1$-$C_6$ alkyl, $C_2$-$C_6$ alkenyl, $C_2$-$C_6$ alkynyl, $C_1$-$C_6$ haloalkyl, G$^{2a}$, or —($C_1$-$C_6$ alkylenyl)-G$^{2a}$;

G$^{2a}$, at each occurrence, are each independently aryl, heteroaryl, $C_3$-$C_7$ heterocycle, $C_3$-$C_8$ cycloalkyl, or $C_5$-$C_8$ cycloalkenyl; and each G$^{2a}$ group is optionally substituted with 1, 2, 3, 4, or 5 R$^{2g}$ groups;

$R^{2g}$, at each occurrence, is independently oxo, $C_1$-$C_6$ alkyl, $C_2$-$C_6$ alkenyl, $C_2$-$C_6$ alkynyl, halogen, $C_1$-$C_6$ haloalkyl, —CN, NO$_2$, —OR$^{z1}$, —OC(O)R$^{z2}$, —OC(O)NR$^{z3}$R$^{z4}$, —SR$^{z1}$, —S(O)$_2$R$^{z1}$, —S(O)$_2$NR$^{z3}$R$^{z4}$, —C(O)R$^{z1}$, —C(O)OR$^{z1}$, —C(O)NR$^{z3}$R$^{z4}$, —NR$^{z3}$R$^{z4}$, —N(R$^{z3}$)C(O)NR$^{z2}$, —N(R$^{z3}$)S(O)$_2$R$^{z2}$, —N(R$^{z3}$)C(O)O(R$^{z2}$), —N(R$^{z3}$)C(O)NR$^{z3}$R$^{z4}$, —N(R$^{z3}$)S(O)$_2$NR$^{z3}$R$^{z4}$, —($C_1$-$C_6$ alkylenyl)-OR$^{z1}$, —($C_1$-$C_6$ alkylenyl)-OC(O)R$^{z2}$, —($C_1$-$C_6$ alkylenyl)-OC(O)NR$^{z3}$R$^{z4}$, —($C_1$-$C_6$ alkylenyl)-S(O)$_2$R$^{z1}$, —($C_1$-$C_6$ alkylenyl)-S(O)$_2$NR$^{z3}$R$^{z4}$, —($C_1$-$C_6$ alkylenyl)-C(O)R$^{z1}$, —($C_1$-$C_6$ alkylenyl)-C(O)OR$^{z1}$, —($C_1$-$C_6$ alkylenyl)-C(O)NR$^{z3}$R$^{z4}$, —($C_1$-$C_6$ alkylenyl)-NR$^{z3}$R$^{z4}$, —($C_1$-$C_6$ alkylenyl)-N(R$^{z3}$)C(O)R$^{z2}$, —($C_1$-$C_6$ alkylenyl)-N(R$^{z3}$)S(O)$_2$R$^{z2}$, —($C_1$-$C_6$ alkylenyl)-N(R$^{z3}$)C(O)O(R$^{z2}$), —($C_1$-$C_6$ alkylenyl)-N(R$^{z3}$)C(O)NR$^{z3}$R$^{z4}$, —($C_1$-$C_6$ alkylenyl)-N(R$^{z3}$)S(O)$_2$NR$^{z3}$R$^{z4}$, or —($C_1$-$C_6$ alkylenyl)-CN;

$R^{z1}$, $R^{z3}$, and $R^{z4}$, at each occurrence, are each independently H, $C_1$-$C_6$ alkyl, $C_2$-$C_6$ alkenyl, $C_2$-$C_6$ alkynyl, or $C_1$-$C_6$ haloalkyl; and $R^{z2}$, at each occurrence, is independently $C_1$-$C_6$ alkyl, $C_2$-$C_6$ alkenyl, $C_2$-$C_6$ alkynyl, or $C_1$-$C_6$ haloalkyl.

In another aspect, the present invention provides for methods for treating or preventing disorders that are ameliorated by inhibition of BET. Such methods comprise of administering to the subject a therapeutically effective amount of a compound of formula (I), alone, or in combination with a pharmaceutically acceptable carrier.

Some of the methods are directed to treating or preventing an inflammatory disease or cancer or AIDS.

In another aspect, the present invention relates to methods of treating cancer in a subject comprising administering a therapeutically effective amount of a compound of formula (I) or a pharmaceutically acceptable salt thereof, to a subject in need thereof. In certain embodiments, the cancer is selected from the group consisting of: acoustic neuroma, acute leukemia, acute lymphocytic leukemia, acute myelocytic leukemia (monocytic, myeloblastic, adenocarcinoma, angiosarcoma, astrocytoma, myelomonocytic and promyelocytic), acute t-cell leukemia, basal cell carcinoma, bile duct carcinoma, bladder cancer, brain cancer, breast cancer, bronchogenic carcinoma, cervical cancer, chondrosarcoma, chordoma, choriocarcinoma, chronic leukemia, chronic lymphocytic leukemia, chronic myelocytic (granulocytic) leukemia, chronic myelogenous leukemia, colon cancer, colorectal cancer, craniopharyngioma, cystadenocarcinoma, diffuse large B-cell lymphoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, follicular lymphoma, germ cell testicular cancer, glioma, glioblastoma, gliosarcoma, heavy chain disease, hemangioblastoma, hepatoma, hepatocellular cancer, hormone insensitive prostate cancer, leiomyosarcoma, leukemia, liposarcoma, lung cancer, lymphagioendotheliosarcoma, lymphangiosarcoma, lymphoblastic leukemia, lymphoma (Hodgkin's and non-Hodgkin's), malignancies and hyperproliferative disorders of the bladder, breast, colon, lung, ovaries, pancreas, prostate, skin and uterus, lymphoid malignancies of T-cell or B-cell origin, leukemia, lymphoma, medullary carcinoma, medulloblastoma, melanoma, meningioma, mesothelioma, multiple myeloma, myelogenous leukemia, myeloma, myxosarcoma, neuroblastoma, NUT midline carcinoma (NMC), non-small cell lung cancer, oligodendroglioma, oral cancer, osteogenic sarcoma, ovarian cancer, pancreatic cancer, papillary adenocarcinomas, papillary carcinoma, pinealoma, polycythemia vera, prostate cancer, rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), small cell lung cancer, stomach cancer, squamous cell carcinoma, synovioma, sweat gland carcinoma, thyroid cancer, Waldenström's macroglobulinemia, testicular tumors, uterine cancer and Wilms' tumor. In certain embodiments, the methods further comprise administering a therapeutically effective amount of at least one additional therapeutic agent. In certain embodiments, the additional therapeutic agent is selected from the group consisting of cytarabine, bortezomib, and 5-azacitidine.

In another aspect, the present invention relates to methods of treating a disease or condition in a subject comprising administering a therapeutically effective amount of a compound of formula (I) or a pharmaceutically acceptable salt thereof, to a subject in need thereof, wherein said disease or condition is selected from the group consisting of: Addison's disease, acute gout, ankylosing spondylitis, asthma, atherosclerosis, Behcet's disease, bullous skin diseases, cardiac myopathy, cardiac hypertrophy, chronic obstructive pulmonary disease (COPD), Crohn's disease, dermatitis, eczema, giant cell arteritis, glomerulonephritis, heart failure, hepatitis, hypophysitis, inflammatory bowel disease, Kawasaki disease, lupus nephritis, multiple sclerosis, myocarditis, myositis, nephritis, organ transplant rejection, osteoarthritis, pancreatitis, pericarditis, Polyarteritis nodosa, pneumonitis, primary biliary cirrhosis, psoriasis, psoriatic arthritis, rheumatoid arthritis, scleritis, sclerosing cholangitis, sepsis, systemic lupus erythematosus, Takayasu's Arteritis, toxic shock, thyroiditis, type I diabetes, ulcerative colitis, uveitis, vitiligo, vasculitis, and Wegener's granulomatosis. In certain embodiments, the methods further comprise administering a therapeutically effective amount of at least one additional therapeutic agent.

In another aspect, the present invention relates to methods of treating a chronic kidney disease or condition in a subject comprising administering a therapeutically effective amount of a compound of formula (I) or a pharmaceutically acceptable salt thereof, to a subject in need thereof, wherein said disease or condition is selected from the group consisting of: diabetic nephropathy, hypertensive nephropathy, HIV-associated nephropathy, glomerulonephritis, lupus nephritis, IgA nephropathy, focal segmental glomerulosclerosis, membranous glomerulonephritis, minimal change disease, polycystic kidney disease and tubular interstitial nephritis. In certain embodiments, the methods further comprise administering a therapeutically effective amount of at least one additional therapeutic agent.

In another aspect, the present invention relates to methods of treating an acute kidney injury or disease or condition in a subject comprising administering a therapeutically effective amount of a compound of formula (I) or a pharmaceutically acceptable salt thereof, to a subject in need thereof, wherein said acute kidney injury or disease or condition is selected from the group consisting of: ischemia-reperfusion induced, cardiac and major surgery induced, percutaneous coronary intervention induced, radio-contrast agent induced, sepsis induced, pneumonia induced, and drug toxicity induced. In certain embodiments, the methods further comprise administering a therapeutically effective amount of at least one additional therapeutic agent.

In another aspect, the present invention relates to methods of treating AIDS in a subject comprising administering a therapeutically effective amount of a compound of formula (I) or a pharmaceutically acceptable salt thereof, to a subject in need thereof. In certain embodiments, the methods further comprise administering a therapeutically effective amount of at least one additional therapeutic agent.

In another aspect, the present invention relates to methods of treating obesity, dyslipidemia, hypercholesterolemia, Alzheimer's disease, metabolic syndrome, hepatic steatosis, type II diabetes, insulin resistance, diabetic retinopathy or diabetic neuropathy in a subject comprising administering a therapeutically effective amount of a compound of formula (I) or a pharmaceutically acceptable salt thereof, to a subject in need thereof. In certain embodiments, the methods further comprise administering a therapeutically effective amount of at least one additional therapeutic agent.

In another aspect, the present invention provides for contraception in a male subject comprising administering a therapeutically effective amount of a compound of formula (I), or a pharmaceutically acceptable salt thereof, to a subject in need thereof. In certain embodiments, the methods further comprise administering a therapeutically effective amount of at least one additional therapeutic agent.

A further aspect of the invention provides the use of a compound of formula (I), alone or in combination with a second active pharmaceutical agent, in the manufacture of a medicament for treating or preventing conditions and disorders disclosed herein, with or without a pharmaceutically acceptable carrier.

Pharmaceutical compositions comprising a compound of formula (I), or a pharmaceutically acceptable salt, alone or in combination with a second active pharmaceutical agent, are also provided. In certain embodiments, pharmaceutical compositions comprise a therapeutically effective amount of a compound of formula (I), or a pharmaceutically acceptable salt thereof, and a pharmaceutically acceptable carrier.

DETAILED DESCRIPTION

Disclosed herein are compounds of formula (I)

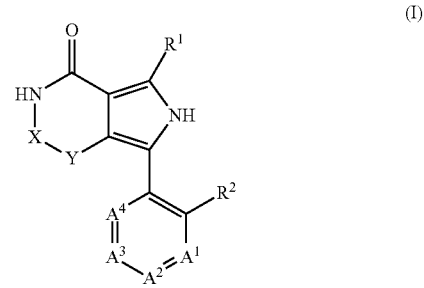

wherein $R^1$, $R^2$, $A^1$, $A^2$, $A^3$, $A^4$, X and Y are defined above in the Summary of the Invention and below in the Detailed Description. Further, compositions comprising such compounds and methods for treating conditions and disorders using such compounds and compositions are also disclosed.

Compounds disclosed herein may contain one or more variable(s) that occur more than one time in any substituent or in the formulae herein. Definition of a variable on each occurrence is independent of its definition at another occurrence. Further, combinations of substituents are permissible only if such combinations result in stable compounds. Stable compounds are compounds, which can be isolated from a reaction mixture.

a). Definitions

It is noted that, as used in this specification and the intended claims, the singular form "a," "an," and "the" include plural referents unless the context clearly dictates otherwise. Thus, for example, reference to "a compound" includes a single compound as well as one or more of the same or different compounds, reference to "optionally a pharmaceutically acceptable carrier" refers to a single optional pharmaceutically acceptable carrier as well as one or more pharmaceutically acceptable carriers, and the like.

As used in the specification and the appended claims, unless specified to the contrary, the following terms have the meaning indicated:

The term "alkenyl" as used herein, means a straight or branched hydrocarbon chain containing from 2 to 10 carbons and containing at least one carbon-carbon double bond, optionally substituted with 1, 2, or 3 halogen atoms. The term "$C_2$-$C_6$ alkenyl" means an alkenyl group containing 2-6 carbon atoms. Non-limiting examples of alkenyl include buta-1,3-dienyl, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkenylene" means a divalent group derived from a straight or branched chain hydrocarbon of 2 to 4 carbon atoms and contains at least one carbon-carbon double bond. Representative examples of alkenylene include, but are not limited to, —CH═CH— and —CH$_2$CH═CH—.

The term "alkyl" as used herein, means a saturated, straight or branched hydrocarbon chain radical. In some instances, the number of carbon atoms in an alkyl moiety is indicated by the prefix "$C_x$—$C_y$", wherein x is the minimum and y is the maximum number of carbon atoms in the substituent. Thus, for example, "$C_1$-$C_6$ alkyl" refers to an alkyl substituent containing from 1 to 6 carbon atoms and "$C_1$-$C_3$ alkyl" refers to an alkyl substituent containing from 1 to 3 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 1-methylbutyl, 2-methylbutyl, 3-methylbutyl, 3,3-dimethylbutyl, 1,1-dimethylpropyl, 1,2-dimethylpropyl, 2,2-dimethylpropyl, 1-methylpropyl, 2-methylpropyl, 1-ethylpropyl, 1,2,2-trimethylpropyl, 3-methylhexyl, 2,2-dimethylpentyl, 2,3-dimethylpentyl, n-heptyl, n-octyl, n-nonyl, and n-decyl.

The term "alkylene" or "alkylenyl" means a divalent radical derived from a straight or branched, saturated hydrocarbon chain, for example, of 1 to 10 carbon atoms or of 1 to 6 carbon atoms ($C_1$-$C_6$ alkylenyl) or of 1 to 4 carbon atoms or of 1 to 3 carbon atoms ($C_1$-$C_3$ alkylenyl). Examples of alkylene and alkylenyl include, but are not limited to, —CH$_2$—, —CH$_2$CH$_2$—, —CH$_2$CH$_2$CH$_2$—, —CH$_2$CH$_2$CH$_2$CH$_2$—, and —CH$_2$CH(CH$_3$)CH$_2$—.

The term "alkynyl" as used herein, means a straight or branched chain hydrocarbon radical containing from 2 to 10 carbon atoms and containing at least one carbon-carbon triple bond, optionally substituted with 1, 2, or 3 halogen atoms. The term "$C_2$-$C_6$ alkynyl" means an alkynyl group of 2 to 6 carbon atoms. Representative examples of alkynyl include, but are not limited, to acetylenyl, 1-propynyl, 2-propynyl, 3-butynyl, 2-pentynyl, and 1-butynyl.

The term "aryl" as used herein, means phenyl or naphthyl. The aryls can be unsubstituted or substituted.

The term "$C_3$-$C_8$ cycloalkyl" as used herein, means a saturated cyclic hydrocarbon group containing from 3 to 8 carbons, examples of $C_3$-$C_8$ cycloalkyl include cyclopropyl, cyclobutyl, cyclopentyl, cyclohexyl, cycloheptyl, and cyclooctyl. The cycloalkyls can be unsubstituted or substituted.

The term "$C_3$-$C_6$ cycloalkyl" as used herein, means cyclopropyl, cyclobutyl, cyclopentyl, and cyclohexyl.

The term "$C_5$-$C_8$ cycloalkenyl" as used herein, means a cyclopentyl, cyclohexyl, cycloheptyl, or cyclooctyl group that contains at least one carbon-carbon double bond. Representative examples of $C_5$-$C_8$ cycloalkenyl include, but are not limited to, cyclohexenyl, cyclohexadienyl, cyclopentenyl, cycloheptenyl, and cyclooctenyl. The cycloalkenyls can be attached to the parent molecular moiety through any substitutable atom contained within the ring systems, and can be unsubstituted or substituted.

The term "halo" or "halogen" as used herein, means Cl, Br, I, and F.

The term "haloalkyl" as used herein, means an alkyl group, as defined herein, in which one, two, three, four, five or six hydrogen atoms are replaced by halogen. The term "$C_1$-$C_6$ haloalkyl" means a $C_1$-$C_6$ alkyl group, as defined herein, in which one, two, three, four, five, six, or seven hydrogen atoms are replaced by halogen. The term "$C_1$-$C_3$ haloalkyl" means a $C_1$-$C_3$ alkyl group, as defined herein, in which one, two, three, four, five, or six hydrogen atoms are replaced by halogen. Representative examples of haloalkyl include, but are not limited to, chloromethyl, 2-fluoroethyl, 2,2-difluoroethyl, 2,2,2-trifluoroethyl, trifluoromethyl, difluoromethyl, pentafluoroethyl, 2-chloro-3-fluoropentyl, trifluorobutyl, trifluoropropyl, 2,2,3,3,3-pentafluoropropyl, and 2,2,3,3,4,4,4-heptafluorobutyl.

The term "$C_3$-$C_7$ heterocycle" or "$C_3$-$C_7$ heterocyclic" as used herein, means a 3, 4, 5, 6 or 7 membered ring containing at least one heteroatom independently selected from the group consisting of O, N, and S. A three- or four-membered ring contains zero or one double bond, and one heteroatom selected from the group consisting of O, N, and S. When two O atoms or one O atom and one S atom are present in a heterocyclic ring, then the two O atoms or one O atom and one S atom are not bonded directly to each other. A five-membered ring contains zero or one double bond and one, two, or three heteroatoms selected from the group consisting of O, N, and S. Examples of five-membered heterocyclic rings include those containing in the ring: 1 O; 1 S; 1 N; 2 N; 3 N; 1 S and 1 N; 1 S, and 2 N; 1 O and 1 N; or 1 O and 2 N. Examples of 5-membered heterocyclic groups include tetrahydrofuranyl, dihydrofuranyl, tetrahydrothienyl, dihydrothienyl, imidazolidinyl, oxazolidinyl, imidazolinyl, isoxazolidinyl, pyrrolidinyl, 2-pyrrolinyl, and 3-pyrrolinyl. A six-membered ring contains zero, one, or two double bonds and one, two, or three heteroatoms selected from the group consisting of O, N, and S. Examples of six-membered heterocyclic rings include those containing in the ring: 1 O; 2 O; 1 S; 2 S; 1 N; 2 N; 3 N; 1 S, 1 O, and 1 N; 1 S and 1 N; 1 S and 2 N; 1 S and 1 O; 1 S and 2 O; 1 Q and 1 N; and 1 O and 2 N. Examples of 6-membered heterocyclic groups include tetrahydropyranyl, dihydropyranyl, dioxanyl, 1,3-dioxolanyl, 1,4-dithianyl, hexahydropyrimidine, morpholinyl, piperazinyl, piperidinyl, 2H-pyranyl, 4H-pyranyl, pyrazolidinyl, pyrazolinyl, 1,2,3,6-tetrahydropyridinyl, tetrahydrothiopyranyl, 1,1-dioxohexahydro-1-thiopyranyl, 1,1-dioxo-1$\lambda^6$-thiomorpholinyl, thiomorpholinyl, thioxanyl, and trithianyl. Seven- and eight-membered rings contains zero, one, two, or three double bonds and one, two, or three heteroatoms selected from the group consisting of O, N, and S. The heterocycles may contain one or two alkylene bridges or an alkenylene bridge, or mixture thereof, each consisting of no more than four carbon atoms and each linking two non adjacent atoms of the ring system. Examples of such bridged heterocycle include, but are not limited to, azabicyclo[2.2.1]heptyl (including 2-azabicyclo[2.2.1]hept-2-yl), 8-azabicyclo[3.2.1]oct-8-yl, aza-admantane (1-azatricyclo[3.3.1.1$^{3,7}$]decane), and oxa-admantane (2-oxatricyclo[3.3.1.1$^{3,7}$]decane). The heterocycles can be unsubstituted or substituted and are connected to the parent molecular moiety through any carbon atom or any nitrogen atom contained within the ring systems. The nitrogen and sulfur heteroatoms in the heterocycle rings may optionally be oxidized (e.g. 1,1-dioxidotetrahydrothienyl, 1,2-dioxido-1,2-thiazolidinyl, 1,1-dioxidothiomorpholinyl)) and the nitrogen atoms may optionally be quarternized.

The term "$C_4$-$C_6$ heterocycle" as used herein, means a four-, five-, or six-membered carbocyclic ring containing at least one heteroatom independently selected from the group consisting of O, N, and S, and zero double bond. Examples of $C_4$-$C_6$ heterocycle include azetidinyl, pyrrolidinyl, tetrahydrofuranyl, tetrahydropyranyl, piperazinyl, piperidinyl, and morpholinyl.

The term "heteroaryl" as used herein, means a monocyclic heteroaryl or a bicyclic heteroaryl. The monocyclic heteroaryl is a 5 or 6 membered ring. The five-membered ring contains two double bonds. The five membered ring may contain one heteroatom selected from O or S; or one, two, three, or four nitrogen atoms and optionally one oxygen or one sulfur atom. The six-membered ring contains three double bonds and one, two, three or four nitrogen atoms. Representative examples of monocyclic heteroaryl include, but are not limited to, furanyl, imidazolyl, isoxazolyl, isothiazolyl, oxadiazolyl, 1,3-oxazolyl, pyridinyl, pyridazinyl, pyrimidinyl, pyrazinyl, pyrazolyl, pyrrolyl, tetrazolyl, thiadiazolyl, 1,3-thiazolyl, thienyl, triazolyl, and triazinyl. The bicyclic heteroaryl consists of a monocyclic heteroaryl fused to a phenyl, or a monocyclic heteroaryl fused to a $C_3$-$C_8$ cycloalkyl, or a monocyclic heteroaryl fused to a monocyclic $C_5$-$C_8$ cycloalkenyl, or a monocyclic heteroaryl fused to a monocyclic heteroaryl, or a monocyclic heteroaryl fused to a $C_3$-$C_7$ heterocycle. Representative examples of bicyclic heteroaryl groups include, but are not limited to, benzofuranyl, benzothienyl, benzoxazolyl, benzimidazolyl, benzoxadiazolyl, phthalazinyl, 2,6-dihydropyrrolo[3,4-c]pyrazol-5(4H)-yl, 6,7-dihydro-pyrazolo[1,5-a]pyrazin-5(4H)-yl, 6,7-dihydro-1,3-benzothiazolyl, imidazo[1,2-a]pyridinyl, indazolyl, indolyl, isoindolyl, isoquinolinyl, naphthyridinyl, pyridoimidazolyl, quinolinyl, 2,4,6,7-tetrahydro-5H-pyrazolo[4,3-c]pyridin-5-yl, thiazolo[5,4-b]pyridin-2-yl, thiazolo[5,4-d]pyrimidin-2-yl, and 5,6,7,8-tetrahydroquinolin-5-yl. The monocyclic and bicyclic heteroaryl groups can be substituted or unsubstituted or are connected to the parent molecular moiety through any substitutable carbon atom or any substitutable nitrogen atom contained within the ring systems. The nitrogen atom in the heteroaryl rings may optionally be oxidized and may optionally be quarternized.

The term "$C_5$-$C_6$ heteroaryl" as used herein, means a monocyclic heteroaryl ring as described above. Examples of $C_5$-$C_6$ heteroaryl include furanyl, thienyl, pyrazolyl, 1,2,4-oxadiazolyl, 1,2,4-trazolyl, 1,3-thiazolyl, pyridinyl, and pyrazinyl.

The term "heteroatom" as used herein, means a nitrogen, oxygen, and sulfur.

The term "oxo" as used herein, means a =O group.

If a moiety is described as "substituted", a non-hydrogen radical is in the place of hydrogen radical of any substitutable atom of the moiety. Thus, for example, a substituted heterocycle moiety is a heterocycle moiety in which at least one non-hydrogen radical is in the place of a hydrogen radical on the heterocycle. It should be recognized that if there are more than one substitution on a moiety, each non-hydrogen radical may be identical or different (unless otherwise stated).

If a moiety is described as being "optionally substituted," the moiety may be either (1) not substituted or (2) substituted. If a moiety is described as being optionally substituted with up to a particular number of non-hydrogen radicals, that moiety may be either (1) not substituted; or (2) substituted by up to that particular number of non-hydrogen radicals or by up to the maximum number of substitutable positions on the moiety, whichever is less. Thus, for example, if a moiety is described as a heteroaryl optionally substituted with up to 3 non-hydrogen radicals, then any heteroaryl with less than 3 substitutable positions would be optionally substituted by up to only as many non-hydrogen radicals as the heteroaryl has substitutable positions. To illustrate, tetrazolyl (which has only one substitutable position) would be optionally substituted with up to one non-hydrogen radical. To illustrate further, if an amino nitrogen is described as being optionally substituted with up to 2 non-hydrogen radicals, then a primary amino nitrogen will be optionally substituted with up to 2 non-hydrogen radicals, whereas a secondary amino nitrogen will be optionally substituted with up to only 1 non-hydrogen radical.

The terms "treat", "treating", and "treatment" refer to a method of alleviating or abrogating a disease and/or its attendant symptoms.

The terms "prevent", "preventing", and "prevention" refer to a method of preventing the onset of a disease and/or its attendant symptoms or barring a subject from acquiring a disease. As used herein, "prevent", "preventing" and "prevention" also include delaying the onset of a disease and/or its attendant symptoms and reducing a subject's risk of acquiring a disease.

The phrase "therapeutically effective amount" means an amount of a compound, or a pharmaceutically acceptable salt thereof, sufficient to prevent the development of or to alleviate to some extent one or more of the symptoms of the condition or disorder being treated when administered alone or in conjunction with another pharmaceutical agent or treatment in a particular subject or subject population. For example in a human or other mammal, a therapeutically effective amount can be determined experimentally in a laboratory or clinical setting, or may be the amount required by the guidelines of the United States Food and Drug Administration, or equivalent foreign agency, for the particular disease and subject being treated.

The term "subject" is defined herein to refer to animals such as mammals, including, but not limited to, primates (e.g., humans), cows, sheep, goats, horses, dogs, cats, rabbits, rats, mice and the like. In preferred embodiments, the subject is a human.

b. Compounds

Compounds of the invention have the general formula (I) as described above.

Particular values of variable groups in compounds of formula (I) are as follows. Such values may be used where appropriate with any of the other values, definitions, claims or embodiments defined hereinbefore or hereinafter.

In certain embodiments of formula (I), $R^1$ is $C_1$-$C_3$ alkyl or $C_1$-$C_3$ haloalkyl.

In certain embodiments, $R^1$ is $C_1$-$C_3$ alkyl. In some such embodiments, $R^1$ is methyl.

In certain embodiments of formula (I), X—Y is —$CR^3$=CH—, —N=$CR^4$—, —$CR^5$=N—, or —$CR^6R^7$—$CR^8R^9$—; wherein the left ends of the moieties are attached to the NH group in the ring.

In certain embodiments wherein X—Y is —$CR^3$=CH— correspond in structure to the following formula (i.e. formula (Ia)):

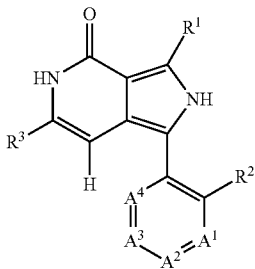

(Ia)

wherein $R^1$, $R^2$, $R^3$, $A^1$, $A^2$, $A^3$, and $A^4$, are as described in the Summary and embodiments herein.

In certain embodiments wherein X—Y is —N═CR⁴— correspond in structure to the following formula (i.e. formula (Ib)):

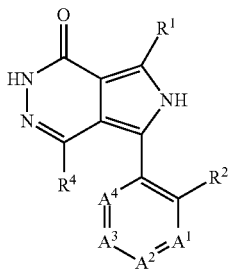

(Ib)

wherein $R^1$, $R^2$, $R^4$, $A^1$, $A^2$, $A^3$, and $A^4$, are as described in the Summary and embodiments herein.

In certain embodiments wherein X—Y is —CR⁵═N— correspond in structure to the following formula (i.e. formula (Ic)):

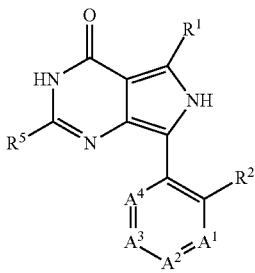

(Ic)

wherein $R^1$, $R^2$, $R^5$, $A^1$, $A^2$, $A^3$, and $A^4$, are as described in the Summary and embodiments herein.

In certain embodiments wherein X—Y is —CR⁶R⁷—CR⁸R⁹— correspond in structure to the following formula (i.e. formula (Id)):

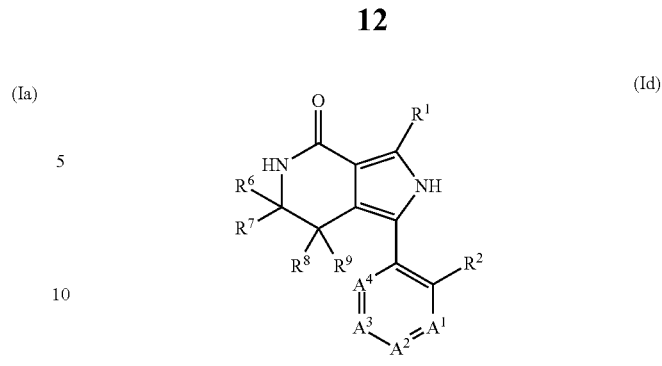

(Id)

wherein $R^1$, $R^2$, $R^6$, $R^7$, $R^8$, $R^9$, $A^1$, $A^2$, $A^3$, and $A^4$, are as described in the Summary and embodiments herein.

In certain embodiments of formula (I), (Ia), (Ib), and (Id), $R^2$ is $R^{xa}$ wherein $R^{xa}$ is as defined in the Summary.

In certain embodiments of formula (I), (Ia), (Ib), and (Id), $R^{xa}$ is hydrogen, $C_1$-$C_6$ alkyl, $C_2$-$C_6$ alkenyl, $C_2$-$C_6$ alkynyl, halogen, $C_1$-$C_6$ haloalkyl, —CN, —OR$^{x1}$, —SR$^{x1}$, —S(O)$_2$R$^{x1}$, —S(O)$_2$NR$^{x3}$R$^{x4}$, —C(O)R$^{x1}$, —C(O)NR$^{x3}$R$^{x4}$, —NR$^{x3}$R$^{x4}$, —N(R$^{x5}$)C(O)R$^{x2}$, —N(R$^{x5}$)S(O)$_2$R$^{x2}$, —(C$_1$-C$_6$ alkylenyl)-G, or —(C$_1$-C$_6$ alkylenyl)-S(O)$_2$R$^{x1}$.

In certain embodiments of formula (I), (Ia), (Ib), and (Id), $R^{xa}$ is hydrogen, $C_1$-$C_6$ alkyl, halogen, $C_1$-$C_6$ haloalkyl, —CN, —OR$^{x1}$, or —NR$^{x3}$R$^{x4}$.

In certain embodiments of formula (I), (Ia), (Ib), and (Id), $R^{xa}$ is —OR$^{x1}$ or —NR$^{x3}$R$^{x4}$.

In certain embodiments of formula (I), (Ia), (Ib), and (Id), $R^{xa}$ is —OR$^{x1}$.

In certain embodiments of formula (I), (Ia), (Ib), and (Id), $R^{xa}$ is —NR$^{x3}$R$^{x4}$.

In some such embodiments, $R^{x1}$ and $R^{x3}$, are each independently G or —C$_1$-C$_6$ alkylenyl-G; and $R^{x4}$ is H or C$_1$-C$_6$ alkyl. In some such embodiments, $R^{x1}$ and $R^{x3}$, are each independently G or —C$_1$-C$_6$ alkylenyl-G; $R^{x4}$ is H or C$_1$-C$_3$ alkyl; and G is optionally substituted aryl or optionally substituted $C_3$-$C_8$ cycloalkyl. In some such embodiments, $R^{x1}$ and $R^{x3}$, are each independently G or —C$_1$-C$_3$ alkylenyl-G; $R^{x4}$ is H or $C_1$-$C_3$ alkyl; and G is optionally substituted phenyl or optionally substituted $C_3$-$C_6$ cycloalkyl. In some such embodiments, $R^{x1}$ and $R^{x3}$, are each independently G or —C$_1$-C$_3$ alkylenyl-G; $R^{x4}$ is H; and G is phenyl, cyclopropyl, or cyclohexyl, each of which is optionally substituted. In some such embodiments, $R^{x1}$ and $R^{x3}$, are each independently G or —CH$_2$-G; $R^{x4}$ is H; and G is phenyl or cyclopropyl, each of which is optionally substituted. Said G groups are optionally substituted as described in the Summary. For example, said G groups are optionally substituted with 1, 2, or 3 $R^g$, wherein $R^g$ is independently selected from the group consisting of $C_1$-$C_6$ alkyl, $C_1$-$C_6$ haloalkyl, halogen, —OH, —O(C$_1$-C$_6$ alkyl), and —O(C$_1$-C$_6$ haloalkyl). In certain embodiments, said G groups are optionally substituted with 1 or 2 halogens, for example, 1 or 2 fluorine.

In certain embodiments of formula (I) and (Ic), $R^2$ is -L-G wherein L is O, N(R$^y$), O—C$_1$-C$_6$ alkylenyl, or N(R$^y$)—C$_1$-C$_6$ alkyenyl, wherein $R^y$ is hydrogen or $C_1$-$C_4$ alkyl.

In certain embodiments of formula (I) and (Ic), $R^2$ is -L-G wherein L is O, O—C$_1$-C$_6$ alkylenyl, or N(R$^y$)—C$_1$-C$_6$ alkylenyl; wherein $R^y$ is hydrogen; and G is optionally substituted phenyl, optionally substituted $C_4$-$C_6$ heterocycle, or optionally substituted $C_3$-$C_6$ cycloalkyl.

In certain embodiments of formula (I) and (Ic), $R^2$ is -L-G wherein L is O or O—C$_1$-C$_3$ alkylenyl; and G is optionally substituted phenyl or optionally substituted $C_3$-$C_6$ cycloalkyl.

In certain embodiments of formula (I) and (Ic), $R^2$ is -L-G wherein L is O, and G is optionally substituted phenyl or optionally substituted $C_3$-$C_6$ cycloalkyl. In some such embodiments, the phenyl group and the $C_3$-$C_6$ cycloalkyl group are optionally substituted with 1, 2, or 3 $R^g$ groups, wherein each $R^g$ is independently $C_1$-$C_6$ alkyl, $C_1$-$C_6$ haloalkyl, halogen, —OH, —O($C_1$-$C_6$ alkyl), or —O($C_1$-$C_6$ haloalkyl).

In certain embodiments of formula (I) and (Ic), $R^2$ is -L-G wherein L is O, and G is optionally substituted phenyl. In some such embodiments, the phenyl group is optionally substituted with 1, 2, or 3 substituents ($R^g$) selected from the group consisting of $C_1$-$C_6$ alkyl, $C_1$-$C_6$ haloalkyl, and halogen. In some such embodiments, the phenyl group is optionally substituted with 1 or 2 halogen.

In certain embodiments of formula (I), (Ia), (Ib), (Ic) and (Id), $A^1$, $A^2$, $A^3$, and $A^4$ are $CR^x$; or one or two of $A^1$, $A^2$, $A^3$, and $A^4$ are N, and the others are $CR^x$.

In certain embodiments, $A^1$, $A^2$, $A^3$, and $A^4$ are $CR^x$.

In certain embodiments, one of $A^1$, $A^2$, $A^3$, and $A^4$ is N, and the others are $CR^x$.

In certain embodiments, two of $A^1$, $A^2$, $A^3$, and $A^4$ are N, and the others are $CR^x$.

In certain embodiments of formula (I), (Ia), (Ib), (Ic) and (Id), $R^x$ is hydrogen, $C_1$-$C_6$ alkyl, $C_2$-$C_6$ alkenyl, $C_2$-$C_6$ alkynyl, halogen, $C_1$-$C_6$ haloalkyl, —CN, $NO_2$, G, —$OR^{x1}$, —OC(O)$R^{x2}$, —OC(O)$NR^{x3}R^{x4}$, —$SR^{x1}$, —S(O)$_2R^{x1}$, —S(O)$_2NR^{x3}R^{x4}$, —C(O)$R^{x1}$, —C(O)$OR^{x1}$, —C(O)$NR^{x3}R^{x4}$, —$NR^{x3}R^{x4}$, —N($R^{x5}$)C(O)$R^{x2}$, —N($R^{x5}$)S(O)$_2R^{x2}$, —N($R^{x5}$)C(O)O($R^{x2}$), —N($R^{x5}$)C(O)$NR^{x3}R^{x4}$, —N($R^{x5}$)S(O)$_2NR^{x3}R^{x4}$, —($C_1$-$C_6$ alkylenyl)-G, —($C_1$-$C_6$ alkylenyl)-$OR^{x1}$, —($C_1$-$C_6$ alkylenyl)-OC(O)$R^{x2}$, —($C_1$-$C_6$ alkylenyl)-OC(O)$NR^{x3}R^{x4}$, —($C_1$-$C_6$ alkylenyl)-S(O)$_2R^{x1}$, —($C_1$-$C_6$ alkylenyl)-S(O)$_2NR^{x3}R^{x4}$, —($C_1$-$C_6$ alkylenyl)-C(O)$R^{x1}$, —($C_1$-$C_6$ alkylenyl)-C(O)$OR^{x1}$, —($C_1$-$C_6$ alkylenyl)-C(O)$NR^{x3}R^{x4}$, —($C_1$-$C_6$ alkylenyl)-$NR^{x3}R^{x4}$, —($C_1$-$C_6$ alkylenyl)-N($R^{x5}$)C(O)$R^{x2}$, —($C_1$-$C_6$ alkylenyl)-N($R^{x5}$)S(O)$_2R^{x2}$, —($C_1$-$C_6$ alkylenyl)-N($R^{x5}$)C(O)O($R^{x2}$), —($C_1$-$C_6$ alkylenyl)-N($R^{x5}$)C(O)$NR^{x3}R^{x4}$, —($C_1$-$C_6$ alkylenyl)-N($R^{x5}$)S(O)$_2$ $NR^{x3}R^{x4}$, and —($C_1$-$C_6$ alkylenyl)-CN.

In certain embodiments, $R^x$ is hydrogen, $C_1$-$C_6$ alkyl, $C_2$-$C_6$ alkenyl, $C_2$-$C_6$ alkynyl, halogen, $C_1$-$C_6$ haloalkyl, —CN, $NO_2$, G, —S(O)$_2R^{x1}$, —$NR^{x3}R^{x4}$, —N($R^{x5}$)S(O)$_2R^{x2}$, —($C_1$-$C_6$ alkylenyl)-G, —($C_1$-$C_6$ alkylenyl)-$OR^{x1}$, or —($C_1$-$C_6$ alkylenyl)-S(O)$_2R^{x1}$. In some such embodiments, G is optionally substituted heteroaryl or optionally substituted $C_3$-$C_7$ heterocycle. In some such embodiments, G is optionally substituted $C_5$-$C_6$ heteroaryl or optionally substituted $C_4$-$C_6$ heterocycle. In some such embodiments, $R^{x1}$, $R^{x3}$, $R^{x4}$, and $R^{x5}$, at each occurrence, are each independently H, $C_1$-$C_6$ alkyl, or $C_1$-$C_6$ haloalkyl. In some such embodiments, $R^{x2}$ is $C_1$-$C_6$ alkyl, $C_1$-$C_6$ haloalkyl, or optionally substituted phenyl. In some such embodiments, $R^{x2}$ is $C_1$-$C_3$ alkyl.

In certain embodiments, $A^1$ is CH, $A^2$ is CH, $A^3$ is $CR^x$, and $A^4$ is CH. In some such embodiments, $R^x$ is hydrogen, halogen, $C_1$-$C_6$ haloalkyl, —CN, $NO_2$, —S(O)$_2R^{x1}$, —$NR^{x3}R^{x4}$, —N($R^{x5}$)S(O)$_2R^{x2}$, or —($C_1$-$C_6$ alkylenyl)-S(O)$_2R^{x1}$. In some such embodiments, $R^{x1}$, $R^{x3}$, $R^{x4}$, and $R^{x5}$, at each occurrence, are each independently H, $C_1$-$C_6$ alkyl, or $C_1$-$C_6$ haloalkyl. In some such embodiments, $R^{x2}$ is $C_1$-$C_6$ alkyl, $C_1$-$C_6$ haloalkyl, or optionally substituted phenyl. In some such embodiments, $R^{x2}$ is $C_1$-$C_3$ alkyl.

In certain embodiments, $A^1$ is CH, $A^2$ is $CR^x$, $A^3$ is CH, and $A^4$ is CH. In some such embodiments, $R^x$ is optionally substituted $C_5$-$C_6$ heteroaryl.

In certain embodiments of formula (I) and (Ia), $R^3$ is H, —CN, $C_1$-$C_6$ alkyl, $C_2$-$C_6$ alkenyl, $C_2$-$C_6$ alkynyl, halogen, $C_1$-$C_6$ haloalkyl, —C(O)$R^{3a}$, —C(O)$OR^{3a}$, —C(O)$NR^{3b}R^{3c}$, —C(O)N($R^{3b}$)$N^{3b}R^{3c}$, —S(O)$R^{3d}$, —S(O)$_2R^{3a}$, —S(O)$_2NR^{3b}R^{3c}$, or $G^1$; wherein the $C_1$-$C_6$ alkyl, $C_2$-$C_6$ alkenyl, and $C_2$-$C_6$ alkynyl are each independently unsubstituted or substituted with 1 or 2 substituents independently selected from the group consisting of $G^1$, —C(O)$R^{3a}$, —C(O)$OR^{3a}$, —C(O)$NR^{3b}R^{3c}$, —C(O)N($R^{3b}$)$NR^{3b}R^{3c}$, —S(O)$R^{3d}$, —S(O)$_2R^{3a}$, —S(O)$_2NR^{3b}R^{3c}$, —$OR^{3a}$, —OC(O)$R^{3d}$, $NR^{3b}R^{3c}$, N($R^{3b}$)C(O)$R^{3d}$, N($R^{3b}$)SO$_2R^{3d}$, N($R^{3b}$)C(O)$OR^{3d}$, N($R^{3b}$)C(O)$NR^{3b}R^{3c}$, and N($R^{3b}$)SO$_2NR^{3b}R^{3c}$.

In certain embodiments, $R^3$ is H, —C(O)$R^{3a}$, —C(O)$OR^{3a}$, —C(O)$NR^{3b}R^{3c}$, $G^1$, or $C_1$-$C_6$ alkyl substituted with one —$OR^{3a}$ group.

In certain embodiments, $R^3$ is —C(O)$OR^{3a}$ or —C(O)$NR^{3b}R^{3c}$.

In certain embodiments, $R^3$ is —C(O)$R^{3a}$ wherein $R^a$ is $G^1$ or —($C_1$-$C_6$ alkylenyl)-$G^1$. In some such embodiments, $G^1$ is optionally substituted $C_3$-$C_7$ heterocycle. In some such embodiments, $G^1$ is morpholinyl, piperazinyl, or piperidinyl, each of which is optionally substituted.

In certain embodiments, $R^3$ is —C(O)$OR^{3a}$. In some such embodiments, $R^{3a}$ is H or $C_1$-$C_6$ alkyl.

In certain embodiments, $R^3$ is —C(O)$NR^{3b}R^{3c}$. In some such embodiments, $R^{3b}$ is H or $C_1$-$C_6$ alkyl and $R^{3c}$ is H, $C_1$-$C_6$ alkyl, $G^1$, —($C_1$-$C_6$ alkylenyl)-$G^1$, —($C_1$-$C_6$ alkylenyl)-$OR^a$, or —($C_1$-$C_6$ alkylenyl)-CN. In some such embodiments, $R^{3b}$ is H or $C_1$-$C_6$ alkyl, and $R^{3c}$ is $C_1$-$C_6$ alkyl or —($C_1$-$C_6$ alkylenyl)-$OR^a$. In the embodiments wherein $R^{3c}$ is $G^1$ or —($C_1$-$C_6$ alkylenyl)-$G^1$; $G^1$ is phenyl, $C_5$-$C_6$ heteroaryl, $C_4$-$C_6$ heterocycle, or $C_3$-$C_6$ cycloalkyl, each of which is optionally substituted.

In certain embodiments, $R^3$ is $G^1$. In some such embodiments, $G^1$ is optionally substituted heteroaryl. In some such embodiments, $G^1$ is optionally substituted $C_5$-$C_6$ heteroaryl. In some such embodiments, $G^1$ is optionally substituted oxadiazolyl.

In certain embodiments of formula (I) and (Ib), $R^4$ is H, —CN, $C_1$-$C_6$ alkyl, $C_2$-$C_6$ alkenyl, $C_2$-$C_6$ alkynyl, halogen, or $C_1$-$C_6$ haloalkyl.

In certain embodiments, $R^4$ is H.

In certain embodiments of formula (I) and (Ic), $R^5$ is H, —CN, $C_1$-$C_6$ alkyl, $C_2$-$C_6$ alkenyl, $C_2$-$C_6$ alkynyl, halogen, $C_1$-$C_6$ haloalkyl, —C(O)$OR^{5a}$, —C(O)$NR^{5b}R^{5c}$, or $G^1$.

In certain embodiments, $R^5$ is H, $C_1$-$C_6$ alkyl, —C(O)$OR^{5a}$, or $G^1$. In some such embodiments, $R^{5a}$ is H or $C_1$-$C_6$ alkyl. In some such embodiments, $G^1$ is optionally substituted heteroaryl. In some such embodiments, $G^1$ is optionally substituted $C_5$-$C_6$ heteroaryl.

In certain embodiments of formula (I) and (Id), $R^6$ is H, —CN, $C_1$-$C_6$ alkyl, $C_2$-$C_6$ alkenyl, $C_2$-$C_6$ alkynyl, halogen, or $C_1$-$C_6$ haloalkyl; $R^8$ and $R^9$, are each independently H, $C_1$-$C_6$ alkyl, $C_2$-$C_6$ alkenyl, $C_2$-$C_6$ alkynyl, halogen, or $C_1$-$C_6$ haloalkyl; and $R^7$ is H, $C_1$-$C_6$ alkyl, $C_2$-$C_6$ alkenyl, $C_2$-$C_6$ alkynyl, halogen, $C_1$-$C_6$ haloalkyl, —C(O)$R^{7a}$, —C(O)$OR^{7a}$, —C(O)$NR^{7b}R^{7c}$, —S(O)$R^{7d}$, —S(O)$_2R^{7a}$, —S(O)$_2NR^{7b}R^{7c}$, or $G^1$; wherein the $C_1$-$C_6$ alkyl, $C_2$-$C_6$ alkenyl, and $C_2$-$C_6$ alkynyl are each independently unsubstituted or substituted with 1 or 2 substituents independently selected from the group consisting of $G^1$, —C(O)$R^{7a}$, —C(O)$OR^{7a}$, —C(O)$NR^{7b}R^{7c}$, —C(O)N($R^{7b}$)$NR^{7b}R^{7c}$, —S(O)$R^{7d}$, —S(O)$_2R^{7a}$, —S(O)$_2NR^{7b}R^{7c}$, —$OR^{7a}$, —OC(O)$R^{7d}$, —$NR^{7b}R^{7c}$, N($R^{7b}$)C(O)$R^{7d}$, N($R^{7b}$)SO$_2R^{7d}$, N($R^{7b}$)C(O)$OR^{7d}$, N($R^{7b}$)C(O)$NR^{7b}R^{7c}$, and N($R^{7b}$)SO$_2NR^{7b}R^{7c}$.

In certain embodiments, $R^6$, $R^8$, and $R^9$ are H, and $R^7$ is H, $C_1$-$C_6$ alkyl, or —C(O)$OR^{7a}$. In some such embodiments, $R^{7a}$ is $C_1$-$C_6$ alkyl. In some such embodiments, $R^7$ is H, $CH_3$, or —C(O)$OCH_3$.

Various embodiments of substituents X, Y, $R^1$, $R^2$, $R^3$, $R^4$, $R^5$, $R^6$, $R^7$, $R^8$, $R^9$, $A^1$, $A^2$, $A^3$, and $A^4$ have been discussed above. These substituents embodiments can be combined to form various embodiments of formula (I), (Ia), (Ib), (Ic), and (Id). All embodiments of formula (I), (Ia), (Ib), (Ic), and (Id) formed by combining the substituent embodiments discussed above are within the scope of Applicant's invention, and some illustrative embodiments of the formula (I), (Ia), (Ib), (Ic), and (Id) are provided below.

In certain embodiments of formula (I), (Ia), (Ib), (Ic), and (Id) wherein
$R^1$ is $C_1$-$C_3$ alkyl; and
$A^1$, $A^2$, $A^3$, and $A^4$ are $CR^x$.

In certain embodiments of formula (I), (Ia), (Ib), and (Id) wherein
$R^1$ is $C_1$-$C_3$ alkyl;
$R^2$ is $R^{xa}$; and
$R^{xa}$ is hydrogen, $C_1$-$C_6$ alkyl, $C_2$-$C_6$ alkenyl, $C_2$-$C_6$ alkynyl, halogen, $C_1$-$C_6$ haloalkyl, —CN, —$OR^{x1}$, —$SR^{x1}$, —$S(O)_2R^{x1}$, —$S(O)_2NR^{x3}R^{x4}$, —$C(O)R^{x1}$, —$C(O)NR^{x3}R^{x4}$, —$NR^{x3}R^{x4}$, —$N(R^{x5})C(O)R^{x2}$, —$N(R^{x5})S(O)_2R^{x2}$, —($C_1$-$C_6$ alkylenyl)-G, or —($C_1$-$C_6$ alkylenyl)-$S(O)_2R^{x1}$.

In certain embodiments of formula (I), (Ia), (Ib), and (Id) wherein
$R^1$ is $C_1$-$C_3$ alkyl;
$R^2$ is $R^{xa}$;
$R^{xa}$ is hydrogen, $C_1$-$C_6$ alkyl, $C_2$-$C_6$ alkenyl, $C_2$-$C_6$ alkynyl, halogen, $C_1$-$C_6$ haloalkyl, —CN, —$OR^{x1}$, —$SR^{x1}$, —$S(O)_2R^{x1}$, —$S(O)_2NR^{x3}R^{x4}$, —$C(O)R^{x1}$, —$C(O)NR^{x3}R^{x4}$, —$NR^{x3}R^{x4}$, —$N(R^{x5})C(O)R^{x2}$, —$N(R^{x5})S(O)_2R^{x2}$, —($C_1$-$C_6$ alkylenyl)-G, or —($C_1$-$C_6$ alkylenyl)-$S(O)_2R^{x1}$; and
$A^1$, $A^2$, $A^3$, and $A^4$ are $CR^x$.

In certain embodiments of formula (I), (Ia), (Ib), and (Id) wherein
$R^1$ is $C_1$-$C_3$ alkyl;
$R^2$ is $R^{xa}$;
$R^{xa}$ is hydrogen, $C_1$-$C_6$ alkyl, halogen, $C_1$-$C_6$ haloalkyl, —CN, —$OR^{x1}$, or —$NR^{x3}R^{x4}$;
$A^1$, $A^2$, $A^3$, and $A^4$ are $CR^x$; and
$R^x$ is hydrogen, $C_1$-$C_6$ alkyl, $C_2$-$C_6$ alkenyl, $C_2$-$C_6$ alkynyl, halogen, $C_1$-$C_6$ haloalkyl, —CN, $NO_2$, G, —$S(O)_2R^{x1}$, —$NR^{x3}R^{x4}$, —$N(R^{x5})S(O)_2R^{x2}$, —($C_1$-$C_6$ alkylenyl)-G, —($C_1$-$C_6$ alkylenyl)-$OR^{x1}$, or —($C_1$-$C_6$ alkylenyl)-$S(O)_2R^{x1}$.

In certain embodiments of formula (I) and (Ic) wherein
$R^1$ is $C_1$-$C_3$ alkyl;
$R^2$ is -L-G;
L is O, O—$C_1$-$C_6$ alkylenyl, or N($R^y$)—$C_1$-$C_6$ alkylenyl; wherein $R^y$ is hydrogen;
G is optionally substituted phenyl, optionally substituted $C_4$-$C_6$ heterocycle, or optionally substituted $C_3$-$C_6$ cycloalkyl.

In certain embodiments of formula (I) and (Ic) wherein
$R^1$ is $C_1$-$C_3$ alkyl;
$R^2$ is -L-G;
L is O or O—$C_1$-$C_3$ alkylenyl;
G is optionally substituted phenyl or optionally substituted $C_3$-$C_6$ cycloalkyl; and
$A^1$, $A^2$, $A^3$, and $A^4$ are $CR^x$.

In certain embodiments of formula (I) and (Ic) wherein
$R^1$ is $C_1$-$C_3$ alkyl;
$R^2$ is -L-G;
L is O;
G is optionally substituted phenyl or optionally substituted $C_3$-$C_6$ cycloalkyl;
$A^1$, $A^2$, $A^3$, and $A^4$ are $CR^x$; and
$R^x$ is hydrogen, $C_1$-$C_6$ alkyl, $C_2$-$C_6$ alkenyl, $C_2$-$C_6$ alkynyl, halogen, $C_1$-$C_6$ haloalkyl, —CN, $NO_2$, G, —$S(O)_2R^{x1}$, —$NR^{x3}R^{x4}$, —$N(R^{x5})S(O)_2R^{x2}$, —($C_1$-$C_6$ alkylenyl)-G, —($C_1$-$C_6$ alkylenyl)-$OR^{x1}$, or —($C_1$-$C_6$ alkylenyl)-$S(O)_2R^{x1}$.

In certain embodiments of formula (Ia), or a pharmaceutically acceptable salt thereof, wherein
$R^1$ is $CH_3$,
$R^2$ is $R^{xa}$,
$R^{xa}$ is —$OR^{xa}$ or —$NR^{x3}R^{x4}$;
$R^{x1}$ and $R^{x3}$ are each independently G or —$C_1$-$C_6$ alkylenyl-G; and
$R^{x4}$ is H or $C_1$-$C_6$ alkyl.

In certain embodiments of formula (Ia), or a pharmaceutically acceptable salt thereof, wherein
$R^1$ is $CH_3$,
$R^2$ is $R^{xa}$,
$R^{xa}$ is —$OR^{x1}$;
$R^{x1}$ is G or —$C_1$-$C_3$ alkylenyl-G;
G is optionally substituted phenyl or optionally substituted $C_3$-$C_6$ cycloalkyl; and
$A^1$, $A^2$, $A^3$, and $A^4$, are $CR^x$.

In certain embodiments of formula (Ia), or a pharmaceutically acceptable salt thereof, wherein
$R^1$ is $CH_3$,
$R^2$ is $R^{xa}$,
$R^{xa}$ is —$OR^{x1}$;
$R^{x1}$ is G or —$C_1$-$C_3$ alkylenyl-G;
G is optionally substituted phenyl or optionally substituted $C_3$-$C_6$ cycloalkyl;
$A^1$, $A^2$, and $A^4$ are CH,
$A^3$ is $CR^x$; and
$R^x$ is hydrogen, halogen, $C_1$-$C_6$ haloalkyl, —CN, $NO_2$, —$S(O)_2R^{x1}$, —$NR^{x3}R^{x4}$, —$N(R^{x5})S(O)_2R^{x2}$, or —($C_1$-$C_6$ alkylenyl)-$S(O)_2R^{x1}$.

In certain embodiments of formula (Ia), or a pharmaceutically acceptable salt thereof, wherein
$R^1$ is $CH_3$,
$R^2$ is $R^{xa}$,
$R^{xa}$ is —$OR^{x1}$;
$R^{x1}$ is G or —$C_1$-$C_3$ alkylenyl-G;
G is optionally substituted phenyl or optionally substituted $C_3$-$C_6$ cycloalkyl;
$A^1$, $A^2$, and $A^4$ are CH,
$A^3$ is $CR^x$;
$R^x$ is hydrogen, halogen, $C_1$-$C_6$ haloalkyl, —CN, $NO_2$, —$S(O)_2R^{x1}$, —$NR^{x3}R^{x4}$, —$N(R^{x5})S(O)_2R^{x2}$, or —($C_1$-$C_6$ alkylenyl)-$S(O)_2R^{x1}$; and
$R^3$ is H, —$C(O)R^{3a}$, —$C(O)OR^{3a}$, —$C(O)NR^{3b}R^{3c}$ $G^1$, or $C_1$-$C_6$ alkyl substituted with one —$OR^{3a}$ group.

In certain embodiments of formula (Ib), or a pharmaceutically acceptable salt thereof, wherein
$R^1$ is $CH_3$,
$R^2$ is $R^{xa}$,
$R^{xa}$ is —$OR^{x1}$ or —$NR^{x3}R^{x4}$;
$R^{x1}$ and $R^{x3}$ are each independently G or —$C_1$-$C_6$ alkylenyl-G; and
$R^{x4}$ is H or $C_1$-$C_6$ alkyl.

In certain embodiments of formula (Ib), or a pharmaceutically acceptable salt thereof, wherein
$R^1$ is $CH_3$,
$R^2$ is $R^{xa}$,
$R^{xa}$ is —$OR^{x1}$ or —$NR^{x3}R^{x4}$;
$R^{x1}$ and $R^{x3}$ are each independently G or —$C_1$-$C_3$ alkylenyl-G;
$R^{x4}$ is H or $C_1$-$C_3$ alkyl;

G is optionally substituted phenyl or optionally substituted $C_3$-$C_6$ cycloalkyl; and $A^1$, $A^2$, $A^3$, and $A^4$, are $CR^x$.

In certain embodiments of formula (Ib), or a pharmaceutically acceptable salt thereof, wherein
$R^1$ is $CH_3$,
$R^2$ is $R^{xa}$,
$R^{xa}$ is $-OR^{x1}$ or $-NR^{x3}R^{x4}$;
$R^{x1}$ and $R^{x3}$ are each independently G or $-C_1$-$C_3$ alkylenyl-G;
$R^{x4}$ is H or $C_1$-$C_3$ alkyl;
G is optionally substituted phenyl or optionally substituted $C_3$-$C_6$ cycloalkyl;
$A^1$, $A^2$, and $A^4$ are CH,
$A^3$ is $CR^x$; and
$R^x$ is hydrogen, halogen, $C_1$-$C_6$ haloalkyl, —CN, $NO_2$, $-S(O)_2R^{x1}$, $-NR^{x3}R^{x4}$, $-N(R^{x5})S(O)_2R^{x2}$, or $-(C_1$-$C_6$ alkylenyl)-$S(O)_2R^{x1}$.

In certain embodiments of formula (Ib), or a pharmaceutically acceptable salt thereof, wherein
$R^1$ is $CH_3$,
$R^2$ is $R^{xa}$,
$R^{xa}$ is $-OR^{x1}$ or $-NR^{x3}R^{x4}$;
$R^{x1}$ and $R^{x3}$ are each independently G or $-C_1$-$C_3$ alkylenyl-G;
$R^{x4}$ is H or $C_1$-$C_3$ alkyl;
G is optionally substituted phenyl or optionally substituted $C_3$-$C_6$ cycloalkyl;
$A^1$, $A^2$, and $A^4$ are CH,
$A^3$ is $CR^x$;
$R^x$ is hydrogen, halogen, $C_1$-$C_6$ haloalkyl, —CN, $NO_2$, $-S(O)_2R^{x1}$, $-NR^{x3}R^{x4}$, $-N(R^{x5})S(O)_2R^{x2}$, or $-(C_1$-$C_6$ alkylenyl)-$S(O)_2R^{x1}$; and
$R^4$ is H.

In certain embodiments of formula (Ic), or a pharmaceutically acceptable salt thereof, wherein
$R^1$ is $CH_3$,
$R^2$ is -L-G,
L is O or O—$C_1$-$C_3$ alkylenyl; and
G is optionally substituted phenyl or optionally substituted $C_3$-$C_6$ cycloalkyl.

In certain embodiments of formula (Ic), or a pharmaceutically acceptable salt thereof, wherein
$R^1$ is $CH_3$,
$R^2$ is -L-G,
L is O;
G is optionally substituted phenyl;
$A^1$, $A^2$, and $A^4$ are CH,
$A^3$ is $CR^x$;
$R^x$ is hydrogen, halogen, $C_1$-$C_6$ haloalkyl, —CN, $NO_2$, $-S(O)_2R^{x1}$, $-NR^{x3}R^{x4}$, $-N(R^{x5})S(O)_2R^{x2}$, or $-(C_1$-$C_6$ alkylenyl)-$S(O)_2R^{x1}$; and
$R^5$ is H, $C_1$-$C_6$ alkyl, $-C(O)OR^{5a}$, or $G^1$.

In certain embodiments of formula (Id), or a pharmaceutically acceptable salt thereof, wherein
$R^1$ is $CH_3$;
$R^2$ is $R^{xa}$;
$R^{xa}$ is $-OR^{x1}$ or $-NR^{x3}R^{x4}$;
$R^{x1}$ and $R^{x3}$ are each independently G or $-C_1$-$C_6$ alkylenyl-G; and
$R^{x4}$ is H or $C_1$-$C_6$ alkyl.

In certain embodiments of formula (Id), or a pharmaceutically acceptable salt thereof, wherein
$R^1$ is $CH_3$;
$R^2$ is $R^{xa}$;
$R^{xa}$ is $-OR^{x1}$;
$R^{x1}$ is G or $-C_1$-$C_3$ alkylenyl-G;

G is optionally substituted phenyl or optionally substituted $C_3$-$C_6$ cycloalkyl; and $A^1$, $A^2$, $A^3$, and $A^4$, are $CR^x$.

In certain embodiments of formula (Id), or a pharmaceutically acceptable salt thereof, wherein
$R^1$ is $CH_3$;
$R^2$ is $R^{xa}$;
$R^{xa}$ is $-OR^{x1}$;
$R^{x1}$ is G or $-C_1$-$C_3$ alkylenyl-G;
G is optionally substituted phenyl or optionally substituted $C_3$-$C_6$ cycloalkyl;
$A^1$, $A^2$, and $A^4$ are CH;
$A^3$ is $CR^x$; and
$R^x$ is hydrogen, halogen, $C_1$-$C_6$ haloalkyl, —CN, $NO_2$, $-S(O)_2R^{x1}$, $-NR^{x3}R^{x4}$, $-N(R^{x5})S(O)_2R^{x2}$, or $-(C_1$-$C_6$ alkylenyl)-$S(O)_2R^{x1}$.

In certain embodiments of formula (Id), or a pharmaceutically acceptable salt thereof, wherein
$R^1$ is $CH_3$;
$R^2$ is $R^{xa}$;
$R^{xa}$ is $-OR^{x1}$;
$R^{x1}$ is G or $-C_1$-$C_3$ alkylenyl-G;
G is optionally substituted phenyl or optionally substituted $C_3$-$C_6$ cycloalkyl;
$A^1$, $A^2$, and $A^4$ are CH;
$A^3$ is $CR^x$;
$R^x$ is hydrogen, halogen, $C_1$-$C_6$ haloalkyl, —CN, $NO_2$, $-S(O)_2R^{x1}$, $-NR^{x3}R^{x4}$, $-N(R^{x5})S(O)_2R^{x2}$, or $-(C_1$-$C_6$ alkylenyl)-$S(O)_2R^{x1}$;
$R^6$, $R^8$, and $R^9$ are H; and
$R^7$ is H, $C_1$-$C_6$ alkyl, or $-C(O)OR^{7a}$.

Compounds of formula (I) may contain one or more asymmetrically substituted atoms. Compounds of formula (I) may also exist as individual stereoisomers (including enantiomers and diastereomers) and mixtures thereof. Individual stereoisomers of compounds of formula (I) may be prepared synthetically from commercially available starting materials that contain asymmetric or chiral centers or by preparation of racemic mixtures followed by resolution of the individual stereoisomer using methods that are known to those of ordinary skill in the art. Examples of resolution are, for example, (i) attachment of a mixture of enantiomers to a chiral auxiliary, separation of the resulting mixture of diastereomers by recrystallization or chromatography, followed by liberation of the optically pure product; or (ii) separation of the mixture of enantiomers or diastereomers on chiral chromatographic columns.

Compounds of formula (I) may also include the various geometric isomers and mixtures thereof resulting from the disposition of substituents around a carbon-carbon double bond, a carbon-nitrogen double bond, a cycloalkyl group, or a heterocycle group. Substituents around a carbon-carbon double bond or a carbon-nitrogen double bond are designated as being of Z or E configuration and substituents around a cycloalkyl or heterocycle are designated as being of cis or trans configuration.

Within the present invention it is to be understood that compounds disclosed herein may exhibit the phenomenon of tautomerism and all tautomeric isomers are included in the scope of the invention.

Thus, the formula drawings within this specification can represent only one of the possible tautomeric, geometric, or stereoisomeric forms. It is to be understood that the invention encompasses any tautomeric, geometric, or stereoisomeric form, and mixtures thereof, and is not to be limited merely to any one tautomeric, geometric, or stereoisomeric form utilized within the formula drawings.

Exemplary compounds of formula (I) include, but are not limited to:

methyl 3-methyl-4-oxo-1-(2-phenoxyphenyl)-4,5-dihydro-2H-pyrrolo[3,4-c]pyridine-6-carboxylate;
methyl 1-(5-amino-2-phenoxyphenyl)-3-methyl-4-oxo-4,5-dihydro-2H-pyrrolo[3,4-c]pyridine-6-carboxylate;
methyl 3-methyl-1-{5-[(methylsulfonyl)amino]-2-phenoxyphenyl}-4-oxo-4,5-dihydro-2H-pyrrolo[3,4-c]pyridine-6-carboxylate;
ethyl 1-[5-amino-2-(2,4-difluorophenoxy)phenyl]-3-methyl-4-oxo-4,5-dihydro-2H-pyrrolo[3,4-c]pyridine-6-carboxylate;
ethyl 3-methyl-1-{5-[(methylsulfonyl)amino]-2-phenoxyphenyl}-4-oxo-4,5-dihydro-2H-pyrrolo[3,4-c]pyridine-6-carboxylate;
ethyl 1-{5-[(ethylsulfonyl)amino]-2-phenoxyphenyl}-3-methyl-4-oxo-4,5-dihydro-2H-pyrrolo[3,4-c]pyridine-6-carboxylate;
methyl 1-{5-[(ethylsulfonyl)amino]-2-phenoxyphenyl}-3-methyl-4-oxo-4,5-dihydro-2H-pyrrolo[3,4-c]pyridine-6-carboxylate;
ethyl 3-methyl-1-[4-(3-methyl-1H-pyrazol-5-yl)phenyl]-4-oxo-4,5-dihydro-2H-pyrrolo[3,4-c]pyridine-6-carboxylate;
ethyl 1-{2-(2,4-difluorophenoxy)-5-[(methylsulfonyl)amino]phenyl}-3-methyl-4-oxo-4,5-dihydro-2H-pyrrolo[3,4-c]pyridine-6-carboxylate;
ethyl 1-{2-(2,4-difluorophenoxy)-5-[(ethylsulfonyl)amino]phenyl}-3-methyl-4-oxo-4,5-dihydro-2H-pyrrolo[3,4-c]pyridine-6-carboxylate;
3-methyl-4-oxo-1-(2-phenoxyphenyl)-4,5-dihydro-2H-pyrrolo[3,4-c]pyridine-6-carboxamide;
3-methyl-4-oxo-1-(2-phenoxyphenyl)-4,5-dihydro-2H-pyrrolo[3,4-c]pyridine-6-carboxylic acid;
N,3-dimethyl-4-oxo-1-(2-phenoxyphenyl)-4,5-dihydro-2H-pyrrolo[3,4-c]pyridine-6-carboxamide;
3-methyl-1-(2-phenoxyphenyl)-2,5-dihydro-4H-pyrrolo[3,4-c]pyridin-4-one;
3-methyl-6-(morpholin-4-ylcarbonyl)-1-(2-phenoxyphenyl)-2,5-dihydro-4H-pyrrolo[3,4-c]pyridin-4-one;
3-methyl-6-[(4-methylpiperazin-1-yl)carbonyl]-1-(2-phenoxyphenyl)-2,5-dihydro-4H-pyrrolo[3,4-c]pyridin-4-one;
3-methyl-N-{4-[(4-methylpiperazin-1-yl)methyl]phenyl}-4-oxo-1-(2-phenoxyphenyl)-4,5-dihydro-2H-pyrrolo[3,4-c]pyridine-6-carboxamide;
6-(hydroxymethyl)-3-methyl-1-(2-phenoxyphenyl)-2,5-dihydro-4H-pyrrolo[3,4-c]pyridin-4-one;
1-{2-(2,4-difluorophenoxy)-5-[(methylsulfonyl)amino]phenyl}-3-methyl-4-oxo-4,5-dihydro-2H-pyrrolo[3,4-c]pyridine-6-carboxamide;
3-methyl-1-{5-[(methylsulfonyl)amino]-2-phenoxyphenyl}-4-oxo-4,5-dihydro-2H-pyrrolo[3,4-c]pyridine-6-carboxamide;
ethyl 1-[2-(2,4-difluorophenoxy)phenyl]-3-methyl-4-oxo-4,5-dihydro-2H-pyrrolo[3,4-c]pyridine-6-carboxylate;
1-[2-(2,4-difluorophenoxy)phenyl]-3-methyl-4-oxo-4,5-dihydro-2H-pyrrolo[3,4-c]pyridine-6-carboxylic acid;
1-[2-(2,4-difluorophenoxy)phenyl]-3-methyl-4-oxo-4,5-dihydro-2H-pyrrolo[3,4-c]pyridine-6-carboxamide;
ethyl 1-[5-chloro-2-(2,4-difluorophenoxy)phenyl]-3-methyl-4-oxo-4,5-dihydro-2H-pyrrolo[3,4-c]pyridine-6-carboxylate;
3-methyl-4-oxo-1-(2-phenoxyphenyl)-N-[2-(pyrrolidin-1-yl)ethyl]-4,5-dihydro-2H-pyrrolo[3,4-c]pyridine-6-carboxamide;
3-methyl-4-oxo-1-(2-phenoxyphenyl)-N-(1,3-thiazol-2-yl)-4,5-dihydro-2H-pyrrolo[3,4-c]pyridine-6-carboxamide;
3-methyl-N-[2-(morpholin-4-yl)ethyl]-4-oxo-1-(2-phenoxyphenyl)-4,5-dihydro-2H-pyrrolo[3,4-c]pyridine-6-carboxamide;
3-methyl-4-oxo-1-(2-phenoxyphenyl)-N-(pyridin-4-yl)-4,5-dihydro-2H-pyrrolo[3,4-c]pyridine-6-carboxamide;
N-(2-methoxyethyl)-3-methyl-4-oxo-1-(2-phenoxyphenyl)-4,5-dihydro-2H-pyrrolo[3,4-c]pyridine-6-carboxamide;
6-[(4-hydroxypiperidin-1-yl)carbonyl]-3-methyl-1-(2-phenoxyphenyl)-2,5-dihydro-4H-pyrrolo[3,4-c]pyridin-4-one;
N-(furan-2-ylmethyl)-3-methyl-4-oxo-1-(2-phenoxyphenyl)-4,5-dihydro-2H-pyrrolo[3,4-c]pyridine-6-carboxamide;
1-[5-chloro-2-(2,4-difluorophenoxy)phenyl]-3-methyl-4-oxo-4,5-dihydro-2H-pyrrolo[3,4-c]pyridine-6-carboxamide;
ethyl 1-[2-(2,4-difluorophenoxy)-5-nitrophenyl]-3-methyl-4-oxo-4,5-dihydro-2H-pyrrolo[3,4-c]pyridine-6-carboxylate;
1-[2-(2,4-difluorophenoxy)-5-(trifluoromethyl)phenyl]-N,3-dimethyl-4-oxo-4,5-dihydro-2H-pyrrolo[3,4-c]pyridine-6-carboxamide;
3-methyl-N-(1-methylpiperidin-4-yl)-4-oxo-1-(2-phenoxyphenyl)-4,5-dihydro-2H-pyrrolo[3,4-c]pyridine-6-carboxamide;
3-methyl-4-oxo-1-(2-phenoxyphenyl)-N-(tetrahydrofuran-3-ylmethyl)-4,5-dihydro-2H-pyrrolo[3,4-c]pyridine-6-carboxamide;
3-methyl-4-oxo-1-(2-phenoxyphenyl)-N-(tetrahydrofuran-3-yl)-4,5-dihydro-2H-pyrrolo[3,4-c]pyridine-6-carboxamide;
3-methyl-4-oxo-1-(2-phenoxyphenyl)-N-(tetrahydro-2H-pyran-4-yl)-4,5-dihydro-2H-pyrrolo[3,4-c]pyridine-6-carboxamide;
ethyl 1-[2-(2,4-difluorophenoxy)-5-(methylsulfonyl)phenyl]-3-methyl-4-oxo-4,5-dihydro-2H-pyrrolo[3,4-c]pyridine-6-carboxylate;
1-[2-(2,4-difluorophenoxy)-5-(methylsulfonyl)phenyl]-3-methyl-4-oxo-4,5-dihydro-2H-pyrrolo[3,4-c]pyridine-6-carboxylic acid;
N,N,3-trimethyl-4-oxo-1-(2-phenoxyphenyl)-4,5-dihydro-2H-pyrrolo[3,4-c]pyridine-6-carboxamide;
1-[2-(2,4-difluorophenoxy)-5-(methylsulfonyl)phenyl]-3-methyl-4-oxo-4,5-dihydro-2H-pyrrolo[3,4-c]pyridine-6-carboxamide;
1-[5-amino-2-(2,4-difluorophenoxy)phenyl]-3-methyl-4-oxo-N-propyl-4,5-dihydro-2H-pyrrolo[3,4-c]pyridine-6-carboxamide;
6-(methoxymethyl)-3-methyl-1-(2-phenoxyphenyl)-2,5-dihydro-4H-pyrrolo[3,4-c]pyridin-4-one;
3-methyl-1-(2-phenoxyphenyl)-6-[3-(pyridin-4-yl)-1,2,4-oxadiazol-5-yl]-2,5-dihydro-4H-pyrrolo[3,4-c]pyridin-4-one;
3-methyl-1-(2-phenoxyphenyl)-6-(3-phenyl-1,2,4-oxadiazol-5-yl)-2,5-dihydro-4H-pyrrolo[3,4-c]pyridin-4-one;
3-methyl-1-(2-phenoxyphenyl)-6-(3-propyl-1,2,4-oxadiazol-5-yl)-2,5-dihydro-4H-pyrrolo[3,4-c]pyridin-4-one;
ethyl 1-[2-(cyclohexyloxy)-5-fluorophenyl]-3-methyl-4-oxo-4,5-dihydro-2H-pyrrolo[3,4-c]pyridine-6-carboxylate;

3-methyl-N-(1-methylazetidin-3-yl)-4-oxo-1-(2-phenoxyphenyl)-4,5-dihydro-2H-pyrrolo[3,4-c]pyridine-6-carboxamide;
N-(trans-3-methoxycyclobutyl)-3-methyl-4-oxo-1-(2-phenoxyphenyl)-4,5-dihydro-2H-pyrrolo[3,4-c]pyridine-6-carboxamide;
3-methyl-N-[(3R)-1-methylpyrrolidin-3-yl]-4-oxo-1-(2-phenoxyphenyl)-4,5-dihydro-2H-pyrrolo[3,4-c]pyridine-6-carboxamide;
N-(2-cyanopropan-2-yl)-3-methyl-4-oxo-1-(2-phenoxyphenyl)-4,5-dihydro-2H-pyrrolo[3,4-c]pyridine-6-carboxamide;
N',N',3-trimethyl-4-oxo-1-(2-phenoxyphenyl)-4,5-dihydro-2H-pyrrolo[3,4-c]pyridine-6-carbohydrazide;
tert-butyl 4-({[3-methyl-4-oxo-1-(2-phenoxyphenyl)-4,5-dihydro-2H-pyrrolo[3,4-c]pyridin-6-yl]carbonyl}amino)piperidine-1-carboxylate;
tert-butyl (3R)-3-[({[3-methyl-4-oxo-1-(2-phenoxyphenyl)-4,5-dihydro-2H-pyrrolo[3,4-c]pyridin-6-yl]carbonyl}amino)methyl]pyrrolidine-1-carboxylate;
tert-butyl 3,3-difluoro-4-[({[3-methyl-4-oxo-1-(2-phenoxyphenyl)-4,5-dihydro-2H-pyrrolo[3,4-c]pyridin-6-yl]carbonyl}amino)methyl]pyrrolidine-1-carboxylate;
3-methyl-4-oxo-1-(2-phenoxyphenyl)-N-(piperidin-4-yl)-4,5-dihydro-2H-pyrrolo[3,4-c]pyridine-6-carboxamide;
3-methyl-4-oxo-1-(2-phenoxyphenyl)-N-[(3S)-pyrrolidin-3-ylmethyl]-4,5-dihydro-2H-pyrrolo[3,4-c]pyridine-6-carboxamide;
N-[(4,4-difluoropyrrolidin-3-yl)methyl]-3-methyl-4-oxo-1-(2-phenoxyphenyl)-4,5-dihydro-2H-pyrrolo[3,4-c]pyridine-6-carboxamide;
3-methyl-1-(2-phenoxyphenyl)-6-[3-(pyridin-3-yl)-1,2,4-oxadiazol-5-yl]-2,5-dihydro-4H-pyrrolo[3,4-c]pyridin-4-one;
3-methyl-6-(3-methyl-1,2,4-oxadiazol-5-yl)-1-(2-phenoxyphenyl)-2,5-dihydro-4H-pyrrolo[3,4-c]pyridin-4-one;
6-{3-[4-(dimethylamino)phenyl]-1,2,4-oxadiazol-5-yl}-3-methyl-1-(2-phenoxyphenyl)-2,5-dihydro-4H-pyrrolo[3,4-c]pyridin-4-one;
6-(3-cyclopropyl-1,2,4-oxadiazol-5-yl)-3-methyl-1-(2-phenoxyphenyl)-2,5-dihydro-4H-pyrrolo[3,4-c]pyridin-4-one;
3-methyl-1-(2-phenoxyphenyl)-6-[3-(1H-1,2,4-triazol-1-ylmethyl)-1,2,4-oxadiazol-5-yl]-2,5-dihydro-4H-pyrrolo[3,4-c]pyridin-4-one;
3-methyl-1-(2-phenoxyphenyl)-6-[3-(pyrazin-2-yl)-1,2,4-oxadiazol-5-yl]-2,5-dihydro-4H-pyrrolo[3,4-c]pyridin-4-one;
3-methyl-1-(2-phenoxyphenyl)-6-[3-(pyridin-3-ylmethyl)-1,2,4-oxadiazol-5-yl]-2,5-dihydro-4H-pyrrolo[3,4-c]pyridin-4-one;
3-methyl-1-(2-phenoxyphenyl)-6-[3-(pyridin-2-yl)-1,2,4-oxadiazol-5-yl]-2,5-dihydro-4H-pyrrolo[3,4-c]pyridin-4-one;
ethyl 1-{2-(2,4-difluorophenoxy)-5-[(methylsulfonyl)methyl]phenyl}-3-methyl-4-oxo-4,5-dihydro-2H-pyrrolo[3,4-c]pyridine-6-carboxylate;
ethyl 1-[2-(cyclopropylmethoxy)-5-fluorophenyl]-3-methyl-4-oxo-4,5-dihydro-2H-pyrrolo[3,4-c]pyridine-6-carboxylate;
1-[2-(cyclopropylmethoxy)-5-fluorophenyl]-3-methyl-4-oxo-4,5-dihydro-2H-pyrrolo[3,4-c]pyridine-6-carboxamide;
1-[2-(cyclopropylmethoxy)-5-fluorophenyl]-3-methyl-6-[3-(pyrazin-2-yl)-1,2,4-oxadiazol-5-yl]-2,5-dihydro-4H-pyrrolo[3,4-c]pyridin-4-one;
7-methyl-5-(2-phenoxyphenyl)-2,6-dihydro-1H-pyrrolo[3,4-d]pyridazin-1-one; N-[3-(7-methyl-1-oxo-2,6-dihydro-1H-pyrrolo[3,4-d]pyridazin-5-yl)-4-phenoxyphenyl]methanesulfonamide;
5-(5-amino-2-phenoxyphenyl)-7-methyl-2,6-dihydro-1H-pyrrolo[3,4-d]pyridazin-1-one;
N-[3-(7-methyl-1-oxo-2,6-dihydro-1H-pyrrolo[3,4-d]pyridazin-5-yl)-4-phenoxyphenyl]ethanesulfonamide;
2,2,2-trifluoro-N-[3-(7-methyl-1-oxo-2,6-dihydro-1H-pyrrolo[3,4-d]pyridazin-5-yl)-4-phenoxyphenyl]ethanesulfonamide;
4-methyl-N-[2-(7-methyl-1-oxo-2,6-dihydro-1H-pyrrolo[3,4-d]pyridazin-5-yl)phenyl]benzenesulfonamide;
5-[5-amino-2-(2,4-difluorophenoxy)phenyl]-7-methyl-2,6-dihydro-1H-pyrrolo[3,4-d]pyridazin-1-one;
N-[4-(2,4-difluorophenoxy)-3-(7-methyl-1-oxo-2,6-dihydro-1H-pyrrolo[3,4-d]pyridazin-5-yl)phenyl]ethanesulfonamide;
N-[4-(2,4-difluorophenoxy)-3-(7-methyl-1-oxo-2,6-dihydro-1H-pyrrolo[3,4-d]pyridazin-5-yl)phenyl]methanesulfonamide;
5-[2-(2,4-difluorophenoxy)-5-(methylsulfonyl)phenyl]-7-methyl-2,6-dihydro-1H-pyrrolo[3,4-d]pyridazin-1-one;
4-(2,4-difluorophenoxy)-3-(7-methyl-1-oxo-2,6-dihydro-1H-pyrrolo[3,4-d]pyridazin-5-yl)benzonitrile;
7-methyl-5-[4-(3-methyl-1H-pyrazol-5-yl)phenyl]-2,6-dihydro-1H-pyrrolo[3,4-d]pyridazin-1-one;
5-{2-[(cyclopropylmethyl)amino]-5-(ethylsulfonyl)phenyl}-7-methyl-2,6-dihydro-1H-pyrrolo[3,4-d]pyridazin-1-one;
5-methyl-7-(2-phenoxyphenyl)-3,6-dihydro-4H-pyrrolo[3,4-d]pyrimidin-4-one;
5-methyl-4-oxo-7-(2-phenoxyphenyl)-4,6-dihydro-3H-pyrrolo[3,4-d]pyrimidine-2-carboxylic acid;
ethyl 5-methyl-4-oxo-7-(2-phenoxyphenyl)-4,6-dihydro-3H-pyrrolo[3,4-d]pyrimidine-2-carboxylate;
2-(furan-2-yl)-5-methyl-7-(2-phenoxyphenyl)-3,6-dihydro-4H-pyrrolo[3,4-d]pyrimidin-4-one;
2,5-dimethyl-7-(2-phenoxyphenyl)-3,6-dihydro-4H-pyrrolo[3,4-d]pyrimidin-4-one;
7-(5-amino-2-phenoxyphenyl)-5-methyl-3,6-dihydro-4H-pyrrolo[3,4-d]pyrimidin-4-one;
N-[3-(5-methyl-4-oxo-4,6-dihydro-3H-pyrrolo[3,4-d]pyrimidin-7-yl)-4-phenoxyphenyl]methanesulfonamide;
3-methyl-1-(2-phenoxyphenyl)-2,5,6,7-tetrahydro-4H-pyrrolo[3,4-c]pyridin-4-one;
N-[4-(2,4-difluorophenoxy)-3-(3-methyl-4-oxo-4,5,6,7-tetrahydro-2H-pyrrolo[3,4-c]pyridin-1-yl)phenyl]methanesulfonamide;
1-(5-amino-2-phenoxyphenyl)-3-methyl-2,5,6,7-tetrahydro-4H-pyrrolo[3,4-c]pyridin-4-one;
N-[3-(3-methyl-4-oxo-4,5,6,7-tetrahydro-2H-pyrrolo[3,4-c]pyridin-1-yl)-4-phenoxyphenyl]methanesulfonamide;
1-[2-(cyclopropylmethoxy)-5-(methylsulfonyl)phenyl]-3-methyl-2,5,6,7-tetrahydro-4H-pyrrolo[3,4-c]pyridin-4-one;
methyl 3-methyl-4-oxo-1-(2-phenoxyphenyl)-4,5,6,7-tetrahydro-2H-pyrrolo[3,4-c]pyridine-6-carboxylate;
1-[2-(2,4-difluorophenoxy)-5-(methylsulfonyl)phenyl]-3-methyl-2,5,6,7-tetrahydro-4H-pyrrolo[3,4-c]pyridin-4-one;

1-[2-fluoro-5-(methylsulfonyl)phenyl]-3-methyl-2,5,6,7-tetrahydro-4H-pyrrolo[3,4-c]pyridin-4-one;

3-methyl-1-phenyl-2,5,6,7-tetrahydro-4H-pyrrolo[3,4-c]pyridin-4-one;

1-[5-amino-2-(2,4-difluorophenoxy)phenyl]-3,6-dimethyl-2,5,6,7-tetrahydro-4H-pyrrolo[3,4-c]pyridin-4-one;

1-{2-(2,4-difluorophenoxy)-5-[(4-methylpiperazin-1-yl)methyl]phenyl}-3-methyl-2,5,6,7-tetrahydro-4H-pyrrolo[3,4-c]pyridin-4-one; and 1-[2-(2,4-difluorophenoxy)-5-(hydroxymethyl)phenyl]-3-methyl-2,5,6,7-tetrahydro-4H-pyrrolo[3,4-c]pyridin-4-one.

Compounds of formula I can be used in the form of pharmaceutically acceptable salts. The phrase "pharmaceutically acceptable salt" means those salts which are, within the scope of sound medical judgement, suitable for use in contact with the tissues of humans and lower animals without undue toxicity, irritation, allergic response and the like and are commensurate with a reasonable benefit/risk ratio.

Pharmaceutically acceptable salts have been described in S. M. Berge et al. J. Pharmaceutical Sciences, 1977, 66: 1-19.

Compounds of formula (I) may contain either a basic or an acidic functionality, or both, and can be converted to a pharmaceutically acceptable salt, when desired, by using a suitable acid or base. The salts may be prepared in situ during the final isolation and purification of the compounds of the invention.

Examples of acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate (isothionate), lactate, malate, maleate, methanesulfonate, nicotinate, 2-naphthalenesulfonate, oxalate, palmitoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quaternized with such agents as lower alkyl halides such as, but not limited to, methyl, ethyl, propyl, and butyl chlorides, bromides and iodides; dialkyl sulfates like dimethyl, diethyl, dibutyl and diamyl sulfates; long chain halides such as, but not limited to, decyl, lauryl, myristyl and stearyl chlorides, bromides and iodides; arylalkyl halides like benzyl and phenethyl bromides and others. Water or oil-soluble or dispersible products are thereby obtained. Examples of acids which may be employed to form pharmaceutically acceptable acid addition salts include such inorganic acids as hydrochloric acid, hydrobromic acid, sulfuric acid, and phosphoric acid and such organic acids as acetic acid, fumaric acid, maleic acid, 4-methylbenzenesulfonic acid, succinic acid and citric acid.

Basic addition salts may be prepared in situ during the final isolation and purification of compounds of this invention by reacting a carboxylic acid-containing moiety with a suitable base such as, but not limited to, the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as, but not limited to, lithium, sodium, potassium, calcium, magnesium and aluminum salts and the like and nontoxic quaternary ammonia and amine cations including ammonium, tetramethylammonium, tetraethylammonium, methylamine, dimethylamine, trimethylamine, triethylamine, diethylamine, ethylamine and the like. Other examples of organic amines useful for the formation of base addition salts include ethylenediamine, ethanolamine, diethanolamine, piperidine, piperazine and the like.

The term "pharmaceutically acceptable prodrug" or "prodrug" as used herein, represents those prodrugs of the compounds of the present invention which are, within the scope of sound medical judgement, suitable for use in contact with the tissues of humans and lower animals without undue toxicity, irritation, allergic response, and the like, commensurate with a reasonable benefit/risk ratio, and effective for their intended use.

The present invention contemplates compounds of formula (I) formed by synthetic means or formed by in vivo biotransformation of a prodrug.

Compounds described herein can exist in unsolvated as well as solvated forms, including hydrated forms, such as hemi-hydrates. In general, the solvated forms, with pharmaceutically acceptable solvents such as water and ethanol among others are equivalent to the unsolvated forms for the purposes of the invention.

General Synthesis

The compounds described herein, including compounds of general formula (I) and specific examples, can be prepared by methodologies known in the art, for example, through the reaction schemes depicted in schemes 1-13. The variables $A^1$, $A^2$, $A^3$, $A^4$, $R^1$, $R^2$, $R^3$, $R^4$, $R^5$, $R^6$, $R^7$, $R^8$, $R^9$, $R^{3a}$, $R^{3b}$, $R^{3c}$, $R^{1g}$, $R^{x1}$, $R^{x2}$, $R^{x3}$, $R^{x4}$, X and Y used in the following schemes have the meanings as set forth in the summary and detailed description sections, unless otherwise noted. PG denotes a protecting group such as, for example, 2-(trimethylsilyl)ethoxymethyl or tri(isopropyl)silyl. Suitable protecting groups and the methods for protecting and deprotecting different substituents using such suitable protecting groups are well known to those skilled in the art; examples of which can be found in T. Greene and P. Wuts, Protecting Groups in Organic Synthesis ($3^{rd}$ ed.), John Wiley & Sons, NY (1999), which is incorporated herein by reference in its entirety.

Abbreviations used in the descriptions of the schemes and the specific examples have the following meanings: DME for 1,2-dimethoxyethane, DMF for N,N-dimethylformamide, DMSO for dimethyl sulfoxide, HATU for O-(7-azabenzotriazol-1-yl)-N,N,N',N'-tetramethyluronium hexafluorophosphate; mCPBA for 3-chloroperbenzoic acid; Pd(PPh$_3$)$_4$ for tetrakis(triphenylphosphine)palladium(0); THF for tetrahydrofuran, TFA for trifluoroacetic acid, TIPS for tri(isopropyl)silyl, SEM for 2-(trimethylsilyl)ethoxymethyl and HPLC for High Performance Liquid chromatography.

Scheme 1

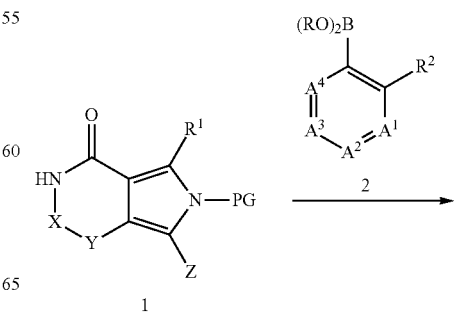

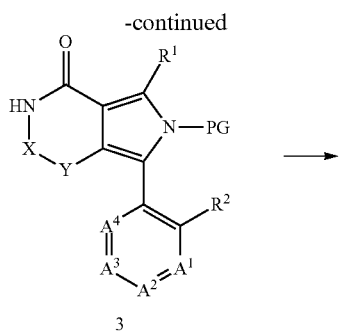

3

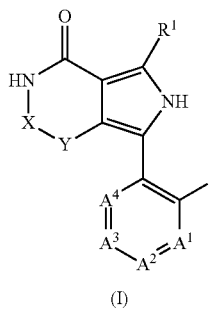

(I)

Compounds of general formula (I) may be prepared using the general procedure as outlined in Scheme 1. Conversion of (1), wherein Z is Cl, Br, or I, and PG is a suitable protecting group such as, for example, SEM to compounds of general formula (3) may be achieved by reaction of (1) with a boronic acid of formula (2) or derivative thereof (e.g. pinacol ester) under Suzuki coupling conditions (N. Miyama and A. Suzuki, Chem. Rev. 1995, 95:2457-2483, J. Organomet. Chem. 1999, 576:147-148). For example, the coupling reaction may be conducted in the presence of a palladium catalyst and a base, and optionally in the presence of a ligand, and in a suitable solvent at elevated temperature (about 60° C. to about 150° C.). The reaction may be facilitated by microwave irradiation. Examples of the palladium catalyst include, but are not limited to, tetrakis(triphenylphosphine)palladium(0), tris(dibenzylideneacetone)dipalladium(0), bis(triphenylphosphine)palladium(II) dichloride, bis(acetonitrile)dichloropalladium (II), chloro(2-dicyclohexylphosphino-2',4',6'-triisopropyl-1,1'-biphenyl)[2-(2'-amino-1,1'-biphenyl)]palladium(II), 1,1'-bis(diphenylphosphino)ferrocene-palladium(II)dichloride dichloromethane complex, and palladium(II)acetate. Examples of suitable bases that may be employed include, but are not limited to, carbonates or phosphates of sodium, potassium, and cesium, and cesium fluoride. Examples of suitable ligands include, but are not limited to, 1,3,5,7-tetramethyl-6-phenyl-2,4,8-trioxa-6-phosphaadamantane, 2-dicyclohexylphosphino-2',4',6'-triisopropylbiphenyl (X-phos), tri-tert-butylphosphine tetrafluoroborate, and 1,1'-bis(diphenylphosphanyl) ferrocene. Non-limiting examples of suitable solvents include methanol, ethanol, 1,2-dimethoxyethane, N,N-dimethylformamide, dimethylsulfoxide, 1,4-dioxane, tetrahydrofuran, toluene, and water, or a mixture thereof. Compounds of general formula (I) may be obtained by the treatment of compounds (3) under conditions appropriate to the protecting group employed; for example, removal of the SEM protecting group can be achieved by treatment with an acid such as, for example, TFA, hydrochloric acid, or p-toluene sulfonic acid in a solvent such as, for example, dichloromethane, at a temperature such as, for example, about 0° C. to about 60° C., followed by treatment with a base such as, for example, sodium carbonate or sodium hydroxide in a solvent such as, for example, methanol, THF, 1,4-dioxane, water, or a mixture thereof, at a temperature such as, for example, about 0° C. to about 60° C.

Scheme 2

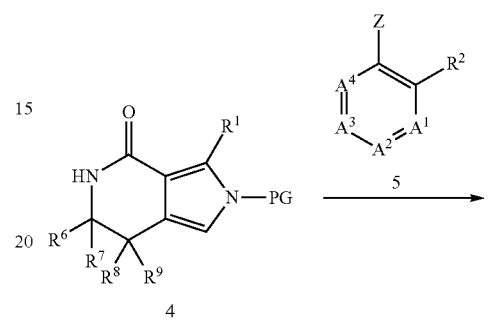

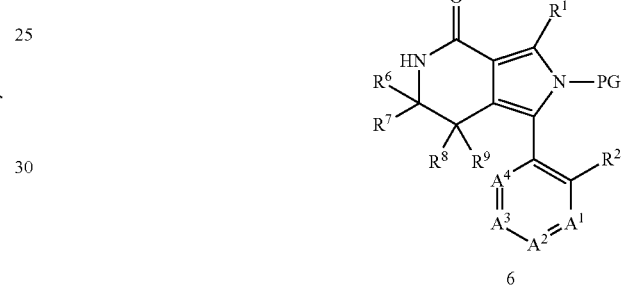

6

Compounds of general formula (3) when X—Y is —CR$^6$R$^7$—CR$^8$R$^9$— may alternatively be prepared using the sequence outlined in Scheme 2. Compounds of general formula (4) wherein PG is a suitable protecting group such as, for example, SEM may be coupled with aryl halides (5) wherein Z is Br by treatment with a palladium source such as, for example, allylpalladium(II)chloride dimer and a base such as, for example, potassium acetate in a solvent such as, for example, N,N-dimethylacetamide at a temperature such as, for example, about 130° C. under an inert atmosphere.

Scheme 3

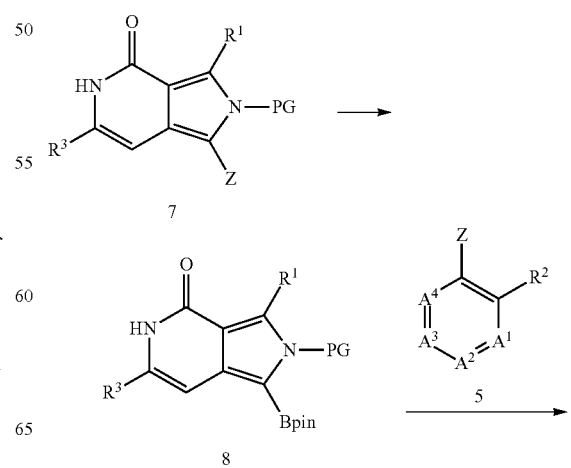

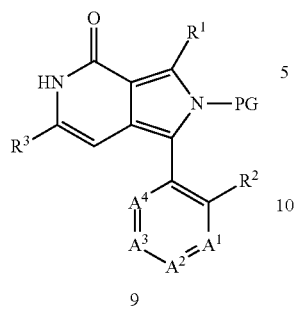

9

Compounds of general formula (3) when X—Y=—CR³=CH— may alternatively be prepared using the sequence outlined in Scheme 3. Pinacol esters of formula (8), may be synthesized, for example, by treatment of compounds of formula (7) wherein Z is Br, Cl, or I, and PG is a suitable protecting group (e.g. SEM) with a reagent such as, but not limited to, bis(pinacolato)diboron or 4,4,5,5-tetramethyl-1,3,2-dioxaborolane in the presence of a palladium catalyst and a base, and optionally in the presence of a ligand, and in a suitable solvent at elevated temperature (about 80° C. to about 150° C.). The reaction may be facilitated by microwave irradiation. Examples of the palladium catalyst include, but are not limited to, tetrakis(triphenylphosphine)palladium(0), tris(dibenzylideneacetone)dipalladium(0), bis(triphenylphosphine)palladium(II) dichloride, and palladium(II)acetate. Examples of suitable bases that may be employed include, but are not limited to, carbonates or phosphates of sodium, potassium, and cesium, and cesium fluoride. Examples of suitable ligands include, but are not limited to, 1,3,5,7-tetramethyl-6-phenyl-2,4,8-trioxa-6-phosphaadamantane, 2-dicyclohexylphosphino-2',4',6'-triisopropylbiphenyl (X-phos), and 1,1'-bis(diphenylphosphino) ferrocene. Non-limiting examples of suitable solvents include methanol, ethanol, 1,2-dimethoxyethane, N,N-dimethylformamide, dimethylsulfoxide, 1,4-dioxane, tetrahydrofuran, and water, or a mixture thereof. Conversion of (8) to compounds of formula (9) may be achieved by reaction of (8) with an aryl halide of formula (5) wherein Z is Cl, Br, or I under Suzuki coupling conditions described in Scheme 1.

Scheme 4

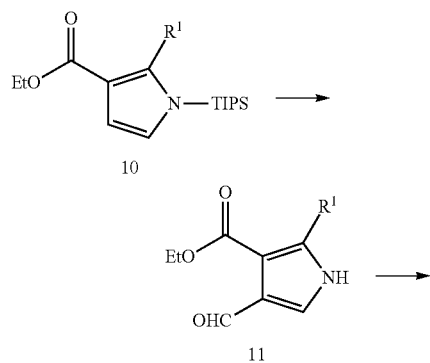

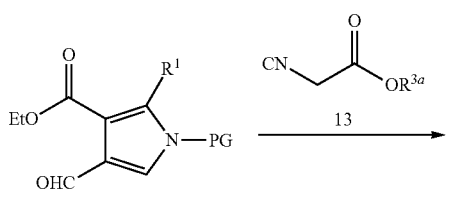

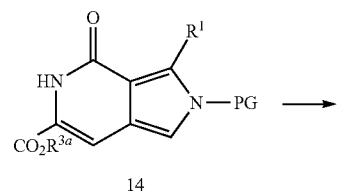

Compounds of formula (7) wherein R³ is CO₂R³ᵃ may be prepared using synthetic routes such as, for example, that illustrated in Scheme 4. Reaction of compounds of formula (10) with the formylating agent generated from DMF and oxalyl chloride in a solvent such as, for example, dichloromethane generated compounds of formula (11). The reaction may be conducted at temperature such as, for example, about 0° C. to about 60° C. Protection with a suitable protecting group such as, for example, SEM provides compounds of formula (12). Condensation of compounds of formula (12) with an appropriate isocyanoacetate ester (13) in the presence of a base, for example, sodium hydride in a solvent, for example, tetrahydrofuran at a temperature such as, for example, about 0° C. to about 60° C. generates compounds of formula (14). Conversion to compounds of formula (15) wherein Z is Br, I, or Cl may be achieved by halogenation with, for example, N-bromosuccinimide, N-iodosuccinimide, or N-chlorosuccinimide in a suitable solvent such as, for example, tetrahydrofuran, at a temperature such as, for example, about −78° C. to about 25° C.

Scheme 5

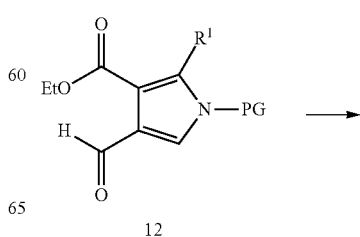

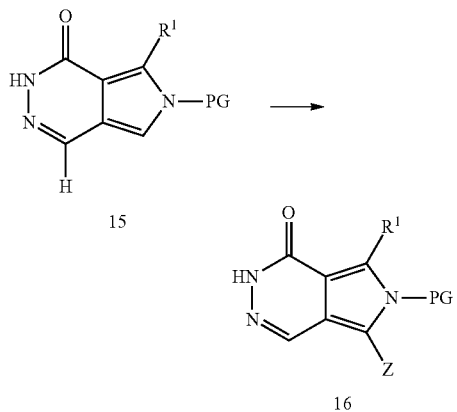

A route for the preparation of intermediates (1) wherein X—Y=-N=CH— is outlined in Scheme 5. Condensation of compounds of formula (12) with hydrazine in a solvent such as, for example, ethanol, at temperatures of about 25° C. to about 80° C., provides compounds (15). Halogenation of compounds (15) using reaction conditions described in Scheme 4 provides compounds of formula (16).

Scheme 6

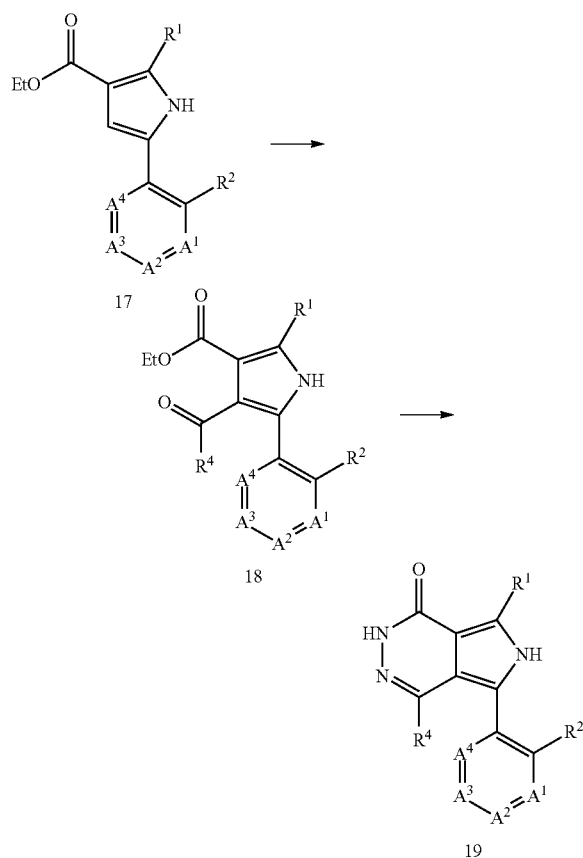

An alternate route for the preparation of compounds (I) wherein X—Y=-N=CR⁴— is outlined in Scheme 6. For example, compounds of formula (17), may be converted to (18) wherein R⁴ is H by treatment with an acylating reagent such as, for example, the formylating agent generated from DMF and oxalyl chloride in a solvent such as, for example, dichloromethane at a temperature such as, for example, about 0° C. to about 60° C. Condensation of compounds of formula (18) with hydrazine utilizing reaction condition as described in Scheme 5 provides compounds (19).

Scheme 7

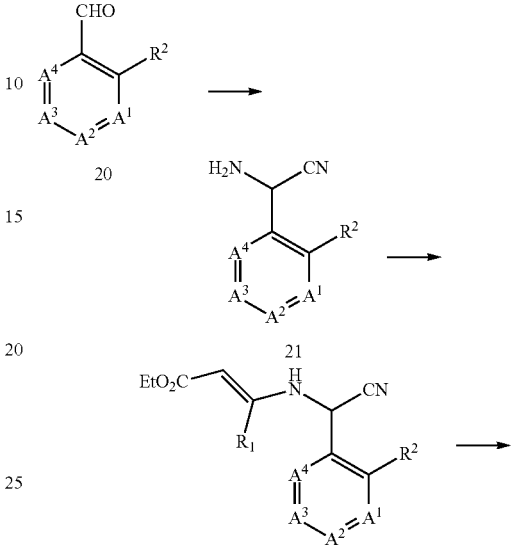

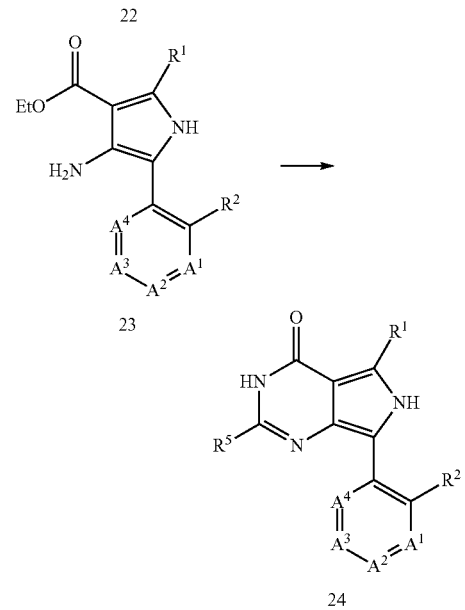

Preparation of compounds (I) wherein X—Y=—CR⁵=N— is outlined in Scheme 7. For example, aldehydes of formula (20) may be converted to compounds of formula (21) by treatment with, for example, sodium cyanide and ammonium chloride in the presence of a base such as, for example, ammonium hydroxide, and in a solvent such as, for example, methanol. The conversion may be achieved at temperatures of about 0° C. to about 25° C. Condensation of (21) with an appropriate beta-keto ester (for example ethyl acetoacetate when R¹ is methyl) in the presence of an acid such as, for example p-toluenesulfonic acid in a solvent such as, for example, toluene and at temperatures of about 60° C. to about 100° C. provides compounds of formula (22). Aminopyrrole salts of formula (23) are formed upon treatment of (22) with a base such as, for example, sodium ethoxide in a solvent such as, for example, ethanol at temperatures of about 0° C. to about 25° C., followed by acidification with hydrochloric acid. Ring closure of (23) provides compounds of formula (24). Such conversion may be achieved by treatment of (23) with an appropriate carboxylic acid derivative such as, for example, formamidine acetate in a solvent such as, for example, ethanol, at elevated temperature (e.g. 50° C. to about 80° C.) to provide compounds (24) wherein $R^5$ is H. Treatment of (23) with ethyl cyanoformate or acetonitrile in HCl/dioxane at about room temperature provides compounds (24) wherein $R^5$ is $CO_2Et$ and $CH_3$ respectively.

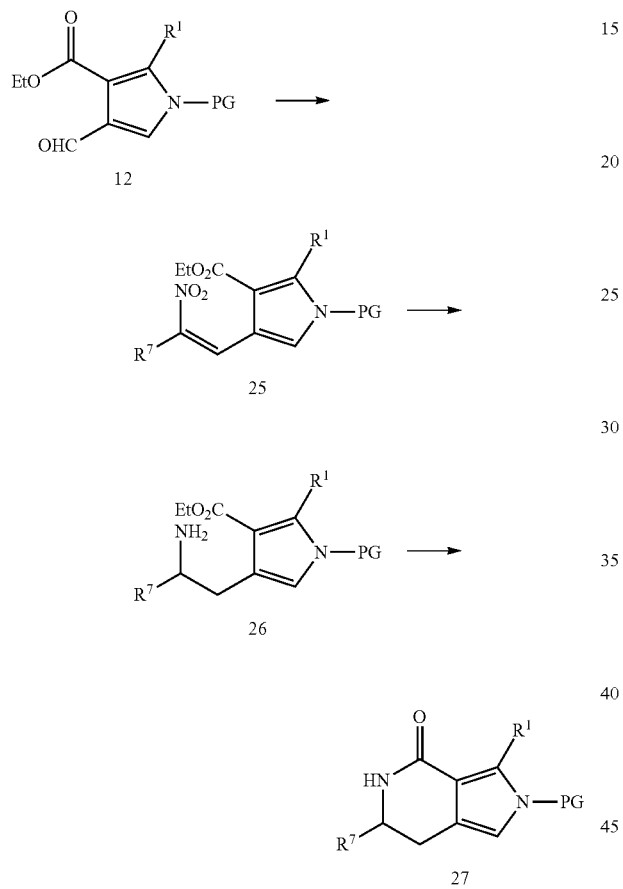

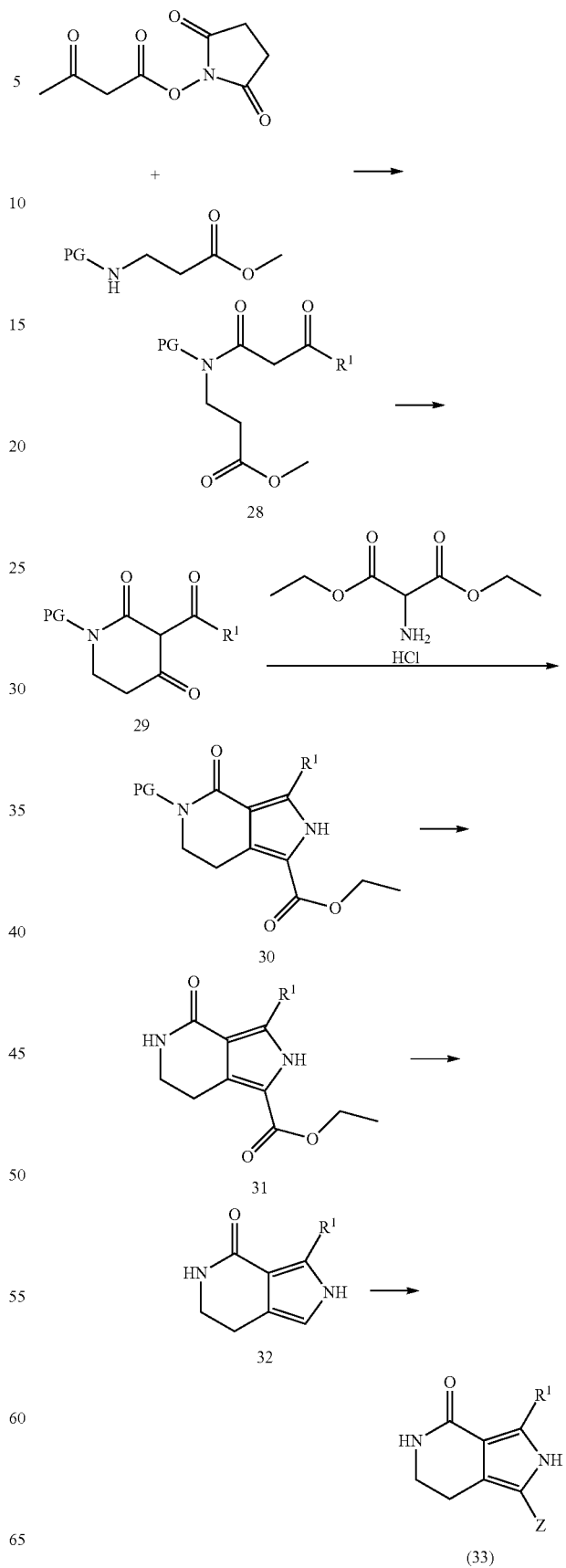

Scheme 8 illustrates general synthetic route for the preparation of intermediates (4) wherein $R^6$, $R^8$, and $R^9$ are H, and $R^7$ is H, $CH_3$, or C(O)Oalkyl. For example, aldehydes of formula (12) may be converted to compounds of formula (25) by treatment with a nitroalkane, for example, nitromethane, nitroethane or alkyl nitroacetate and a base such as, for example, ammonium acetate, optionally in a solvent such as, for example, THF and at temperatures of about 0° C. to about 90° C. Reduction of the resulting nitro compounds (25) with hydrogen using washed Raney-Ni in THF provides compounds of formula (26). Ester hydrolysis of (26) provides compounds of formula (27). The conversion may be facilitated with a base such as, for example, lithium hydroxide in a solvent such as, for example, THF, water, or a mixture thereof, at temperatures of, for example, about 100° C. to about 130° C.

Scheme 9 illustrates an alternate route for the preparation of unprotected intermediates of formula (1) wherein X—Y is CH$_2$—CH$_2$—. Condensation of an appropriate beta-keto active ester (for example N-hydroxysuccinimidyl acetoacetate when R$^1$ is methyl) with a suitably protected 3-aminopropionate ester, for example, methyl 3-(4-methoxybenzylamino)propanoate in a solvent such as, for example, dichloromethane at temperatures of about 25° C. to about 60° C. provides compounds of formula (28). Lactams of formula (29) may be prepared upon treatment of (28) with a base such as, for example, sodium methoxide in a solvent such as, for example, methanol at temperatures of, for example, about 60° C., followed by acidification with, for example, HCl. Reaction of compounds of formula (29) with diethyl 2-aminomalonate in the presence of sodium acetate and in a solvent such as, but not limited to, acetic acid, provides intermediates of formula (30). The reaction may be conducted at elevated temperature such as, but not limited to, about 80° C. to about 120° C. Deprotection of (30) provides intermediates (31). Ester hydrolysis of (31) followed by decarboxylation of the resulting carboxylic acid affords compounds of formula (32). Ester hydrolysis may be accomplished in the presence of a base such as, for example, hydroxides of lithium, potassium, or sodium. The reaction is generally conducted in a solvent such as, but not limited to, tetrahydrofuran or water, and at temperatures ranging from about room temperature to about 80° C. Heating of the resulting carboxylic acid in an alcoholic solvent (e.g., ethanol), and in the presence of an acid such as, but not limited to, hydrochloric acid or sulfuric acid, at a temperature from about 50° C. to about 100° C. provides compounds of formula (32). Halogenation of compounds (32) using reaction conditions as described in Scheme 4 provides compounds (33) wherein Z is I, Br, or Cl.

Scheme 10

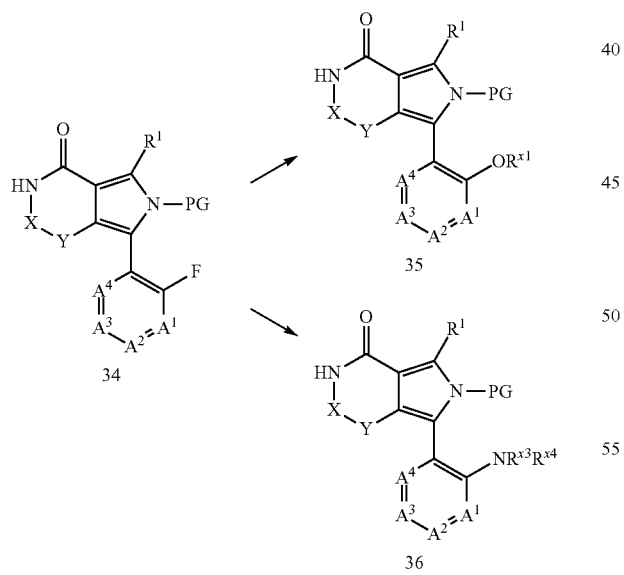

Compounds of formula (3) wherein R$^2$ is OR$^{x1}$ and NR$^{x1}$R$^{x2}$ may be prepared from displacement of fluorine atom with alcohols R$^{x1}$OH and amines of formula NR$^{x1}$R$^{x2}$ respectively as shown in Scheme 10. Displacement of the fluorine atom may be accomplished in a solvent such as, for example, dimethylsulfoxide, N,N-dimethylformamide, 1,4-dioxane, or tetrahydrofuran, and in the presence of a base such as, for example, carbonates of cesium, potassium, or sodium, or sodium hydride, and at a temperature from about 40° C. to about 120° C.

Scheme 11

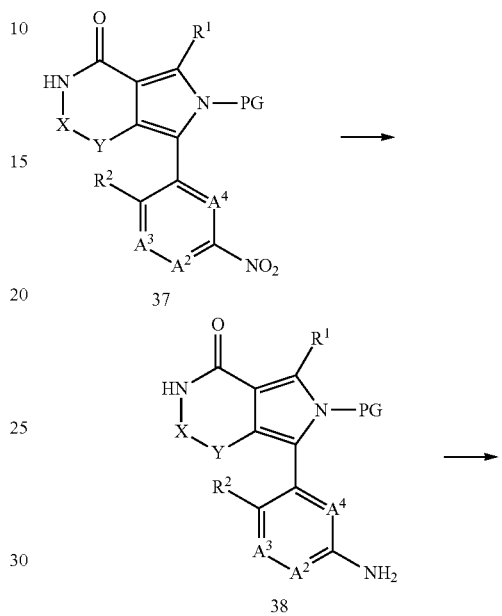

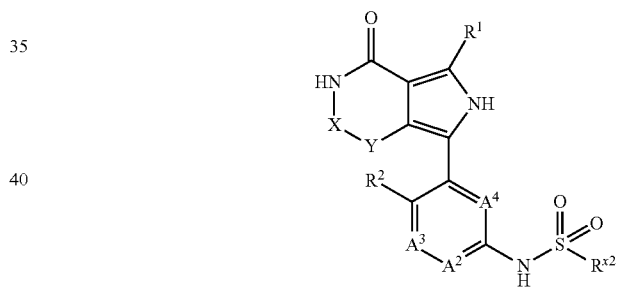

Compounds of formula (I) wherein A$^3$ is C(R$^x$) and R$^x$ is N(H)SO$_2$R$^{x2}$ may be synthesized as shown in Scheme 11. Reduction of the nitro compounds of formula (37) to compounds (38) may be achieved using iron powder in the presence of ammonium chloride in a solvent such as, for example, tetrahydrofuran, ethanol, or water, or a mixture thereof, and at a temperature of about 80° C. to about 120° C. The reduction may also be achieved by treatment of (37) with tin chloride in hydrochloric acid at a temperature of about 80° C. to about 120° C. Transformation of (37) to (38) may also be conducted in the presence of a catalyst such as platinum oxide or palladium on charcoal, in a solvent such as ethanol or methanol and under hydrogen pressure. Treatment of compounds (38) with sulfonyl chlorides of formula R$^{x2}$SO$_2$Cl, in the presence of a base such as triethylamine or diisopropylethylamine in a solvent such as dichloromethane or tetrahydrofuran and at a temperature of about 0° C. to about 40° C. provides sulfonamides (39).

Scheme 12

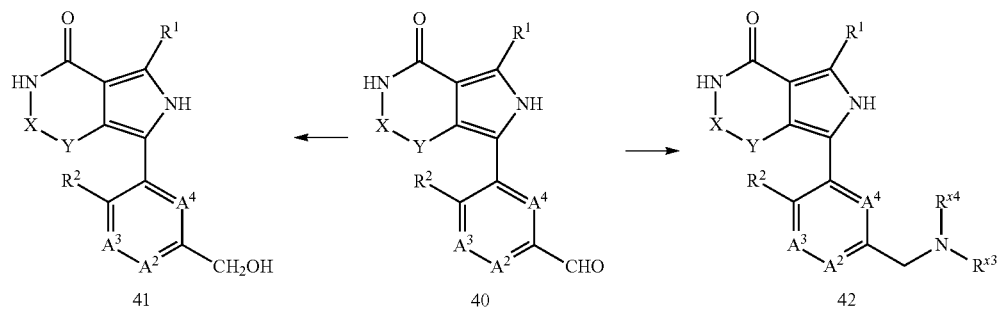

Compounds of formula (I) wherein $A^3$ is $C(R^x)$ and $R^x$ is $CH_2OH$ and compounds of formula (I) wherein $A^3$ is $C(R^x)$ and $R^x$ is $CH_2NR^{x3}R^{x4}$ may be synthesized as shown in Scheme 12. Reduction of the formyl compounds of formula (40) to the alcohols (41) may be achieved using, for example, sodium borohydride in a solvent such as, for example, THF at a temperature of, for example about 0° C. to about 40° C. Reductive alkylation of compounds (40) with amines $HNR^{x3}R^{x4}$ in the presence of a reducing agent such as, for example, sodium triacetoxyhydroborate, sodium borohydride, or sodium cyanoborohydride, and an acid (e.g. acetic acid), provide compounds (42). The reaction is generally conducted in a solvent such as, for example, dichloromethane, methanol, or ethanol, at a temperature of about 0° C. to about 100° C.

hydroxide in a mixture of water and an organic solvent such as, for example, THF or methanol, at a temperature of, for example, about 0° C. to about 100° C. Conversion of acids (44) to esters (43) or amides (45) may be achieved by carboxyl activation with a coupling reagent, for example, 2-(3H-[1,2,3]triazolo[4,5-b]pyridin-3-yl)-1,1,3,3-tetramethylisouronium hexafluorophosphate(V), in the presence of a tertiary amine base such as, for example, diisopropylethylamine, in a solvent such as, for example N,N-dimethylacetamide and at a temperature of, for example, about 0° C. to about 125° C.; followed by treatment of the activated ester with an alcohol $R^{3a}OH$ or an amine $HNR^{3a}R^{3b}$. Alternatively, direct conversion of esters of general formula (43) to amides (45) may be achieved by heating of (43) with an excess of amine $HNR^{3a}R^{3b}$. Oxadiazoles of formula (46) may be prepared Scheme 13

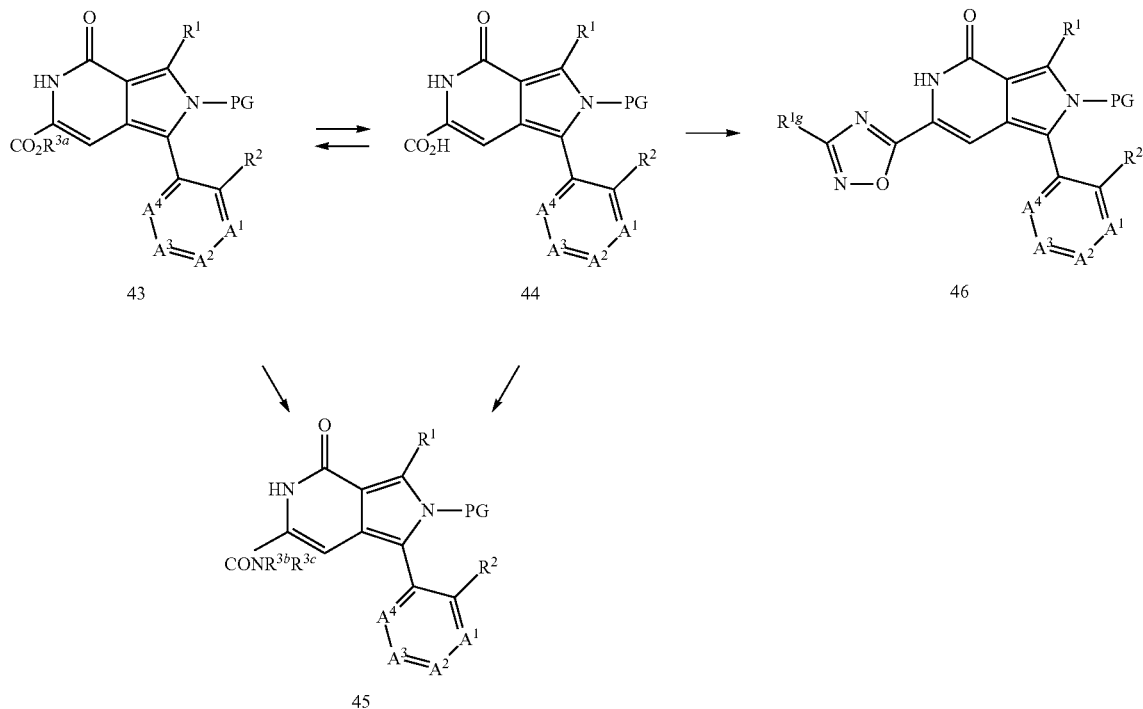

As shown in Scheme 13, compounds of general formula (43) may be converted to carboxylic acids of formula (44) by hydrolysis with an aqueous base, for example, lithium from acids of formula (44) by carboxyl activation with, for example, carbonyldiimidazole and condensation with a (Z)—N'-hydroxyimidamide (for example (Z)—N'-hydroxybenzimidamide when $R^{1g}$ is phenyl) in a solvent such as, for example, DMF, at a temperature of, for example, about 180° C.

It can be appreciated that the synthetic schemes and specific examples as illustrated in the synthetic examples section are illustrative and are not to be read as limiting the scope of the invention as it is defined in the appended claims. All alternatives, modifications, and equivalents of the synthetic methods and specific examples are included within the scope of the claims.

Optimum reaction conditions and reaction times for each individual step can vary depending on the particular reactants employed and substituents present in the reactants used. Unless otherwise specified, solvents, temperatures and other reaction conditions can be readily selected by one of ordinary skill in the art. Specific procedures are provided in the Synthetic Examples section. Reactions can be worked up in the conventional manner, e.g. by eliminating the solvent from the residue and further purified according to methodologies generally known in the art such as, but not limited to, crystallization, distillation, extraction, trituration and chromatography. Unless otherwise described, the starting materials and reagents are either commercially available or can be prepared by one skilled in the art from commercially available materials using methods described in the chemical literature.

Routine experimentations, including appropriate manipulation of the reaction conditions, reagents and sequence of the synthetic route, protection of any chemical functionality that can not be compatible with the reaction conditions, and deprotection at a suitable point in the reaction sequence of the method are included in the scope of the invention. Suitable protecting groups and the methods for protecting and deprotecting different substituents using such suitable protecting groups are well known to those skilled in the art; examples of which can be found in T. Greene and P. Wuts, Protecting Groups in Organic Synthesis ($3^{rd}$ ed.), John Wiley & Sons, NY (1999), which is incorporated herein by reference in its entirety. Synthesis of the compounds of the invention can be accomplished by methods analogous to those described in the synthetic schemes described hereinabove and in specific examples.

Starting materials, if not commercially available, can be prepared by procedures selected from standard organic chemical techniques, techniques that are analogous to the synthesis of known, structurally similar compounds, or techniques that are analogous to the above described schemes or the procedures described in the synthetic examples section.

When an optically active form of a compound is required, it can be obtained by carrying out one of the procedures described herein using an optically active starting material (prepared, for example, by asymmetric induction of a suitable reaction step), or by resolution of a mixture of the stereoisomers of the compound or intermediates using a standard procedure (such as chromatographic separation, recrystallization or enzymatic resolution).

Similarly, when a pure geometric isomer of a compound is required, it can be prepared by carrying out one of the above procedures using a pure geometric isomer as a starting material, or by resolution of a mixture of the geometric isomers of the compound or intermediates using a standard procedure such as chromatographic separation.

Pharmaceutical Compositions

This invention also provides for pharmaceutical compositions comprising a therapeutically effective amount of a compound of Formula I, or a pharmaceutically acceptable salt thereof together with a pharmaceutically acceptable carrier, diluent, or excipient therefor. The phrase "pharmaceutical composition" refers to a composition suitable for administration in medical or veterinary use.

The pharmaceutical compositions that comprise a compound of formula (I), alone or or in combination with a second active pharmaceutical agent, may be administered to the subjects orally, rectally, parenterally, intracisternally, intravaginally, intraperitoneally, topically (as by powders, ointments or drops), bucally or as an oral or nasal spray. The term "parenterally" as used herein, refers to modes of administration which include intravenous, intramuscular, intraperitoneal, intrasternal, subcutaneous and intraarticular injection and infusion.

The term "pharmaceutically acceptable carrier" as used herein, means a non-toxic, inert solid, semi-solid or liquid filler, diluent, encapsulating material or formulation auxiliary of any type. Some examples of materials which can serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols; such a propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Pharmaceutical compositions for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), vegetable oils (such as olive oil), injectable organic esters (such as ethyl oleate) and suitable mixtures thereof. Proper fluidity can be maintained, for example, by the use of coating materials such as lecithin, by the maintenance of the required particle size in the case of dispersions and by the use of surfactants.

These compositions may also contain adjuvants such as preservatives, wetting agents, emulsifying agents and dispersing agents. Prevention of the action of microorganisms can be ensured by the inclusion of various antibacterial and antifungal agents, for example, paraben, chlorobutanol, phenol sorbic acid and the like. It may also be desirable to include isotonic agents such as sugars, sodium chloride and the like. Prolonged absorption of the injectable pharmaceutical form can be brought about by the inclusion of agents, which delay absorption such as aluminum monostearate and gelatin.

In some cases, in order to prolong the effect of the drug, it is desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally-administered drug form may be accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Solid dosage forms for oral administration include capsules, tablets, pills, powders and granules. In certain embodiments, solid dosage forms may contain from 1% to 95% (w/w) of a compound of formula I. In certain embodiments, the compound of formula I may be present in the solid dosage form in a range of from 5% to 70% (w/w). In such solid dosage forms, the active compound may be mixed with at least one inert, pharmaceutically acceptable excipient or carrier, such as sodium citrate or dicalcium phosphate and/or a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form may also comprise buffering agents.

The pharmaceutical composition may be a unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampules. Also, the unit dosage form can be a capsule, tablet, cachet, or lozenge itself, or it can be the appropriate number of any of these in packaged form. The quantity of active component in a unit dose preparation may be varied or adjusted from 0.1 mg to 1000 mg, from 1 mg to 100 mg, or from 1% to 95% (w/w) of a unit dose, according to the particular application and the potency of the active component. The composition can, if desired, also contain other compatible therapeutic agents.

The dose to be administered to a subject may be determined by the efficacy of the particular compound employed and the condition of the subject, as well as the body weight or surface area of the subject to be treated. The size of the dose also will be determined by the existence, nature, and extent of any adverse side-effects that accompany the administration of a particular compound in a particular subject. In determining the effective amount of the compound to be administered in the treatment or prophylaxis of the disorder being treated, the physician can evaluate factors such as the circulating plasma levels of the compound, compound toxicities, and/or the progression of the disease, etc. In general, the dose equivalent of a compound is from about 1 µg/kg to 100 mg/kg for a typical subject.

For administration, compounds of the formula I can be administered at a rate determined by factors that can include, but are not limited to, the $LD_{50}$ of the compound, the pharmacokinetic profile of the compound, contraindicated drugs, and the side-effects of the compound at various concentrations, as applied to the mass and overall health of the subject. Administration can be accomplished via single or divided doses.

The compounds utilized in the pharmaceutical method of the invention can be administered at the initial dosage of about 0.001 mg/kg to about 100 mg/kg daily. In certain embodiments, the daily dose range is from about 0.1 mg/kg to about 10 mg/kg. The dosages, however, may be varied depending upon the requirements of the subject, the severity of the condition being treated, and the compound being employed. Determination of the proper dosage for a particular situation is within the skill of the practitioner. Treatment may be initiated with smaller dosages, which are less than the optimum dose of the compound. Thereafter, the dosage is increased by small increments until the optimum effect under circumstances is reached. For convenience, the total daily dosage may be divided and administered in portions during the day, if desired.

Solid compositions of a similar type may also be employed as fillers in soft and hard-filled gelatin capsules using such carriers as lactose or milk sugar as well as high molecular weight polyethylene glycols and the like.

The solid dosage forms of tablets, dragees, capsules, pills and granules can be prepared with coatings and shells such as enteric coatings and other coatings well-known in the pharmaceutical formulating art. They may optionally contain opacifying agents and may also be of a composition such that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned carriers.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols and fatty acid esters of sorbitan and mixtures thereof.

Besides inert diluents, the oral compositions may also include adjuvants such as wetting agents, emulsifying and suspending agents, sweetening, flavoring and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, tragacanth and mixtures thereof.

Compositions for rectal or vaginal administration are preferably suppositories which can be prepared by mixing the compounds of this invention with suitable non-irritating carriers or carriers such as cocoa butter, polyethylene glycol or a suppository wax which are solid at room temperature but liquid at body temperature and therefore melt in the rectum or vaginal cavity and release the active compound.

Compounds of formula I may also be administered in the form of liposomes. Liposomes generally may be derived from phospholipids or other lipid substances. Liposomes are formed by mono- or multi-lamellar hydrated liquid crystals which are dispersed in an aqueous medium. Any non-toxic, physiologically acceptable and metabolizable lipid capable of forming liposomes can be used. The present compositions in liposome form may contain, in addition to a compound of formula (I), stabilizers, preservatives, excipients and the like. Examples of lipids include, but are not limited to, natural and synthetic phospholipids and phosphatidyl cholines (lecithins), used separately or together.

Methods to form liposomes have been described, see example, Prescott, Ed., Methods in Cell Biology, Volume XIV, Academic Press, New York, N.Y. (1976), p. 33 et seq.

Dosage forms for topical administration of a compound described herein include powders, sprays, ointments and inhalants. The active compound may be mixed under sterile conditions with a pharmaceutically acceptable carrier and any needed preservatives, buffers or propellants which may be required. Opthalmic formulations, eye ointments, powders and solutions are also contemplated as being within the scope of this invention.

Methods of Use

The compounds of formula I, or pharmaceutically acceptable salts thereof, and pharmaceutical compositions comprising a compound of formula I, or a pharmaceutically acceptable salt thereof, can be administered to a subject suffering from a bromodomain-mediated disorder or condition. The term "administering" refers to the method of contacting a compound with a subject. Thus, the compounds of formula I can be administered by injection, that is, intravenously, intramuscularly, intracutaneously, subcutaneously, intraduodenally, parentally, or intraperitoneally. Also, the compounds described herein can be administered by inhalation, for example, intranasally. Additionally, the compounds of formula I can be administered transdermally, topically, via implantation, transdermally, topically, and via implantation. In certain embodiments, the compounds of the formula I may be delivered orally. The compounds can also be delivered rectally, bucally, intravaginally, ocularly, andially, or by insufflation. Bromodomain-mediated disorders and conditions can be treated prophylactically, acutely, and chronically using compounds of formula I, depending on the nature of the disorder or condition. Typically, the host or subject in each of these methods is human, although other mammals can also benefit from the administration of a compound of formula I.

A "bromodomain-mediated disorder or condition" is characterized by the participation of one or more bromodomains (e.g., BRD4) in the inception, manifestation of one or more symptoms or disease markers, severity, or progression of a disorder or condition. Accordingly, compounds of formula I may be used to treat cancer, including, but not limited to acoustic neuroma, acute leukemia, acute lymphocytic leukemia, acute myelocytic leukemia (monocytic, myeloblastic, adenocarcinoma, angiosarcoma, astrocytoma, myelomonocytic and promyelocytic), acute t-cell leukemia, basal cell carcinoma, bile duct carcinoma, bladder cancer, brain cancer, breast cancer, bronchogenic carcinoma, cervical cancer, chondrosarcoma, chordoma, choriocarcinoma, chronic leukemia, chronic lymphocytic leukemia, chronic myelocytic (granulocytic) leukemia, chronic myelogenous leukemia, colon cancer, colorectal cancer, craniopharyngioma, cystadenocarcinoma, diffuse large B-cell lymphoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, follicular lymphoma, germ cell testicular cancer, glioma, glioblastoma, gliosarcoma, heavy chain disease, hemangioblastoma, hepatoma, hepatocellular cancer, hormone insensitive prostate cancer, leiomyosarcoma, leukemia, liposarcoma, lung cancer, lymphagioendotheliosarcoma, lymphangiosarcoma, lymphoblastic leukemia, lymphoma (Hodgkin's and non-Hodgkin's), malignancies and hyperproliferative disorders of the bladder, breast, colon, lung, ovaries, pancreas, prostate, skin and uterus, lymphoid malignancies of T-cell or B-cell origin, leukemia, lymphoma, medullary carcinoma, medulloblastoma, melanoma, meningioma, mesothelioma, multiple myeloma, myelogenous leukemia, myeloma, myxosarcoma, neuroblastoma, NUT midline carcinoma (NMC), non-small cell lung cancer, oligodendroglioma, oral cancer, osteogenic sarcoma, ovarian cancer, pancreatic cancer, papillary adenocarcinomas, papillary carcinoma, pinealoma, polycythemia vera, prostate cancer, rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), small cell lung cancer, stomach cancer, squamous cell carcinoma, synovioma, sweat gland carcinoma, thyroid cancer, Waldenström's macroglobulinemia, testicular tumors, uterine cancer and Wilms' tumor.

Further, compounds of formula I may be used to treat inflammatory diseases, inflammatory conditions, and autoimmune diseases, including, but not limited to: Addison's disease, acute gout, ankylosing spondylitis, asthma, atherosclerosis, Behcet's disease, bullous skin diseases, chronic obstructive pulmonary disease (COPD), Crohn's disease, dermatitis, eczema, giant cell arteritis, glomerulonephritis, hepatitis, hypophysitis, inflammatory bowel disease, Kawasaki disease, lupus nephritis, multiple sclerosis, myocarditis, myositis, nephritis, organ transplant rejection, osteoarthritis, pancreatitis, pericarditis, Polyarteritis nodosa, pneumonitis, primary biliary cirrhosis, psoriasis, psoriatic arthritis, rheumatoid arthritis, scleritis, sclerosing cholangitis, sepsis, systemic lupus erythematosus, Takayasu's Arteritis, toxic shock, thyroiditis, type I diabetes, ulcerative colitis, uveitis, vitiligo, vasculitis, and Wegener's granulomatosis.

Compounds of formula I, or pharmaceutically acceptable salts thereof, may be used to treat AIDS.

The compounds of formula I can be co-administered to a subject. The term "co-administered" means the administration of two or more different pharmaceutical agents or treatments (e.g., radiation treatment) that are administered to a subject by combination in the same pharmaceutical composition or separate pharmaceutical compositions. Thus co-administration involves administration at the same time of a single pharmaceutical composition comprising two or more pharmaceutical agents or administration of two or more different compositions to the same subject at the same or different times.

The compounds of the invention can be co-administered with a therapeutically effective amount of one or more agents to treat a cancer, where examples of the agents include, such as radiation, alkylating agents, angiogenesis inhibitors, antibodies, antimetabolites, antimitotics, antiproliferatives, antivirals, aurora kinase inhibitors, apoptosis promoters (for example, Bcl-xL, Bcl-w and Bfl-1) inhibitors, activators of death receptor pathway, Bcr-Abl kinase inhibitors, BiTE (Bi-Specific T cell Engager) antibodies, antibody drug conjugates, biologic response modifiers, cyclin-dependent kinase inhibitors, cell cycle inhibitors, cyclooxygenase-2 inhibitors, DVDs (dual variable domain antibodies), leukemia viral oncogene homolog (ErbB2) receptor inhibitors, growth factor inhibitors, heat shock protein (HSP)-90 inhibitors, histone deacetylase (HDAC) inhibitors, hormonal therapies, immunologicals, inhibitors of inhibitors of apoptosis proteins (IAPs), intercalating antibiotics, kinase inhibitors, kinesin inhibitors, Jak2 inhibitors, mammalian target of rapamycin inhibitors, microRNA's, mitogen-activated extracellular signal-regulated kinase inhibitors, multivalent binding proteins, non-steroidal anti-inflammatory drugs (NSAIDs), poly ADP (adenosine diphosphate)-ribose polymerase (PARP) inhibitors, platinum chemotherapeutics, polo-like kinase (Plk) inhibitors, phosphoinositide-3 kinase (bromodomain) inhibitors, proteosome inhibitors, purine analogs, pyrimidine analogs, receptor tyrosine kinase inhibitors, etinoids/deltoids plant alkaloids, small inhibitory ribonucleic acids (siRNAs), topoisomerase inhibitors, ubiquitin ligase inhibitors, and the like, and in combination with one or more of these agents.

BiTE antibodies are bi-specific antibodies that direct T-cells to attack cancer cells by simultaneously binding the two cells. The T-cell then attacks the target cancer cell. Examples of BiTE antibodies include adecatumumab (Micromet MT201), blinatumomab (Micromet MT103) and the like. Without being limited by theory, one of the mechanisms by which T-cells elicit apoptosis of the target cancer cell is by exocytosis of cytolytic granule components, which include perforin and granzyme B. In this regard, Bcl-2 has been shown to attenuate the induction of apoptosis by both perforin and granzyme B. These data suggest that inhibition of Bcl-2 could enhance the cytotoxic effects elicited by T-cells when targeted to cancer cells (V. R. Sutton, D. L. Vaux and J. A. Trapani, *J. of Immunology* 1997, 158 (12), 5783).

SiRNAs are molecules having endogenous RNA bases or chemically modified nucleotides. The modifications do not abolish cellular activity, but rather impart increased stability and/or increased cellular potency. Examples of chemical modifications include phosphorothioate groups, 2'-deoxynucleotide, 2'—OCH$_3$-containing ribonucleotides, 2'-F-ribonucleotides, 2'-methoxyethyl ribonucleotides, combinations thereof and the like. The siRNA can have varying lengths (e.g., 10-200 bps) and structures (e.g., hairpins, single/double strands, bulges, nicks/gaps, mismatches) and are processed in cells to provide active gene silencing. A double-stranded siRNA (dsRNA) can have the same number of nucleotides on each strand (blunt ends) or asymmetric ends (overhangs). The overhang of 1-2 nucleotides can be present on the sense and/or the antisense strand, as well as present on the 5'- and/or the 3'-ends of a given strand.

Multivalent binding proteins are binding proteins comprising two or more antigen binding sites. Multivalent binding proteins are engineered to have the three or more antigen binding sites and are generally not naturally occurring antibodies. The term "multispecific binding protein" means a binding protein capable of binding two or more related or unrelated targets. Dual variable domain (DVD) binding proteins are tetravalent or multivalent binding proteins binding proteins comprising two or more antigen binding sites. Such DVDs may be monospecific (i.e., capable of binding one antigen) or multispecific (i.e., capable of binding two or more antigens). DVD binding proteins comprising two heavy chain DVD polypeptides and two light chain DVD polypeptides are referred to as DVD Ig's. Each half of a DVD Ig comprises a heavy chain DVD polypeptide, a light chain DVD polypeptide, and two antigen binding sites. Each binding site comprises a heavy chain variable domain and a light chain variable domain with a total of 6 CDRs involved in antigen binding per antigen binding site. Multispecific DVDs include DVD binding proteins that bind DLL4 and VEGF, or C-met and EFGR or ErbB3 and EGFR.

Alkylating agents include altretamine, AMD-473, AP-5280, apaziquone, bendamustine, brostallicin, busulfan, carboquone, carmustine (BCNU), chlorambucil, CLORETAZINE® (laromustine, VNP 40101M), cyclophosphamide, decarbazine, estramustine, fotemustine, glufosfamide, ifosfamide, KW-2170, lomustine (CCNU), mafosfamide, melphalan, mitobronitol, mitolactol, nimustine, nitrogen mustard N-oxide, ranimustine, temozolomide, thiotepa, TREANDA® (bendamustine), treosulfan, rofosfamide and the like.

Angiogenesis inhibitors include endothelial-specific receptor tyrosine kinase (Tie-2) inhibitors, epidermal growth factor receptor (EGFR) inhibitors, insulin growth factor-2 receptor (IGFR-2) inhibitors, matrix metalloproteinase-2 (MMP-2) inhibitors, matrix metalloproteinase-9 (MMP-9) inhibitors, platelet-derived growth factor receptor (PDGFR) inhibitors, thrombospondin analogs, vascular endothelial growth factor receptor tyrosine kinase (VEGFR) inhibitors and the like.

Antimetabolites include ALIMTA® (pemetrexed disodium, LY231514, MTA), 5-azacitidine, XELODA® (capecitabine), carmofur, LEUSTAT® (cladribine), clofarabine, cytarabine, cytarabine ocfosfate, cytosine arabinoside, decitabine, deferoxamine, doxifluridine, eflornithine, EICAR (5-ethynyl-1-β-D-ribofuranosylimidazole-4-carboxamide), enocitabine, ethnylcytidine, fludarabine, 5-fluorouracil alone or in combination with leucovorin, GEMZAR® (gemcitabine), hydroxyurea, ALKERAN®(melphalan), mercaptopurine, 6-mercaptopurine riboside, methotrexate, mycophenolic acid, nelarabine, nolatrexed, ocfosfate, pelitrexol, pentostatin, raltitrexed, Ribavirin, triapine, trimetrexate, S-1, tiazofurin, tegafur, TS-1, vidarabine, UFT and the like.

Antivirals include ritonavir, hydroxychloroquine and the like.

Aurora kinase inhibitors include ABT-348, AZD-1152, MLN-8054, VX-680, Aurora A-specific kinase inhibitors, Aurora B-specific kinase inhibitors and pan-Aurora kinase inhibitors and the like.

Bcl-2 protein inhibitors include AT-101 ((−)gossypol), GENASENSE® (G3139 or oblimersen (Bcl-2-targeting antisense oligonucleotide)), IPI-194, IPI-565, N-(4-(4-((4'-chloro(1,1'-biphenyl)-2-yl)methyl)piperazin-1-yl)benzoyl)-4-(((1R)-3-(dimethylamino)-1-((phenylsulfanyl)methyl)propyl)amino)-3-nitrobenzenesulfonamide) (ABT-737), N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide (ABT-263), GX-070 (obatoclax), ABT-199, and the like.

Bcr-Abl kinase inhibitors include DASATINIB® (BMS-354825), GLEEVEC® (imatinib) and the like.

CDK inhibitors include AZD-5438, BMI-1040, BMS-032, BMS-387, CVT-2584, flavopyridol, GPC-286199, MCS-5A, PD0332991, PHA-690509, seliciclib (CYC-202, R-roscovitine), ZK-304709 and the like.

COX-2 inhibitors include ABT-963, ARCOXIA® (etoricoxib), BEXTRA® (valdecoxib), BMS347070, CELEBREX® (celecoxib), COX-189 (lumiracoxib), CT-3, DERAMAXX® (deracoxib), JTE-522, 4-methyl-2-(3,4-dimethylphenyl)-1-(4-sulfamoylphenyl-1H-pyrrole), MK-663 (etoricoxib), NS-398, parecoxib, RS-57067, SC-58125, SD-8381, SVT-2016, S-2474, T-614, VIOXX® (rofecoxib) and the like.

EGFR inhibitors include EGFR antibodies, ABX-EGF, anti-EGFR immunoliposomes, EGF-vaccine, EMD-7200, ERBITUX® (cetuximab), HR3, IgA antibodies, IRESSA® (gefitinib), TARCEVA® (erlotinib or OSI-774), TP-38, EGFR fusion protein, TYKERB® (lapatinib) and the like.

ErbB2 receptor inhibitors include CP-724-714, CI-1033 (canertinib), HERCEPTIN® (trastuzumab), TYKERB® (lapatinib), OMNITARG® (2C4, petuzumab), TAK-165, GW-572016 (ionafarnib), GW-282974, EKB-569, PI-166, dHER2 (HER2 vaccine), APC-8024 (HER-2 vaccine), anti-HER/2neu bispecific antibody, B7.her2IgG3, AS HER2 trifunctional bispecfic antibodies, mAB AR-209, mAB 2B-1 and the like.

Histone deacetylase inhibitors include depsipeptide, LAQ-824, MS-275, trapoxin, suberoylanilide hydroxamic acid (SAHA), TSA, valproic acid and the like.

HSP-90 inhibitors include 17-AAG-nab, 17-AAG, CNF-101, CNF-1010, CNF-2024, 17-DMAG, geldanamycin, IPI-504, KOS-953, MYCOGRAB® (human recombinant antibody to HSP-90), NCS-683664, PU24FC1, PU-3, radicicol, SNX-2112, STA-9090 VER49009 and the like.

Inhibitors of inhibitors of apoptosis proteins include HGS1029, GDC-0145, GDC-0152, LCL-161, LBW-242 and the like.

Antibody drug conjugates include anti-CD22-MC-MMAF, anti-CD22-MC-MMAE, anti-CD22-MCC-DM1, CR-011-vcMMAE, PSMA-ADC, MEDI-547, SGN-19Am SGN-35, SGN-75 and the like.

Activators of death receptor pathway include TRAIL, antibodies or other agents that target TRAIL or death receptors (e.g., DR4 and DR5) such as Apomab, conatumumab, ETR2-ST01, GDC0145, (lexatumumab), HGS-1029, LBY-135, PRO-1762 and trastuzumab.

Kinesin inhibitors include Eg5 inhibitors such as AZD4877, ARRY-520; CENPE inhibitors such as GSK923295A and the like.

JAK-2 inhibitors include CEP-701 (lesaurtinib), XL019 and INCB018424 and the like.

MEK inhibitors include ARRY-142886, ARRY-438162 PD-325901, PD-98059 and the like.

mTOR inhibitors include AP-23573, CCI-779, everolimus, RAD-001, rapamycin, temsirolimus, ATP-competitive TORC1/TORC2 inhibitors, including PI-103, PP242, PP30, Torin 1 and the like.

Non-steroidal anti-inflammatory drugs include AMIGESIC® (salsalate), DOLOBID® (diflunisal), MOTRIN® (ibuprofen), ORUDIS® (ketoprofen), RELAFEN® (nabumetone), FELDENE® (piroxicam), ibuprofen cream, ALEVE® (naproxen) and NAPROSYN® (naproxen), VOLTAREN® (diclofenac), INDOCIN® (indomethacin), CLINORIL® (sulindac), TOLECTIN® (tolmetin), LODINE® (etodolac), TORADOL® (ketorolac), DAYPRO® (oxaprozin) and the like.

PDGFR inhibitors include C-451, CP-673, CP-868596 and the like.

Platinum chemotherapeutics include cisplatin, ELOXATIN® (oxaliplatin) eptaplatin, lobaplatin, nedaplatin, PARAPLATIN® (carboplatin), satraplatin, picoplatin and the like.

Polo-like kinase inhibitors include BI-2536 and the like.

Phosphoinositide-3 kinase (PI3K) inhibitors include wortmannin, LY294002, XL-147, CAL-120, ONC-21, AEZS-127, ETP-45658, PX-866, GDC-0941, BGT226, BEZ235, XL765 and the like.

Thrombospondin analogs include ABT-510, ABT-567, ABT-898, TSP-1 and the like.

VEGFR inhibitors include AVASTIN® (bevacizumab), ABT-869, AEE-788, ANGIOZYME™ (a ribozyme that inhibits angiogenesis (Ribozyme Pharmaceuticals (Boulder, Colo.) and Chiron, (Emeryville, Calif.)), axitinib (AG-13736), AZD-2171, CP-547,632, IM-862, MACUGEN (pegaptamib), NEXAVAR® (sorafenib, BAY43-9006), pazopanib (GW-786034), vatalanib (PTK-787, ZK-222584), SUTENT® (sunitinib, SU-11248), VEGF trap, ZACTIMA™ (vandetanib, ZD-6474), GA101, ofatumumab, ABT-806 (mAb-806), ErbB3 specific antibodies, BSG2 specific antibodies, DLL4 specific antibodies and C-met specific antibodies, and the like.

Antibiotics include intercalating antibiotics aclarubicin, actinomycin D, amrubicin, annamycin, adriamycin, BLENOXANE® (bleomycin), daunorubicin, CAELYX® or MYOCET® (liposomal doxorubicin), elsamitrucin, epirubicin, glarbuicin, ZAVEDOS® (idarubicin), mitomycin C, nemorubicin, neocarzinostatin, peplomycin, pirarubicin, rebeccamycin, stimalamer, streptozocin, VALSTAR® (valrubicin), zinostatin and the like.

Topoisomerase inhibitors include aclarubicin, 9-aminocamptothecin, amonafide, amsacrine, becatecarin, belotecan, BN-80915, CAMPTOSAR® (irinotecan hydrochloride), camptothecin, CARDIOXANE® (dexrazoxine), diflomotecan, edotecarin, ELLENCE® or PHARMORUBICIN® (epirubicin), etoposide, exatecan, 10-hydroxycamptothecin, gimatecan, lurtotecan, mitoxantrone, orathecin, pirarbucin, pixantrone, rubitecan, sobuzoxane, SN-38, tafluposide, topotecan and the like.

Antibodies include AVASTIN® (bevacizumab), CD40-specific antibodies, chTNT-1/B, denosumab, ERBITUX® (cetuximab), HUMAX-CD4® (zanolimumab), IGF1R-specific antibodies, lintuzumab, PANOREX® (edrecolomab), RENCAREX® (WX G250), RITUXAN® (rituximab), ticilimumab, trastuzimab, CD20 antibodies types I and II and the like.

Hormonal therapies include ARIMIDEX® (anastrozole), AROMASIN® (exemestane), arzoxifene, CASODEX® (bicalutamide), CETROTIDE® (cetrorelix), degarelix, deslorelin, DESOPAN® (trilostane), dexamethasone, DROGENIL® (flutamide), EVISTA® (raloxifene), AFEMA™ (fadrozole), FARESTON® (toremifene), FASLODEX® (fulvestrant), FEMARA® (letrozole), formestane, glucocorticoids, HECTOROL® (doxercalciferol), RENAGEL® (sevelamer carbonate), lasofoxifene, leuprolide acetate, MEGACE® (megesterol), MIFEPREX® (mifepristone), NILANDRON™ (nilutamide), NOLVADEX® (tamoxifen citrate), PLENAXIS™ (abarelix), prednisone, PROPECIA® (finasteride), rilostane, SUPREFACT® (buserelin), TRELSTAR® (luteinizing hormone releasing hormone (LHRH)), VANTAS® (Histrelin implant), VETORYL® (trilostane or modrastane), ZOLADEX® (fosrelin, goserelin) and the like.

Deltoids and retinoids include seocalcitol (EB1089, CB1093), lexacalcitrol (KH1060), fenretinide, PANRETIN® (aliretinoin), ATRAGEN® (liposomal tretinoin), TARGRETIN® (bexarotene), LGD-1550 and the like.

PARP inhibitors include ABT-888 (veliparib), olaparib, KU-59436, AZD-2281, AG-014699, BSI-201, BGP-15, INO-1001, ONO-2231 and the like.

Plant alkaloids include, but are not limited to, vincristine, vinblastine, vindesine, vinorelbine and the like.

Proteasome inhibitors include VELCADE® (bortezomib), MG132, NPI-0052, PR-171 and the like.

Examples of immunologicals include interferons and other immune-enhancing agents. Interferons include interferon alpha, interferon alpha-2a, interferon alpha-2b, interferon beta, interferon gamma-1a, ACTIMMUNE® (interferon gamma-1b) or interferon gamma-n1, combinations thereof and the like. Other agents include ALFAFERONE®, (IFN-α), BAM-002 (oxidized glutathione), BEROMUN® (tasonermin), BEXXAR® (tositumomab), CAMPATH® (alemtuzumab), CTLA4 (cytotoxic lymphocyte antigen 4), decarbazine, denileukin, epratuzumab, GRANOCYTE® (lenograstim), lentinan, leukocyte alpha interferon, imiquimod, MDX-010 (anti-CTLA-4), melanoma vaccine, mitumomab, molgramostim, MYLOTARG™ (gemtuzumab ozogamicin), NEUPOGEN® (filgrastim), OncoVAC-CL, OVAREX® (oregovomab), pemtumomab (Y-muHMFG1), PROVENGE® (sipuleucel-T), sargaramostim, sizofilan, teceleukin, THERACYS® (Bacillus Calmette-Guerin), ubenimex, VIRULIZIN® (immunotherapeutic, Lorus Pharmaceuticals), Z-100 (Specific Substance of Maruyama (SSM)), WF-10 (Tetrachlorodecaoxide (TCDO)), PROLEUKIN® (aldesleukin), ZADAXIN® (thymalfasin), ZENAPAX® (daclizumab), ZEVALIN® (90Y-Ibritumomab tiuxetan) and the like.

Biological response modifiers are agents that modify defense mechanisms of living organisms or biological responses, such as survival, growth or differentiation of tissue cells to direct them to have anti-tumor activity and include krestin, lentinan, sizofiran, picibanil PF-3512676 (CpG-8954), ubenimex and the like.

Pyrimidine analogs include cytarabine (ara C or Arabinoside C), cytosine arabinoside, doxifluridine, FLUDARA® (fludarabine), 5-FU (5-fluorouracil), floxuridine, GEMZAR® (gemcitabine), TOMUDEX® (ratitrexed), TROXATYL™ (triacetyluridine troxacitabine) and the like.

Purine analogs include LANVIS® (thioguanine) and PURI-NETHOL® (mercaptopurine).

Antimitotic agents include batabulin, epothilone D (KOS-862), N-(2-((4-hydroxyphenyl)amino)pyridin-3-yl)-4-methoxybenzenesulfonamide, ixabepilone (BMS 247550), paclitaxel, TAXOTERE® (docetaxel), PNU100940 (109881), patupilone, XRP-9881 (larotaxel), vinflunine, ZK-EPO (synthetic epothilone) and the like.

Ubiquitin ligase inhibitors include MDM2 inhibitors, such as nutlins, NEDD8 inhibitors such as MLN4924 and the like.

Compounds of this invention can also be used as radiosensitizers that enhance the efficacy of radiotherapy. Examples of radiotherapy include external beam radiotherapy, teletherapy, brachytherapy and sealed, unsealed source radiotherapy and the like.

Additionally, compounds having Formula (I) may be combined with other chemotherapeutic agents such as ABRAXANE™ (ABI-007), ABT-100 (farnesyl transferase inhibitor), ADVEXIN® (Ad5CMV-p53 vaccine), ALTOCOR® or MEVACOR® (lovastatin), AMPLIGEN® (poly I:poly C12U, a synthetic RNA), APTOSYN® (exisulind), AREDIA® (pamidronic acid), arglabin, L-asparaginase, atamestane (1-methyl-3,17-dione-androsta-1,4-diene), AVAGE® (tazarotene), AVE-8062 (combreastatin derivative) BEC2 (mitumomab), cachectin or cachexin (tumor necrosis factor), canvaxin (vaccine), CEAVAC® (cancer vaccine), CELEUK® (celmoleukin), CEPLENE® (histamine dihydrochloride), CERVARIX® (human papillomavirus vaccine), CHOP® (C: CYTOXAN® (cyclophosphamide); H: ADRIAMYCIN® (hydroxydoxorubicin); O: Vincristine)(ONCOVIN®); P: prednisone), CYPAT™ (cyproterone acetate), combrestatin A4P, DAB(389)EGF (catalytic and translocation domains of diphtheria toxin fused via a His-Ala linker to human epidermal growth factor) or TransMID-107R™ (diphtheria toxins), dacarbazine, dactinomycin, 5,6-dimethylxanthenone-4-acetic acid (DMXAA), eniluracil, EVIZON™ (squalamine lactate), DIMERICINE® (T4N5 liposome lotion), discodermolide, DX-8951f (exatecan mesylate), enzastaurin, EP0906 (epithilone B), GARDASIL® (quadrivalent human papillomavirus (Types 6, 11, 16, 18) recombinant vaccine), GASTRIMMUNE®, GENASENSE®, GMK (ganglioside conjugate vaccine), GVAX® (prostate cancer vaccine), halofuginone, histerelin, hydroxycarbamide, ibandronic acid, IGN-101, IL-13-PE38, IL-13-PE38QQR (cintredekin besudotox), IL-13-pseudomonas exotoxin, interferon-α, interferon-γ, JUNOVAN™ or MEPACT™ (mifamurtide), lonafarnib, 5,10-methylenetetrahydrofolate, miltefosine (hexadecylphosphocholine), NEOVASTAT® (AE-941), NEUTREXIN® (trimetrexate glucuronate), NIPENT® (pentostatin), ONCONASE® (a ribonuclease enzyme), ONCOPHAGE® (melanoma vaccine treatment), ONCOVAX® (IL-2 Vaccine), ORATHECIN™ (rubitecan), OSIDEM® (antibody-based cell drug), OVAREX® MAb (murine monoclonal antibody), paclitaxel, PANDIMEX™ (aglycone saponins from ginseng comprising 20(S)protopanaxadiol (aPPD) and 20(S)protopanaxatriol (aPPT)), panitumumab, PANVAC-VF (investigational cancer vaccine), pegaspargase, PEG Interferon A, phenoxodiol, procarbazine, rebimastat, REMOVAB® (catumaxomab), REVLIMID® (lenalidomide), RSR13 (efaproxiral), SOMATULINE® LA (lanreotide), SORIATANE® (acitretin), staurosporine (Streptomyces staurospores), talabostat (PT100), TARGRETIN® (bexarotene), TAXOPREXIN® (DHA-paclitaxel), TELCYTA® (canfosfamide, TLK286), temilifene, TEMODAR® (temozolomide), tesmilifene, thalidomide, THERATOPE® (STn-KLH), thymitaq (2-amino-3,4-dihydro-6-methyl-4-oxo-5-(4-pyridylthio)quinazoline dihydrochloride), TNFERADE™ (adenovector: DNA carrier containing the gene for tumor necrosis factor-α), TRACLEER® or ZAVESCA® (bosentan), tretinoin (Retin-A), tetrandrine, TRISENOX® (arsenic trioxide), VIRULIZIN®, ukrain (derivative of alkaloids from the greater celandine plant), vitaxin (anti-alphavbeta3 antibody), XCYTRIN® (motexafin gadolinium), XINLAY™ (atrasentan), XYOTAX™ (paclitaxel poliglumex), YONDELIS® (trabectedin), ZD-6126, ZINECARD® (dexrazoxane), ZOMETA® (zolendronic acid), zorubicin and the like.

The compounds of the invention can also be co-administered with a therapeutically effective amount of one or more agents to treat an inflammatory disease or condition, or autoimmune disease, where examples of the agents include, such as methotrexate, 6-mercaptopurine, azathioprine sulphasalazine, mesalazine, olsalazine chloroquinine/hydroxychloroquine, pencillamine, aurothiomalate (intramuscular and oral), azathioprine, cochicine, corticosteroids (oral, inhaled and local injection), beta-2 adrenoreceptor agonists (salbutamol, terbutaline, salmeteral), xanthines (theophylline, aminophylline), cromoglycate, nedocromil, ketotifen, ipratropium and oxitropium, cyclosporin, FK506, rapamycin, mycophenolate mofetil, leflunomide, NSAIDs, for example, ibuprofen, corticosteroids such as prednisolone, phosphodiesterase inhibitors, adensosine agonists, antithrombotic agents, complement inhibitors, adrenergic agents, agents which interfere with signalling by proinflammatory cytokines such as TNFα or IL-1 (e.g., NIK, IKK, p38 or MAP kinase inhibitors), IL-1β converting enzyme inhibitors, T-cell signalling inhibitors such as kinase inhibitors, metalloproteinase inhibitors, sulfasalazine, 6-mercaptopurines, angiotensin converting enzyme inhibitors, soluble cytokine receptors and derivatives thereof (e.g. soluble p55 or p75 TNF receptors and the derivatives p75TNFRIgG (etanercept) and p55TNFRIgG (Lenercept), sIL-1RI, sIL-1RII, sIL-6R), anti-inflammatory cytokines (e.g. IL-4, IL-10, IL-11, IL-13 and TGFβ), celecoxib, folic acid, hydroxychloroquine sulfate, rofecoxib, etanercept, infliximab, naproxen, valdecoxib, sulfasalazine, methylprednisolone, meloxicam, methylprednisolone acetate, gold sodium thiomalate, aspirin, triamcinolone acetonide, propoxyphene napsylate/apap, folate, nabumetone, diclofenac, piroxicam, etodolac, diclofenac sodium, oxaprozin, oxycodone HCl, hydrocodone bitartrate/apap, diclofenac sodium/misoprostol, fentanyl, anakinra, tramadol HCl, salsalate, sulindac, cyanocobalamin/fa/pyridoxine, acetaminophen, alendronate sodium, prednisolone, morphine sulfate, lidocaine hydrochloride, indomethacin, glucosamine sulf/chondroitin, amitriptyline HCl, sulfadiazine, oxycodone HCl/acetaminophen, olopatadine HCl misoprostol, naproxen sodium, omeprazole, cyclophosphamide, rituximab, IL-1 TRAP, MRA, CTLA4-IG, IL-18 BP, anti-IL-12, Anti-IL15, BIRB-796, SCIO-469, VX-702, AMG-548, VX-740, Roflumilast, IC-485, CDC-801, S1P1 agonists (such as FTY720), PKC family inhibitors (such as Ruboxistaurin or AEB-071) and Mesopram. In certain embodiments, combinations include methotrexate or leflunomide and in moderate or severe rheumatoid arthritis cases, cyclosporine and anti-TNF antibodies as noted above.

Non-limiting examples of therapeutic agents for inflammatory bowel disease with which a compound of Formula (I) of the invention may be co-administered include the following: budenoside; epidermal growth factor; corticosteroids; cyclosporin, sulfasalazine; aminosalicylates; 6-mercaptopurine; azathioprine; metronidazole; lipoxygenase inhibitors; mesalamine; olsalazine; balsalazide; antioxidants; thromboxane inhibitors; IL-1 receptor antagonists; anti-IL-1β monoclonal antibodies; anti-IL-6 monoclonal antibodies; growth factors; elastase inhibitors; pyridinyl-imidazole compounds; antibodies to or antagonists of other human cytokines or growth factors, for example, TNF, LT, IL-1, IL-2, IL-6, IL-7, IL-8, IL-12, IL-15, IL-16, IL-23, EMAP-II, GM-CSF, FGF, and PDGF; cell surface molecules such as CD2, CD3, CD4, CD8, CD25, CD28, CD30, CD40, CD45, CD69, CD90 or their ligands; methotrexate; cyclosporine; FK506; rapamycin; mycophenolate mofetil; leflunomide; NSAIDs, for example, ibuprofen; corticosteroids such as prednisolone; phosphodiesterase inhibitors; adenosine agonists; antithrombotic agents; complement inhibitors; adrenergic agents; agents which interfere with signalling by proinflammatory cytokines such as TNFα or IL-1 (e.g. NIK, IKK, or MAP kinase inhibitors); IL-1β converting enzyme inhibitors; TNFα converting enzyme inhibitors; T-cell signalling inhibitors such as kinase inhibitors; metalloproteinase inhibitors; sulfasalazine; azathioprine; 6-mercaptopurines; angiotensin converting enzyme inhibitors; soluble cytokine receptors and derivatives thereof (e.g. soluble p55 or p75 TNF receptors, sIL-1RI, sIL-1RII, sIL-6R) and antiinflammatory cytokines (e.g. IL-4, IL-10, IL-11, IL-13 and TGFβ). Preferred examples of therapeutic agents for Crohn's disease with which a compound of Formula (I) can be combined include the following: TNF antagonists, for example, anti-TNF antibodies, D2E7 (adalimumab), CA2 (infliximab), CDP 571, TNFR-Ig constructs, (p75TNFRIgG (etanercept) and p55TNFRIgG (LENERCEPT™) inhibitors and PDE4 inhibitors. A compound of Formula (I) can be combined with corticosteroids, for example, budenoside and dexamethasone; sulfasalazine, 5-aminosalicylic acid; olsalazine; and agents which interfere with synthesis or action of proinflammatory cytokines such as IL-1, for example, IL-1β converting enzyme inhibitors and IL-1ra; T cell signaling inhibitors, for example, tyrosine kinase inhibitors; 6-mercaptopurine; IL-11; mesalamine; prednisone; azathioprine; mercaptopurine; infliximab; methylprednisolone sodium succinate; diphenoxylate/atrop sulfate; loperamide hydrochloride; methotrexate; omeprazole; folate; ciprofloxacin/dextrose-water; hydrocodone bitartrate/apap; tetracycline hydrochloride; fluocinonide; metronidazole; thimerosal/boric acid; cholestyramine/sucrose; ciprofloxacin hydrochloride; hyoscyamine sulfate; meperidine hydrochloride; midazolam hydrochloride; oxycodone HCl/acetaminophen; promethazine hydrochloride; sodium phosphate; sulfamethoxazole/trimethoprim; celecoxib; polycarbophil; propoxyphene napsylate; hydrocortisone; multivitamins; balsalazide disodium; codeine phosphate/apap; colesevelam HCl; cyanocobalamin; folic acid; levofloxacin; methylprednisolone; natalizumab and interferon-gamma.

Non-limiting examples of therapeutic agents for multiple sclerosis with which a compound of Formula (I) may be co-administered include the following: corticosteroids; prednisolone; methylprednisolone; azathioprine; cyclophosphamide; cyclosporine; methotrexate; 4-aminopyridine; tizanidine; interferon-β1a (AVONEX®; Biogen); interferon-β1b (BETASERON®; Chiron/Berlex); interferon α-n3) (Interferon Sciences/Fujimoto), interferon-α (Alfa Wassermann/J&J), interferon β1A-IF (Serono/Inhale Therapeutics), Peginterferon α 2b (Enzon/Schering-Plough), Copolymer 1 (Cop-1; COPAXONE®; Teva Pharmaceutical Industries, Inc.); hyperbaric oxygen; intravenous immunoglobulin; cladribine; antibodies to or antagonists of other human cytokines or growth factors and their receptors, for example, TNF, LT, IL-1, IL-2, IL-6, IL-7, IL-8, IL-12, IL-23, IL-15, IL-16, EMAP-II, GM-CSF, FGF, and PDGF. A compound of Formula (I) can be combined with antibodies to cell surface molecules such as CD2, CD3, CD4, CD8, CD19, CD20, CD25, CD28, CD30, CD40, CD45, CD69, CD80, CD86, CD90 or their ligands. A compound of Formula (I) may also be combined with agents such as methotrexate, cyclosporine, FK506, rapamycin, mycophenolate mofetil, leflunomide, an S1P1 agonist, NSAIDs, for example, ibuprofen, corticosteroids such as prednisolone, phosphodiesterase inhibitors, adensosine agonists, antithrombotic agents, complement inhibitors, adrenergic agents, agents which interfere with signalling by proinflammatory cytokines such as TNFα or IL-1 (e.g., NIK, IKK, p38 or MAP kinase inhibitors), IL-1β converting enzyme inhibitors, TACE inhibitors, T-cell signaling inhibitors such as kinase inhibitors, metalloproteinase inhibitors, sulfasalazine, azathioprine, 6-mercaptopurines, angiotensin converting enzyme inhibitors, soluble cytokine receptors and derivatives thereof (e.g. soluble p55 or p75 TNF receptors, sIL-1RI, sIL-1RII, sIL-6R) and antiinflammatory cytokines (e.g. IL-4, IL-10, IL-13 and TGFβ).

A compound of Formula (I) may also be co-administered with agents, such as alemtuzumab, dronabinol, daclizumab, mitoxantrone, xaliproden hydrochloride, fampridine, glatiramer acetate, natalizumab, sinnabidol, α-immunokine NNSO3, ABR-215062, AnergiX.MS, chemokine receptor antagonists, BBR-2778, calagualine, CPI-1189, LEM (liposome encapsulated mitoxantrone), THC.CBD (cannabinoid agonist), MBP-8298, mesopram (PDE4 inhibitor), MNA-715, anti-IL-6 receptor antibody, neurovax, pirfenidone allotrap 1258 (RDP-1258), sTNF-R1, talampanel, teriflunomide, TGF-beta2, tiplimotide, VLA-4 antagonists (for example, TR-14035, VLA4 Ultrahaler, Antegran-ELAN/Biogen), interferon gamma antagonists and IL-4 agonists.

Non-limiting examples of therapeutic agents for ankylosing spondylitis with which a compound of Formula (I) can be co-administered include the following: ibuprofen, diclofenac, misoprostol, naproxen, meloxicam, indomethacin, diclofenac, celecoxib, rofecoxib, sulfasalazine, methotrexate, azathioprine, minocyclin, prednisone, and anti-TNF antibodies, D2E7 (HUMIRA®), CA2 (infliximab), CDP 571, TNFR-Ig constructs, (p75TNFRIgG (ENBREL®) and p55TNFRIgG (LENERCEPT®).

Non-limiting examples of therapeutic agents for asthma with which a compound of Formula (I) may be co-administered include the following: albuterol, salmeterol/fluticasone, montelukast sodium, fluticasone propionate, budesonide, prednisone, salmeterol xinafoate, levalbuterol HCl, albuterol sulfate/ipratropium, prednisolone sodium phosphate, triamcinolone acetonide, beclomethasone dipropionate, ipratropium bromide, azithromycin, pirbuterol acetate, prednisolone, theophylline anhydrous, methylprednisolone sodium succinate, clarithromycin, zafirlukast, formoterol fumarate, influenza virus vaccine, amoxicillin trihydrate, flunisolide, allergy injection, cromolyn sodium, fexofenadine hydrochloride, flunisolide/menthol, amoxicillin/clavulanate, levofloxacin, inhaler assist device, guaifenesin, dexamethasone sodium phosphate, moxifloxacin HCl, doxycycline hyclate, guaifenesin/d-methorphan, p-ephedrine/cod/chlorphenir, gatifloxacin, cetirizine hydrochloride, mometasone furoate, salmeterol xinafoate, benzonatate, cephalexin, pe/hydrocodone/chlorphenir, cetirizine HCl/pseudoephed, phenylephrine/cod/promethazine, codeine/promethazine, cefprozil, dexamethasone, guaifenesin/pseudoephedrine, chlorpheniramine/hydrocodone, nedocromil sodium, terbutaline sulfate, epinephrine, methylprednisolone, anti-IL-13 antibody, and metaproterenol sulfate.

Non-limiting examples of therapeutic agents for COPD with which a compound of Formula (I) may be co-administered include the following: albuterol sulfate/ipratropium, ipratropium bromide, salmeterol/fluticasone, albuterol, salmeterol xinafoate, fluticasone propionate, prednisone, theophylline anhydrous, methylprednisolone sodium succinate, montelukast sodium, budesonide, formoterol fumarate, triamcinolone acetonide, levofloxacin, guaifenesin, azithromycin, beclomethasone dipropionate, levalbuterol HCl, flunisolide, ceftriaxone sodium, amoxicillin trihydrate, gatifloxacin, zafirlukast, amoxicillin/clavulanate, flunisolide/menthol, chlorpheniramine/hydrocodone, metaproterenol sulfate, methylprednisolone, mometasone furoate, p-ephedrine/cod/chlorphenir, pirbuterol acetate, p-ephedrine/loratadine, terbutaline sulfate, tiotropium bromide, (R,R)-formoterol, TgAAT, cilomilast and roflumilast.

Non-limiting examples of therapeutic agents for psoriasis with which a compound of Formula (I) may be co-administered include the following: calcipotriene, clobetasol propionate, triamcinolone acetonide, halobetasol propionate, tazarotene, methotrexate, fluocinonide, betamethasone diprop augmented, fluocinolone acetonide, acitretin, tar shampoo, betamethasone valerate, mometasone furoate, ketoconazole, pramoxine/fluocinolone, hydrocortisone valerate, flurandrenolide, urea, betamethasone, clobetasol propionate/emoll, fluticasone propionate, azithromycin, hydrocortisone, moisturizing formula, folic acid, desonide, pimecrolimus, coal tar, diflorasone diacetate, etanercept folate, lactic acid, methoxsalen, hc/bismuth subgal/znox/resor, methylprednisolone acetate, prednisone, sunscreen, halcinonide, salicylic acid, anthralin, clocortolone pivalate, coal extract, coal tar/salicylic acid, coal tar/salicylic acid/sulfur, desoximetasone, diazepam, emollient, fluocinonide/emollient, mineral oil/castor oil/na lact, mineral oil/peanut oil, petroleum/isopropyl myristate, psoralen, salicylic acid, soap/tribromsalan, thimerosal/boric acid, celecoxib, infliximab, cyclosporine, alefacept, efalizumab, tacrolimus, pimecrolimus, PUVA, UVB, sulfasalazine, ABT-874 and ustekinamab.

Non-limiting examples of therapeutic agents for psoriatic arthritis with which a compound of Formula (I) may be co-administered include the following: methotrexate, etanercept, rofecoxib, celecoxib, folic acid, sulfasalazine, naproxen, leflunomide, methylprednisolone acetate, indomethacin, hydroxychloroquine sulfate, prednisone, sulindac, betamethasone diprop augmented, infliximab, methotrexate, folate, triamcinolone acetonide, diclofenac, dimethylsulfoxide, piroxicam, diclofenac sodium, ketoprofen, meloxicam, methylprednisolone, nabumetone, tolmetin sodium, calcipotriene, cyclosporine, diclofenac sodium/misoprostol, fluocinonide, glucosamine sulfate, gold sodium thiomalate, hydrocodone bitartrate/apap, ibuprofen, risedronate sodium, sulfadiazine, thioguanine, valdecoxib, alefacept, D2E7 (adalimumab), and efalizumab.

Preferred examples of therapeutic agents for SLE (Lupus) with which a compound of Formula (I) may be co-administered include the following: NSAIDS, for example, diclofenac, naproxen, ibuprofen, piroxicam, indomethacin; COX2 inhibitors, for example, celecoxib, rofecoxib, valdecoxib; anti-malarials, for example, hydroxychloroquine; steroids, for example, prednisone, prednisolone, budenoside, dexamethasone; cytotoxics, for example, azathioprine, cyclophosphamide, mycophenolate mofetil, methotrexate; inhibitors of PDE4 or purine synthesis inhibitor, for example Cellcept®. A compound of Formula (I) may also be combined with agents such as sulfasalazine, 5-aminosalicylic acid, olsalazine, Imuran® and agents which interfere with synthesis, production or action of proinflammatory cytokines such as IL-1, for example, caspase inhibitors like IL-1β converting enzyme inhibitors and IL-1ra. A compound of Formula (I) may also be used with T cell signaling inhibitors, for example, tyrosine kinase inhibitors; or molecules that target T cell activation molecules, for example, CTLA-4-IgG or anti-B7 family antibodies, anti-PD-1 family antibodies. A compound of Formula (I) can be combined with IL-11 or anti-cytokine antibodies, for example, fonotolizumab (anti-IFNg antibody), or anti-receptor receptor antibodies, for example, anti-IL-6 receptor antibody and antibodies to B-cell surface molecules. A compound of Formula (I) may also be used with UP 394 (abetimus), agents that deplete or inactivate B-cells, for example, Rituximab (anti-CD20 antibody), lymphostat-B (anti-BlyS antibody), TNF antagonists, for example, anti-TNF antibodies, D2E7 (adalimumab), CA2 (infliximab), CDP 571, TNFR-Ig constructs, (p75TNFRIgG (etanercept) and p55TNFRIgG (LENERCEPT™).

A compound of Formula (I) may also be co-administered with insulin for the treatment of type I diabetes.

The compounds of the invention can also be co-administered with a therapeutically effective amount of one or more agents used in the prevention or treatment of AIDS, where examples of the agents include, HIV reverse transcriptase inhibitors, HIV protease inhibitors, immunomodulators, and other retroviral drugs. Examples of reverse transcriptase inhibitors include, but are not limited to, abacavir, adefovir, didanosine, dipivoxil delavirdine, efavirenz, emtricitabine, lamivudine, nevirapine, rilpivirine, stavudine, tenofovir, zalcitabine, and zidovudine. Examples of protease inhibitors include, but are not limited to, amprenavir, atazanavir, darunavir, indinavir, fosamprenavir, lopinavir, nelfinavir, ritonavir, saquinavir, and tipranavir. Examples of other retroviral drugs include, but are not limited to, elvitegravir, enfuvirtide, maraviroc and raltegravir.

The compounds of the invention can also be co-administered with a therapeutically effective amount of one or more agents used in the treatment of obesity, where examples of the agents include orlistat.

The compounds of the invention can also be co-administered with a therapeutically effective amount of one or more agents used in the treatment of type II diabetes, where examples of the agents include, alpha glucosidase inhibitors, insulin, metformin, sulfonylureas (e.g., carbutamide, acetohexamide, chlorpropamide, glibenclamide, glibornuride, gliclazide, glimepiride, glipizide, gliquidone, glisoxepide, glyclopyramide, tolbutamide, and tolazamide), nonsulfonylureas (e.g., nateglinide, and repaglinide), and thiazolidinediones (e.g., pioglitazone).

The compounds of the invention can be co-administered with a therapeutically effective amount of one or more agents to prevent or treat type II diabetes, hepatic steatosis, insulin resistance, metabolic syndrome and related disorders, where examples of the agents include, but are not limited to, insulin and insulins that have been modified to improve the duration of action in the body; agents that stimulate insulin secretion such as acetohexamide, chlorpropamide, glyburide, glimepiride, glipizide, glicazide, glycopyramide, gliquidone, rapaglinide, nataglinide, tolazamide and tolbutamide; agents that are glucagon-like peptide agonists such as exanatide, liraglutide and taspoglutide; agents that inhibit dipeptidyl-peptidase IV such as vildagliptin, sitagliptin, saxagliptin, linagliptin, allogliptin and septagliptin; agents that bind to the peroxisome proliferator-activated receptor gamma such as rosiglitazone and pioglitazone; agents that decrease insulin resistance such as metformin; agents that reduce glucose absorbance in the small intestine such as acarbose, miglitol and voglibose.

The compounds of the invention can be co-administered with a therapeutically effective amount of one or more agents to prevent or treat acute kidney disorders and chronic kidney diseases, where examples of the agents include, but are not limited to, dopamine, diuretics such as furosemide, bumetanide, thiazide and the like, mannitol, calcium gluconate, sodium bicarbonate, albuterol, paricalcitol, doxercalciferol, and cinacalcet. The following Examples may be used for illustrative purposes and should not be deemed to narrow the scope of the invention.

EXAMPLES

Example 1 methyl 3-methyl-4-oxo-1-(2-phenoxyphenyl)-4,5-dihydro-2H-pyrrolo[3,4-c]pyridine-6-carboxylate Example 1a ethyl 2-methyl-1-(triisopropylsilyl)-1H-pyrrole-3-carboxylate Ethyl 2-methyl-1H-pyrrole-3-carboxylate (1 g, 6.53 mmol) in tetrahydrofuran (15 mL) at 0° C. was treated with sodium hydride (60% oil dispersion, 0.39 g, 9.8 mmol), stirred for twenty minutes, and then treated with chlorotriisopropylsilane (1.676 mL, 7.83 mmol). The reaction mixture was stirred for three hours and allowed to reach ambient temperature. The reaction mixture was partitioned between ethyl acetate and water, washed with saturated aqueous sodium chloride, dried over anhydrous magnesium sulfate, filtered and concentrated. The residue was purified by flash chromatography (silica gel, 1-8% ethyl acetate in hexanes) to give 1.85 g (91%) of the title compound.

Example 1b ethyl 4-formyl-2-methyl-1H-pyrrole-3-carboxylate

N,N-dimethylformamide (5.5 mL, 71 mmol) in dichloromethane (126 mL) at 0° C. was treated dropwise with oxalyl dichloride (6 mL, 71 mmol). The mixture was stirred at 0° C. for 30 minutes and then at ambient temperature for 1 hour. The mixture was again cooled to 0° C. and treated with a mixture of Example 1a (20 g, 64.6 mmol) in dichloromethane (126 mL). The reaction mixture was stirred at 0° C. for 2 hours and then at ambient temperature for 48 hours. The reaction mixture was again cooled to 0° C. and slowly quenched with 4 N aqueous sodium hydroxide solution. The mixture was then extracted with ethyl acetate (2×300 mL). The combined organic layers were washed with saturated aqueous sodium chloride, dried over anhydrous magnesium sulfate, filtered and concentrated. The residue was triturated with a mixture of 9:1 hexanes/ethyl acetate, filtered, and dried under high vacuum to give 8.67 g (74%) of the title compound.

Example 1c ethyl 4-formyl-2-methyl-1-((2-(trimethylsilyl)ethoxy)methyl)-1H-pyrrole-3-carboxylate Example 1b (1.8 g, 10 mmol) was dissolved in tetrahydrofuran (100 mL), treated with sodium hydride (60% oil dispersion, 0.8 g, 20 mmol) and stirred at ambient temperature for 20 minutes. (2-(Chloromethoxy)ethyl)trimethylsilane (2.65 mL, 15 mmol) was added and the mixture was stirred at ambient temperature for 4 hours. The mixture was carefully quenched with saturated aqueous ammonium chloride solution and concentrated to half the volume. The concentrated material was extracted with ethyl acetate. The combined organic layers were washed with saturated aqueous sodium chloride, dried over anhydrous magnesium sulfate, filtered and concentrated. The residue was purified by flash chromatography (silica gel, 0-45% ethyl acetate in hexanes) to give 2.93 g (94%) of the title compound.

Example 1d methyl 3-methyl-4-oxo-2-((2-(trimethylsilyl)ethoxy)methyl)-4,5-dihydro-2H-pyrrolo[3,4-c]pyridine-6-carboxylate To a solution of methyl 2-isocyanoacetate (0.198 g, 2 mmol) and Example 1c (0.311 g, 1 mmol) in tetrahydrofuran (10 mL) was added sodium hydride (60% oil dispersion, 0.12 g, 3 mmol). The reaction mixture was stirred at ambient temperature for one hour. A spatula tip of silica gel and methanol (5 mL) were added and the mixture was heated at 50° C. for 4 hours. The reaction mixture was concentrated, slurried in a 1:1 mixture of dichloromethane/ethyl acetate, filtered through Celite and concentrated. The residue was purified by flash chromatography (silica gel, 5-80% ethyl acetate in dichloromethane) to give 0.114 g (34%) of the title compound.

Example 1e methyl 1-bromo-3-methyl-4-oxo-2-((2-(trimethylsilyl)ethoxy)methyl)-4,5-dihydro-2H-pyrrolo[3,4-c]pyridine-6-carboxylate Example 1d (0.11 g, 0.33 mmol) in tetrahydrofuran (3.3 mL) at −78° C. was treated with 1-bromopyrrolidine-2,5-dione (0.059 g, 0.33 mmol) and stirred at −78° C. for 1.5 hours. The reaction mixture was quenched with saturated aqueous sodium thiosulfate solution and then partitioned between ethyl acetate and water. The organic layer was washed with saturated sodium bicarbonate solution (2×50 mL), water, and saturated aqueous sodium chloride, dried over anhydrous magnesium sulfate, filtered and concentrated.

The residue was purified by flash chromatography (silica gel, 0-50% ethyl acetate in hexanes) to give 0.099 g (72%) of the title compound.

Example 1f methyl 3-methyl-4-oxo-1-(2-phenoxyphenyl)-2-((2-(trimethylsilyl)ethoxy)methyl)-4,5-dihydro-2H-pyrrolo[3,4-c]pyridine-6-carboxylate Example 1e (0.083 g, 0.2 mmol), 2-phenoxyphenylboronic acid (0.064 g, 0.3 mmol), bis(dibenzylideneacetone)palladium(0) (0.0055 g, 6 μmol), (1S,3R,5R,7S)-1,3,5,7-tetramethyl-8-phenyl-2,4,6-trioxa-8-phosphaadamantane (0.0064 g, 0.022 mmol) and sodium carbonate (0.106 g, 1 mmol) were combined and sparged with nitrogen for 40 minutes. Nitrogen-sparged dioxane (1 mL) and water (0.250 mL) were added. The mixture was stirred at 60° C. for five hours and then at ambient temperature overnight. The reaction mixture was partitioned between ethyl acetate and water, washed with saturated aqueous sodium chloride, dried over anhydrous magnesium sulfate, filtered and concentrated. The residue was purified by flash chromatography (silica gel, 25-55% ethyl acetate in hexanes) to give 0.03 g (30%) of the title compound.

Example 1g methyl 3-methyl-4-oxo-1-(2-phenoxyphenyl)-4,5-dihydro-2H-pyrrolo[3,4-c]pyridine-6-carboxylate Example 1f (0.03 g, 0.059 mmol) in dichloromethane (1 mL) at ambient temperature was treated with 2,2,2-trifluoroacetic acid (0.045 mL, 0.59 mmol) and stirred at ambient temperature for two hours. Additional 2,2,2-trifluoroacetic acid (0.045 mL, 0.59 mmol) was added and stirring was continued at ambient temperature for six hours. Additional 2,2,2-trifluoroacetic acid (0.045 mL, 0.59 mmol) was added and stirring was continued at ambient temperature overnight. The reaction mixture was concentrated to dryness. Neat 2,2,2-trifluoroacetic acid (0.3 mL, 3.93 mmol) was added and the mixture was stirred at ambient temperature for thirty minutes. The reaction mixture was concentrated and dried on house vacuum for 10 minutes. Acetonitrile (1 mL) and a solution of sodium acetate (0.145 g, 1.77 mmol) in water (0.3 mL) were added and the mixture was heated at 50° C. for two hours. The reaction mixture was partitioned between ethyl acetate and water, washed with saturated aqueous sodium chloride, dried over anhydrous magnesium sulfate, filtered and concentrated. The residue was purified by flash chromatography (silica gel, 0-100% ethyl acetate in dichloromethane) to give 0.011 g (48%) of the title compound. $^1$H NMR (400 MHz, DMSO-$d_6$) δ 12.29 (s, 1H), 9.47 (s, 1H), 7.56 (dd, J=7.63, 1.53 Hz, 1H), 7.39 (m, 1H), 7.31 (m, 4H), 7.05 (m, 2H), 6.88 (m, 2H), 3.79 (s, 3H), 2.60 (s, 3H). MS (ESI+) m/z 375.1 (M+H)$^+$.

Example 2 methyl 1-(5-amino-2-phenoxyphenyl)-3-methyl-4-oxo-4,5-dihydro-2H-pyrrolo[3,4-c]pyridine-6-carboxylate

Example 2a methyl 1-(5-amino-2-phenoxyphenyl)-3-methyl-4-oxo-2-((2-(trimethylsilyl)ethoxy)methyl)-4,5-dihydro-2H-pyrrolo[3,4-c]pyridine-6-carboxylate Example 1e (0.085 g, 0.2 mmol), Example 74e (0.095 g, 0.31 mmol), bis(dibenzylideneacetone)palladium(0) (0.0056 g, 6.1 μmol), (1S,3R,5R,7S)-1,3,5,7-tetramethyl-8-phenyl-2,4,6-trioxa-8-phosphaadamantane (0.0066 g, 0.022 mmol) and sodium carbonate (0.108 g, 1.02 mmol) were combined and sparged with nitrogen for 40 minutes. Nitrogen-sparged N,N-dimethylformamide (2 mL) was added. The mixture was stirred at 60° C. for one day and then at ambient temperature for 2.5 days. The reaction mixture was partitioned between ethyl acetate and water, washed with saturated aqueous sodium chloride, dried over anhydrous magnesium sulfate, filtered and concentrated. The residue was purified by flash chromatography (silica gel, 7-70% ethyl acetate in dichloromethane). The material was purified by flash chromatography a second time (silica gel, 0-4% methanol in dichloromethane) to give 0.038 g (29%) of the title compound.

Example 2b methyl 1-(5-amino-2-phenoxyphenyl)-3-methyl-4-oxo-4,5-dihydro-2H-pyrrolo[3,4-c]pyridine-6-carboxylate Example 2a (0.0573 g, 0.11 mmol) in dichloromethane (1 mL) was treated with 2,2,2-trifluoroacetic acid (0.17 mL, 2.2 mmol) and stirred at ambient temperature for 6 hours. The reaction mixture was concentrated and dried under high vacuum. The concentrate was taken up in acetonitrile (1 mL) and water (0.15 mL), treated with sodium acetate (0.09 g, 1.1 mmol) and stirred at ambient temperature overnight. Additional sodium acetate (0.18 g, 2.2 mmol) was added and stirring was continued for 4 hours at 50° C. The reaction mixture was partitioned between ethyl acetate and water, washed with saturated aqueous sodium chloride, dried over anhydrous magnesium sulfate, filtered and concentrated. The residue was purified by flash chromatography (silica gel, 5-80% ethyl acetate with 1% methanol in dichloromethane, then 3% methanol in dichloromethane) to give 0.0064 g (13%) of the title compound. $^1$H NMR (300 MHz, DMSO-$d_6$) δ 12.18 (s, 1H), 9.35 (s, 1H), 7.30 (d, J=1.36 Hz, 1H), 7.15 (m, 2H), 6.86 (m, 2H), 6.74 (d, J=2.71 Hz, 1H), 6.67 (m, 2H), 6.62 (dd, J=8.48, 2.71 Hz, 1H), 5.20 (s, 2H), 3.80 (s, 3H), 2.54 (s, 3H). MS (ESI+) m/z 390.1 (M+H)$^+$.

Example 3 methyl 3-methyl-1-(5-(methylsulfonamido)-2-phenoxyphenyl)-4-oxo-4,5-dihydro-2H-pyrrolo[3,4-c]pyridine-6-carboxylate

Example 3a methyl 3-methyl-1-(5-(N-(methylsulfonyl)methylsulfonamido)-2-phenoxyphenyl)-4-oxo-2-((2-(trimethylsilyl)ethoxy)methyl)-4,5-dihydro-2H-pyrrolo[3,4-c]pyridine-6-carboxylate Example 2a (0.0472 g, 0.091 mmol) in tetrahydrofuran (0.9 mL) at ambient temperature was treated sequentially with methanesulfonyl chloride (0.018 mL, 0.227 mmol) and triethylamine (0.038 mL, 0.272 mmol). The reaction mixture was stirred at ambient temperature for 3.6 hours and then concentrated. The residue was taken up in tetrahydrofuran (0.9 mL) and treated with a solution of sodium acetate (0.075 g, 0.908 mmol) in water (0.9 mL). The reaction mixture was stirred at 50° C. for 45 minutes. Sodium carbonate (0.048 g, 0.454 mmol) was added and the mixture was stirred at 50° C. for 2 hours and then at ambient temperature overnight. The organic layer was washed with saturated aqueous sodium chloride, dried over anhydrous magnesium sulfate, filtered and concentrated to give the title compound which was utilized in the next step without additional purification.

Example 3b methyl 3-methyl-1-(5-(methylsulfonamido)-2-phenoxyphenyl)-4-oxo-4,5-dihydro-2H-pyrrolo[3,4-c]pyridine-6-carboxylate Example 3a in a mixture of dichloromethane (1.5 mL) and methanol (1.5 mL) was treated with 2,2,2-trifluoroacetic acid (0.14 mL, 1.82 mmol) and stirred at ambient temperature for two hours. Additional 2,2,2-trifluoroacetic acid (0.14 mL, 1.82 mmol) was added and stirring was continued at ambient temperature overnight and then at 40° C. for 2 hours. The reaction mixture was concentrated. Neat 2,2,2-trifluoroacetic acid (0.28 mL, 3.64 mmol) was added and the mixture was stirred at ambient temperature for 6 hours. The reaction mixture was concentrated and dried under high vacuum. The residue was taken up in methanol (1.5 mL), treated with potassium carbonate (0.25 g, 1.82 mmol) and stirred overnight at ambient temperature. The reaction mixture was partitioned between ethyl acetate and water, washed with saturated aqueous sodium chloride, dried over anhydrous magnesium sulfate, filtered and concentrated. The residue and N1-((ethylimino)methylene)-N3,N3-dimethylpropane-1,3-diamine hydrochloride (0.035 g, 0.182 mmol) were taken up in dichloromethane (1 mL) and methanol (0.25 mL), treated with triethylamine (0.05 mL, 0.36 mmol) and stirred at ambient temperature for 23 hours. Additional $N^1$-((ethylimino)methylene)-$N^3$,$N^3$-dimethylpropane-1,3-diamine hydrochloride (0.035 g, 0.18 mmol), triethylamine (0.05 mL, 0.36 mmol) and methanol (0.25 mL) were added and stirring was continued for another 25 hours. The reaction mixture was partitioned between ethyl acetate and water, washed with saturated aqueous sodium chloride, dried over anhydrous magnesium sulfate, filtered and concentrated. The residue was purified by flash chromatography (silica gel, 0-10% methanol in dichloromethane) to give 0.11 g (27%) of the title compound. $^1$H NMR (400 MHz, DMSO-$d_6$) δ 12.32 (s, 1H), 9.83 (s, 1H), 9.52 (d, J=1.22 Hz, 1H), 7.40 (d, J=2.44 Hz, 1H), 7.28 (m, 3H), 7.22 (dd, J=8.70, 2.59 Hz, 1H), 7.10 (d, J=8.85 Hz, 1H), 7.01 (m, 1H), 6.85 (m, 2H), 3.79 (s, 3H), 3.06 (s, 3H), 2.60 (s, 3H). MS (ESI+) m/z 468.1 (M+H)$^+$.

Example 4 ethyl 1-[5-amino-2-(2,4-difluorophenoxy)phenyl]-3-methyl-4-oxo-4,5-dihydro-2H-pyrrolo[3,4-c]pyridine-6-carboxylate

Example 4a ethyl 3-methyl-4-oxo-2-((2-(trimethylsilyl)ethoxy)methyl)-4,5-dihydro-2H-pyrrolo[3,4-c]pyridine-6-carboxylate To Example 1c (3.1 g, 10 mmol) and ethyl 2-isocyanoacetate (2.2 mL, 20 mmol) in tetrahydrofuran (100 mL) was added sodium hydride (60% oil dispersion, 1.2 g, 30 mmol). The mixture was heated at 70° C. for 5 hours. The reaction mixture was cooled to ambient temperature and partitioned between ethyl acetate and water. The organic layer was washed with water and saturated aqueous sodium chloride, dried over anhydrous magnesium sulfate, filtered, and concentrated. The residue was purified by flash chromatography (silica gel, 0-60% ethyl acetate in hexanes) and trituration of impure fractions with diethyl ether to give 1.2 g (34%) of the title compound.

Example 4b ethyl 1-bromo-3-methyl-4-oxo-2-((2-(trimethylsilyl)ethoxy)methyl)-4,5-dihydro-2H-pyrrolo[3,4-c]pyridine-6-carboxylate Example 4b was prepared according to the procedure used for the preparation of Example 1e, substituting Example 4a for Example 1d and stirring for 1.25 hours. Purification by flash chromatography (silica gel, 0-40% ethyl acetate in hexanes) gave 1.4 g (100%) of the title compound.

Example 4c ethyl 1-(2-fluoro-5-nitrophenyl)-3-methyl-4-oxo-2-((2-(trimethylsilyl)ethoxy)methyl)-4,5-dihydro-2H-pyrrolo[3,4-c]pyridine-6-carboxylate Example 4b (0.086 g, 0.2 mmol), 2-fluoro-5-nitrophenylboronic acid (0.044 g, 0.24 mmol), bis(dibenzylideneacetone)palladium(0) (0.013 g, 0.014 mmol), tri-tert-butylphosphine tetrafluoroborate (0.0081 g, 0.028 mmol) and cesium fluoride (0.091 g, 0.6 mmol) were combined and sparged with nitrogen for thirty minutes Nitrogen-sparged tetrahydrofuran (2 mL) was added and the mixture was reacted in a Biotage microwave reactor at 110° C. for 25 minutes. The reaction mixture was partitioned between ethyl acetate and water, washed with saturated aqueous sodium chloride, dried over anhydrous magnesium sulfate, filtered and concentrated. The residue was purified by flash chromatography (silica gel, 0-40% ethyl acetate in hexanes) to give 0.079 g, (81%) of the title compound.

Example 4d ethyl 1-(2-(2,4-difluorophenoxy)-5-nitrophenyl)-3-methyl-4-oxo-2-((2-(trimethylsilyl)ethoxy)methyl)-4,5-dihydro-2H-pyrrolo[3,4-c]pyridine-6-carboxylate Example 4c (0.123 g, 0.25 mmol), 2,4-difluorophenol (0.053 g, 0.41 mmol) and cesium carbonate (0.223 g, 0.68 mmol) were combined with dimethyl sulfoxide (3.4 mL) and stirred at 50° C. for 45 minutes. The reaction mixture was partitioned between ethyl acetate and saturated aqueous ammonium chloride solution and washed with water and saturated aqueous sodium chloride. The combined aqueous layers were acidified to pH 5 and extracted with ethyl acetate. The combined organic layers were dried over anhydrous magnesium sulfate, filtered and concentrated. The residue was purified by flash chromatography (silica gel, 0-20% ethyl acetate in dichloromethane to give 0.13 g (86%) of the title compound.

Example 4e ethyl 1-(5-amino-2-(2,4-difluorophenoxy)phenyl)-3-methyl-4-oxo-2-((2-(trimethylsilyl)ethoxy)methyl)-4,5-dihydro-2H-pyrrolo[3,4-c]pyridine-6-carboxylate Example 4d (0.127 g, 0.212 mmol) in ethanol (2 mL) and tetrahydrofuran (2 mL) at 65° C. was treated sequentially with iron powder (0.12 g, 2.12 mmol) and a solution of ammonium chloride (0.023 g, 0.424 mmol) in water (1 mL). The resulting mixture was stirred vigorously at 65° C. for 1 hour. The reaction mixture was cooled to ambient temperature and filtered through diatomaceous earth, rinsing with ethyl acetate. The filtrate was washed with water and saturated aqueous sodium chloride, dried over anhydrous magnesium sulfate, filtered, and concentrated to give the title compound.

Example 4f ethyl 1-[5-amino-2-(2,4-difluorophenoxy)phenyl]-3-methyl-4-oxo-4,5-dihydro-2H-pyrrolo[3,4-c]pyridine-6-carboxylate Example 4e was treated with neat 2,2,2-trifluoroacetic acid (1 mL, 13.1 mmol) and stirred at ambient temperature for 25 minutes. The reaction mixture was concentrated and dried under high vacuum. The residue was taken up in acetonitrile (3 mL) and treated with a solution of sodium acetate (0.174 g, 2.12 mmol) in water (1 mL). The mixture was stirred at 50° C. for 2 hours, at ambient temperature overnight and then for another 2 hours at 50° C. The reaction mixture was cooled to ambient temperature, partitioned between ethyl acetate and water, washed with saturated aqueous sodium chloride, dried over anhydrous magnesium sulfate, filtered, and concentrated. The residue was purified by reverse phase HPLC (C18, acetonitrile/water (0.1% TFA), 0-70%) to give 0.062 g (53%) of the title compound as the TFA salt. $^1$H NMR (300 MHz, DMSO-$d_6$) δ 12.28 (s, 1H), 9.44 (s, 1H), 7.36 (m, 1H), 7.26 (d, J=1.19 Hz, 1H), 6.95 (m, 3H), 6.84 (m, 2H), 4.24 (q, J=7.14 Hz, 2H), 2.61 (s, 3H), 1.27 (t, J=6.94 Hz, 3H). MS (ESI+) m/z 440.0 (M+H)$^+$.

Example 5 ethyl 3-methyl-1-(5-(methylsulfonamido)-2-phenoxyphenyl)-4-oxo-4,5-dihydro-2H-pyrrolo[3,4-c]pyridine-6-carboxylate Example 4e (0.048 g, 0.09 mmol) in tetrahydrofuran (0.9 mL) was treated sequentially with methanesulfonyl chloride (0.017 mL, 0.22 mmol) and triethylamine (0.037 mL, 0.27 mmol) and stirred at ambient temperature for 3 hours. The reaction mixture was partitioned between ethyl acetate and water, washed with saturated sodium bicarbonate solution and saturated aqueous sodium chloride, dried over anhydrous magnesium sulfate, filtered, and concentrated. The residue was treated with neat 2,2,2-trifluoroacetic acid (0.5 mL, 6.5 mmol), stirred at ambient temperature for 30 minutes, concentrated, and dried under high vacuum. The residue was suspended in ethanol (1 mL), treated with potassium carbonate (0.123 g, 0.89 mmol) and stirred at ambient temperature for 5 hours. The mixture was then filtered through a syringe filter. The filtrate was concentrated and the residue was purified by reverse phase HPLC (C18, acetonitrile/water (0.1% TFA), 10-80%) to give 0.025 g (59%) of the title compound. $^1$H NMR (300 MHz, DMSO-$d_6$) δ 12.30 (s, 1H), 9.80 (s, 1H), 9.47 (s, 1H), 7.41 (d, J=2.38 Hz, 1H), 7.29 (m, 3H), 7.20 (dd, J=8.73, 2.78 Hz, 1H), 7.04 (m, 2H), 6.89 (d, J=7.93 Hz, 2H), 4.25 (q, J=7.14 Hz, 2H), 3.05 (s, 3H), 2.60 (s, 3H), 1.28 (t, J=7.14 Hz, 3H). MS (ESI+) m/z 482.1 (M+H)$^+$.

Example 6 ethyl 1-(5-(ethylsulfonamido)-2-phenoxyphenyl)-3-methyl-4-oxo-4,5-dihydro-2H-pyrrolo[3,4-c]pyridine-6-carboxylate Example 6 was prepared according to the procedure used for the preparation of Example 5, substituting ethanesulfonyl chloride for methanesulfonyl chloride and stirring the second step for 45 minutes instead of 30 minutes to give 0.023 g (49%) of the title compound. $^1$H NMR (400 MHz, DMSO-$d_6$) δ 12.30 (s, 1H), 9.87 (s, 1H), 9.48 (s, 1H), 7.42 (d, J=2.44 Hz, 1H), 7.29 (m, 3H), 7.21 (dd, J=8.70, 2.59 Hz, 1H), 7.06 (d, J=8.54 Hz, 1H), 7.02 (m, 1H), 6.88 (m, 2H), 4.25 (q, J=7.12 Hz, 2H), 3.15 (q, J=7.32 Hz, 2H), 2.60 (s, 3H), 1.29 (t, J=7.17 Hz, 3H), 1.25 (t, J=7.32 Hz, 3H). MS (ESI+) m/z 496.1 (M+H)$^+$.

Example 7 methyl 1-(5-(ethylsulfonamido)-2-phenoxyphenyl)-3-methyl-4-oxo-4,5-dihydro-2H-pyrrolo[3,4-c]pyridine-6-carboxylate Example 7 was obtained during the purification of Example 6 by trans-esterification as a result of methanol used to dissolve Example 6 for HPLC purification. 0.0035 g (8%) of the title compound was obtained. $^1$H NMR (400 MHz, DMSO-$d_6$) δ 12.30 (s, 1H), 9.89 (s, 1H), 9.52 (s, 1H), 7.41 (d, J=2.75 Hz, 1H), 7.27 (m, 3H), 7.22 (dd, J=8.70, 2.59 Hz, 1H), 7.09 (d, J=8.85 Hz, 1H), 7.00 (m, 1H), 6.85 (m, 2H), 3.79 (s, 3H), 3.16 (q, J=7.12 Hz, 2H), 2.59 (s, 3H), 1.26 (t, J=7.32 Hz, 3H). MS (ESI+) m/z 482.2 (M+H)$^+$.

Example 8 ethyl 3-methyl-1-[4-(3-methyl-1H-pyrazol-5-yl)phenyl]-4-oxo-4,5-dihydro-2H-pyrrolo[3,4-c]pyridine-6-carboxylate Example 8a 3-methyl-5-(4-(4,4,5,5-tetramethyl-1,3,2-dioxaborolan-2-yl)phenyl)-1H-pyrazole 5-(4-Bromophenyl)-3-methyl-1H-pyrazole (95 mg, 0.40 mmol), 4,4,4',4',5,5,5',5'-octamethyl-2,2'-bi(1,3,2-dioxaborolane) (203 mg, 0.800 mmol), potassium acetate (137 mg, 1.40 mmol), tris(dibenzylideneacetone)dipalladium (11 mg, 0.012 mmol) and 2-dicyclohexylphosphino-2',4',6-triisopropylbiphenyl (17 mg, 0.036 mmol) were combined and purged with nitrogen for 30 minutes. Dioxane (2 mL) was purged with nitrogen for 30 minutes and transferred to the reaction flask. The reaction mixture was heated at 80° C. for 2 hours. The reaction mixture was partitioned with ethyl acetate and water. The organic layer was washed with saturated aqueous sodium chloride, dried over anhydrous sodium sulfate, filtered, and concentrated. The residue was purified by flash chromatography (silica gel, 2% methanol in dichloromethane) to give a solid. The solid was triturated with heptanes to afford the title compound (87 mg, 77%).

Example 8b ethyl 3-methyl-1-(4-(3-methyl-1H-pyrazol-5-yl)phenyl)-4-oxo-2-((2-(trimethylsilyl)ethoxy)methyl)-4,5-dihydro-2H-pyrrolo[3,4-c]pyridine-6-carboxylate Example 4b (60 mg, 0.14 mmol), Example 8a (60 mg, 0.21 mmol), sodium carbonate (69 mg, 0.63 mmol), tris(dibenzylideneacetone)dipalladium (3.9 mg, 4.2 μmol) and 1,3,5,7-tetramethyl-6-phenyl-2,4,8-trioxa-6-phosphaadamante (3.7 mg, 0.013 mmol) were combined and purged with nitrogen for 15 minutes. A mixture of dioxane (2 mL) and water (0.5 mL) was purged with nitrogen for 15 minutes and transferred to the reaction flask. The reaction mixture was heated at 60° C. for 4 hours. The reaction mixture was partitioned with ethyl acetate and water. The organic layer was washed with saturated aqueous sodium chloride, dried over anhydrous sodium sulfate, treated with 3-mercaptopropyl functionalized silica gel, filtered, and concentrated. The residue was purified by flash chromatography (silica gel, 2-4% methanol in dichloromethane) to afford the title compound (41 mg, 58%).

Example 8c ethyl 3-methyl-1-[4-(3-methyl-1H-pyrazol-5-yl)phenyl]-4-oxo-4,5-dihydro-2H-pyrrolo[3,4-c]pyridine-6-carboxylate Example 8b (40 mg, 0.079 mmol) was treated with 2,2,2-trifluoroacetic acid (1.0 mL, 13 mmol). The reaction mixture was stirred at ambient temperature for 30 minutes, concentrated, and dried under high vacuum. To this residue was added acetonitrile (3 mL) and a solution of sodium acetate (65 mg, 0.79 mmol) in water (1 mL). The reaction mixture was stirred at 50° C. for 3 hours. The reaction mixture was partitioned with ethyl acetate and water. The organic layer was washed with saturated aqueous sodium chloride, dried over anhydrous sodium sulfate, filtered, and concentrated. The residue was purified by flash chromatography (silica gel, 2-6% methanol in dichloromethane) to afford the title compound (22 mg, 74%). $^1$H NMR (300 MHz, DMSO-$d_6$) δ 12.57 (s, 1 H) 12.41 (s, 1 H) 9.54 (s, 1 H) 7.88 (d, J=7.80 Hz, 2 H) 7.64 (d, J=8.14 Hz, 2 H) 7.38 (d, J=1.36 Hz, 1 H) 6.49 (s, 1 H) 4.30 (q, J=7.01 Hz, 2 H) 2.67 (s, 3 H) 2.28 (s, 3 H) 1.32 (t, J=7.12 Hz, 3 H). MS (ESI+) m/z 377 (M+H)$^+$.

Example 9 ethyl 1-{2-(2,4-difluorophenoxy)-5-[(methylsulfonyl)amino]phenyl}-3-methyl-4-oxo-4,5-dihydro-2H-pyrrolo[3,4-c]pyridine-6-carboxylate Example 4f (0.05 g, 0.114 mmol) in tetrahydrofuran (2 mL) was treated sequentially with methanesulfonyl chloride (0.022 mL, 0.284 mmol) and triethylamine (0.048 mL, 0.34 mmol), stirred at ambient temperature for 2.8 hours, concentrated and dried under high vacuum. The residue was taken up in tetrahydrofuran (2 mL), treated with potassium carbonate (0.157 g, 1.138 mmol) and stirred at ambient temperature overnight. The reaction mixture was partitioned between ethyl acetate and water, washed with saturated aqueous sodium chloride, dried over anhydrous magnesium sulfate, filtered and concentrated. The residue was again taken up in tetrahydrofuran (2 mL), treated with potassium carbonate (0.157 g, 1.138 mmol) and heated at 50° C. for 45 minutes. The reaction mixture was partitioned between ethyl acetate and water, washed with saturated aqueous sodium chloride, dried over anhydrous magnesium sulfate, filtered and concentrated. The product was purified by reverse phase HPLC (C18, acetonitrile/water (0.1% TFA), 10-80%) to give 0.048 g (82%) of the title compound. $^1$H NMR (400 MHz, DMSO-$d_6$) δ 12.34 (s, 1H), 9.76 (s, 1H), 9.48 (s, 1H), 7.44 (m, 1H), 7.38 (d, J=2.44 Hz, 1H), 7.30 (d, J=1.53 Hz, 1H), 7.16 (m, 2H), 7.07 (m, 1H), 6.90 (d, J=8.85 Hz, 1H), 4.23 (q, J=7.02 Hz, 2H), 3.03 (s, 3H), 2.65 (s, 3H), 1.27 (t, J=7.17 Hz, 3H). MS (ESI+) m/z 518.0 (M+H)$^+$.

Example 10 ethyl 1-(2-(2,4-difluorophenoxy)-5-(ethylsulfonamido)phenyl)-3-methyl-4-oxo-4,5-dihydro-2H-pyrrolo[3,4-c]pyridine-6-carboxylate Example 10 (0.04 g, 67%) was prepared according to the procedure used for the preparation of Example 9, substituting ethanesulfonyl chloride for methanesulfonyl chloride. $^1$H NMR (400 MHz, DMSO-$d_6$) δ 12.32 (s, 1H), 9.83 (s, 1H), 9.49 (s, 1H), 7.44 (m, 1H), 7.39 (d, J=2.75 Hz, 1H), 7.29 (d, J=1.22 Hz, 1H), 7.15 (m, 2H), 7.07 (m, 1H), 6.89 (d, J=8.85 Hz, 1H), 4.23 (q, J=7.22 Hz, 2H), 3.13 (q, J=7.32 Hz, 2H), 2.64 (s, 3H), 1.27 (t, J=6.26 Hz, 3H), 1.24 (t, J=7.32 Hz, 3H). MS (ESI+) m/z 532.0 (M+H)$^+$.

Example 11

3-methyl-4-oxo-1-(2-phenoxyphenyl)-4,5-dihydro-2H-pyrrolo[3,4-c]pyridine-6-carboxamide Example 11a ethyl 3-methyl-4-oxo-1-(2-phenoxyphenyl)-2-((2-(trimethylsilyl)ethoxy)methyl)-4,5-dihydro-2H-pyrrolo[3,4-c]pyridine-6-carboxylate Example 11a was prepared according to the procedure used for Example 1f, substituting Example 4b for Example 1e. In the current example, the reaction mixture was heated for 3.5 hours and then stirred overnight at ambient temperature. Purification by flash chromatography (silica gel, 7 to 60% ethyl acetate in hexanes) gave 0.91 g (65%) of the title compound.

Example 11b 3-methyl-4-oxo-1-(2-phenoxyphenyl)-2-((2-(trimethylsilyl)ethoxy)methyl)-4,5-dihydro-2H-pyrrolo[3,4-c]pyridine-6-carboxamide Example 11a (0.026 g, 0.05 mmol) was treated with ammonia (7 N in methanol, 2 mL, 14 mmol) solution, heated at 50° C. for 24 hours, concentrated and dried under high vacuum to give the title compound.

Example 11c 3-methyl-4-oxo-1-(2-phenoxyphenyl)-4,5-dihydro-2H-pyrrolo[3,4-c]pyridine-6-carboxamide Example 11b was treated with neat 2,2,2-trifluoroacetic acid (1 mL, 13.1 mmol), stirred at ambient temperature for 30 minutes, concentrated and dried under high vacuum. The residue was dissolved in methanol (2 mL), treated with potassium carbonate (0.138 g, 1 mmol) and heated at 50° C. for 1.5 hours. The reaction mixture was then partitioned between ethyl acetate and water, washed with saturated aqueous sodium chloride, dried over anhydrous magnesium sulfate, filtered and concentrated. The residue was taken up in a mixture of acetonitrile (3 mL) and water (1 mL), treated with sodium acetate (0.082 g, 1 mmol) and heated at 50° C. overnight. Additional sodium acetate (0.082 g, 1 mmol) was added and heating was continued for six hours at 60° C. Sodium acetate (0.082 g, 1 mmol) was again added and heating was continued overnight at 60° C. The reaction mixture was cooled to ambient temperature, partitioned between ethyl acetate and water, washed with saturated aqueous sodium chloride, dried over anhydrous magnesium sulfate, filtered and concentrated. The residue was purified by reverse phase HPLC (C18, acetonitrile/water (0.1% TFA), 10-80%) to give 0.019 g (53%) of the title compound. $^1$H NMR (400 MHz, DMSO-$d_6$) δ 12.14 (s, 1H), 8.87 (s, 1H), 8.07 (s, 1H), 7.58 (d, J=7.02 Hz, 1H), 7.46 (s, 1H), 7.33 (m, 5H), 7.03 (m, 2H), 6.95 (d, J=7.93 Hz, 2H), 2.60 (s, 3H). MS (ESI+) m/z 360.1 (M+H)$^+$.

Example 12

3-methyl-4-oxo-1-(2-phenoxyphenyl)-4,5-dihydro-2H-pyrrolo[3,4-c]pyridine-6-carboxylic acid Example 12a 3-methyl-4-oxo-1-(2-phenoxyphenyl)-2-((2-(trimethylsilyl)ethoxy)methyl)-4,5-dihydro-2H-pyrrolo[3,4-c]pyridine-6-carboxylic acid Example 11a (0.104 g, 0.2 mmol) in a mixture of tetrahydrofuran (1 mL), water (1 mL) and methanol (1 mL) was treated with lithium hydroxide monohydrate (0.084 g, 2 mmol), heated at 50° C. for 1.75 hours, cooled to ambient temperature, partitioned between ethyl acetate and water, washed with saturated aqueous sodium chloride, dried over anhydrous magnesium sulfate, filtered and concentrated. The residue was dried under high vacuum to give 0.096 g (98%) of the title compound.

Example 12b 3-methyl-4-oxo-1-(2-phenoxyphenyl)-4,5-dihydro-2H-pyrrolo[3,4-c]pyridine-6-carboxylic acid Example 12a (0.025 g, 0.05 mmol) in ethanol (0.25 mL) was treated with concentrated aqueous hydrogen chloride solution (0.5 mL, 6 mmol) and heated at 80° C. for 1 hour. Sodium hydroxide solution (4 N aqueous, 2 mL, 8 mmol) was added and the mixture was stirred at 80° C. for 45 minutes and then at ambient temperature overnight. The pH was adjusted to 5 with hydrogen chloride solution (2 N aqueous). The mixture was then extracted with ethyl acetate (2×60 mL). The combined organic layers were washed with saturated aqueous sodium chloride, dried over anhydrous magnesium sulfate, filtered and concentrated. The product was purified by reverse phase HPLC (C18, acetonitrile/water (0.1% TFA), 10-80%) to give 0.009 g (50%) of the title compound. $^1$H NMR (400 MHz, DMSO-$d_6$) δ 13.20 (s, 1H), 12.25 (s, 1H), 9.12 (s, 1H), 7.57 (dd, J=7.63, 1.53 Hz, 1H), 7.38 (m, 1H), 7.30 (m, 4H), 7.04 (m, 2H), 6.87 (m, 2H), 2.60 (s, 3H). MS (ESI+) m/z 361.0 (M+H)$^+$.

Example 13

N,3-dimethyl-4-oxo-1-(2-phenoxyphenyl)-4,5-dihydro-2H-pyrrolo[3,4-c]pyridine-6-carboxamide Example 13a N,3-dimethyl-4-oxo-1-(2-phenoxyphenyl)-2-((2-(trimethylsilyl)ethoxy)methyl)-4,5-dihydro-2H-pyrrolo[3,4-c]pyridine-6-carboxamide Example 11a (0.052 g, 0.1 mmol) was treated with methanamine (2 M in tetrahydrofuran, 2 mL, 4 mmol) and heated at 50° C. overnight. Methanamine hydrochloride (0.675 g, 10 mmol), N-ethyl-N-isopropylpropan-2-amine (1.7 mL, 10 mmol) and methanol (2 mL) were added and heating was continued at 50° C. for 4.5 hours. Additional methanamine (2 M in tetrahydrofuran, 2 mL, 4 mmol) was added and heating was continued overnight at 55° C. Additional methanamine hydrochloride (0.675 g, 10 mmol), N-ethyl-N-isopropylpropan-2-amine (1.7 mL, 10 mmol) and methanamine (2 M in tetrahydrofuran) (2 mL, 4 mmol) were added and heating was continued over another night at 55° C. The reaction mixture was concentrated. The residue was partitioned between ethyl acetate and water, washed with water and saturated aqueous sodium chloride, dried over anhydrous magnesium sulfate, filtered and concentrated.

Example 13b

N,3-dimethyl-4-oxo-1-(2-phenoxyphenyl)-4,5-dihydro-2H-pyrrolo[3,4-c]pyridine-6-carboxamide Example 13a was treated with neat 2,2,2-trifluoroacetic acid (0.011 g, 0.1 mmol), stirred at ambient temperature for 25 minutes, concentrated and dried under high vacuum. The residue was taken up in a mixture of acetonitrile (1.2 mL) and water (0.4 mL), treated with sodium acetate (0.246 g, 3 mmol) and heated at 50° C. overnight. Additional sodium acetate (0.246 g, 3 mmol) was added and heating was continued for 24 hours. The reaction mixture was then cooled to ambient temperature, partitioned between ethyl acetate and water, washed with saturated aqueous sodium chloride, dried over anhydrous magnesium sulfate, filtered and concentrated. The product was purified by reverse phase HPLC (C18, acetonitrile/water (0.1% TFA), 10-80%) to give 0.026 g (69%) of the title compound. $^1$H NMR (500 MHz, DMSO-$d_6$) δ 12.13 (s, 1H), 8.91 (s, 1H), 8.53 (q, J=4.37 Hz, 1H), 7.58 (dd, J=7.48, 1.68 Hz, 1H), 7.37 (td, J=7.78, 1.83 Hz, 1H), 7.30 (m, 3H), 7.23 (d, J=1.22 Hz, 1H), 7.04 (m, 2H), 6.92 (d, J=7.93 Hz, 2H), 2.75 (d, J=4.58 Hz, 3H), 2.59 (s, 3H). MS (ESI+) m/z 374.1 (M+H)$^+$.

Example 14

3-methyl-1-(2-phenoxyphenyl)-2H-pyrrolo[3,4-c]pyridin-4(5H)-one

Example 14a 3-methyl-1-(2-phenoxyphenyl)-2-((2-(trimethylsilyl)ethoxy)methyl)-2H-pyrrolo[3,4-c]pyridin-4(5H)-one To a solution of Example 12a (0.037 g, 0.075 mmol) in a mixture of N-methyl-2-pyrrolidinone (0.3 mL) and quinoline (0.100 mL) were added 1,10-phenanthroline (0.027 g, 0.15 mmol) and copper(I) oxide (0.01 g, 0.075 mmol). The mixture sparged with nitrogen for 30 minutes and heated in a Biotage microwave reactor at 190° C. for 1 hour. The reaction mixture was partitioned between ethyl acetate and water, washed with saturated aqueous sodium chloride, dried over anhydrous magnesium sulfate, filtered and concentrated to afford a mixture of products containing the title compound.

Example 14b 3-methyl-1-(2-phenoxyphenyl)-2H-pyrrolo[3,4-c]pyridin-4(5H)-one

Example 14a was treated with neat 2,2,2-trifluoroacetic acid (3 mL, 39.2 mmol) and stirred at ambient temperature overnight. The reaction mixture was concentrated and dried under high vacuum. The residue was dissolved in acetonitrile (1.5 mL) and water (0.5 mL), treated with sodium acetate (0.308 g, 3.75 mmol) and heated at 50° C. for 2 hours. Additional sodium acetate (0.308 g, 3.75 mmol) was added and heating was continued overnight. The reaction mixture was cooled to ambient temperature, partitioned between ethyl acetate and water, washed with saturated aqueous sodium chloride, dried over anhydrous magnesium sulfate, filtered and concentrated. The residue was purified by reverse phase HPLC (C18, acetonitrile/water (0.1% TFA), 10-80%) to give 0.006 g (15%) of the title compound. $^1$H NMR (300 MHz, DMSO-$d_6$) δ 11.82 (s, 1H), 9.90 (d, J=5.16 Hz, 1H), 7.52 (dd, J=7.34, 2.18 Hz, 1H), 7.26 (m, 4H), 7.01 (m, 2H), 6.90 (d, J=7.93 Hz, 2H), 6.54 (dd, J=7.14, 5.55 Hz, 1H), 6.31 (d, J=7.14 Hz, 1H), 2.58 (s, 3H). MS (ESI+) m/z 317.2 (M+H)$^+$.

Example 15

3-methyl-6-(morpholine-4-carbonyl)-1-(2-phenoxyphenyl)-2H-pyrrolo[3,4-c]pyridin-4(5H)-one Example 15a 3-methyl-6-(morpholine-4-carbonyl)-1-(2-phenoxyphenyl)-2-((2-(trimethylsilyl)ethoxy)methyl)-2H-pyrrolo[3,4-c]pyridin-4(5H)-one Example 11a (0.052 g, 0.1 mmol) was treated with morpholine (1 mL, 11.4 mmol) and heated at 60° C. overnight. Heating was continued for 24 hours at 100° C. and then for 24 hours at 115° C. Additional morpholine (1 mL, 11.4 mmol) was added and heating was continued for 3 days at 110° C. The reaction mixture was cooled to ambient temperature, partitioned between ethyl acetate and water, washed with hydrochloric acid solution (1 N, aqueous) and saturated aqueous sodium chloride, dried over anhydrous magnesium sulfate, filtered and concentrated. Flash chromatography (silica gel, 0-8% methanol in dichloromethane) gave the title compound as a mixture.

Example 15b 3-methyl-6-(morpholine-4-carbonyl)-1-(2-phenoxyphenyl)-2H-pyrrolo[3,4-c]pyridin-4(5H)-one Example 15a was treated with neat 2,2,2-trifluoroacetic acid (2 mL, 26 mmol), stirred at ambient temperature for 35 minutes and concentrated to dryness. The residue was dissolved in acetonitrile (1 mL) and water (0.33 mL), treated with sodium acetate (0.054 g, 0.66 mmol) and stirred at 50° C. overnight. The reaction mixture was cooled to ambient temperature, partitioned between ethyl acetate and water, washed with saturated aqueous sodium chloride, dried over anhydrous magnesium sulfate, filtered and concentrated. The residue was purified by reverse phase HPLC (C18, acetonitrile/water (0.1% TFA), 10-80%) to give 0.005 g (35%) of the title compound. $^1$H NMR (500 MHz, DMSO-$d_6$) δ 12.03 (s, 1H), 10.03 (s, 1H), 7.53 (dd, J=7.48, 1.68 Hz, 1H), 7.30 (m, 4H), 7.05 (t, J=7.32 Hz, 1H), 7.02 (dd, J=7.93, 0.92 Hz, 1H), 6.90 (d, J=7.93 Hz, 2H), 6.42 (d, J=0.92 Hz, 1H), 3.54 (m, J=4.58 Hz, 4H), 3.43 (m, 4H), 2.59 (s, 3H). MS (ESI+) m/z 430.1 (M+H)$^+$ Example 16

3-methyl-6-(4-methylpiperazine-1-carbonyl)-1-(2-phenoxyphenyl)-2H-pyrrolo[3,4-c]pyridin-4(5H)-one Example 16a 3-methyl-6-(4-methylpiperazine-1-carbonyl)-1-(2-phenoxyphenyl)-2-((2-(trimethylsilyl)ethoxy)methyl)-2H-pyrrolo[3,4-c]pyridin-4(5H)-one 1-Methylpiperazine (0.022 mL, 0.2 mmol), Example 12a (0.049 g, 0.1 mmol), and 2-(3H-[1,2,3]triazolo[4,5-b]pyridin-3-yl)-1,1,3,3-tetramethylisouronium hexafluorophosphate(V) (0.057 g, 0.15 mmol) were combined, dissolved in N,N-dimethylformamide (1 mL), treated with N-ethyl-N-isopropylpropan-2-amine (0.052 mL, 0.3 mmol) and stirred overnight at ambient temperature. The reaction mixture was partitioned between ethyl acetate and water, washed with saturated aqueous sodium chloride, dried over anhydrous magnesium sulfate, filtered and concentrated. The residue was purified by flash chromatography (silica gel, 0-16% methanol in dichloromethane) to afford the title compound.

Example 16b 3-methyl-6-(4-methylpiperazine-1-carbonyl)-1-(2-phenoxyphenyl)-2H-pyrrolo[3,4-c]pyridin-4(5H)-one Example 16b was prepared according to the procedure used for the preparation of Example 15b, substituting Example 16a for Example 15a, to give 0.02 g (36%) of the title compound as the TFA salt. $^1$H NMR (500 MHz, DMSO-$d_6$) δ 12.08 (s, 1H), 10.03 (s, 1H), 10.00 (s, 1H), 7.54 (dd, J=7.63, 1.53 Hz, 1H), 7.34 (td, J=7.71, 1.68 Hz, 1H), 7.29 (m, 3H), 7.04 (m, 2H), 6.89 (d, J=7.93 Hz, 2H), 6.52 (d, J=1.22 Hz, 1H), 4.14 (s, 1H), 3.44 (m, J=9.77 Hz, 3H), 3.24 (m, 2H), 3.01 (m, 2H), 2.82 (s, 3H), 2.59 (s, 3H). MS (ESI+) m/z 443.1 (M+H)$^+$.

Example 17

3-methyl-N-(4-((4-methylpiperazin-1-yl)methyl)phenyl)-4-oxo-1-(2-phenoxyphenyl)-4,5-dihydro-2H-pyrrolo[3,4-c]pyridine-6-carboxamide Example 17 was prepared according to the procedure used for the preparation of Example 16a, substituting Example 12b for Example 12a and 4-((4-methylpiperazin-1-yl)methyl)aniline for 1-methylpiperazine. Purification by reverse phase HPLC (C18, acetonitrile/water (0.1% TFA), 10-80%) gave 0.0085 g (51%) of the title compound. $^1$H NMR (500 MHz, DMSO-$d_6$) δ 12.24 (s, 1H), 10.31 (s, 1H), 9.22 (s, 1H), 7.73 (d, J=8.24 Hz, 2H), 7.62 (dd, J=7.63, 1.53 Hz, 1H), 7.50 (d, J=1.22 Hz, 1H), 7.39 (td, J=7.78, 1.53 Hz, 1H), 7.35 (d, J=8.24 Hz, 2H), 7.31 (m, 4H), 7.05 (t, J=7.48 Hz, 1H), 7.02 (d, J=8.24 Hz, 1H), 6.98 (d, J=7.93 Hz, 2H), 3.76 (m, 2H), 3.06 (m, 8H), 2.78 (s, 3H), 2.62 (s, 3H). MS (ESI+) m/z 548.0 (M+H)$^+$.

Example 18

6-(hydroxymethyl)-3-methyl-1-(2-phenoxyphenyl)-2H-pyrrolo[3,4-c]pyridin-4(5H) one

Example 18a ethyl 3-methyl-4-oxo-1-(2-phenoxyphenyl)-4,5-dihydro-2H-pyrrolo[3,4-c]pyridine-6-carboxylate Example 18a was prepared according to the procedure used for the preparation of Example 15b, substituting Example 11a for Example 15a. Purification by flash chromatography (silica gel, 6-50% ethyl acetate in dichloromethane) gave 0.108 g (92%) of the title compound.

Example 18b 6-(hydroxymethyl)-3-methyl-1-(2-phenoxyphenyl)-2H-pyrrolo[3,4-c]pyridin-4(5H)-one To Example 18a (0.05 g, 0.129 mmol) in tetrahydrofuran (1.3 mL) at −78° C. was added aluminum(III) lithium hydride (2 M in tetrahydrofuran, 0.1 mL, 0.2 mmol). The reaction mixture was stirred at −78° C. for 30 minutes, then at 0° C. for 30 minutes and then for another 30 minutes without cooling. The reaction mixture was cooled to 0° C., quenched by sequential addition of 0.02 mL water, 0.02 mL of 4 N aqueous sodium hydroxide solution, and finally 0.06 mL water. The reaction mixture was then partitioned between ethyl acetate and water, washed with saturated aqueous sodium chloride, dried over anhydrous magnesium sulfate, filtered and concentrated. The residue was purified by reverse phase HPLC (C18, acetonitrile/water (0.1% TFA), 10-80%). The material was purified further by flash chromatography (silica gel, 0-8% methanol in dichloromethane) to give 0.021 g (47%) of the title compound. $^1$H NMR (400 MHz, DMSO-$d_6$) δ 11.76 (s, 1 H), 9.65 (s, 1 H), 7.52 (m, 1 H), 7.27 (m, 4 H), 7.02 (m, 2 H), 6.90 (m, J=8.70, 1.07 Hz, 2 H), 6.33 (d, J=0.92 Hz, 1 H), 5.09 (t, J=5.95 Hz, 1 H), 4.17 (d, J=5.49 Hz, 2 H), 2.57 (s, 3 H). MS (ESI+) m/z 347.0 (M+H)$^+$.

Example 19

1-(2-(2,4-difluorophenoxy)-5-(methylsulfonamido)phenyl)-3-methyl-4-oxo-4,5-dihydro-2H-pyrrolo[3,4-c]pyridine-6-carboxamide Example 9 (0.035 g, 0.068 mmol) was treated with ammonia (7 N in methanol, 3 mL, 21 mmol) and heated at 55° C. for 24 hours. Additional ammonia (7 N in methanol, 1 mL, 7 mmol) was added and heating was continued at 55° C. for 4 hours. The reaction mixture was then cooled to ambient temperature and concentrated to dryness. The residue was purified by flash chromatography (silica gel, 5% methanol in dichloromethane) to provide 0.027 g (82%) of the title compound. $^1$H NMR (400 MHz, DMSO-$d_6$) δ 12.19 (s, 1H), 9.73 (s, 1H), 8.95 (s, 1H), 7.94 (s, 1H), 7.48 (s, 1H), 7.40 (m, 1H), 7.35 (d, J=2.75 Hz, 1H), 7.20 (m, 3H), 7.06 (m, 1H), 6.89 (d, J=8.85 Hz, 1H), 3.03 (s, 3H), 2.63 (s, 3H). MS (ESI+) m/z 489.0 (M+H)$^+$.

Example 20

3-methyl-1-(5-(methylsulfonamido)-2-phenoxyphenyl)-4-oxo-4,5-dihydro-2H-pyrrolo[3,4-c]pyridine-6-carboxamide Example 5 (0.015 g, 0.032 mmol) was treated with ammonia (7 N in methanol, 1 mL, 7 mmol) and heated at 55° C. for 24 hours. Additional ammonia (7 N in methanol, 1 mL, 7 mmol) was added and heating was continued over a second night. The reaction mixture was then concentrated to dryness. The residue was purified by flash chromatography (silica gel, 2-10% methanol in dichloromethane) to give 0.012 g (84%) of the title compound. $^1$H NMR (400 MHz, DMSO-$d_6$) δ 12.19 (s, 1H), 9.76 (s, 1H), 8.95 (s, 1H), 7.96 (s, 1H), 7.49 (s, 1H), 7.37 (d, J=2.44 Hz, 1H), 7.28 (m, 3H), 7.21 (dd, J=8.54, 2.75 Hz, 1H), 7.02 (m, 2H), 6.89 (m, 2H), 3.05 (s, 3H), 2.59 (s, 3H). MS (ESI+) m/z 453.1 (M+H)$^+$.

Example 21 ethyl 1-[2-(2,4-difluorophenoxy)phenyl]-3-methyl-4-oxo-4,5-dihydro-2H-pyrrolo[3,4-c]pyridine-6-carboxylate

Example 21a ethyl 1-(2-(2,4-difluorophenoxy)phenyl)-3-methyl-4-oxo-2-((2-(trimethylsilyl)ethoxy)methyl)-4,5-dihydro-2H-pyrrolo[3,4-c]pyridine-6-carboxylate Example 4e (228 mg, 0.400 mmol) and tert-butyl nitrite (0.285 mL, 2.40 mmol) were combined in tetrahydrofuran (2 mL). The reaction mixture was stirred at ambient temperature for 30 minutes. To this reaction mixture was added ethanol (2 mL) and a solution of sodium bisulfite (416 mg, 4.00 mmol) in water (2 mL). The reaction mixture was stirred at ambient temperature for 1 hour. The reaction mixture was partitioned with ethyl acetate and water. The organic layer was washed with saturated aqueous sodium chloride, dried over anhydrous sodium sulfate, filtered, and concentrated. The residue was purified by flash chromatography (silica gel, 20-40% ethyl acetate in heptanes) to afford the title compound (175 mg, 79%).

Example 21b ethyl 1-[2-(2,4-difluorophenoxy)phenyl]-3-methyl-4-oxo-4,5-dihydro-2H-pyrrolo[3,4-c]pyridine-6-carboxylate Example 21a (172 mg, 0.310 mmol) was treated with 2,2,2-trifluoroacetic acid (2.0 mL, 26 mmol). The reaction mixture was stirred at ambient temperature for 30 minutes, concentrated, and dried under high vacuum. To this residue was added acetonitrile (6 mL) and a solution of sodium acetate (254 mg, 3.10 mmol) in water (2 mL). The reaction mixture was stirred at 50° C. for 3 hours. The reaction mixture was partitioned with ethyl acetate and water. The organic layer was washed with saturated aqueous sodium chloride, dried over anhydrous sodium sulfate, filtered, and concentrated. The residue was purified by flash chromatography (silica gel, 20-50% ethyl acetate in heptanes) to give a solid. The solid was triturated with 10% ethyl acetate/heptanes to afford the title compound (83 mg, 63%). $^1$H NMR (300 MHz, DMSO-$d_6$) δ 12.30 (s, 1 H) 9.39 (s, 1 H) 7.54 (dd, J=7.46, 1.70 Hz, 1 H) 7.40-7.51 (m, 1 H) 7.03-7.38 (m, 5 H) 6.84 (d, J=7.80 Hz, 1 H) 4.22 (q, J=7.12 Hz, 2 H) 2.65 (s, 3 H) 1.26 (t, J=7.12 Hz, 3 H). MS (ESI+) m/z 425 (M+H)$^+$.

Example 22

1-[2-(2,4-difluorophenoxy)phenyl]-3-methyl-4-oxo-4,5-dihydro-2H-pyrrolo[3,4-c]pyridine-6-carboxylic acid Example 21b (20 mg, 0.047 mmol) and lithium hydroxide (11.3 mg, 0.471 mmol were combined in the mixture of tetrahydrofuran (1 mL)/methanol (1 mL)/water (1 mL). The reaction mixture was heated at 80° C. for 1 hour, cooled to ambient temperature, diluted with water, and adjusted to pH 4 by addition of 1M HCl. The resulting solid was filtered, washed with water, and dried to afford the title compound (17 mg, 91%). $^1$H NMR (300 MHz, DMSO-$d_6$) δ 13.16 (s, 1 H) 12.23 (s, 1 H) 9.07 (s, 1 H) 7.54 (dd, J=7.46, 1.70 Hz, 1 H) 7.01-7.49 (m, 6 H) 6.86 (d, J=8.14 Hz, 1 H) 2.64 (s, 3 H). MS (ESI+) m/z 397 (M+H)$^+$.

Example 23

1-[2-(2,4-difluorophenoxy)phenyl]-3-methyl-4-oxo-4,5-dihydro-2H-pyrrolo[3,4-c]pyridine-6-carboxamide Example 22 (42.0 mg, 0.106 mmol), HATU (48.4 mg, 0.127 mmol) and N,N-diisopropylethylamine (0.093 mL, 0.53 mmol) were combined in dimethylformamide (1 mL). To this solution was added 0.5M ammonia in dioxane (0.848 mL, 0.424 mmol). The reaction mixture was stirred at ambient temperature for 1 hour. The reaction mixture was partitioned with ethyl acetate and water. The organic layer was washed with saturated aqueous sodium chloride twice, dried over anhydrous sodium sulfate, filtered, and concentrated. The residue was purified by flash chromatography (silica gel, 2-6% methanol in dichloromethane). The fractions were collected and concentrated to give a solid. The solid was triturated with 50% dichloromethane/heptanes to afford the title compound (17 mg, 41%). $^1$H NMR (300 MHz, DMSO-$d_6$) δ 12.12 (s, 1 H) 8.87 (s, 1 H) 8.03 (s, 1 H) 7.56 (dd, J=7.46, 2.03 Hz, 1 H) 7.19-7.48 (m, 6 H) 7.01-7.16 (m, 1 H) 6.84 (d, J=7.80 Hz, 1 H) 2.63 (s, 3 H). MS (ESI+) m/z 396 (M+H)$^+$.

Example 24 ethyl 1-[5-chloro-2-(2,4-difluorophenoxy)phenyl]-3-methyl-4-oxo-4,5-dihydro-2H-pyrrolo[3,4-c]pyridine-6-carboxylate Example 24a ethyl 1-(5-chloro-2-(2,4-difluorophenoxy)phenyl)-3-methyl-4-oxo-2-((2-(trimethylsilyl)ethoxy)methyl)-4,5-dihydro-2H-pyrrolo[3,4-c]pyridine-6-carboxylate A mixture of Example 4e (359 mg, 0.63 mmol) and copper (II) chloride (847 mg, 6.30 mmol) in dimethyl sulfoxide (10 mL) was stirred for 10 minutes, treated with tert-butyl nitrite (0.225 mL, 1.890 mmol) and heated at 50° C. for 1 hour. The mixture was partitioned with ethyl acetate and water. The organic layer was washed with saturated aqueous sodium chloride, dried with sodium sulfate, filtered and evaporated. Purification by chromatography (silica gel, 20-40% ethyl acetate in heptanes) afforded the title compound (0.238 g, 64%).

Example 24b ethyl 1-[5-chloro-2-(2,4-difluorophenoxy)phenyl]-3-methyl-4-oxo-4,5-dihydro-2H-pyrrolo[3,4-c]pyridine-6-carboxylate Example 24a (0.235 g, 0.399 mmol) was stirred in 2,2,2,-trifluoroacetic acid (3 mL for 30 minutes at ambient temperature, concentrated and azeotroped with toluene (3×10 mL). The resulting intermediate was re-dissolved in a mixture of tetrahydrofuran (6 mL) and water (2 mL), treated with sodium acetate (0.327 g, 3.99 mmol) and heated at 50° C. for 2 hours. The reaction mixture was cooled and partitioned between ethyl acetate and water. The organic layer was washed with saturated aqueous sodium chloride, dried (anhydrous sodium sulfate), filtered, and concentrated. Purification by chromatography (silica gel, 15-60% ethyl acetate in heptanes) afforded the title compound as a yellow powder (0.15 g, 82%). $^1$H NMR (300 MHz, DMSO-$d_6$) δ 12.40 (s, 1H), 9.47 (s, 1H), 7.59 (d, J=2.71 Hz, 1H), 7.45-7.53 (m, 1H), 7.33-7.38 (m, 2H), 7.21-7.30 (m, 1H), 7.08-7.16 (m, 1H), 6.86 (d, J=8.48 Hz, 1H), 4.22 (q, J=7.12 Hz, 2H), 2.65 (s, 3H) 1.25 (t, J=7.12 Hz, 3H). MS (ESI+) m/z 359 [M+H]$^+$.

Example 25

3-methyl-4-oxo-1-(2-phenoxyphenyl)-N-[2-(pyrrolidin-1-yl)ethyl]-4,5-dihydro-2H-pyrrolo[3,4-c]pyridine-6-carboxamide A stock solution of Example 12b and N,N-diisopropylethylamine (0.11 M and 0.35 M in N,N-dimethylacetamide, respectively, 329 μL, 0.039 mmol Example 12b and 0.11 mmol N,N-diisopropylethylamine), 2-(3H-[1,2,3]triazolo[4,5-b]pyridin-3-yl)-1,1,3,3-tetramethylisouronium hexafluorophosphate(V) (0.14 M in N,N-dimethylacetamide, 329 μL, 0.047 mmol), and 2-(1-pyrrolidinyl)ethanamine (0.40 M in N,N-dimethylacetamide, 115 μL, 0.047 mmol) were aspirated from their respective source vials, mixed through a perfluoroalkoxy mixing tube (0.2 mm inner diameter), and loaded into an injection loop. The reaction segment was injected into the flow reactor (Hastelloy coil, 0.75 mm inner diameter, 1.8 mL internal volume) set at 125° C., and passed through the reactor at 180 μL min$^{-1}$ (10 minute residence time). Upon exiting the reactor, the reaction mixture was loaded directly into an injection loop and purified by reverse phase HPLC (C8, acetonitrile/water (0.1% TFA), 5-100%) to yield the title compound as the TFA salt (0.0107 g, 49% yield). $^1$H NMR (400 MHz, DMSO-$d_6$/D$_2$O) δ 7.57 (dd, J=7.63, 1.83 Hz, 1H), 7.39 (td, J=7.78, 1.83 Hz, 1H), 7.28 (m, 3H), 7.20 (s, 1H), 7.04 (m, 2H), 6.89 (m, 2H), 3.60 (m, 4H), 3.33 (m, 3H), 3.10 (m, 1H), 2.61 (s, 3H), 2.00 (m, 4H). MS (APCI+) m/z 457.1 (M+H)$^+$.

Example 26

3-methyl-4-oxo-1-(2-phenoxyphenyl)-N-(thiazol-2-yl)-4,5-dihydro-2H-pyrrolo[3,4-c]pyridine-6-carboxamide Example 26 was prepared according to the procedure used for the preparation of Example 25 substituting 2-aminothiazole for 2-(1-pyrrolidinyl)ethanamine, to give 0.0065 g (30%) of the title compound as the TFA salt. $^1$H NMR (400 MHz, DMSO-$d_6$/D$_2$O) δ 7.68 (s, 1H), 7.63 (dd, J=7.63, 1.53 Hz, 1H), 7.49 (d, J=3.36 Hz, 1H), 7.41 (td, J=7.63, 1.83 Hz, 1H), 7.32 (td, J=7.48, 1.22 Hz, 1H), 7.26 (m, 2H), 7.18 (m, 1H), 7.06 (dd, J=8.09, 1.07 Hz, 1H), 7.00 (m, 1H), 6.90 (m, 2H), 2.62 (s, 3H). MS (APCI+) m/z 443.0 (M+H)$^+$.

Example 27

3-methyl-N-(2-morpholinoethyl)-4-oxo-1-(2-phenoxyphenyl)-4,5-dihydro-2H-pyrrolo[3,4-c]pyridine-6-carboxamide Example 27 was prepared according to the procedure used for the preparation of Example 25 substituting 2-morpholinoethanamine for 2-(1-pyrrolidinyl)ethanamine, to give 0.0148 g (66%) of the title compound as the TFA salt. $^1$H NMR (400 MHz, DMSO-$d_6$/$D_2$O) δ 7.57 (dd, J=7.48, 1.68 Hz, 1H), 7.39 (td, J=7.78, 1.83 Hz, 1H), 7.28 (m, 2H), 7.20 (s, 1H), 7.04 (m, 2H), 6.90 (m, 2H), 3.86 (m, 4H), 3.64 (t, J=6.10 Hz, 2H), 3.31 (m, 7H), 2.61 (s, 3H). MS (APCI+) m/z 473.1 (M+H)$^+$.

Example 28

3-methyl-4-oxo-1-(2-phenoxyphenyl)-N-(pyridin-4-yl)-4,5-dihydro-2H-pyrrolo[3,4-c]pyridine-6-carboxamide Example 28 was prepared according to the procedure used for the preparation of Example 25 substituting 4-aminopyridine for 2-(1-pyrrolidinyl)ethanamine, to give 0.0125 g (59%) of the title compound as the TFA salt. $^1$H NMR (400 MHz, DMSO-$d_6$/$D_2$O) δ 8.63 (d, J=3.97 Hz, 2H), 8.11 (d, J=7.02 Hz, 2H), 7.62 (m, 1H), 7.58 (s, 1H), 7.41 (td, J=7.71, 1.68 Hz, 1H), 7.32 (td, J=7.55, 1.07 Hz, 1H), 7.26 (m, 2H), 7.05 (dd, J=8.24, 0.92 Hz, 1H), 7.02 (m, 1H), 6.93 (m, 2H), 2.64 (s, 3H). MS (APCI+) m/z 437.1 (M+H)$^+$.

Example 29

N-(2-methoxyethyl)-3-methyl-4-oxo-1-(2-phenoxyphenyl)-4,5-dihydro-2H-pyrrolo[3,4-c]pyridine-6-carboxamide Example 29 was prepared according to the procedure used for the preparation of Example 25 substituting 2-methoxyethanamine for 2-(1-pyrrolidinyl)ethanamine, to give 0.0099 g (49%) of the title compound as the TFA salt. $^1$H NMR (400 MHz, DMSO-$d_6$/$D_2$O) δ 7.58 (dd, J=7.48, 1.68 Hz, 1 H), 7.37 (td, J=7.78, 1.83 Hz, 1 H), 7.28 (m, 4 H), 7.02 (m, 2 H), 6.91 (m, 2 H), 3.48 (m, 2 H), 3.41 (m, 2 H), 3.29 (s, 3 H), 2.60 (s, 3 H). MS (APCI+) m/z 418.1 (M+H)$^+$.

Example 30

6-(4-hydroxypiperidine-1-carbonyl)-3-methyl-1-(2-phenoxyphenyl)-2H-pyrrolo[3,4-c]pyridin-4(5H)-one Example 30 was prepared according to the procedure used for the preparation of Example 25 substituting piperidin-4-ol for 2-(1-pyrrolidinyl)ethanamine, to give 0.0119 g (56%) of the title compound as the TFA salt. $^1$H NMR (400 MHz, DMSO-$d_6$/$D_2$O) δ 7.53 (m, 1 H), 7.33 (m, 1 H), 7.27 (m, 3 H), 7.02 (m, 2 H), 6.87 (m, 2 H), 6.44 (s, 1 H), 3.76 (m, 2 H), 3.53 (m, 1 H), 3.20 (m, 2 H), 2.60 (s, 3 H), 1.75 (m, 2 H), 1.39 (m, 2 H). MS (APCI+) m/z 444.1 (M+H)$^+$.

Example 31

N-(furan-2-ylmethyl)-3-methyl-4-oxo-1-(2-phenoxyphenyl)-4,5-dihydro-2H-pyrrolo[3,4-c]pyridine-6-carboxamide Example 31 was prepared according to the procedure used for the preparation of Example 25 substituting furan-2-ylmethanamine for 2-(1-pyrrolidinyl)ethanamine, to give 0.0121 g (57%) of the title compound as the TFA salt. $^1$H NMR (400 MHz, DMSO-$d_6$/$D_2$O) δ 7.57 (dd, J=7.63, 1.83 Hz, 1 H), 7.50 (dd, J=1.83, 0.92 Hz, 1 H), 7.37 (td, J=7.78, 1.83 Hz, 1 H), 7.27 (m, 4 H), 7.02 (m, 2 H), 6.89 (m, 2 H), 6.39 (dd, J=3.36, 1.83 Hz, 1 H), 6.27 (dd, J=3.20, 0.76 Hz, 1 H), 4.44 (s, 2 H), 2.60 (s, 3 H). MS (APCI+) m/z 440.1 (M+H)$^+$.

Example 32

1-[5-chloro-2-(2,4-difluorophenoxy)phenyl]-3-methyl-4-oxo-4,5-dihydro-2H-pyrrolo[3,4-c]pyridine-6-carboxamide

Example 32a 1-(5-chloro-2-(2,4-difluorophenoxy)phenyl)-3-methyl-4-oxo-4,5-dihydro-2H-pyrrolo[3,4-c]pyridine-6-carboxylic acid A mixture of Example 24b (0.14 g, 0.305 mmol) and lithium hydroxide (0.073 g, 3.05 mmol) in tetrahydrofuran/methanol/water (2 mL each) was stirred at 80° C. for 2 hours. The mixture was cooled, diluted with water and brought to pH 4 with 1M HCl producing a yellow solid that was collected by filtration, washed with water and dried to constant mass (0.10 g, 76%).

Example 32b

1-[5-chloro-2-(2,4-difluorophenoxy)phenyl]-3-methyl-4-oxo-4,5-dihydro-2H-pyrrolo[3,4-c]pyridine-6-carboxamide A mixture of Example 32a (0.07 g, 0.162 mmol), 2-(3H-[1,2,3]triazolo[4,5-b]pyridin-3-yl)-1,1,3,3-tetramethylisouronium hexafluorophosphate(V) (0.074 g, 0.195 mmol), N-ethyl-N-isopropylpropan-2-amine (0.142 mL, 0.812 mmol) and 0.5 M ammonia (1.625 mL, 0.812 mmol) in dimethylformamide (1 mL) was stirred at ambient temperature for two hours. The mixture was partitioned between ethyl acetate and water. The organic layer was washed with saturated aqueous sodium chloride, dried (anhydrous sodium sulfate), filtered and concentrated. Purification by reverse phase chromatography (C18, CH$_3$CN/10 mM ammonium acetate in water, 10-100% gradient) afforded the title compound (0.022 mg, 31%). $^1$H NMR (400 MHz, DMSO-$d_6$) δ 12.23 (s, 1H), 8.95 (s, 1H), 8.07 (s, 1H), 7.56 (d, J=2.44 Hz, 1H), 7.40-7.52 (m, 2H), 7.26-7.39 (m, 3H), 7.06-7.15 (m, 1H), 6.87 (d, J=8.85 Hz, 1H), 2.63 (s, 3H). MS (APCI+) m/z 430 [M+H]$^+$.

Example 33 ethyl 1-[2-(2,4-difluorophenoxy)-5-nitrophenyl]-3-methyl-4-oxo-4,5-dihydro-2H-pyrrolo[3,4-c]pyridine-6-carboxylate Example 33 was prepared according to the procedure used for the preparation of Example 15b substituting Example 4d for Example 15a and stirring with 2,2,2-trifluoroacetic acid for one hour instead of 35 minutes. Purification by flash chromatography (silica gel, 0-4% methanol in dichloromethane) gave 0.037 g (95%) of the title compound. $^1$H NMR (300 MHz, DMSO-$d_6$) δ 12.59 (s, 1H), 9.57 (s, 1H), 8.40 (d, J=2.71 Hz, 1H), 8.15 (dd, J=9.16, 3.05 Hz, 1H), 7.61 (ddd, J=11.27, 8.73, 3.05 Hz, 1H), 7.51 (td, J=9.16, 5.76 Hz, 1H), 7.37 (d, J=1.70 Hz, 1H), 7.25 (m, 1H), 6.97 (dd, J=9.16, 1.02 Hz, 1H), 4.22 (q, J=7.12 Hz, 2H), 2.69 (s, 3H), 1.25 (t, J=7.12 Hz, 3H). MS (ESI+) m/z 469.9 (M+H)+.

Example 34

1-[2-(2,4-difluorophenoxy)-5-(trifluoromethyl)phenyl]-N,3-dimethyl-4-oxo-4,5-dihydro-2H-pyrrolo[3,4-c]pyridine-6-carboxamide Example 34a 2-bromo-1-(2,4-difluorophenoxy)-4-(trifluoromethyl)benzene A mixture of 3-bromo-4-fluorobenzotrifluoride (0.5 mL, 3.52 mmol), 2,4-difluorophenol (0.337 mL, 3.52 mmol), and potassium carbonate (0.486 g, 3.52 mmol) in dimethylformamide (7 mL) was heated at 80° C. overnight. The reaction mixture was cooled to ambient temperature and partitioned between ethyl acetate and water. The layers were separated, and the aqueous layer was extracted with ethyl acetate. The combined organics were washed with water and saturated aqueous sodium chloride, dried over anhydrous sodium sulfate, filtered, and concentrated by rotary evaporation. The crude material was purified by flash chromatography (ethyl acetate/hexanes) to provide the title compound (1.0 g, 80% yield).

Example 34b (2-(2,4-difluorophenoxy)-5-(trifluoromethyl)phenyl)boronic acid

To a suspension of magnesium (0.083 g, 3.42 mmol) in tetrahydrofuran (1.000 mL) was added 0.5 mL of a solution of example 34a (1.099 g, 3.11 mmol) in tetrahydrofuran (1.5 mL). The reaction mixture was warmed (about 40-50° C.) until reaction commenced. The remaining solution of starting bromide was added dropwise. The reaction mixture was stirred at ambient temperature for 1 hour. The resulting Grignard solution was added dropwise to a solution of trimethyl borate (0.696 mL, 6.23 mmol) in tetrahydrofuran (1.5 mL) at 0° C. The reaction mixture was stirred at ambient temperature. After 1 hour at ambient temperature, the reaction mixture was quenched with ice water and then neutralized with 2 M HCl. The mixture was extracted with ethyl acetate (3×). The combined organics were washed with saturated aqueous sodium chloride, dried over anhydrous sodium sulfate, filtered, and concentrated. The crude material was purified by flash chromatography (silica gel, 10-33% ethyl acetate/hexanes) to provide the title compound (0.650 g, 65.7% yield).

Example 34c ethyl 1-(2-(2,4-difluorophenoxy)-5-(trifluoromethyl) phenyl)-3-methyl-4-oxo-2-((2-(trimethylsilyl) ethoxy)methyl)-4,5-dihydro-2H-pyrrolo[3,4-c]pyridine-6-carboxylate Nitrogen was bubbled through a 4:1 DME/ethanol solution for 20 minutes. A microwave vial was charged with Example 4b (0.05 g, 0.116 mmol), Example 34b (0.041 g, 0.128 mmol), Pd(PPh3)4 (6.73 mg, 5.82 µmol), and CsF (0.053 g, 0.349 mmol). The vial was sealed and flushed with nitrogen. The 4:1 DME/ethanol (0.5 mL) was added. The reaction mixture was heated in a microwave reactor at 120° C. for 40 minutes. The reaction mixture was partitioned between water and ethyl acetate. The layers were separated. The aqueous layer was extracted with ethyl acetate (2×). The combined organics were dried over sodium sulfate, filtered, and concentrated. The crude material was purified by flash chromatography (silica gel, 10-50% ethyl acetate in hexanes) to give the title compound (0.039 g, 53.8% yield).

Example 34d 1-(2-(2,4-difluorophenoxy)-5-(trifluoromethyl)phenyl)-N,3-dimethyl-4-oxo-2-((2-(trimethylsilyl) ethoxy)methyl)-4,5-dihydro-2H-pyrrolo[3,4-c]pyridine-6-carboxamide To a high pressure glass tube charged with Example 34c (0.023 g, 0.037 mmol) was added methylamine (1.380 mL, 11.08 mmol) (33 wt % in ethanol). The reaction vessel was sealed and heated at 80° C. overnight. The reaction mixture was concentrated to give the title compound (0.020 g, 89% yield).

Example 34e

1-[2-(2,4-difluorophenoxy)-5-(trifluoromethyl)phenyl]-N,3-dimethyl-4-oxo-4,5-dihydro-2H-pyrrolo[3,4-c]pyridine-6-carboxamide To a solution of Example 34d (0.023 g, 0.038 mmol) in dichloromethane was added TFA (0.5 mL, 6.49 mmol). The reaction mixture was stirred at ambient temperature for 1 hour and then concentrated by rotary evaporation. The residue was concentrated down from toluene (2×), then taken up in methanol/tetrahydrofuran. Sodium acetate (0.124 g, 1.514 mmol) was added, and the reaction mixture was heated at reflux for 2 hours. The reaction mixture was concentrated by rotary evaporation. The residue was partitioned between ethyl acetate and water. The layers were separated, and the organic layer was dried over anhydrous sodium sulfate, filtered, and concentrated. The crude material was purified by flash chromatography (silica gel, 20-80% ethyl acetate in hexanes) to give the title compound (0.004 g, 22% yield). $^1$H NMR (300 MHz, DMSO-$d_6$) δ 12.20-12.46 (m, 1 H), 9.06 (s, 1 H), 8.41-8.52 (m, 1H), 7.82 (d, J=2.03 Hz, 1 H), 7.66 (dd, J=8.82, 1.70 Hz, 1 H), 7.44-7.54 (m, 2 H), 7.15-7.23 (m, 2 H), 6.99 (d, J=8.48 Hz, 1 H), 2.74 (d, J=4.41 Hz, 3 H), 2.65 (s, 3H). MS (ESI+) m/z 478.0)+.

Example 35

3-methyl-N-(1-methylpiperidin-4-yl)-4-oxo-1-(2-phenoxyphenyl)-4,5-dihydro-2H-pyrrolo[3,4-c]pyridine-6-carboxamide A stock solution of Example 12b and N,N-diisopropylethylamine (0.12 M and 0.36 M in N,N-dimethylacetamide, respectively, 350 µL, 0.042 mmol Example 12b and 0.12 mmol N,N-diisopropylethylamine), 2-(3H-[1,2,3]triazolo[4,5-b]pyridin-3-yl)-1,1,3,3-tetramethylisouronium hexafluorophosphate(V) (0.14 M in N,N-dimethylacetamide, 350 µL, 0.050 mmol), and 4-amino-N-methylpiperidine (0.40 M in N,N-dimethylacetamide, 125 µL, 0.050 mmol) were aspirated from their respective source vials, mixed through a perfluoroalkoxy mixing tube (0.2 mm inner diameter), and loaded into an injection loop. The reaction segment was injected into the flow reactor (Hastelloy coil, 0.75 mm inner diameter, 1.8 mL internal volume) set at 125° C., and passed through the reactor at 180 µL min$^{-1}$ (10 minute residence time). Upon exiting the reactor, the reaction mixture was loaded directly into an injection loop and purified by reverse phase HPLC (C8, acetonitrile/water (0.1% TFA), 5-100%) to yield the title compound as the TFA salt (19.1 mg, 80% yield). $^1$H NMR (500 MHz, DMSO-$d_6$/D$_2$O) δ 7.57 (dd, J=7.63, 1.83 Hz, 1 H), 7.39 (td, J=7.86, 1.68 Hz, 1 H), 7.32 (m, 4 H), 7.09 (t, J=7.48 Hz, 1 H), 6.99 (t, J=8.24 Hz, 3 H), 3.97 (m, J=11.67, 11.67, 4.12, 3.97 Hz, 1 H), 3.47 (d, J=12.51 Hz, 2 H), 3.09 (m, 2 H), 2.79 (s, 3 H), 2.61 (s, 3 H), 2.02 (d, J=14.04 Hz, 2 H), 1.75 (m, 2 H). MS (APCI+) m/z 457.1 (M+H)$^+$.

Example 36

3-methyl-4-oxo-1-(2-phenoxyphenyl)-N-(tetrahydrofuran-3-ylmethyl)-4,5-dihydro-2H-pyrrolo[3,4-c]pyridine-6-carboxamide Example 36 was prepared according to the procedure used for the preparation of Example 35, substituting (tetrahydrofuran-3-yl)methanamine for 4-amino-N-methylpiperidine, to give 0.0176 g (76%) of the title compound as the TFA salt. $^1$H NMR (500 MHz, DMSO-$d_6$/D$_2$O) δ 7.58 (dd, J=7.63, 1.53 Hz, 1 H), 7.39 (td, J=7.78, 1.83 Hz, 1 H), 7.31 (m, 4 H), 7.07 (t, J=7.32 Hz, 1 H), 7.00 (dd, J=8.24, 0.92 Hz, 1 H), 6.96 (m, J=7.63 Hz, 2 H), 3.67 (dd, J=8.54, 7.02 Hz, 1 H), 3.63 (m, 1 H), 3.45 (dd, J=8.70, 5.34 Hz, 1 H), 3.22 (m, J=23.19, 13.58, 8.09 Hz, 2 H), 2.61 (s, 3 H), 2.53 (m, 1 H), 2.46 (m, 1 H), 1.93 (m, 1 H), 1.58 (m, 1 H). MS (APCI+) m/z 444.1 (M+H)$^+$.

Example 37

3-methyl-4-oxo-1-(2-phenoxyphenyl)-N-(tetrahydrofuran-3-yl)-4,5-dihydro-2H-pyrrolo[3,4-c]pyridine-6-carboxamide Example 37 was prepared according to the procedure used for the preparation of Example 35, substituting tetrahydrofuran-3-amine for 4-amino-N-methylpiperidine, to give 0.0186 g (82%) of the title compound as the TFA salt. $^1$H NMR (500 MHz, DMSO-$d_6$/D$_2$O) δ 7.58 (dd, J=7.63, 1.83 Hz, 1H), 7.38 (m, 2H), 7.30 (m, 3H), 7.08 (t, J=7.48 Hz, 1H), 6.98 (m, 3H), 4.42 (m, 1H), 3.85 (m, 2H), 3.71 (m, 1H), 3.57 (dd, J=9.00, 4.12 Hz, 1H), 2.61 (s, 3H), 2.17 (m, 1H), 1.89 (m, 1H). MS (APCI+) m/z 430.1 (M+H)$^+$.

Example 38

3-methyl-4-oxo-1-(2-phenoxyphenyl)-N-(tetrahydro-2H-pyran-4-yl)-4,5-dihydro-2H-pyrrolo[3,4-c]pyridine-6-carboxamide Example 38 was prepared according to the procedure used for the preparation of Example 35, substituting tetrahydro-2H-pyran-4-amine for 4-amino-N-methylpiperidine, to give 0.0148 g (64%) of the title compound as the TFA salt. $^1$H NMR (500 MHz, DMSO-$d_6$/D$_2$O) δ 7.58 (dd, J=7.63, 1.83 Hz, 1 H), 7.38 (td, J=7.78, 1.83 Hz, 1 H), 7.36 (s, 1 H), 7.32 (m, 3 H), 7.09 (t, J=7.48 Hz, 1 H), 6.99 (d, J=7.63 Hz, 3 H), 3.94 (m, 1 H), 3.89 (m, 2 H), 3.37 (m, 2 H), 2.61 (s, 3 H), 1.73 (dd, J=12.51, 2.44 Hz, 2 H), 1.56 (m, 2 H). MS (APCI+) m/z 444.1 (M+H)$^+$.

Example 39 ethyl 1-[2-(2,4-difluorophenoxy)-5-(methylsulfonyl)phenyl]-3-methyl-4-oxo-4,5-dihydro-2H-pyrrolo[3,4-c]pyridine-6-carboxylate Example 39a ethyl 1-(2-fluoro-5-(methylsulfonyl)phenyl)-3-methyl-4-oxo-2-((2-(trimethylsilyl)ethoxy)methyl)-4,5-dihydro-2H-pyrrolo[3,4-c]pyridine-6-carboxylate Example 81a (0.734 g, 2.445 mmol), Example 4b (0.7 g, 1.630 mmol), tris(dibenzylideneacetone)dipalladium(0) (0.045 g, 0.049 mmol), 1,3,5,7-tetramethyl-6-phenyl-2,4,8-trioxa-6-phosphaadamantane (0.048 g, 0.163 mmol) and sodium carbonate (0.691 g, 6.52 mmol) were combined and sparged with argon for 15 minutes. Meanwhile a solution of 4:1 dioxane/water (0.8 mL) was sparged with nitrogen for 15 minutes and transferred by syringe into the reaction vessel under argon. The mixture was stirred at 60° C. for 4 hours and partitioned between ethyl acetate and water. The organic layer was washed with saturated aqueous sodium chloride, dried (anhydrous sodium sulfate), treated with 3-mercaptopropyl functionalized silica gel, filtered and concentrated. Purification by chromatography (silica gel, 0-3% methanol in dichloromethane) afforded the title compound (0.23 g, 27%).

Example 39b ethyl 1-(2-(2,4-difluorophenoxy)-5-(methylsulfonyl)phenyl)-3-methyl-4-oxo-2-((2-(trimethylsilyl)ethoxy)methyl)-4,5-dihydro-2H-pyrrolo[3,4-c]pyridine-6-carboxylate Example 39a (0.23 g, 0.440 mmol), 2,4-difluorophenol (0.172 g, 1.320 mmol) and cesium carbonate (0.358 g, 1.100 mmol) were combined in dimethyl sulfoxide (4.40 mL) under argon and heated at 95° C. for 30 minutes, cooled and partitioned between ethyl acetate and water, adjusting the pH to 7 with 1M HCl. The organic layer was washed with saturated aqueous sodium chloride, dried (anhydrous sodium sulfate) filtered, and concentrated. Purification by chromatography (silica gel, 0-60% ethyl acetate in heptanes) afforded the title compound (0.24 g, 86%).

Example 39c ethyl 1-[2-(2,4-difluorophenoxy)-5-(methylsulfonyl)phenyl]-3-methyl-4-oxo-4,5-dihydro-2H-pyrrolo[3,4-c]pyridine-6-carboxylate Example 39b (0.24 g, 0.379 mmol) was stirred in TFA (3 mL) for 60 minutes at ambient temperature, concentrated, and azeotroped with toluene (3×10 mL). The residue was re-dissolved in a mixture of tetrahydrofuran (6 mL) and water (2 mL), treated with sodium acetate (0.311 g, 3.79 mmol), and heated at 50° C. for 2 hours. The reaction mixture was cooled and partitioned between ethyl acetate and water. The organic layer was washed with saturated aqueous sodium chloride, dried (anhydrous sodium sulfate), filtered, and concentrated. Purification by chromatography (silica gel, 0.5-3.5% methanol in dichloromethane) afforded the title compound as a yellow powder (0.15 g, 79%). $^1$H NMR (400 MHz, DMSO-$d_6$) δ 12.55 (s, 1H), 9.55 (s, 1H), 8.06 (d, J=2.44 Hz, 1H), 7.81 (dd, J=8.85, 2.44 Hz, 1H), 7.55-7.63 (m, 1H), 7.41-7.50 (m, 1H), 7.36 (d, J=1.22 Hz, 1H), 7.16-7.27 (m, 1H), 6.98 (d, J=8.85 Hz, 1H), 4.22 (q, J=7.22 Hz, 2H), 3.26 (s, 3H), 2.70 (s, 3H), 1.25 (t, J=7.02 Hz, 3H). MS (ESI+) m/z 503 [M+H]$^+$.

Example 40

1-[2-(2,4-difluorophenoxy)-5-(methylsulfonyl)phenyl]-3-methyl-4-oxo-4,5-dihydro-2H-pyrrolo[3,4-c]pyridine-6-carboxylic acid Example 39c (0.14 g, 0.279 mmol) and lithium hydroxide (0.067 g, 2.79 mmol) were combined in methanol (2 mL), tetrahydrofuran (2 mL) and water (2 mL) and heated at 80° C. for 2 hours. The mixture was cooled, concentrated, and the residue was partitioned between ethyl acetate and water, carefully adjusting the pH to 2 with 1M HCl. The organic layer was washed with saturated aqueous sodium chloride, dried (anhydrous sodium sulfate), filtered, and concentrated to afford the title compound (0.13 g, 98%). $^1$H NMR (300 MHz, DMSO-$d_6$) δ 13.19 (s, 1H), 12.47 (s, 1H), 9.22 (s, 1H), 8.04 (d, J=2.37 Hz, 1H), 7.81 (dd, J=8.82, 2.37 Hz, 1H), 7.49-7.61 (m, 1H), 7.37-7.47 (m, 1H), 7.28 (d, J=1.36 Hz, 1H), 7.15-7.25 (m, 1H), 6.99 (d, J=8.82 Hz, 1H), 3.25 (s, 3H), 2.69 (s, 3H). MS (ESI+) m/z 475 [M+H]$^+$.

Example 41

N,N,3-trimethyl-4-oxo-1-(2-phenoxyphenyl)-4,5-dihydro-2H-pyrrolo[3,4-c]pyridine-6-carboxamide Example 41 was prepared according to the procedure used for the preparation of Example 16a, substituting Example 12b for Example 12a and dimethylamine (2 M solution in tetrahydrofuran) for 1-methylpiperazine. Purification by flash chromatography (silica gel, 0-8% methanol in dichloromethane) gave 0.029 g (88%) of the title compound. $^1$H NMR (300 MHz, DMSO-$d_6$) δ 12.01 (s, 1H), 9.87 (s, 1H), 7.53 (dd, J=7.29, 1.86 Hz, 1H), 7.30 (m, 4H), 7.03 (m, 2H), 6.89 (m, 2H), 6.42 (d, J=1.70 Hz, 1H), 2.91 (s, 6H), 2.59 (s, 3H). MS (ESI+) m/z 388.0 (M+H)$^+$.

Example 42

1-[2-(2,4-difluorophenoxy)-5-(methylsulfonyl)phenyl]-3-methyl-4-oxo-4,5-dihydro-2H-pyrrolo[3,4-c]pyridine-6-carboxamide A mixture of Example 40 (0.05 g, 0.105 mmol), 2-(3H-[1,2,3]triazolo[4,5-b]pyridin-3-yl)-1,1,3,3-tetramethylisouronium hexafluorophosphate(V) (0.048 g, 0.126 mmol), N-ethyl-N-isopropylpropan-2-amine (0.092 mL, 0.527 mmol) and 0.5 M ammonia (1.054 mL, 0.527 mmol) in dimethylformamide (1 mL) was stirred at ambient temperature for 4 hours. The mixture was partitioned between ethyl acetate and water. The organic layer was washed with saturated aqueous sodium chloride, dried (anhydrous sodium sulfate), filtered, and concentrated. Purification by reverse phase chromatography (C18, CH$_3$CN/10 mM ammonium acetate in water, 10-100% gradient) afforded the title compound (0.011 mg, 22%). $^1$H NMR (300 MHz, DMSO-$d_6$) δ 8.96-9.08 (m, 1H), 8.00 (d, J=2.37 Hz, 1H), 7.96-7.99 (m, 1H), 7.82 (dd, J=8.48, 2.37 Hz, 1H), 7.44-7.63 (m, 3H), 7.28 (s, 1H), 7.18-7.27 (m, 1H), 6.99 (d, J=7.46 Hz, 1H), 3.26 (s, 3H), 2.67 (s, 3H). MS (ESI+) m/z 474 [M+H]$^+$.

Example 43

1-[5-amino-2-(2,4-difluorophenoxy)phenyl]-3-methyl-4-oxo-N-propyl-4,5-dihydro-2H-pyrrolo[3,4-c]pyridine-6-carboxamide Example 43a 1-(5-amino-2-(2,4-difluorophenoxy)phenyl)-3-methyl-4-oxo-N-propyl-2-((2-(trimethylsilyl)ethoxy)methyl)-4,5-dihydro-2H-pyrrolo[3,4-c]pyridine-6-carboxamide A mixture of Example 4e (0.05 g, 0.088 mmol) and propan-1-amine (1 mL, 12.16 mmol) in methanol (0.5 mL) in a sealed tube was heated by microwave at 120° C. for 2 hours, cooled and concentrated to afford the title compound (0.05 g, 98%). The product was used without purification.

Example 43b

1-[5-amino-2-(2,4-difluorophenoxy)phenyl]-3-methyl-4-oxo-N-propyl-4,5-dihydro-2H-pyrrolo[3,4-c]pyridine-6-carboxamide Example 43a (0.05 g, 0.086 mmol) was stirred in TFA (3 mL) for 60 minutes at ambient temperature, concentrated, and azeotroped with toluene (3×10 mL). The resulting intermediate was re-dissolved in a mixture of tetrahydrofuran (6 mL) and water (2 mL), treated with sodium acetate (0.070 g, 0.858 mmol) and heated at 50° C. for 3 hours. The reaction mixture was cooled and partitioned between ethyl acetate and water. The organic layer was washed with saturated aqueous sodium chloride, dried (anhydrous sodium sulfate), filtered, and concentrated. Purification by reverse phase chromatography (C18, CH$_3$CN/0.1% TFA in water, 10-100% gradient) afforded the title compound as the TFA salt (0.028 g, 58%). $^1$H NMR (300 MHz, DMSO-$d_6$) δ 12.10 (s, 1H), 8.99 (s, 1H), 8.47 (t, J=5.76 Hz, 1H), 7.24-7.36 (m, 1H), 7.20 (d, J=1.36 Hz, 1H), 6.66-7.05 (m, 6H), 3.07-3.22 (m, 2H), 2.58 (s, 3H), 1.41-1.59 (m, 2H), 0.88 (t, J=7.46 Hz, 3H). MS (ESI+) m/z 453 [M+H]$^+$.

Example 44

6-(methoxymethyl)-3-methyl-1-(2-phenoxyphenyl)-2,5-dihydro-4H-pyrrolo[3,4-c]pyridin-4-one Example 44a ethyl 4-methoxy-3-methyl-1-(2-phenoxyphenyl)-2-((2-(trimethylsilyl)ethoxy)methyl)-2H-pyrrolo[3,4-c]pyridine-6-carboxylate Example 12a (1 g, 1.93 mmol) was dissolved in 1,2-dichloroethane (12 mL), treated sequentially with silver carbonate (1.6 g, 5.78 mmol) and iodomethane (1.2 mL, 19.3 mmol), and heated at 50° C. overnight. Additional silver carbonate (0.532 g, 1.93 mmol) and iodomethane (1.2 mL, 19.3 mmol) were added and heating was continued at 55° C. for 8 hours and then at ambient temperature overnight. The reaction mixture was filtered through a pad of Celite rinsing with dichloromethane. The filtrate was concentrated. The residue was purified by flash chromatography (silica gel, 0-50% ethyl acetate in heptanes) to give 0.864 g (84%) of the title compound.

Example 44b (4-methoxy-3-methyl-1-(2-phenoxyphenyl)-2-((2-(trimethylsilyl)ethoxy)methyl)-2H-pyrrolo[3,4-c]pyridin-6-yl)methanol Example 44a (0.86 g, 1.614 mmol) in tetrahydrofuran (16.1 mL) was treated with lithium tetrahydroborate (0.176 g, 8.07 mmol) and heated at 55° C. for 4.5 hours. Additional lithium tetrahydroborate (0.106 g, 4.84 mmol) was added and heating was continued for another 3.75 hours. The reaction mixture was cooled to ambient temperature, quenched with methanol and water, and partitioned between ethyl acetate and water. The organic layer was washed with saturated aqueous sodium chloride, dried over anhydrous magnesium sulfate, filtered, and concentrated. The residue was purified by flash chromatography (silica gel, 10-80% ethyl acetate in heptanes) to give 0.555 g (70%) of the title compound.

Example 44c 4-methoxy-6-(methoxymethyl)-3-methyl-1-(2-phenoxyphenyl)-2-((2-(trimethylsilyl)ethoxy)methyl)-2H-pyrrolo[3,4-c]pyridine Example 44b (0.097 g, 0.2 mmol) in tetrahydrofuran (2 mL) was treated with sodium hydride (60% oil dispersion, 0.012 g, 0.3 mmol) and stirred at ambient temperature for 10 minutes. Iodomethane (0.037 mL, 0.6 mmol) was added and the resulting mixture was stirred at ambient temperature for 3 hours. The reaction mixture was quenched with saturated aqueous ammonium chloride solution and then partitioned between ethyl acetate and water. The organic layer was washed with saturated aqueous sodium chloride, dried over anhydrous magnesium sulfate, filtered, and concentrated. The residue was purified by flash chromatography (silica gel, 0-12% ethyl acetate in heptanes) to provide 0.09 g (91%) of the title compound.

Example 44d 6-(methoxymethyl)-3-methyl-1-(2-phenoxyphenyl)-2-((2-(trimethylsilyl)ethoxy)methyl)-2H-pyrrolo[3,4-c]pyridin-4(5H)-one A mixture of Example 44c (0.0816 g, 0.162 mmol) and lithium iodide (0.65 g, 4.85 mmol) in pyridine (1 mL) was heated at 160° C. for 1 hour in a Biotage microwave reactor. The reaction mixture was partitioned between ethyl acetate and water, washed with saturated aqueous sodium chloride, dried over anhydrous magnesium sulfate, filtered and concentrated. The residue was purified by flash chromatography (silica gel, 20-80% ethyl acetate in heptanes) to provide 0.034 g (43%) of the title compound.

Example 44e 6-(methoxymethyl)-3-methyl-1-(2-phenoxyphenyl)-2H-pyrrolo[3,4-c]pyridin-4(5H)-one Example 44d (0.033 g, 0.067 mmol) was treated with neat 2,2,2-trifluoroacetic acid (1 mL, 0.067 mmol), stirred for 1 hour at ambient temperature and concentrated to dryness. The residue in a mixture of acetonitrile (1.5 mL) and water (0.5 mL) was treated with sodium acetate (0.137 g, 1.68 mmol) and heated at 60° C. overnight. Additional sodium acetate (0.137 g, 1.68 mmol) was added and heating was continued for another 4 hours. The reaction mixture was cooled to ambient temperature, partitioned between ethyl acetate and water, washed with saturated aqueous sodium chloride, dried over anhydrous magnesium sulfate, filtered and concentrated. The residue was purified by reverse phase HPLC (C18, acetonitrile/water (0.1% TFA), 10-80%) to give the title compound as an impure mixture. The material was further purified by flash chromatography (silica gel, 0-4% methanol in dichloromethane) to provide 0.0064 g (27%) of the title compound. $^1$H NMR (400 MHz, DMSO-$d_6$) δ 11.81 (s, 1H), 9.82 (s, 1H), 7.51 (dd, J=7.32, 1.83 Hz, 1H), 7.27 (m, 4H), 7.01 (m, 2H), 6.89 (d, J=8.24 Hz, 2H), 6.31 (s, 1H), 4.07 (s, 2H), 3.18 (s, 3H), 2.57 (s, 3H). MS (ESI+) m/z 462.1 (M+H)$^+$.

Example 45

3-methyl-1-(2-phenoxyphenyl)-6-(3-(pyridin-4-yl)-1,2,4-oxadiazol-5-yl)-2H-pyrrolo[3,4-c]pyridin-4(5H)-one Example 45 was prepared according to the procedure used for the preparation of Example 46, substituting (Z)—N'-hydroxyisonicotinimidamide for (Z)—N'-hydroxybenzimidamide. Purification by reverse phase HPLC (C8, acetonitrile/water (0.1% ammonium acetate), 45-75%) gave 0.0012 g (10%) of the title compound as the acetic acid salt. $^1$H NMR (400 MHz, DMSO-$d_6$/$D_2O$) δ 12.42 (s, 1H), 10.39 (s, 1H), 8.85 (m, 2H), 8.01 (m, 2H), 7.63 (dd, J=7.63, 1.53 Hz, 1H), 7.57 (s, 1H), 7.42 (td, J=7.78, 1.83 Hz, 1H), 7.33 (m, 3H), 7.07 (m, 2H), 6.95 (m, 2H), 2.65 (s, 3H). MS (ESI+) m/z 462.1 (M+H)$^+$.

Example 46

3-methyl-1-(2-phenoxyphenyl)-6-(3-phenyl-1,2,4-oxadiazol-5-yl)-2H-pyrrolo[3,4-c]pyridin-4(5H)-one A solution of Example 12b (500 µL, 0.005 g, 0.0139 mmol) in N,N-dimethylformamide and a solution of 1,1'-carbonyldiimidazole (500 µL, 0.0113 g, 0.069 mmol) in N,N-dimethylformamide were combined and shaken for 1 hour at ambient temperature. A solution of (Z)—N'-hydroxybenzimidamide (69.4 µL, 0.042 mmol) in N,N-dimethylformamide was added and the resulting mixture was reacted in an Anton Paar Synthos 3000 microwave optimizer at 180° C. for 45 minutes. Upon completion, the crude material was concentrated to dryness and purified by reverse phase HPLC (C8, acetonitrile/water (0.1% ammonium acetate), 25-55%) to yield 0.0027 g (37%) of the title compound as the acetic acid salt. $^1$H NMR (400 MHz, DMSO-$d_6$/$D_2O$) δ 12.39 (s, 1 H), 10.30 (s, 1 H), 8.09 (m, 2 H), 7.61 (m, 4 H), 7.54 (m, 1 H), 7.41 (m, 1 H), 7.33 (m, 3 H), 7.07 (m, 2 H), 6.95 (d, J=7.93 Hz, 2 H), 2.65 (s, 3 H). MS (ESI+) m/z 461.1 (M+H)$^+$.

Example 47

3-methyl-1-(2-phenoxyphenyl)-6-(3-propyl-1,2,4-oxadiazol-5-yl)-2H-pyrrolo[3,4-c]pyridin-4(5H)-one Example 47 was prepared according to the procedure used for the preparation of Example 46, substituting (Z)—N'-hydroxybutyrimidamide for (Z)—N'-hydroxybenzimidamide. Purification by reverse phase HPLC (C8, acetonitrile/water (0.1% ammonium acetate), 45-75%) gave 0.0029 g (43%) of the title compound as the acetic acid salt. $^1$H NMR (400 MHz, DMSO-$d_6$/$D_2O$) δ 12.36 (s, 1 H), 10.11 (s, 1 H), 7.61 (dd, J=7.63, 1.53 Hz, 1 H), 7.42 (s, 1 H), 7.39 (dd, J=7.78, 1.68 Hz, 1 H), 7.32 (m, 3 H), 7.06 (m, 2 H), 6.89 (m, 2 H), 2.72 (t, J=7.32 Hz, 2 H), 2.62 (s, 3 H), 1.74 (m, 2 H), 0.96 (t, J=7.32 Hz, 3 H). MS (ESI+) m/z 427.1 (M+H)+.

Example 48 ethyl 1-[2-(cyclohexyloxy)-5-fluorophenyl]-3-methyl-4-oxo-4,5-dihydro-2H-pyrrolo[3,4-c]pyridine-6-carboxylate Example 48a ethyl 1-(2-(cyclohexyloxy)-5-fluorophenyl)-3-methyl-4-oxo-2-((2-(trimethylsilyl)ethoxy)methyl)-4,5-dihydro-2H-pyrrolo[3,4-c]pyridine-6-carboxylate Example 48a was prepared according to the procedure used for the preparation of Example 34c, substituting 2-(cyclohexyloxy)-5-fluorophenylboronic acid (0.10 g, 0.233 mmol) for Example 34b. The crude material was purified by flash chromatography (silica gel, 10-50% ethyl acetate in hexanes) to give the title compound (0.022 g, 17% yield).

Example 48b ethyl 1-[2-(cyclohexyloxy)-5-fluorophenyl]-3-methyl-4-oxo-4,5-dihydro-2H-pyrrolo[3,4-c]pyridine-6-carboxylate To a solution of Example 48a (0.020 g, 0.037 mmol) in dichloromethane was added TFA (2.84 µL, 0.037 mmol). The reaction mixture was stirred at ambient temperature for 1 hour and then concentrated by rotary evaporation. The residue was concentrated down from toluene (2×) then taken up in methanol/tetrahydrofuran. Potassium acetate (0.145 g, 1.474 mmol) was added, and the reaction mixture was heated at reflux for 2 hours. The reaction mixture was concentrated by rotary evaporation. The residue was partitioned between ethyl acetate and water. The layers were separated, and the organic layer was dried over anhydrous sodium sulfate, filtered, and concentrated. The crude material was purified by flash chromatography (silica gel, 20-80% ethyl acetate in hexanes) to give the title compound (0.010 g, 66% yield). $^1$H NMR (300 MHz, DMSO-$d_6$) δ 12.01 (s, 1 H), 9.29 (s, 1 H), 7.18 (s, 1 H), 6.93-7.09 (m, 3 H), 4.15-4.21 (m, 1 H), 4.12 (q, J=7.12 Hz, 2 H), 2.49 (s, 3 H), 1.69-1.75 (m, 2 H), 1.38-1.45 (m, 2 H), 1.20-1.33 (m, 2 H), 1.13 (t, J=7.02 Hz, 3 H), 1.07-1.18 (m, 4 H). MS (ESI+) m/z 413.1 (M+H)+.

Example 49

3-methyl-N-(1-methylazetidin-3-yl)-4-oxo-1-(2-phenoxyphenyl)-4,5-dihydro-2H-pyrrolo[3,4-c]pyridine-6-carboxamide A stock solution of 12b and N,N-diisopropylethylamine (0.13 M and 0.39 M in N,N-dimethylacetamide, respectively, 317 µL, 0.042 mmol Example 12b and 0.12 mmol N,N-diisopropylethylamine), 2-(3H-[1,2,3]triazolo[4,5-b]pyridin-3-yl)-1,1,3,3-tetramethylisouronium hexafluorophosphate(V) (0.16 M in N,N-dimethylacetamide, 317 µL, 0.050 mmol), and 3-amino-N-methylazetidine (0.40 M in N,N-dimethylacetamide, 125 µL, 0.050 mmol) were aspirated from their respective source vials, mixed through a perfluoroalkoxy mixing tube (0.2 mm inner diameter), and loaded into an injection loop. The reaction segment was injected into the flow reactor (Hastelloy coil, 0.75 mm inner diameter, 1.8 mL internal volume) set at 125° C., and passed through the reactor at 180 µL min$^{-1}$ (10 minute residence time). Upon exiting the reactor, the reaction mixture was loaded directly into an injection loop and purified by reverse phase HPLC (C8, acetonitrile/water (0.1% TFA), 5-100%) to yield the title compound as the TFA salt (0.008 g, 36% yield). $^1$H NMR (400 MHz, DMSO-$d_6$/D$_2$O) δ 7.57 (dd, J=7.63, 1.53 Hz, 1 H), 7.39 (td, J=7.78, 1.83 Hz, 1 H), 7.29 (m, 3 H), 7.22 (s, 1 H), 7.04 (m, 2 H), 6.90 (m, 2 H), 4.71 (m, 1 H), 4.35 (m, 4 H), 2.93 (s, 3 H), 2.61 (s, 3 H). MS (APCI+) m/z 429.1 (M+H)+.

Example 50

N-(trans-3-methoxycyclobutyl)-3-methyl-4-oxo-1-(2-phenoxyphenyl)-4,5-dihydro-2H-pyrrolo[3,4-c]pyridine-6-carboxamide Example 50 was prepared according to the procedure used for the preparation of Example 49, substituting (trans)-3-methoxycyclobutanamine for 3-amino-N-methylazetidine, to give 0.0162 g (70%) of the title compound as the TFA salt. $^1$H NMR (400 MHz, DMSO-$d_6$/D$_2$O) δ 7.58 (dd, J=7.63, 1.83 Hz, 1 H), 7.37 (td, J=7.63, 1.83 Hz, 1 H), 7.29 (m, 4 H), 7.03 (m, 2 H), 6.94 (m, 2 H), 4.37 (m, 1 H), 4.03 (m, 1 H), 3.18 (s, 3 H), 2.61 (s, 3 H), 2.27 (dd, J=7.02, 5.49 Hz, 4 H). MS (APCI+) m/z 444.1 (M+H)+.

Example 51

(R)-3-methyl-N-(1-methylpyrrolidin-3-yl)-4-oxo-1-(2-phenoxyphenyl)-4,5-dihydro-2H-pyrrolo[3,4-c]pyridine-6-carboxamide Example 51 was prepared according to the procedure used for the preparation of Example 49, substituting (R)-1-methylpyrrolidin-3-amine for 3-amino-N-methylazetidine, to give 0.0134 g (58%) of the title compound as the TFA salt. $^1$H NMR (400 MHz, DMSO-$d_6$/D$_2$O) δ 7.57 (dd, J=7.63, 1.53 Hz, 1 H), 7.38 (td, J=7.78, 1.53 Hz, 1 H), 7.29 (m, 3 H), 7.22 (s, 1 H), 7.04 (m, 2 H), 6.91 (m, J=7.93 Hz, 2 H), 4.53 (m, 1 H), 3.60 (m, 4 H), 2.91 (s, 3 H), 2.61 (s, 3 H), 2.41 (m, 1 H), 2.12 (m, 1 H). MS (APCI+) m/z 443.1 (M+H)+.

Example 52

N-(2-cyanopropan-2-yl)-3-methyl-4-oxo-1-(2-phenoxyphenyl)-4,5-dihydro-2H-pyrrolo[3,4-c]pyridine-6-carboxamide Example 52 was prepared according to the procedure used for the preparation of Example 49, substituting 2-amino-2-methylpropanenitrile for 3-amino-N-methylazetidine, to give 0.0058 g (26%) of the title compound as the TFA salt. $^1$H NMR (400 MHz, DMSO-$d_6$/D$_2$O) δ 7.58 (dd, J=7.63, 1.83 Hz, 1 H), 7.37 (m, 1 H), 7.29 (m, 4 H), 7.04 (m, 2 H), 6.93 (m, 2 H), 2.61 (s, 3 H), 1.69 (s, 6 H). MS (APCI+) m/z 427.1 (M+H)+.

Example 53

N',N',3-trimethyl-4-oxo-1-(2-phenoxyphenyl)-4,5-dihydro-2H-pyrrolo[3,4-c]pyridine-6-carbohydrazide Example 53 was prepared according to the procedure used for the preparation of Example 49, substituting 1,1-dimethylhydrazine for 3-amino-N-methylazetidine, to give 0.0042 g (20%) of the title compound as the TFA salt. $^1$H NMR (400

MHz, DMSO-$d_6$/$D_2O$) δ 7.57 (dd, J=7.48, 1.68 Hz, 1 H), 7.37 (td, J=7.78, 1.83 Hz, 1 H), 7.29 (m, 3 H), 7.20 (s, 1 H), 7.03 (m, 2 H), 6.93 (dd, J=8.70, 0.76 Hz, 2 H), 2.63 (s, 6 H), 2.61 (s, 3 H). MS (APCI+) m/z 427.1 (M+H)$^+$.

Example 54 tert-butyl 4-(3-methyl-4-oxo-1-(2-phenoxyphenyl)-4,5-dihydro-2H-pyrrolo[3,4-c]pyridine-6-carboxamido)piperidine-1-carboxylate Example 54 was prepared according to the procedure used for the preparation of Example 49, substituting tert-butyl 4-aminopiperidine-1-carboxylate for 3-amino-N-methylazetidine, to give 0.0185 g (68%) of the title compound as the TFA salt. $^1$H NMR (400 MHz, DMSO-$d_6$/$D_2O$) δ 7.57 (dd, J=7.63, 1.83 Hz, 1 H), 7.36 (td, J=7.78, 1.83 Hz, 1H), 7.28 (m, 4 H), 7.02 (m, 2 H), 6.94 (m, 2 H), 3.92 (m, 3 H), 2.86 (m, 2 H), 2.61 (s, 3 H), 1.79 (dd, J=12.66, 3.20 Hz, 2 H), 1.42 (s, 9 H), 1.44 (m, 2 H). MS (APCI+) m/z 543.1 (M+H)$^+$.

Example 55

(R)-tert-butyl 3-((3-methyl-4-oxo-1-(2-phenoxyphenyl)-4,5-dihydro-2H-pyrrolo[3,4-c]pyridine-6-carboxamido)methyl)pyrrolidine-1-carboxylate Example 55 was prepared according to the procedure used for the preparation of Example 49, substituting (R)-tert-butyl 3-(aminomethyl)pyrrolidine-1-carboxylate for 3-amino-N-methylazetidine, to give 0.0202 g (74%) of the title compound as the TFA salt. $^1$H NMR (400 MHz, DMSO-$d_6$/$D_2O$) δ 7.58 (dd, J=7.63, 1.83 Hz, 1 H), 7.37 (td, J=7.78, 1.83 Hz, 1 H), 7.28 (m, 4 H), 7.03 (m, 2 H), 6.92 (m, 2 H), 3.35 (m, 3 H), 3.22 (m, 2 H), 3.00 (dd, J=10.83, 6.87 Hz, 1 H), 2.61 (s, 3 H), 2.42 (m, 1 H), 1.92 (m, 1 H), 1.59 (m, 1 H), 1.39 (s, 9 H). MS (APCI+) m/z 543.1 (M+H)$^+$.

Example 56 tert-butyl 3,3-difluoro-4-((3-methyl-4-oxo-1-(2-phenoxyphenyl)-4,5-dihydro-2H-pyrrolo[3,4-c]pyridine-6-carboxamido)methyl)pyrrolidine-1-carboxylate Example 56 was prepared according to the procedure used for the preparation of Example 49, substituting tert-butyl 4-(aminomethyl)-3,3-difluoropyrrolidine-1-carboxylate for 3-amino-N-methylazetidine, to give 0.0069 g (24%) of the title compound as the TFA salt. $^1$H NMR (400 MHz, DMSO-$d_6$/$D_2O$) δ 7.57 (dd, J=7.48, 1.68 Hz, 1 H), 7.38 (m, 1 H), 7.29 (m, 3 H), 7.23 (s, 1 H), 7.03 (m, 2 H), 6.90 (m, 2H), 3.68 (m, 3H), 3.56 (dd, J=13.89, 5.95 Hz, 1 H), 3.36 (m, 1 H), 3.23 (m, 1 H), 2.89 (m, 1 H), 2.61 (s, 3 H), 1.40 (s, 9 H). MS (APCI+) m/z 579.0 (M+H)$^+$.

Example 57

3-methyl-4-oxo-1-(2-phenoxyphenyl)-N-(piperidin-4-yl)-4,5-dihydro-2H-pyrrolo[3,4-c]pyridine-6-carboxamide Example 54 (0.014 g, 0.026 mmol) was dissolved in 1,4-dioxane (1 mL), treated with 4 N HCl in 1,4-dioxane (0.75 mL, excess) and stirred at ambient temperature until complete conversion was evident by HPLC. The reaction mixture was dried down under a stream of nitrogen and then placed under vacuum to yield the title compound as the HCl salt (9.5 mg, 77% yield). $^1$H NMR (400 MHz, DMSO-$d_6$/$D_2O$) δ 7.58 (dd, J=7.48, 1.68 Hz, 1 H), 7.37 (m, J=7.78, 7.78, 1.53 Hz, 1 H), 7.29 (m, 4 H), 7.04 (m, 2 H), 6.93 (m, 2H), 4.01 (m, 1H), 3.34 (m, 2 H), 3.03 (m, 2 H), 2.61 (s, 3 H), 2.02 (m, 2 H), 1.79 (m, 2H).

Example 58

(S)-3-methyl-4-oxo-1-(2-phenoxyphenyl)-N-(pyrrolidin-3-ylmethyl)-4,5-dihydro-2H-pyrrolo[3,4-c]pyridine-6-carboxamide Example 58 was prepared according to the procedure used for the preparation of Example 57, substituting Example 55 for Example 54, to give 0.0113 g (92%) of the title compound as the HCl salt. $^1$H NMR (400 MHz, DMSO-$d_6$/$D_2O$) δ 7.58 (dd, J=7.63, 1.53 Hz, 1 H), 7.38 (m, 1 H), 7.29 (m, 3 H), 7.24 (s, 1 H), 7.04 (m, 2 H), 6.91 (m, 2 H), 3.33 (m, 3 H), 3.27 (m, 1H), 3.17 (m, 1H), 2.94 (dd, J=11.60, 7.93 Hz, 1 H), 2.61 (s, 3 H), 2.57 (m, 1 H), 2.06 (m, 1 H), 1.70 (m, 1 H).

Example 59

N-[(4,4-difluoropyrrolidin-3-yl)methyl]-3-methyl-4-oxo-1-(2-phenoxyphenyl)-4,5-dihydro-2H-pyrrolo[3,4-c]pyridine-6-carboxamide Example 59 was prepared according to the procedure used for the preparation of Example 57, substituting Example 56 for Example 54, to give 0.0023 g (18%) of the title compound as the HCl salt. $^1$H NMR (400 MHz, DMSO-$d_6$/$D_2O$) δ 7.57 (dd, J=7.63, 1.83 Hz, 1H), 7.38 (td, J=7.71, 1.68 Hz, 1H), 7.29 (m, 3H), 7.23 (s, 1H), 7.03 (m, J=7.32, 7.32 Hz, 2H), 6.90 (m, J=7.63 Hz, 2H), 3.71 (m, 4H), 3.52 (m, 3H), 3.04 (m, 1H), 2.60 (s, 3H).

Example 60

3-methyl-1-(2-phenoxyphenyl)-6-(3-(pyridin-3-yl)-1,2,4-oxadiazol-5-yl)-2H-pyrrolo[3,4-c]pyridin-4(5H)-one A solution of Example 12b (200 μL, 0.0275 g, 0.076 mmol) in N,N-dimethylformamide/pyridine (1:1 v/v), a solution of 1-ethyl-3-(3-dimethylaminopropyl)carbodiimide (200 μL, 0.0225 g, 0.145 mmol) in N,N-dimethylformamide/pyridine (1:1 v/v), and a solution of (Z)—N'-hydroxynicotinimidamide (173.0 μL, 0.103 mmol) in 1 mL of N,N-dimethylformamide/pyridine (1:1 v/v) were combined and shaken at ambient temperature overnight. Upon completion, the reaction mixture was concentrated to dryness. The residue was purified by reverse phase HPLC (C8, acetonitrile/water (0.1% ammonium acetate), 45-75%) to give 0.0031 g (9%) of the title compound. $^1$H NMR (400 MHz, DMSO-$d_6$/$D_2O$) δ 9.24 (dd, J=2.14, 0.61 Hz, 1H), 8.81 (dd, J=4.88, 1.83 Hz, 1 H), 8.45 (ddd, J=8.09, 1.83, 1.68 Hz, 1 H), 7.67 (m, 1 H), 7.64 (dd, J=7.63, 1.83 Hz, 1 H), 7.59 (s, 1 H), 7.44 (m, 1 H), 7.34 (m, 3 H), 7.07 (m, 2 H), 6.95 (m, 2 H), 2.66 (s, 3 H). MS (ESI+) m/z 562.0 (M+H)$^+$.

Example 61

3-methyl-6-(3-methyl-1,2,4-oxadiazol-5-yl)-1-(2-phenoxyphenyl)-2H-pyrrolo[3,4-c]pyridin-4(5H)-one Example 61 was prepared according to the procedure used for the preparation of Example 60, substituting (Z)—N'-hydroxyacetimidamide for (Z)—N'-hydroxynicotinimidamide. Purification by reverse phase HPLC (C8, acetonitrile/water (0.1% ammonium acetate), 30-100%) gave 0.0003 g (1%) of the title compound. $^1$H NMR (400 MHz, DMSO-d$_6$/D$_2$O) δ 7.61 (m, 1 H), 7.44 (m, 2 H), 7.32 (m, 3 H), 7.07 (m, 2 H), 6.88 (m, 2 H), 2.62 (s, 3 H), 2.40 (s, 3 H). MS (APCI+) m/z 462.2 (M+H)$^+$.

Example 62

6-(3-(4-(dimethylamino)phenyl)-1,2,4-oxadiazol-5-yl)-3-methyl-1-(2-phenoxyphenyl)-2H-pyrrolo[3,4-c]pyridin-4(5H)-one Example 62 was prepared according to the procedure used for the preparation of Example 60, substituting (Z)-4-(dimethylamino)-N'-hydroxybenzimidamide for (Z)—N'-hydroxynicotinimidamide. Purification by reverse phase HPLC (C8, acetonitrile/water (0.1% ammonium acetate), 50-80%) gave 0.001 g (2.6%) of the title compound. $^1$H NMR (400 MHz, DMSO-d$_6$/D$_2$O) δ 7.62 (m, 1 H), 7.46 (m, 1 H), 7.34 (m, 4 H), 7.21 (m, 2 H), 7.08 (m, 2 H), 6.94 (m, 2 H), 6.80 (m, 2 H), 2.95 (m, 6 H), 2.64 (m, 3H). MS (ESI+) m/z 505.1 [M+2H]$^+$.

Example 63

6-(3-cyclopropyl-1,2,4-oxadiazol-5-yl)-3-methyl-1-(2-phenoxyphenyl)-2H-pyrrolo[3,4-c]pyridin-4(5H)-one Example 63 was prepared according to the procedure used for the preparation of Example 60, substituting (Z)—N'-hydroxycyclopropanecarboximidamide for (Z)—N'-hydroxynicotinimidamide. Purification by reverse phase HPLC (C8, acetonitrile/water (0.1% ammonium acetate), 50-80%) gave 0.0014 g (4.3%) of the title compound. $^1$H NMR (400 MHz, DMSO-d$_6$/D$_2$O) δ 7.60 (dd, J=7.63, 1.53 Hz, 1 H), 7.42 (m, 2H), 7.32 (m, 3H), 7.06 (m, 2 H), 6.90 (m, 2 H), 2.63 (s, 3 H), 2.15 (m, 1H), 1.12 (m, 2 H), 0.99 (m, 2 H). MS (ESI+) m/z 425.1 (M+H)$^+$.

Example 64

6-(3-((1H-1,2,4-triazol-1-yl)methyl)-1,2,4-oxadiazol-5-yl)-3-methyl-1-(2-phenoxyphenyl)-2H-pyrrolo[3,4-c]pyridin-4(5H)-one Example 64 was prepared according to the procedure used for the preparation of Example 60, substituting (Z)—N'-hydroxy-2-(1H-1,2,4-triazol-1-yl)acetimidamide for (Z)—N'-hydroxynicotinimidamide. Purification by reverse phase HPLC (C8, acetonitrile/water (0.1% ammonium acetate), 35-65%) gave 0.0023 g (6.5%) of the title compound. $^1$H NMR (400 MHz, DMSO-d$_6$/D$_2$O) δ 12.37 (s, 1H), 10.31 (s, 1H), 8.77 (s, 1H), 8.05 (s, 1H), 7.59 (dd, J=7.63, 1.53 Hz, 1H), 7.44 (s, 1H), 7.40 (td, J=7.71, 1.68 Hz, 1H), 7.31 (m, 3H), 7.05 (m, 2H), 6.87 (d, J=7.63 Hz, 2H), 5.72 (s, 2H), 2.62 (s, 3H). MS (ESI+) m/z 466.2 (M+H)$^+$.

Example 65

3-methyl-1-(2-phenoxyphenyl)-6-(3-(pyrazin-2-yl)-1,2,4-oxadiazol-5-yl)-2H-pyrrolo[3,4-c]pyridin-4(5H)-one Example 65 was prepared according to the procedure used for the preparation of Example 60, substituting (Z)—N'-hydroxypyrazine-2-carboximidamide for (Z)—N'-hydroxynicotinimidamide. Purification by reverse phase HPLC (C8, acetonitrile/water (0.1% ammonium acetate), 40-70%) gave 0.0026 g (7.4%) of the title compound. $^1$H NMR (500 MHz, DMSO-d$_6$/D$_2$O) δ 12.42 (s, 1H), 10.41 (s, 1H), 9.36 (d, J=0.92 Hz, 1H), 8.90 (m, J=7.93, 1.83 Hz, 2H), 7.64 (dd, J=7.63, 1.22 Hz, 1H), 7.58 (s, 1H), 7.42 (m, 1H), 7.35 (t, J=7.78 Hz, 1H), 7.31 (t, J=7.93 Hz, 2H), 7.09 (d, J=7.93 Hz, 1H), 7.05 (t, J=7.48 Hz, 1H), 6.95 (d, J=7.93 Hz, 2H), 2.65 (s, 3H). MS (ESI+) m/z 463.2 (M+H)$^+$.

Example 66

3-methyl-1-(2-phenoxyphenyl)-6-(3-(pyridin-3-ylmethyl)-1,2,4-oxadiazol-5-yl)-2H-pyrrolo[3,4-c]pyridin-4(5H)-one Example 66 was prepared according to the procedure used for the preparation of Example 60, substituting (Z)—N'-hydroxy-2-(pyridin-3-yl)acetimidamide for (Z)—N'-hydroxynicotinimidamide. Purification by reverse phase HPLC (C8, acetonitrile/water (0.1% ammonium acetate), 40-70%) gave 0.001.5 g (4.1%) of the title compound. $^1$ H NMR (400 MHz, DMSO-d$_6$/D$_2$O) δ 8.61 (d, J=2.14 Hz, 1 H), 8.49 (dd, J=4.73, 1.68 Hz, 1 H), 7.82 (m, 1H), 7.60 (dd, J=7.63, 1.83 Hz, 1 H), 7.45 (s, 1 H), 7.42 (m, 2 H), 7.34 (m, 1 H), 7.29 (m, 2H), 7.05 (m, 2 H), 6.88 (m, 2 H), 4.21 (s, 2 H), 2.62 (s, 3 H). MS (ESI+) m/z 476.1 (M+H)$^+$.

Example 67

3-methyl-1-(2-phenoxyphenyl)-6-(3-(pyridin-2-yl)-1,2,4-oxadiazol-5-yl)-2H-pyrrolo[3,4-c]pyridin-4(5H)-one Example 67 was prepared according to the procedure used for the preparation of Example 60, substituting (Z)—N'-hydroxypicolinimidamide for (Z)—N'-hydroxynicotinimidamide. Purification by reverse phase HPLC (C8, acetonitrile/water (0.1% ammonium acetate), 45-75%) gave 0.001.5 g (4.1%) of the title compound. $^1$ H NMR (400 MHz, DMSO-d$_6$/D$_2$O) δ 8.79 (m, 1 H), 8.20 (m, 1 H), 8.08 (td, J=7.71, 1.68 Hz, 1 H), 7.65 (m, 2 H), 7.59 (s, 1 H), 7.45 (td, J=7.78, 1.83 Hz, 1 H), 7.33 (m, 3H), 7.10 (dd, J=8.24, 1.22 Hz, 1 H), 7.05 (m, 1 H), 6.93 (m, 2 H), 2.65 (s, 3 H). MS (ESI+) m/z 462.0 (M+H)$^+$.

Example 68 ethyl 1-{2-(2,4-difluorophenoxy)-5-[(methylsulfonyl)methyl]phenyl}-3-methyl-4-oxo-4,5-dihydro-2H-pyrrolo[3,4-c]pyridine-6-carboxylate Example 68a 3-bromo-4-(2,4-difluorophenoxy)benzaldehyde A mixture of 3-bromo-4-fluorobenzaldehyde (4.06 g, 20.0 mmol), 2,4-difluorophenol (2.60 g, 20.0 mmol) and cesium carbonate (7.17 g, 22.0 mmol) in dimethyl sulfoxide (20 mL) was heated at 100° C. for 1 hour. The reaction mixture was partitioned with ethyl acetate and water. The organic layer was washed with saturated aqueous sodium chloride twice, dried over anhydrous sodium sulfate, filtered, and concentrated. The residue was purified by flash chromatography (silica gel, 20% ethyl acetate in heptanes) to provide the title compound (5.94 g, 95%).

Example 68b (3-bromo-4-(2,4-difluorophenoxy)phenyl)methanol

To Example 68a (3.76 g, 12.0 mmol) in a mixture of ethanol (10 mL) and tetrahydrofuran (10 mL) was added sodium borohydride (0.136 g, 3.60 mmol). The reaction mixture was stirred at ambient temperature for 1 hour. The solvent was evaporated and the residue was partitioned with ethyl acetate and water. The organic layer was washed with saturated aqueous sodium chloride, dried over anhydrous sodium sulfate, filtered, and concentrated to provide the title compound (3.72 g, 98%).

Example 68c 2-bromo-4-(bromomethyl)-1-(2,4-difluorophenoxy) benzene

To Example 68b (3.70 g, 11.7 mmol) in dichloromethane (20 mL) was added phosphorus tribromide (1.107 mL, 11.74 mmol) dropwise. The reaction mixture was stirred at ambient temperature for 3 hours, poured into ice water, the pH adjusted to basic by the addition of saturated aqueous sodium bicarbonate slowly, and extracted by dichloromethane. The organic layer was washed with saturated aqueous sodium chloride, dried over anhydrous sodium sulfate, filtered, and concentrated to provide the title compound (4.15 g, 93%).

Example 68d (3-bromo-4-(2,4-difluorophenoxy)benzyl)(methyl) sulfane

A mixture of Example 68c (1.51 g, 4.00 mmol) and sodium thiomethoxide (0.280 g, 4.00 mmol) in dimethylformamide (8 mL) was stirred at ambient temperature for 6 hours. The reaction mixture was partitioned with ethyl acetate and water. The organic layer was washed with saturated aqueous sodium chloride twice, dried over anhydrous sodium sulfate, filtered, and concentrated to provide the title compound (1.38 g, 100%).

Example 68e 2-bromo-1-(2,4-difluorophenoxy)-4-(methylsulfonylmethyl)benzene

To Example 68d (1.38 g, 4.00 mmol) in methanol (15 mL) was added oxone (5.16 g, 8.40 mmol) in water (15 mL) at 0° C. The reaction mixture was stirred at ambient temperature for 1 hour. The reaction mixture was partitioned with ethyl acetate and water. The organic layer was washed with saturated aqueous sodium chloride, dried over anhydrous sodium sulfate, filtered, and concentrated. The residue was purified by flash chromatography (silica gel, 20-40% ethyl acetate in heptanes) to provide the title compound (1.485 g, 98%).

Example 68f ethyl 3-methyl-4-oxo-1-(4,4,5,5-tetramethyl-1,3,2-dioxaborolan-2-yl)-2-((2-(trimethylsilyl)ethoxy)methyl)-4,5-dihydro-2H-pyrrolo[3,4-c]pyridine-6-carboxylate Example 4b (515 mg, 1.20 mmol), bis(acetonitrile)dichloropalladium (II) (7.8 mg, 0.030 mmol) and 2-(dicyclohexylphosphino)-2',4',6'-triisopropylbiphenyl (57.2 mg, 0.120 mmol) were combined and purged with nitrogen for 5 minutes. To this mixture was added dioxane (3 mL), 4,4,5,5-tetramethyl-1,3,2-dioxaborolane (0.260 mL, 1.80 mmol) and triethylamine (0.502 mL, 3.60 mmol) by syringe. The reaction mixture was heated at 80° C. for 1 hour. The reaction mixture was partitioned with ethyl acetate and water. The organic layer was washed with saturated aqueous sodium chloride, dried over anhydrous sodium sulfate, treated with 3-mercaptopropyl functionalized silica gel, filtered and concentrated. The residue was purified by flash chromatography (silica gel, 10-40% ethyl acetate in heptanes) to provide the title compound (389 mg, 68%)

Example 68g ethyl 1-(2-(2,4-difluorophenoxy)-5-(methylsulfonylmethyl)phenyl)-3-methyl-4-oxo-2-((2-(trimethylsilyl)ethoxy)methyl)-4,5-dihydro-2H-pyrrolo[3,4-c]pyridine-6-carboxylate Example 68e (94 mg, 0.25 mmol), Example 68f (143 mg, 0.300 mmol), cesium fluoride (114 mg, 0.750 mmol) and tetrakis(triphenylphosphine)palladium(0) (14 mg, 0.013 mmol) were combined in a microwave tube and purged with nitrogen for 15 minutes. A mixture of dimethoxyethane (2 mL) and ethanol (1 mL) was purged with nitrogen for 15 minutes and transferred to the microwave tube. The reaction mixture was heated in a microwave reactor at 120° C. for 30 minutes. The reaction mixture was partitioned with ethyl acetate and water. The organic layer was washed with saturated aqueous sodium chloride, dried over anhydrous sodium sulfate, treated with 3-mercaptopropyl functionalized silica gel, filtered, and concentrated. The residue was purified by flash chromatography (silica gel, 20-60% ethyl acetate in heptanes) to afford the title compound (17 mg, 11%).

Example 68h ethyl 1-{2-(2,4-difluorophenoxy)-5-[(methylsulfonyl)methyl]phenyl}-3-methyl-4-oxo-4,5-dihydro-2H-pyrrolo[3,4-c]pyridine-6-carboxylate Example 68h was prepared according to the procedure used for the preparation of Example 8c, substituting 68g for 8b. Purification by flash chromatography (silica gel, 2-4% methanol in dichloromethane) afforded the title compound (9 mg, 70%). $^1$H NMR (300 MHz, DMSO-$d_6$) δ 12.32 (s, 1 H) 9.44 (s, 1 H) 7.57 (d, J=2.03 Hz, 1H) 7.42-7.53 (m, 1H) 7.23-7.39 (m, 3 H) 7.05-7.20 (m, 1 H) 6.86 (d, J=8.14 Hz, 1 H) 4.52 (s, 2 H) 4.22 (q, J=7.12 Hz, 2 H) 2.96 (s, 3 H) 2.66 (s, 3 H) 1.27 (t, J=7.12 Hz, 3 H). MS (ESI+) m/z 517 (M+H)$^+$.

Example 69 ethyl 1-[2-(cyclopropylmethoxy)-5-fluorophenyl]-3-methyl-4-oxo-4,5-dihydro-2H-pyrrolo[3,4-c]pyridine-6-carboxylate

Example 69a ethyl 1-(2-(cyclopropylmethoxy)-5-fluorophenyl)-3-methyl-4-oxo-2-((2-(trimethylsilyl)ethoxy)methyl)-4,5-dihydro-2H-pyrrolo[3,4-c]pyridine-6-carboxylate Example 4b (0.215 g, 0.5 mmol), 2-(2-(cyclopropylmethoxy)-5-fluorophenyl)-4,4,5,5-tetramethyl-1,3,2-dioxaborolane (0.183 g, 0.625 mmol), chloro(2-dicyclohexylphosphino-2',4',6'-triisopropyl-1,1'-biphenyl)[2-(2'-amino-1,1'-biphenyl)]palladium(II) (0.039 g, 0.05 mmol) and potassium phosphate (0.212 g, 1 mmol) were combined and sparged with nitrogen for 30 minutes. Nitrogen-sparged tetrahydrofuran (1 mL) and water (2 mL) were added and the mixture was stirred at 40° C. for 8 hours and then at ambient temperature overnight. The reaction mixture was partitioned between ethyl acetate and water, washed with saturated aqueous sodium chloride, treated with 3-mercaptopropyl-functionalized silica gel for 20 minutes, dried over anhydrous magnesium sulfate, filtered through a plug of Celite and concentrated. The residue was purified by flash chromatography (silica gel, 0-40% ethyl acetate in dichloromethane) to give the title compound as an impure mixture. The material was further purified by a second flash chromatography (silica gel, 5-25% ethyl acetate in dichloromethane) to give 0.087 g (34%) of the title compound.

Example 69b ethyl 1-(2-(cyclopropylmethoxy)-5-fluorophenyl)-3-methyl-4-oxo-4,5-dihydro-2H-pyrrolo[3,4-c]pyridine-6-carboxylate Example 69a (0.05 g, 0.090 mmol) was treated with neat 2,2,2-trifluoroacetic acid (1 mL, 13 mmol), stirred at ambient for 50 minutes and concentrated to dryness. The residue in a mixture of acetonitrile (2 mL) and water (0.5 mL) was treated with sodium acetate (0.220 g, 2.68 mmol) and heated at 70° C. for 2 hours. The reaction mixture was cooled to ambient temperature and then partitioned between ethyl acetate and water. The organic layer was washed with saturated aqueous sodium chloride, dried over anhydrous magnesium sulfate, filtered and concentrated. The residue was purified by reverse phase HPLC (C18, acetonitrile/water (0.1% TFA), 10-90%) to give 0.014 g (40%) of the title compound. $^1$H NMR (400 MHz, DMSO-$d_6$) δ 12.18 (s, 1H), 9.43 (s, 1H), 7.29 (s, 1H), 7.22 (dd, J=9.46, 2.14 Hz, 1H), 7.13 (m, 2H), 4.27 (q, J=7.02 Hz, 2H), 3.85 (d, J=7.02 Hz, 2H), 2.65 (s, 3H), 1.29 (t, J=7.02 Hz, 3H), 1.18 (m, 1H), 0.46 (m, 2H), 0.29 (q, J=4.68 Hz, 2H). MS (ESI+) m/z 385.0 (M+H)$^+$.

Example 70

1-[2-(cyclopropylmethoxy)-5-fluorophenyl]-3-methyl-4-oxo-4,5-dihydro-2H-pyrrolo[3,4-c]pyridine-6-carboxamide

Example 70a 1-(2-(cyclopropylmethoxy)-5-fluorophenyl)-3-methyl-4-oxo-2-((2-(trimethylsilyl)ethoxy)methyl)-4,5-dihydro-2H-pyrrolo[3,4-c]pyridine-6-carboxamide Example 69a (0.042 g, 0.082 mmol) was treated with ammonia (7 N in methanol, 1 mL, 7 mmol) solution and heated at 60° C. overnight. Additional ammonia (7 N in methanol, 1 mL, 7 mmol) solution was added and heating was continued for 6 hours. The reaction mixture was cooled to ambient temperature and concentrated to dryness to give 0.029 g (73%) of the title compound.

Example 70b

1-[2-(cyclopropylmethoxy)-5-fluorophenyl]-3-methyl-4-oxo-4,5-dihydro-2H-pyrrolo[3,4-c]pyridine-6-carboxamide Example 70b was prepared according to the procedure used for the preparation of Example 69b, substituting Example 70a for Example 69a. In the current example, the first stage was run for 1 hour and the second stage was run for 8 hours to give 0.007 g (33%) of the title compound. $^1$H NMR (400 MHz, DMSO-$d_6$) δ 11.99 (s, 1 H), 8.85 (s, 1 H), 8.08 (s, 1 H), 7.45 (s, 1 H), 7.29 (d, J=1.22 Hz, 1 H), 7.23 (m, 1 H), 7.11 (m, 2 H), 3.84 (d, J=7.02 Hz, 2 H), 2.64 (s, 3 H), 1.15 (m, 1 H), 0.45 (m, 2 H), 0.28 (m, J=5.26, 5.26, 4.12 Hz, 2 H). MS (ESI+) m/z 356.1 (M+H)$^+$.

Example 71

1-(2-(cyclopropylmethoxy)-5-fluorophenyl)-3-methyl-6-(3-(pyrazin-2-yl)-1,2,4-oxadiazol-5-yl)-2H-pyrrolo[3,4-c]pyridin-4(5H)-one

Example 71a 1-(2-(cyclopropylmethoxy)-5-fluorophenyl)-3-methyl-6-(3-(pyrazin-2-yl)-1,2,4-oxadiazol-5-yl)-2-((2-(trimethylsilyl)ethoxy)methyl)-2H-pyrrolo[3,4-c]pyridin-4(5H)-one Example 69a (0.057 g, 0.11 mmol), (Z)—N'-hydroxypyrazine-2-carboximidamide (0.030 g, 0.22 mmol), and cesium carbonate (0.054 g, 0.165 mmol) were combined with toluene (1 mL) and reacted for 60 minutes at 180° C. in a Biotage microwave reactor. The reaction mixture was concentrated to dryness. The residue was partitioned between ethyl acetate and water, washed with saturated aqueous sodium chloride, dried over anhydrous magnesium sulfate, filtered, and concentrated. The residue was purified by flash chromatography (silica gel, 0-90% methanol in dichloromethane) to give 0.033 g (51%) of the title compound.

Example 71b 1-(2-(cyclopropylmethoxy)-5-fluorophenyl)-3-methyl-6-(3-(pyrazin-2-yl)-1,2,4-oxadiazol-5-yl)-2H-pyrrolo[3,4-c]pyridin-4(5H)-one Example 71b was prepared according to the procedure used for the preparation of Example 69b, substituting Example 71a for Example 69a. In the current example, the second stage was run overnight and the residue was purified by flash chromatography (silica gel, 0 to 100% ethyl acetate in dichloromethane) to give 0.018 g (38%) of the title compound. $^1$H NMR (400 MHz, DMSO-$d_6$) δ 12.29 (s, 1H), 10.38 (s, 1H), 9.36 (d, J=1.53 Hz, 1H), 8.89 (m, 2H), 7.60 (s, 1H), 7.30 (dd, J=9.31, 2.59 Hz, 1H), 7.16 (m, 2H), 3.89 (d, J=7.02 Hz, 2H), 2.69 (s, 3H), 1.20 (m, 1H), 0.42 (m, 2H), 0.30 (m, 2H). MS (ESI+) m/z 459.1 (M+H)$^+$.

Example 72

7-methyl-5-(2-phenoxyphenyl)-2,6-dihydro-1H-pyrrolo[3,4-d]pyridazin-1-one

Example 72a ethyl 2-acetyl-4-oxo-4-(2-phenoxyphenyl)butanoate

A mixture of sodium hydride (60% oil dispersion, 0.157 g, 3.92 mmol) and tetrahydrofuran (6.1 mL) was cooled to 0° C., treated dropwise with ethyl 3-oxobutanoate (0.413 mL, 3.27 mmol) and stirred at 0° C. for 30 minutes. A solution of 2-bromo-1-(2-phenoxyphenyl)ethanone (1.05 g, 3.6 mmol) in tetrahydrofuran (2 mL) was added dropwise and stirring was continued for 5.5 hours. The reaction mixture was partitioned between ethyl acetate and saturated aqueous ammonium chloride solution and washed with saturated aqueous sodium chloride. The combined aqueous layers were extracted with ethyl acetate. The combined organic layers were dried over anhydrous magnesium sulfate, filtered and concentrated. The residue was purified by flash chromatography (silica gel, 2-20% ethyl acetate in hexanes) to give 1.1 g (100%) of the title compound.

Example 72b ethyl 2-methyl-5-(2-phenoxyphenyl)-1H-pyrrole-3-carboxylate

Example 72a (1.1 g, 3.25 mmol), ammonium acetate (1.25 g, 16.2 mmol) and acetic acid (3 mL) were combined and heated to 80° C. for 40 minutes. The reaction mixture was cooled to near ambient temperature and partially concentrated to induce formation of a solid. Water (30 mL) was added and the mixture was stirred for 20 minutes. The solid was collected by filtration, rinsed with 200 mL of water and dried under vacuum to give 1.01 g (95%) of the title compound with 11% acetic acid as an excipient.

Example 72c ethyl 4-formyl-2-methyl-5-(2-phenoxyphenyl)-1H-pyrrole-3-carboxylate

Oxalyl dichloride (0.053 mL, 0.625 mmol) was added dropwise to N,N-dimethylformamide (0.387 mL, 5 mmol) at 0° C. The reaction mixture was removed from the cooling bath and stirred for thirty minutes at ambient temperature. N,N-Dimethylformamide (1 mL) was added to the reaction mixture and stirring was continued for another 30 minutes. The mixture was again cooled to 0° C. and a solution of Example 72b (0.161 g, 0.5 mmol) in N,N-dimethylformamide (2 mL) was added. Stirring was continued at 0° C. for two hours and then at ambient temperature for 3.5 hours. A solution of sodium hydroxide (10 mL, 4 N aqueous) was added and the mixture was stirred for 20 minutes. The reaction mixture was then partitioned between ethyl acetate and water, washed with water and saturated aqueous sodium chloride, dried over anhydrous magnesium sulfate, filtered and concentrated. The residue was purified by flash chromatography (silica gel, 5-50% ethyl acetate in hexanes) to give 0.16 g (92%) of the title compound.

Example 72d

7-methyl-5-(2-phenoxyphenyl)-2,6-dihydro-1H-pyrrolo[3,4-d]pyridazin-1-one

Example 72c (0.05 g, 0.143 mmol) in ethanol (1 mL) at ambient temperature was treated with hydrazine monohydrate (0.044 mL, 1.431 mmol) and stirred at ambient temperature for 1.5 hours and then at 60° C. for 2.5 days. The reaction mixture was concentrated and the residue was purified by reverse phase HPLC (C8, acetonitrile/water (0.1% TFA), 10-95%) to give 0.037 g (81%) of the title compound. $^1$H NMR (300 MHz, DMSO-d$_6$) δ 12.42 (s, 1H), 11.37 (s, 1H), 8.05 (s, 1H), 7.61 (dd, J=7.46, 1.70 Hz, 1H), 7.34 (m, 4H), 7.07 (m, 1H), 7.01 (dd, J=8.14, 1.02 Hz, 1H), 6.94 (m, 2H), 2.60 (s, 3H). MS (ESI+) m/z 318.2 (M+H)$^+$.

Example 73

N-[3-(7-methyl-1-oxo-2,6-dihydro-1H-pyrrolo[3,4-d]pyridazin-5-yl)-4-phenoxyphenyl]methanesulfonamide Example 74f (0.0203 g, 0.061 mmol) in tetrahydrofuran (1 mL) was treated sequentially with methanesulfonyl chloride (0.012 mL, 0.153 mmol) and triethylamine (0.026 mL, 0.183 mmol) and stirred at ambient temperature for 3 hours. A solution of sodium hydroxide (1 M aqueous) (0.611 mL, 0.611 mmol) was added and the mixture was heated at 45° C. for 1 hour. The reaction mixture was neutralized with 2 N aqueous hydrochloric acid and partitioned between ethyl acetate and water. The organic layer was washed with saturated aqueous sodium chloride, dried over anhydrous magnesium sulfate, filtered, and concentrated. The residue was purified by reverse phase HPLC (C8, acetonitrile/water (0.1% TFA), 10-95%) and then by flash chromatography (silica gel, 0-10% methanol in dichloromethane to give 0.013 g (52%) of the title compound. $^1$H NMR (300 MHz, DMSO-d$_6$) δ 12.43 (s, 1H), 11.41 (s, 1H), 9.77 (s, 1H), 8.06 (s, 1H), 7.43 (d, J=2.37 Hz, 1H), 7.30 (m, 2H), 7.21 (dd, J=8.82, 2.71 Hz, 1H), 7.03 (m, 2H), 6.91 (m, 2H), 3.05 (s, 3H), 2.59 (s, 3H). MS (ESI+) m/z 411 (M+H)$^+$.

Example 74

5-(5-amino-2-phenoxyphenyl)-7-methyl-2,6-dihydro-1H-pyrrolo[3,4-d]pyridazin-1-one

Example 74a

7-methyl-2,6-dihydro-1H-pyrrolo[3,4-d]pyridazin-1-one

Example 93b (5 g, 27.6 mmol) and hydrazine monohydrate (41.4 g, 828 mmol) were combined in ethanol (110 mL) and heated at 60° C. for 24 hours. The mixture was cooled and concentrated to leave about 30 mL of solvent. The resulting solid was collected by filtration, rinsed with a minimal amount of cold ethanol, and dried to constant mass affording the title compound as a fine, white powder (3.59 g, 87%).

Example 74b

5-bromo-7-methyl-2,6-dihydro-1H-pyrrolo[3,4-d]pyridazin-1-one

To a suspension of Example 74a (1.1 g, 7.38 mmol) in dimethylformamide (12.29 mL) at −20° C. was added dropwise a solution of N-bromosuccinimide (1.313 g, 7.38 mmol) in tetrahydrofuran (24.58 mL). The mixture was stirred at −20° C. and allowed to slowly warm to 0° C. over 3 hours. The reaction mixture was diluted with ethyl acetate and washed with 10% aqueous sodium thiosulfate, water, saturated aqueous sodium chloride, dried (anhydrous sodium sulfate), filtered and concentrated. The residue was triturated in a minimal volume of 9:1 ethyl acetate/hexanes to afford the title compound (1.42 g, 84%).

Example 74c

2-bromo-4-nitro-1-phenoxybenzene

2-Bromo-1-fluoro-4-nitrobenzene (2.5 g, 11.4 mmol), phenol (1.28 g, 13.6 mmol), and cesium carbonate (4.44 g, 13.6 mmol) were combined in dimethyl sulfoxide (140 mL) and heated at 110° C. for 1 hour. The reaction mixture was partitioned between ethyl acetate and saturated aqueous sodium chloride. The combined organics were washed with saturated aqueous sodium chloride, dried (anhydrous magnesium sulfate), filtered, and concentrated to afford the title compound.

Example 74d 3-bromo-4-phenoxyaniline

Example 74c (3.43 g, 11.7 mmol), iron powder (3.26 g, 58.4 mmol), and ammonium chloride (1.25 g, 23.4 mmol) were combined in ethanol (50 mL), tetrahydrofuran (50 mL), and water (16.7 mL), and heated at 100° C. for 2 hour. The reaction mixture was cooled to just below reflux, vacuum filtered through diatomaceous earth, the filter cake washed with warm methanol (3×35 mL), and the filtrate concentrated under reduced pressure. The residue was partitioned between saturated aqueous NaHCO$_3$ and ethyl acetate (3×125 mL). The combined organics were washed with saturated aqueous sodium chloride, dried (anhydrous magnesium sulfate), gravity filtered, then concentrated to afford the title compound.

Example 74e 4-phenoxy-3-(4,4,5,5-tetramethyl-1,3,2-dioxaborolan-2-yl)aniline

Example 74d (4.38 g, 16.58 mmol), 4,4,4',4',5,5,5',5'-octamethyl-2,2'-bi(1,3,2-dioxaborolane) (8.42 g, 33.2 mmol), potassium acetate (3.58 g, 36.5 mmol), tris(dibenzylideneacetone)dipalladium(0) (0.456 g, 0.498 mmol) and 1,3,5,7-tetramethyl-6-phenyl-2,4,8-trioxa-6-phosphaadamantane (0.436 g, 1.493 mmol) were combined and sparged with argon for 30 minutes. Meanwhile, anhydrous dioxane (83 mL) was sparged with nitrogen for 30 minutes and added via syringe to the solids. The mixture was stirred under nitrogen for 20 hours at 80° C., cooled and partitioned between ethyl acetate and water. The organic layer was washed with water, saturated aqueous sodium chloride, dried (anhydrous sodium sulfate), filtered and concentrated. Purification by chromatography (silica gel, 0-40% ethyl acetate in hexanes) provided an oil that was triturated in a minimal volume of hexanes to afford the title compound (3.64 g).

Example 74f 5-(5-amino-2-phenoxyphenyl)-7-methyl-2,6-dihydro-1H-pyrrolo[3,4-d]pyridazin-1-one Example 74b (0.046 g, 0.2 mmol), Example 74e (0.081 g, 0.260 mmol), tris(dibenzylideneacetone)dipalladium(0) (5.49 mg, 6.00 µmol), 1,3,5,7-tetramethyl-6-phenyl-2,4,8-trioxa-6-phosphaadamantane (6.43 mg, 0.022 mmol) and sodium carbonate (0.085 g, 0.800 mmol) were combined in a sealed 5 mL microwave tube and sparged with argon for 15 minutes. Meanwhile a solution of dioxane (0.80 mL) and water (0.20 mL) was sparged with nitrogen for 15 minutes and transferred into the reaction vessel under argon. The mixture was stirred at 60° C. for 5 hours, cooled and partitioned between ethyl acetate and water. The organic layer was washed with saturated aqueous sodium chloride, dried (anhydrous sodium sulfate), treated with 3-mercaptopropyl functionalized silica gel, filtered and concentrated. Purification by chromatography (silica gel, 0-6% methanol in dichloromethane) afforded the title compound (0.042 g, 63% yield). $^1$H NMR (300 MHz, DMSO-d$_6$) δ 12.30 (s, 1H), 11.31 (s, 1H), 8.04 (s, 1H), 7.11-7.24 (m, 2H), 6.85-6.93 (m, 2H), 6.80 (d, J=2.71 Hz, 1H), 6.72 (d, J=7.80 Hz, 2H), 6.62 (dd, J=8.48, 2.71 Hz, 1H), 5.18 (s, 2H), 2.53 (s, 3H). MS (ESI+) m/z 333 [M+H]$^+$.

Example 75

N-[3-(7-methyl-1-oxo-2,6-dihydro-1H-pyrrolo[3,4-d]pyridazin-5-yl)-4-phenoxyphenyl]ethanesulfonamide To a solution of Example 74f (0.05 g, 0.150 mmol) and triethylamine (0.084 mL, 0.602 mmol) in dichloromethane (1.504 mL) and tetrahydrofuran (1.504 mL) was added dropwise ethanesulfonyl chloride (0.046 mL, 0.481 mmol). The reaction mixture was stirred for three hours at ambient temperature and concentrated. The residue was diluted with dioxane (3 mL) and 1 M sodium hydroxide (1 mL) and heated at 60° C. for 1 hour. The mixture was cooled and diluted with water and ethyl acetate adjusting the pH to 6 with 1 M HCl. The organic layer was washed with saturated aqueous sodium chloride, dried (anhydrous sodium sulfate), filtered, and concentrated. Purification by chromatography (silica gel, 1-5% methanol in dichloromethane) afforded the title compound (0.03 g, 45%). $^1$H NMR (300 MHz, DMSO-d$_6$) δ 12.43 (s, 1H), 11.41 (s, 1H), 9.83 (s, 1H), 8.04 (s, 1H), 7.43 (d, J=2.71 Hz, 1H), 7.26-7.33 (m, 2H), 7.22 (dd, J=8.82, 2.71 Hz, 1H), 7.00-7.08 (m, 2H), 6.90 (d, J=7.46 Hz, 2H), 3.15 (q, J=7.23 Hz, 2H), 2.59 (s, 3H), 1.24 (t, J=7.46 Hz, 3H). MS (ESI+) m/z 425 [M+H]$^+$.

Example 76

2,2,2-trifluoro-N-[3-(7-methyl-1-oxo-2,6-dihydro-1H-pyrrolo[3,4-d]pyridazin-5-yl)-4-phenoxyphenyl]ethanesulfonamide Example 76 was prepared according to the procedure used for the preparation of Example 75, substituting 2,2,2-trifluoroethanesulfonyl chloride for ethanesulfonyl chloride, to afford the title compound (0.01 g, 12%). $^1$H NMR (300 MHz, DMSO-d$_6$) δ 12.42 (s, 1H), 11.41 (s, 1H), 10.48 (s, 1H), 8.06 (s, 1H), 7.45 (d, J=2.71 Hz, 1H), 7.27-7.34 (m, 2H), 7.21 (dd, J=8.82, 2.37 Hz, 1H), 7.01-7.08 (m, 2H), 6.93 (d, J=7.46 Hz, 2H), 4.58 (q, J=9.72 Hz, 2H), 2.59 (s, 3H). MS (ESI+) m/z 479 [M+H]$^+$.

Example 77

4-methyl-N-[2-(7-methyl-1-oxo-2,6-dihydro-1H-pyrrolo[3,4-d]pyridazin-5-yl)phenyl]benzenesulfonamide Example 77 was prepared according to the procedure used for the preparation of Example 74f, substituting 4-methyl-N-(2-(4,4,5,5-tetramethyl-1,3,2-dioxaborolan-2-yl)phenyl)benzenesulfonamide for Example 74e. Purification by reverse phase HPLC (C18, CH$_3$CN/water (0.1% TFA), 0-100% gradient) afforded the title compound as a TFA salt (0.007 g, 5%). $^1$H NMR (300 MHz, DMSO-d$_6$) δ 12.10 (s, 1H), 11.33 (s, 1H), 9.52 (s, 1H), 7.67 (s, 1H), 7.27-7.39 (m, 5H), 7.05-7.21 (m, 3H), 2.61 (s, 3H), 2.27 (s, 3H). MS (ESI+) m/z 395 [M+H]$^+$.

Example 78

5-[5-amino-2-(2,4-difluorophenoxy)phenyl]-7-methyl-2,6-dihydro-1H-pyrrolo[3,4-d]pyridazin-1-one

Example 78a 5-(2-fluoro-5-nitrophenyl)-7-methyl-2,6-dihydro-1H-pyrrolo[3,4-d]pyridazin-1-one Example 74b (100 mg, 0.439 mmol), 2-fluoro-5-nitrophenylboronic acid (122 mg, 0.658 mmol), sodium carbonate (209 mg, 1.97 mmol), tris(dibenzylideneacetone)dipalladium (12 mg, 0.013 mmol) and 1,3,5,7-tetramethyl-6-phenyl-2,4,8-trioxa-6-phosphaadamante (11.5 mg, 0.039 mmol) were combined and purged with nitrogen for 15 minutes. The mixture of dioxane (2 mL) and water (0.5 mL) was purged with nitrogen for 15 minutes and transferred to the reaction flask. The reaction mixture was heated at 60° C. for 4 hours. A small amount of water was added to the reaction mixture and the pH adjusted to 7 by addition of 1M HCl. The resulting solid was filtered, and triturated with 50% ethyl acetate/hexane to afford the title compound (108 mg, 85%).

Example 78b 5-(2-(2,4-difluorophenoxy)-5-nitrophenyl)-7-methyl-2,6-dihydro-1H-pyrrolo[3,4-d]pyridazin-1-one Example 78a (105 mg, 0.364 mmol), 2,4-difluorophenol (52.1 mg, 0.401 mmol) and cesium carbonate (356 mg, 1.09 mmol) were combined in dimethylformamide (2 mL). The reaction mixture was heated at 50° C. for 22 hours. The reaction mixture was partitioned with ethyl acetate and water. The organic layer was washed with saturated aqueous sodium chloride twice, dried over anhydrous sodium sulfate, filtered, and concentrated. The residue was triturated with a small amount of ethyl acetate to afford the title compound (96 mg, 66%).

Example 78c

5-[5-amino-2-(2,4-difluorophenoxy)phenyl]-7-methyl-2,6-dihydro-1H-pyrrolo[3,4-d]pyridazin-1-one A mixture of Example 78b (80 mg, 0.20 mmol) and 10% palladium on carbon (42.7 mg, 0.040 mmol) in ethyl acetate (20 mL) was treated with a balloon of hydrogen gas. The reaction mixture was stirred at ambient temperature for 16 hours. The solid was removed by filtration, and the filtrate was concentrated. The residue was purified by flash chromatography (silica gel, 2-6% methanol in dichloromethane) to afford the title compound (54 g, 73%). $^1$H NMR (300 MHz, DMSO-$d_6$) δ 12.35 (s, 1 H) 11.34 (s, 1 H) 8.00 (s, 1 H) 7.20-7.37 (m, 1 H) 6.85-6.97 (m, 1 H) 6.71-6.83 (m, 3 H) 6.59 (dd, J=8.73, 2.78 Hz, 1 H) 5.18 (s, 2 H) 2.56 (s, 3 H). MS (ESI+) m/z 369 (M+H)$^+$.

Example 79

N-[4-(2,4-difluorophenoxy)-3-(7-methyl-1-oxo-2,6-dihydro-1H-pyrrolo[3,4-d]pyridazin-5-yl)phenyl]ethanesulfonamide To a solution of Example 78c (40.5 mg, 0.110 mmol) and triethylamine (0.077 mL, 0.55 mmol) in the mixture of dichloromethane (2 mL) and tetrahydrofuran (2 mL) was added ethanesulfonyl chloride (0.038 mL, 0.40 mmol) dropwise. The reaction mixture was stirred at ambient temperature for 6 hours and concentrated. The residue was diluted with dioxane (2 mL) and 1M sodium hydroxide (1.1 mL), and heated at 50° C. for 1 hour. The reaction mixture was cooled to ambient temperature, diluted with water and ethyl acetate, adjusted the pH to 7 by addition of 1M HCl and separated. The organic layer was washed with saturated aqueous sodium chloride, dried over anhydrous sodium sulfate, filtered, and concentrated. The residue was purified by flash chromatography (silica gel, 1-5% methanol in dichloromethane) to afford the title compound (20 mg, 40%). $^1$H NMR (300 MHz, DMSO-$d_6$) δ 12.45 (s, 1 H) 11.45 (s, 1 H) 9.81 (s, 1 H) 8.04 (s, 1 H) 7.36-7.50 (m, 2 H) 7.13-7.27 (m, 2 H) 7.02-7.12 (m, 1 H) 6.88 (d, J=8.73 Hz, 1 H) 3.13 (q, J=7.14 Hz, 2 H) 2.63 (s, 3 H) 1.23 (t, J=7.34 Hz, 3 H). MS (ESI+) m/z 461 (M+H)$^+$.

Example 80

N-[4-(2,4-difluorophenoxy)-3-(7-methyl-1-oxo-2,6-dihydro-1H-pyrrolo[3,4-d]pyridazin-5-yl)phenyl]methanesulfonamide Example 80 was prepared according to the procedure used for the preparation of Example 79, substituting methanesulfonyl chloride for ethanesulfonyl chloride. Purification by flash chromatography (silica gel, 1-6% methanol in dichloromethane) afforded the title compound (30 mg, 75%). $^1$H NMR (300 MHz, DMSO-$d_6$) δ 12.45 (s, 1 H) 11.44 (s, 1 H) 9.73 (s, 1 H) 8.06 (s, 1 H) 7.39-7.48 (m, 2 H) 7.14-7.26 (m, 2 H) 7.03-7.12 (m, 1 H) 6.89 (d, J=8.82 Hz, 1 H) 3.03 (s, 3 H) 2.63 (s, 3 H). MS (ESI+) m/z 447 (M+H)$^+$.

Example 81

5-[2-(2,4-difluorophenoxy)-5-(methylsulfonyl)phenyl]-7-methyl-2,6-dihydro-1H-pyrrolo[3,4-d]pyridazin-1-one

Example 81a 2-(2-fluoro-5-(methylsulfonyl)phenyl)-4,4,5,5-tetramethyl-1,3,2-dioxaborolane 4,4,4',4',5,5,5',5'-octamethyl-2,2'-bi(1,3,2-dioxaborolane) (3.91 g, 15.41 mmol), 2-bromo-1-fluoro-4-(methylsulfonyl)benzene (2.6 g, 10.27 mmol), potassium acetate (2.016 g, 20.55 mmol), and 1,1'-bis(diphenylphosphino)ferrocene-palladium(II)dichloride dichloromethane complex (0.419 g, 0.514 mmol) were combined in dioxane (33.6 mL)/dimethyl sulfoxide (0.685 mL), sparged with argon for 30 minutes and heated at 90° C. under argon for 24 hours. The reaction mixture was partitioned between ethyl acetate and water and filtered through a plug of Celite to remove elemental Pd. The layers were separated and the organic layer was washed with saturated aqueous sodium chloride, dried (anhydrous sodium sulfate), treated with 3-mercaptopropyl functionalized silica gel for 15 minutes, filtered and concentrated. Purification by recrystallization from heptanes/ethyl acetate (9:1) afforded the title compound as amber crystals (1.77 g, 57%).

Example 81b 5-(2-fluoro-5-(methylsulfonyl)phenyl)-7-methyl-2,6-dihydro-1H-pyrrolo[3,4-d]pyridazin-1-one Example 81a (0.137 g, 0.456 mmol), Example 74b (0.08 g, 0.351 mmol), tris(dibenzylideneacetone)dipalladium(0)

(9.64 mg, 10.52 μmol), 1,3,5,7-tetramethyl-6-phenyl-2,4,8-trioxa-6-phosphaadamantane (10.25 mg, 0.035 mmol) and sodium carbonate (0.149 g, 1.403 mmol) were combined in a sealed tube and sparged with argon for 30 minutes. Meanwhile a solution of dioxane (1.604 mL) and water (0.401 mL) was sparged with nitrogen for thirty minutes and added to the solids. The mixture was stirred under argon at 60° C. for three hours, cooled, diluted with water and filtered to collect a dark tan solid. The solid was triturated in a minimal volume of ethyl acetate and filtered to afford the title compound (0.09 g, 80%).

Example 81c

5-[2-(2,4-difluorophenoxy)-5-(methylsulfonyl)phenyl]-7-methyl-2,6-dihydro-1H-pyrrolo[3,4-d]pyridazin-1-one 2,4-difluorophenol (0.039 g, 0.300 mmol), Example 81b (0.048 g, 0.15 mmol) and cesium carbonate (0.122 g, 0.375 mmol) were combined in dimethyl sulfoxide (1 mL) and heated by microwave at 120° C. for two hours. The mixture was cooled and partitioned between ethyl acetate and water adjusting the pH to 1 with 1 M HCl. The organic layer was washed with saturated aqueous sodium chloride, dried (anhydrous sodium sulfate), filtered and concentrated. Purification by chromatography (silica gel, eluting with 1-5% methanol in dichloromethane) afforded the title compound (0.007 g, 11%). $^1$H NMR (300 MHz, DMSO-$d_6$) δ 12.70 (s, 1H), 11.52 (s, 1H), 8.12 (s, 1H), 8.08 (d, J=2.38 Hz, 1H), 7.83 (dd, J=8.73, 1.98 Hz, 1H), 7.51-7.63 (m, 2H), 7.19-7.28 (m, 1H), 6.98 (d, J=8.73 Hz, 1H), 3.27 (s, 3H), 2.68 (s, 3H). MS (ESI+) m/z 432 [M+H]$^+$.

Example 82

4-(2,4-difluorophenoxy)-3-(7-methyl-1-oxo-2,6-dihydro-1H-pyrrolo[3,4-d]pyridazin-5-yl)benzonitrile

Example 82a 4-fluoro-3-(7-methyl-1-oxo-2,6-dihydro-1H-pyrrolo[3,4-d]pyridazin-5-yl)benzonitrile Example 82a was prepared according to the procedure used in Example 81b, substituting 5-cyano-2-fluorophenylboronic acid for Example 81a, to afford the title compound (0.290 g, 62%).

Example 82b 4-(2,4-difluorophenoxy)-3-(7-methyl-1-oxo-2,6-dihydro-1H-pyrrolo[3,4-d]pyridazin-5-yl)benzonitrile 2,4-difluorophenol (0.087 g, 0.671 mmol), Example 82a (0.06 g, 0.224 mmol) and cesium carbonate (0.219 g, 0.671 mmol) were combined in dimethyl sulfoxide (2 mL) and heated at 100° C. for three hours. The mixture was cooled and partitioned between ethyl acetate and water adjusting the pH to 6 with 1 M HCl. The organic layer was washed with saturated aqueous sodium chloride, dried (anhydrous sodium sulfate), filtered and concentrated. Purification by chromatography (silica gel, eluting with 1-4% methanol in dichloromethane) afforded the title compound (0.032 g, 38%). $^1$H NMR (300 MHz, DMSO-$d_6$) δ 12.60 (s, 1H), 11.49 (s, 1H), 8.11 (s, 1H), 8.06 (d, J=2.03 Hz, 1H), 7.76 (dd, J=8.82, 2.03 Hz, 1H), 7.49-7.62 (m, 2H), 7.13-7.30 (m, 1H), 6.92 (d, J=8.48 Hz, 1H), 2.66 (s, 3H). MS (ESI+) m/z 379 [M+H]$^+$.

Example 83

7-methyl-5-[4-(3-methyl-1H-pyrazol-5-yl)phenyl]-2,6-dihydro-1H-pyrrolo[3,4-d]pyridazin-1-one Example 74b (50 mg, 0.22 mmol), Example 8a (75 mg, 0.26 mmol), sodium carbonate (105 mg, 0.99 mmol), tris(dibenzylideneacetone)dipalladium (6 mg, 0.007 mmol) and 1,3,5,7-tetramethyl-6-phenyl-2,4,8-trioxa-6-phosphaadamante (5.8 mg, 0.020 mmol) were combined and purged with nitrogen for 15 minutes. The mixture of dioxane (2 mL) and water (0.5 mL) was purged with nitrogen for 15 minutes and transferred to the reaction flask. The reaction mixture was heated at 60° C. for 4 hours. The reaction mixture was partitioned between ethyl acetate and water. The organic layer was washed with saturated aqueous sodium chloride, dried over anhydrous sodium sulfate, treated with 3-mercaptopropyl functionalized silica gel, filtered, and concentrated. The residue was purified by reverse phase HPLC (C8, CH$_3$CN/water (10 mM ammonium carbonate), 30-60%) to afford the title compound (30 mg, 45%). $^1$H NMR (300 MHz, DMSO-$d_6$) δ 12.52 (s, br, 1 H) 11.46 (s, 1 H) 8.31 (s, 1 H) 7.80-7.88 (m, 2 H) 7.68-7.77 (m, 2 H) 6.49 (s, 1 H) 2.65 (s, 3 H) 2.26 (s, 3 H). MS (ESI+) m/z 306 (M+H)$^+$.

Example 84

5-{2-[(cyclopropylmethyl)amino]-5-(ethylsulfonyl)phenyl}-7-methyl-2,6-dihydro-1H-pyrrolo[3,4-d]pyridazin-1-one

Example 84a (3-bromo-4-fluorophenyl)(ethyl)sulfane

A mixture of 3-bromo-4-fluorobenzenethiol (3.89 g, 18.8 mmol) and 5M sodium hydroxide (3.95 mL, 19.7 mmol) in methanol (40 mL) was stirred at 0° C. for 10 minutes. To this solution was added iodoethane (1.803 mL, 22.54 mmol). The reaction mixture was stirred at ambient temperature for 6 hours. The solvent was removed, and the residue was partitioned between water and ethyl acetate. The aqueous layer was extracted with addition ethyl acetate three times. The combined organic layers were washed with saturated aqueous sodium chloride, dried over anhydrous magnesium sulfate, filtered, and concentrated to give the title compound (4.35 g, 98%). It was used directly for the next reaction.

Example 84b 2-bromo-4-(ethylsulfonyl)-1-fluorobenzene

Example 84a (4.4 g, 18.7 mmol) in dichloromethane (250 mL) was cooled to 0° C. To this solution was added mCPBA (10.2 g, 41.2 mmol) portionwise. The reaction mixture was stirred at ambient temperature for 6 hours. The solid from the reaction mixture was removed by filtration. The filtrate was washed with saturated aqueous sodium bicarbonate several times. The aqueous layer was then extracted with additional dichloromethane three times. The combined organic layers were washed with saturated aqueous sodium chloride, dried over anhydrous magnesium sulfate, filtered, and concentrated. The residue was purified by flash chromatography (silica gel, 15% ethyl acetate in hexanes) to afford the title compound (4.4 g, 88%).

Example 84c 2-bromo-N-(cyclopropylmethyl)-4-(ethylsulfonyl) aniline

A mixture of Example 84b (0.534 g, 2.00 mmol) and cyclopropylmethanamine (0.427 g, 6.00 mmol) in dioxane (5 mL) was heated at 100° C. for overnight. The reaction mixture was cooled to ambient temperature and filtered to remove the solid. The filtrate was concentrated. The residue was purified by flash chromatography (silica gel, 40% ethyl acetate in hexanes) to afford the title compound (0.63 g, 99%).

Example 84d

N-(cyclopropylmethyl)-4-(ethylsulfonyl)-2-(4,4,5,5-tetramethyl-1,3,2-dioxaborolan-2-yl)aniline Example 84d was prepared according to the procedure used for the preparation of Example 8a, substituting Example 84c for 5-(4-bromophenyl)-3-methyl-1H-pyrazole and the reaction time was 22 hours instead of 2 hours. Purification by flash chromatography (silica gel, 10-20% ethyl acetate in heptanes) and trituration with heptanes afforded the title compound (90 mg, 62%).

Example 84e

5-{2-[(cyclopropylmethyl)amino]-5-(ethylsulfonyl) phenyl}-7-methyl-2,6-dihydro-1H-pyrrolo[3,4-d] pyridazin-1-one Example 84e was prepared according to the procedure used for the preparation of Example 83, substituting 84d for 8a, to provide the title compound (13 mg, 21%). $^1$H NMR (300 MHz, DMSO-$d_6$) δ 12.51 (s, 1 H) 11.43 (s, 1 H) 7.85 (s, 1 H) 7.63 (dd, J=8.73, 2.38 Hz, 1 H) 7.48 (d, J=1.98 Hz, 1 H) 6.90 (d, J=8.73 Hz, 1 H) 5.94 (s, 1 H) 3.18 (q, J=7.14 Hz, 2 H) 3.06 (t, J=6.15 Hz, 2 H) 2.64 (s, 3 H) 0.99-1.17 (m, 4 H) 0.35-0.50 (m, 2 H) 0.16-0.27 (m, 4.89 Hz, 2 H). MS (ESI+) m/z 387 (M+H)$^+$.

Example 85

5-methyl-7-(2-phenoxyphenyl)-3,6-dihydro-4H-pyrrolo[3,4-d]pyrimidin-4-one

Example 85a 2-amino-2-(2-phenoxyphenyl)acetonitrile

A solution of 2-phenoxybenzaldehyde (1.0 g, 5.04 mmol) in methanol (10 mL) was added to a solution of sodium cyanide (0.297 g, 6.05 mmol) and ammonium chloride (0.494 g, 9.23 mmol) in ammonium hydroxide (10 mL, 85 mmol) at 0° C. The reaction mixture was stirred at ambient temperature for 4 hours. The reaction mixture was concentrated by rotary evaporation. The residue was taken up in water and extracted with dichloromethane (2×). The combined organics were washed with water, dried over anhydrous sodium sulfate, filtered, and concentrated. The crude product was purified by flash chromatography (silica gel, 50% ethyl acetate in hexanes) to provide the title compound (1.065 g, 94% yield).

Example 85b (E)-ethyl 3-((cyano(2-phenoxyphenyl)methyl)amino) but-2-enoate

A mixture of Example 85a (1.063 g, 4.74 mmol), ethyl acetoacetate (0.602 mL, 4.74 mmol), and p-toluenesulfonic acid (0.05 g, 0.263 mmol) in toluene (10 mL) was heated at 80° C. for 4 hours. The reaction mixture was cooled to 0° C. and added to cold saturated NaHCO$_3$. The mixture was extracted with ethyl acetate (2×). The combined organics were dried over anhydrous sodium sulfate, filtered, and concentrated to give the title compound (1.57 g, 98% yield) which was used without purification.

Example 85c 4-(ethoxycarbonyl)-5-methyl-2-(2-phenoxyphenyl)-1H-pyrrol-3-aminium chloride A sodium ethoxide solution was prepared by adding sodium (0.118 g, 5.13 mmol) to anhydrous ethanol (8 mL). The solution was cooled to 0° C., and a solution of Example 85b (1.57 g, 4.67 mmol) in ethanol (8 mL) was added. The reaction mixture was allowed to stand overnight at ambient temperature. The reaction mixture was cooled to 0° C. Hydrochoric acid (5.02 mL, 10.03 mmol) (2M in ether) was added with stirring. A precipitate formed. The mixture was diluted with ether to further precipitate product. The solid was collected by vacuum filtration and washed with ether to provide the title compound as the hydrochloride salt+sodium chloride (1.7 g, 84% yield).

Example 85d 5-methyl-7-(2-phenoxyphenyl)-3,6-dihydro-4H-pyrrolo[3,4-d]pyrimidin-4-one A mixture of Example 85c (0.1 g, 0.232 mmol) and formamidine acetate (0.072 g, 0.696 mmol) in ethanol (0.6 mL) was heated at 80° C. for 2 hours. The reaction mixture was concentrated. The crude material was purified by flash chromatography (silica gel, 5% methanol in 1:1 hexanes/dichloromethane) to give the title compound (0.039 g, 53% yield).
$^1$H NMR (300 MHz, DMSO-$d_6$) δ 11.77 (s, 1 H), 11.02 (s, 1 H), 8.17-8.21 (m, 1 H), 7.56 (d, J=3.39 Hz, 1 H), 7.29-7.37 (m, 2 H), 7.15-7.27 (m, 2 H), 7.03-7.12 (m, 1 H), 6.97-7.02 (m, 2 H), 6.91-6.96 (m, 1 H), 2.50-2.60 (m, 3 H). MS (ESI+) m/z 318.2 (M+H)$^+$.

Example 86

5-methyl-4-oxo-7-(2-phenoxyphenyl)-4,6-dihydro-3H-pyrrolo[3,4-d]pyrimidine-2-carboxylic acid A mixture of Example 85c (0.05 g, 0.116 mmol) and ethyl cyanoformate (0.013 mL, 0.128 mmol) in 4M HCl in dioxane (0.25 mL, 1.000 mmol) was stirred at ambient temperature overnight. The solvent was evaporated under a stream of nitrogen. The residue was taken up in water and dioxane, and sodium carbonate (0.037 g, 0.348 mmol) was added. The reaction mixture was stirred at ambient temperature. Solvent was evaporated under a stream of nitrogen. The residue was taken up in methanol. The mixture was filtered, and the crude product was purified by reverse phase HPLC (10-70% acetonitrile in 0.1% aq TFA) to provide the title compound (0.018 g, 43% yield). $^1$ H NMR (300 MHz, DMSO-d$_6$) δ 12.12 (s, 1 H), 10.88 (s, 1 H), 8.10 (dd, J=7.54, 1.98 Hz, 1 H), 7.22-7.36 (m, 4 H), 7.05-7.12 (m, 1 H), 7.00-7.05 (m, 2 H), 6.95 (dd, J=8.13, 1.39 Hz, 1 H), 2.57 (s, 3 H). MS (ESI+) m/z 362.1 (M+H)$^+$.

Example 87 ethyl 5-methyl-4-oxo-7-(2-phenoxyphenyl)-4,6-dihydro-3H-pyrrolo[3,4-d]pyrimidine-2-carboxylate A mixture of Example 85c (0.05 g, 0.116 mmol) and ethyl cyanoformate (0.013 mL, 0.128 mmol) in 4M HCl in dioxane (0.25 mL, 1.000 mmol) was stirred at ambient temperature overnight. The solvent was evaporated under a stream of nitrogen. The residue was taken up in dimethylformamide (0.5 mL). The reaction mixture was heated at 80° C. for 2 hours and then stirred at ambient temperature 2 days. Water was added. The precipitate was collected by vacuum filtration and washed with water. The crude material was purified by reverse phase HPLC (10-100% acetonitrile in 0.1% aq TFA) to give the title compound (0.015 g, 33% yield). $^1$ H NMR (300 MHz, DMSO-d$_6$) δ 12.17 (s, 1 H), 11.08 (s, 1 H), 8.01 (dd, J=7.46, 2.03 Hz, 1 H), 7.31-7.37 (m, 2 H), 7.21-7.33 (m, 2 H), 7.09 (t, J=7.29 Hz, 1 H), 7.03 (d, J=7.80 Hz, 2 H), 6.94 (dd, J=8.14, 1.36 Hz, 1 H), 4.32 (q, J=7.12 Hz, 2 H), 2.58 (s, 3H), 1.32 (t, J=7.12 Hz, 3 H). MS (ESI+) m/z 390.1 (M+H)$^+$.

Example 88

2-(furan-2-yl)-5-methyl-7-(2-phenoxyphenyl)-3,6-dihydro-4H-pyrrolo[3,4-d]pyrimidin-4-one A mixture of Example 85c (0.05 g, 0.116 mmol) and 2-furonitrile (10.16 μL, 0.116 mmol) in 4M HCl in dioxane (0.25 mL, 1.000 mmol) was stirred at ambient temperature overnight. The solvent was evaporated under a stream of nitrogen. The residue was taken up in dimethylformamide (1 mL), and Na$_2$CO$_3$ (0.012 g, 0.116 mmol) and water (0.25 mL) were added. The reaction mixture was stirred at ambient temperature overnight. Water was added. The precipitate was collected by vacuum filtration and washed with water. The crude material was purified by reverse phase HPLC (20-100% acetonitrile in 0.1% aq TFA) to give the title compound (0.027 g, 60.7% yield). $^1$ H NMR (300 MHz, DMSO-d$_6$) δ 11.83 (s, 1 H), 11.20 (s, 1 H), 8.22 (dd, J=6.10, 3.39 Hz, 1 H), 7.89 (d, J=1.70 Hz, 1 H), 7.41 (d, J=3.73 Hz, 1 H), 7.34 (t, J=7.80 Hz, 2 H), 7.24-7.28 (m, 2 H), 7.00-7.12 (m, 3 H), 6.92-6.98 (m, 1H), 6.66 (dd, J=3.39, 1.70 Hz, 1 H), 2.57 (s, 3 H). MS (ESI+) m/z 384.2 (M+H)$^+$.

Example 89

2,5-dimethyl-7-(2-phenoxyphenyl)-3,6-dihydro-4H-pyrrolo[3,4-d]pyrimidin-4-one

A mixture of Example 85c and acetonitrile (0.024 mL, 0.464 mmol) in 4M HCl in dioxane (0.25 mL, 1.000 mmol) was stirred at ambient temperature overnight. Another 48 μL of acetonitrile was added, and the reaction mixture was stirred overnight. The solvent was evaporated under a stream of nitrogen. The residue was taken up in dimethylformamide (1 mL). The slurry was heated at 80° C. for 2 hours. To the reaction mixture was added Na$_2$CO$_3$ (0.012 g, 0.116 mmol) and water (0.250 mL). The reaction mixture was stirred at ambient temperature overnight. Water was added. The precipitate was collected by vacuum filtration and washed with water. The crude material was purified by reverse phase HPLC (20-100% acetonitrile in 0.1% aq TFA) to give the title compound (0.026 g, 67.7% yield). $^1$ H NMR (300 MHz, CD$_3$OD) δ 7.61 (dd, J=7.46, 1.70 Hz, 1 H), 7.44-7.51 (m, 1 H), 7.30-7.36 (m, 1 H), 7.20-7.26 (m, 2 H), 7.14 (dd, J=8.14, 1.02 Hz, 1 H), 6.97-7.03 (m, 1 H), 6.79-6.84 (m, 2 H), 2.61 (s, 3 H), 2.60 (s, 3 H). MS (ESI+) m/z 3322 (M+H)$^+$.

Example 90

7-(5-amino-2-phenoxyphenyl)-5-methyl-3,6-dihydro-4H-pyrrolo[3,4-d]pyrimidin-4-one Example 90a 5-nitro-2-phenoxybenzaldehyde A mixture of 2-fluoro-5-nitrobenzaldehyde (1.0 g, 5.91 mmol), phenol (0.557 g, 5.91 mmol), and K$_2$CO$_3$ (1.635 g, 11.83 mmol) in dioxane (6 mL) was heated at 70° C. overnight. The reaction mixture was cooled to ambient temperature and diluted with ethyl acetate (60 mL). The solution was washed with water (2×30 mL) and saturated aqueous sodium chloride. The organic layer was dried over sodium sulfate, filtered, and concentrated by rotary evaporation to give the title compound (1.43 g, 99% yield).

Example 90b 2-amino-2-(5-nitro-2-phenoxyphenyl)acetonitrile

Example 90b was prepared according to the procedure used for the preparation of Example 85a, substituting Example 90a (1.43 g, 5.88 mmol) for 2-phenoxybenzaldehyde. The crude material was purified by flash chromatography (silica gel, 20-50% ethyl acetate in hexanes) to give the title compound (0.450 g, 28.4% yield).

Example 90c (E)-ethyl 3-((cyano(5-nitro-2-phenoxyphenyl)methyl)amino)but-2-enoate Example 90c was prepared according to the procedure used for the preparation of Example 85b, substituting Example 90b (0.430 g, 1.597 mmol) for Example 85a to provide the title compound (0.6 g, 99% yield).

Example 90d 4-(ethoxycarbonyl)-5-methyl-2-(5-nitro-2-phenoxyphenyl)-1H-pyrrol-3-aminium chloride Example 90d was prepared according to the procedure used for the preparation of Example 85c, substituting Example 90c (0.6 g, 1.573 mmol) for Example 85b to provide the title compound (0.330 g, 44% yield).

Example 90e 5-methyl-7-(5-nitro-2-phenoxyphenyl)-3H-pyrrolo[3,4-d]pyrimidin-4(6H)-one Example 90e was prepared according to the procedure used for the preparation of Example 85d, substituting Example 90d (0.277 g, 0.582 mmol) for Example 85c to provide the title compound (0.080 g, 38% yield).

Example 90f

7-(5-amino-2-phenoxyphenyl)-5-methyl-3,6-dihydro-4H-pyrrolo[3,4-d]pyrimidin-4-one A slurry of Example 90e (0.078 g, 0.215 mmol) and 10% Pd-C (0.046 g, 0.043 mmol) in methanol (5 mL) was heated at 50° C. under an atmosphere of hydrogen (H$_2$ balloon) for 4 hours. The reaction mixture was flushed with nitrogen and filtered through Celite. The filtrate was concentrated by rotary evaporation. The crude material was purified by flash chromatography (silica gel, 5% methanol in ethyl acetate) to give the title compound (0.056 g, 78% yield). $^1$H NMR (300 MHz, DMSO-d$_6$) δ 11.66 (s, 1 H), 10.94 (s, 1 H), 7.49 (s, 1 H), 7.31 (d, J=2.78 Hz, 1 H), 7.18 (dd, J=8.73, 7.14 Hz, 2 H), 6.84-6.91 (m, 1 H), 6.76-6.83 (m, 3 H), 6.49 (dd, J=8.73, 2.78 Hz, 1 H), 5.03 (s, 2 H), 2.48 (s, 3 H). MS (ESI+) m/z 333.2 (M+H)$^+$.

Example 91

N-[3-(5-methyl-4-oxo-4,6-dihydro-3H-pyrrolo[3,4-d]pyrimidin-7-yl)-4-phenoxyphenyl]methanesulfonamide To a solution/suspension Example 90f (0.053 g, 0.159 mmol) in dichloromethane (2 mL) at 0° C. were added triethylamine (0.067 mL, 0.478 mmol) and methanesulfonyl chloride (0.030 mL, 0.383 mmol). The reaction mixture was stirred at ambient temperature for 1 hour. The solvent was evaporated under a stream of nitrogen. The residue was partitioned between ethyl acetate and water and stirred at ambient temperature for 30 minutes until all solids dissolved. The layers were separated, and the organic layer was washed with saturated aqueous sodium chloride, dried over anhydrous sodium sulfate, filtered, and concentrated. The residue was taken up in dioxane (0.8 mL). Aqueous 1M sodium hydroxide (1.595 mL, 1.595 mmol) was added. The mixture was heated at 50° C. for 1 hour. The solvent was evaporated under a stream of nitrogen. The residue was partitioned between ethyl acetate and aqueous saturated ammonium chloride and stirred at ambient temperature 30 minutes until all solids dissolved. The layers were separated, and the organic layer was washed with saturated aqueous sodium chloride, dried over anhydrous sodium sulfate, filtered, and concentrated. The crude material was filtered through a plug of silica gel (5% methanol in dichloromethane). The solid obtained was triturated from 2% methanol in dichloromethane to provide the title compound (0.008 g, 12.3% yield). $^1$H NMR (300 MHz, DMSO-d$_6$) δ 11.82 (s, 1 H), 11.05 (s, 1 H), 9.71 (s, 1 H), 8.00 (d, J=2.38 Hz, 1 H), 7.56 (d, J=3.57 Hz, 1 H), 7.25-7.35 (m, 2H), 7.07-7.13 (m, 1 H), 7.04 (t, J=7.34 Hz, 1 H), 6.92-6.99 (m, Hz, 3 H), 3.03 (s, 3 H), 2.54 (s, 3H). MS (ESI+) m/z 411.2 (M+H)$^+$.

Example 92

3-methyl-1-(2-phenoxyphenyl)-2,5,6,7-tetrahydro-4H-pyrrolo[3,4-c]pyridin-4-one

Example 92a methyl 3-(N-(4-methoxybenzyl)-3-oxobutanamido)propanoate

A flask with stirbar was charged with 2,5-dioxopyrrolidin-1-yl 3-oxobutanoate (6.47 g, 32.5 mmol), methyl 3-(4-methoxybenzylamino)propanoate (prepared as described in Bew, S. et al, Chem Commun. 2006 (41), 4338-40, 7.7 g, 34.5 mmol) and triethylamine (5 mL, 35.9 mmol) in dichloromethane (125 mL). The solution was stirred overnight at ambient temperature, then shaken in a separatory funnel with saturated aqueous sodium chloride. The organics were then washed with saturated aqueous sodium chloride containing 0.1M HCl and dried over anhydrous sodium sulfate. Filtration and solvent removal provided the title compound.

Example 92b

3-acetyl-1-(4-methoxybenzyl)piperidine-2,4-dione

A flask with stirbar and reflux condenser was charged with Example 92a (9.96 g, 32.4 mmol) in toluene (120 mL). Sodium methoxide (1.75 g, 32.4 mmol) in methanol (30 mL) was added, and the mixture heated in an 85° C. oil bath for 18 hours. The mixture was acidified with 4 mL concentrated HCl and then shaken in a separatory funnel with 250 mL each of ethyl acetate and saturated aqueous sodium chloride. The organics were dried over anhydrous magnesium sulfate. Filtration and solvent removal gave a yellow oil which was chromatographed on a 330 g silica cartridge eluting with 5-70% ethyl acetate/hexanes to provide the title compound.

Example 92c ethyl 5-(4-methoxybenzyl)-3-methyl-4-oxo-4,5,6,7-tetrahydro-2H-pyrrolo[3,4-c]pyridine-1-carboxylate A flask with stirbar and reflux condenser was charged with Example 92b (5.06 g, 18.38 mmol), diethyl 2-aminomalonate, hydrochloric acid salt (4.46 g, 21.07 mmol) and sodium acetate (4.65 g, 56.7 mmol) in acetic acid (40 mL). The well-stirred mixture was placed in an 125° C. oil bath. After 4 days, the mixture was cooled and concentrated by rotovap. The residues were shaken in a separatory funnel with 250 mL each of saturated aqueous sodium chloride and ethyl acetate. The organics were washed with aqueous sodium hydroxide and dried over anhydrous magnesium sulfate. Filtration and solvent removal gave a red-brown oil which was adsorbed on silica and chromatographed on a 330 g silica gel cartridge eluting with 10-100% ethyl acetate/hexanes to provide the title compound as the second eluting isomer.

Example 92d ethyl 3-methyl-4-oxo-4,5,6,7-tetrahydro-2H-pyrrolo[3,4-c]pyridine-1-carboxylate A flask with stirbar and reflux condenser was charged with Example 92c (0.52 g, 1.519 mmol) in TFA (18.00 mL) and anisole (2 mL). The solution was heated at 70° C. for 3 hours, cooled and concentrated by rotovap. The residues were partitioned between dichloromethane (2×125 mL) and aqueous sodium bicarbonate (100 mL). The organics were dried over anhydrous sodium sulfate. Filtration, solvent removal and vacuum drying provided the title compound.

Example 92e

3-methyl-6,7-dihydro-2H-pyrrolo[3,4-c]pyridin-4(5H)-one

A flask with stirbar was charged with Example 92d (0.338 g, 1.521 mmol) and lithium hydroxide monohydrate (0.281 g, 6.70 mmol) in tetrahydrofuran (10 mL) and water (5.00 mL). The mixture was stirred in a 60° C. oil bath for 16 hours. The reaction vessel was removed from the oil bath and acidified with 0.6 mL of TFA, then concentrated under reduced pressure and vacuum dried. The residues were adsorbed on silica, then chromatographed on a 40 g silica gel cartridge eluting with 0-10% methanol/dichloromethane to provide the title compound.

Example 92f 1-bromo-3-methyl-6,7-dihydro-2H-pyrrolo[3,4-c]pyridin-4(5H)-one

A flask with stirbar was charged with Example 92e (0.228 g, 1.52 mmol) in tetrahydrofuran (10 mL) and cooled to −78° C. under nitrogen. Recrystallized N-bromosuccinimide (0.328 g, 1.843 mmol) was added and the mixture was stirred for 50 minutes. The reaction mixture was poured into a separatory funnel containing aqueous sodium sulfite and extracted into 50 mL ether. The organics were washed with aqueous sodium bicarbonate and dried over anhydrous magnesium sulfate. After filtration and solvent removal the residue was chromatographed on a 40 g silica gel cartridge and eluting with 10% methanol/dichloromethane to provide the title compound.

Example 92g 3-methyl-1-(2-phenoxyphenyl)-6,7-dihydro-2H-pyrrolo[3,4-c]pyridin-4(5H)-one A 2 mL microwave reaction vessel equipped with stirbar was charged with Example 92f (0.010 g, 0.044 mmol), 2-phenoxyphenylboronic acid (0.023 g, 0.109 mmol), 2 M aqueous sodium carbonate (0.218 mL, 0.437 mmol) and bis(triphenylphosphine)palladium(II) dichloride (3.06 mg, 4.37 µmol) in ethanol (0.200 mL)/DME (0.200 mL) and sealed. The mixture was heated at 120° C. for 30 minutes in a Biotage Initiator 2 monomode microwave reactor, then cooled to ambient temperature. The mixture was shaken in a separatory funnel with 75 mL ethyl acetate and 50 mL saturated aqueous sodium chloride. The organics were dried over anhydrous sodium sulfate. After filtration and solvent removal the residue was purified by reverse phase HPLC (C18, 0-100% $CH_3CN$/water (0.1% TFA)) to afford the title compound (7.3 mg, 53%). $^1$H NMR (300 MHz, $CD_3OD$) δ 10.74 (bds, 1H), 7.42 (dd, J=1.9, 7.6 Hz, 1H), 7.31-7.18 (m, 4H), 7.02-6.96 (m, 2H), 6.85 (m, 2H), 3.36 (m, 2H), 2.73 (m, 2H), 2.44 (s, 3H). MS (ESI+) m/z 319.2 $(M+H)^+$.

Example 93

N-[4-(2,4-difluorophenoxy)-3-(3-methyl-4-oxo-4,5,6,7-tetrahydro-2H-pyrrolo[3,4-c]pyridin-1-yl)phenyl]methanesulfonamide Example 93a ethyl 2-methyl-1-(triisopropylsilyl)-1H-pyrrole-3-carboxylate A solution of ethyl 2-methyl-1H-pyrrole-3-carboxylate (purchased from Beta Pharma Scientific, 9.91 g, 64.7 mmol) in tetrahydrofuran (200 mL) at 0° C. under $N_2$ was treated portionwise with sodium hydride (dry, 95%) (2.06 g, 82 mmol). The resulting mixture was stirred for 20 minutes and treated with triisopropylchlorosilane (16.5 mL, 78 mmol). The mixture was stirred for 30 minutes, then the ice bath was removed. After warming to ambient temperature over 90 minutes, the mixture was partitioned between ethyl acetate and water. The organic layer was washed with saturated aqueous sodium chloride, dried (anhydrous magnesium sulfate) filtered and concentrated. Purification by chromatography on a 330 g silica cartridge eluting with 0-20% ethyl acetate in hexane afforded the title compound.

Example 93b ethyl 4-formyl-2-methyl-1H-pyrrole-3-carboxylate

N,N-Dimethylformamide (3.35 mL, 43.2 mmol) in dichloromethane (80 mL) at 0° C. was treated dropwise with oxalyl chloride (3.66 mL, 43.2 mmol). The mixture was stirred at 0° C. for 30 minutes and then at ambient temperature for 1 hour. The mixture was then cooled to 0° C. and Example 93a (12.16 g, 39.3 mmol) in dichloromethane (80 mL) was added dropwise by addition funnel. The reaction mixture was allowed to warm to ambient temperature for 60 hours. The mixture was then heated at reflux for 24 hours. The reaction mixture was then cooled to 0° C. and quenched slowly with 60 mL of 1 N NaOH solution. The mixture was then diluted with water (300 mL) and extracted with ethyl acetate (2×300 mL). The combined organic layers were washed with saturated aqueous sodium chloride, dried (anhydrous magnesium sulfate), filtered and concentrated and slurried in 35 mL of a mixture of 9:1 heptane/ethyl acetate. The solids were collected by filtration and vacuum dried to provide the title compound. Chromatography of the concentrated filtrate on a 220 g silica gel cartridge eluting with 10 to 90% ethyl acetate/heptane to provided additional title compound.

Example 93c ethyl 4-formyl-2-methyl-1-((2-(trimethylsilyl)ethoxy)methyl)-1H-pyrrole-3-carboxylate A solution of Example 93b (8.826 g, 48.7 mmol) in tetrahydrofuran (325 mL) was chilled in an ice bath and treated with sodium hydride (dry, 95%) (2.454 g, 97 mmol) added portionwise over 15 minutes. The mixture was stirred under $N_2$ for 10 minutes and treated with (2-(chloromethoxy)ethyl)trimethylsilane (12 mL, 67.8 mmol), then stirred for 50 minutes. The reaction vessel was removed from the ice bath and allowed to warm to ambient temperature. The reaction mixture was carefully quenched with 200 mL of saturated aqueous ammonium chloride, reduced in volume by rotovap and shaken in a separatory funnel with 350 mL each of ethyl acetate and water. The organic layer was washed with saturated aqueous sodium chloride, dried (anhydrous magnesium sulfate), filtered and concentrated. The crude material was chromatographed on a 330 g silica gel cartridge eluting with 0-50% ethyl acetate/heptane to provide the title compound.

Example 93d (E)-ethyl 2-methyl-4-(2-nitrovinyl)-1-((2-(trimethylsilyl)ethoxy)methyl)-1H-pyrrole-3-carboxylate A 200 mL recovery flask with stirbar and condenser was charged with Example 93c (3.94 g, 12.65 mmol) and ammonium acetate (0.44 g, 5.71 mmol) in nitromethane (45 mL). The mixture was heated at 90° C. for 60 minutes in an oil bath, then cooled to ambient temperature. The crude reaction mixture was concentrated by rotovap, giving a dark yellow oil which was adsorbed on silica gel and chromatographed on a 150 g silica gel cartridge eluting with 0-40% ethyl acetate/heptane to provide the title compound.

Example 93e ethyl 4-(2-aminoethyl)-2-methyl-1-((2-(trimethylsilyl)ethoxy)methyl)-1H-pyrrole-3-carboxylate Example 93d (3.83 g, 10.80 mmol) and tetrahydrofuran (150 mL) were added to a Ra—Ni 2800, water slurry (38.3 g, 653 mmol) in a 250 mL stainless steel pressure bottle and stirred for 16 hours at 30 psi of hydrogen and ambient temperature. The mixture was filtered through a nylon membrane, stripped down and vacuum dried to provide the title compound.

Example 93f 3-methyl-2-((2-(trimethylsilyl)ethoxy)methyl)-6,7-dihydro-2H-pyrrolo[3,4-c]pyridin-4(5H)-one A solution of Example 93e (3.36 g, 10.29 mmol) and lithium hydroxide monohydrate (3.17 g, 76 mmol) in ethanol (47.5 mL) and water (2.5 mL) was added to 100 mL microwave reaction vessel with stir bar. The mixture was heated at 120° C. for 30 minutes in a Ethos Microsynth multimode microwave reactor (Milestone Inc.), then cooled to ambient temperature. The reaction mixture was added to 200 mL water and stirred for 15 minutes. The mixture extracted with 3×200 mL 10% methanol/dichloromethane and the combined dichloromethane extracts dried over anhydrous sodium sulfate. Filtration and solvent removal provided a brown oil which was chromatographed on a 40 g silica cartridge eluting with 0-10% methanol/dichloromethane to provide the title compound.

Example 93g 1-bromo-3-methyl-2-((2-(trimethylsilyl)ethoxy)methyl)-6,7-dihydro-2H-pyrrolo[3,4-c]pyridin-4(5H)-one A flask with stirbar was charged Example 93f (0.651 g, 2.321 mmol) in tetrahydrofuran (6 mL) and cooled to −78° C. A solution of N-bromosuccinimide (0.519 g, 2.92 mmol) in tetrahydrofuran (6.00 mL) was added in six portions about a minute apart, then the mixture was stirred for 60 minutes. The reaction mixture was poured into a separatory funnel containing aqueous sodium sulfite and extracted into 100 mL ethyl acetate. The organics were washed with aqueous sodium bicarbonate, concentrated and chromatographed on a 12 g silica cartridge eluting with 0-100% ethyl acetate/heptane to provide the title compound.

Example 93h 1-(2-fluoro-5-nitrophenyl)-3-methyl-2-((2-(trimethylsilyl)ethoxy)methyl)-6,7-dihydro-2H-pyrrolo[3,4-c]pyridin-4(5H)-one 2-fluoro-5-nitrophenylboronic acid (0.134 g, 0.725 mmol), tris(dibenzylidineacetone)dipalladium(0) (0.0157 g, 0.017 mmol), 1,3,5,7-tetramethyl-6-phenyl-2,4,8-trioxa-6-phosphaadamantane (0.0165 g, 0.056 mmol) and tris-potassium phosphate (0.280 g, 1.319 mmol) were combined in a sealed 5 mL microwave tube with stir bar and sparged with nitrogen for 15 minutes. A solution of Example 93g (0.173 g, 0.481 mmol) in a degassed mixture of 4:1 dioxane/water (5.0 mL) was added by syringe into the reaction vessel which was heated at 110° C. for 25 minutes in a Biotage Initiator 2 monomode microwave reactor, then cooled to ambient temperature. The reaction mixture was shaken in a separatory funnel with 75 mL ethyl acetate and 40 mL saturated aqueous sodium chloride. The organics were dried over anhydrous sodium sulfate. Filtration and solvent removal gave a yellow oil which was chromatographed on a 40 g silica gel cartridge eluting with 0-100% ethyl acetate/heptane to provide the title compound.

Example 93i 1-(2-(2,4-difluorophenoxy)-5-nitrophenyl)-3-methyl-2-((2-(trimethylsilyl)ethoxy)methyl)-6,7-dihydro-2H-pyrrolo[3,4-c]pyridin-4(5H)-one A flask with stirbar was charged with Example 93h (0.075 g, 0.179 mmol), 2,4-difluorophenol (25 µL, 0.262 mmol) and cesium carbonate (0.118 g, 0.362 mmol) in dimethyl sulfoxide (2 mL) and stirred at 50° C. for 45 minutes. The reaction mixture was diluted with ethyl acetate then washed twice with saturated aqueous sodium chloride and dried over anhydrous sodium sulfate. Filtration and solvent removal provided the title compound.

Example 93j 1-(5-amino-2-(2,4-difluorophenoxy)phenyl)-3-methyl-2-((2-(trimethylsilyl)ethoxy)methyl)-6,7-dihydro-2H-pyrrolo[3,4-c]pyridin-4(5H)-one Example 93i (0.095 g, 0.179 mmol) in ethanol (2 mL) and tetrahydrofuran (2 mL) at 65° C. was treated sequentially with iron powder (<10 micron, 0.096 g, 1.719 mmol) and a solution of ammonium chloride (0.0218 g, 0.408 mmol) in water (1 mL). The resulting mixture was stirred vigorously at 65° C. for 5 hours. The reaction mixture was cooled to ambient temperature and filtered through a fritted funnel containing a pad of Celite 503 filter aid rinsing with ethyl acetate. The filtrate was washed with aqueous sodium bicarbonate and saturated aqueous sodium chloride then dried over anhydrous sodium sulfate. Filtration and solvent removal provided the title compound.

Example 93k

N-(4-(2,4-difluorophenoxy)-3-(3-methyl-4-oxo-2-((2-(trimethylsilyl)ethoxy)methyl)-4,5,6,7-tetrahydro-2H-pyrrolo[3,4-c]pyridin-1-yl)phenyl)-N-(methylsulfonyl)methanesulfonamide Example 93j (0.089 g, 0.179 mmol) in tetrahydrofuran (2 mL) was treated sequentially with triethylamine (0.075 mL, 0.537 mmol) and methanesulfonyl chloride (0.035 mL, 0.448 mmol) then stirred at ambient temperature for 60 minutes. The mixture was diluted with 60 mL ethyl acetate, washed with saturated aqueous sodium chloride, and dried over anhydrous magnesium sulfate. Filtration and solvent removal provided the title compound.

Example 931

N-(4-(2,4-difluorophenoxy)-3-(3-methyl-4-oxo-4,5,6,7-tetrahydro-2H-pyrrolo[3,4-c]pyridin-1-yl)phenyl)methanesulfonamide A flask with stirbar was charges with Example 93k (0.117 g, 179 mmol) and 2,2,2-trifluoroacetic acid (2 mL, 26.1 mmol) and stirred at ambient temperature. After 45 minutes the reaction mixture was concentrated, chased with ether, and vacuum dried overnight. The residues were dissolved in methanol (3 mL) and stirred with a suspension of potassium carbonate (0.247 g, 1.790 mmol) for 2 hour at ambient temperature. The reaction mixture was partitioned between dichloromethane and aqueous ammonium chloride. The organics were dried over anhydrous sodium sulfate. After filtration and solvent removal, the crude material was chromatographed on a 12 g silica gel cartridge eluting with 10% ammonia saturated methanol/dichloromethane to provide the title compound. $^1$H NMR (300 MHz, DMSO-$d_6$) δ 11.05 (bds, 1H), 7.41 (m, 1H), 7.23 (d, J=3.5 Hz, 1H), 7.09-7.03 (m, 2H), 6.96 (m, 1H), 6.82 (d, J=8.8 Hz, 1H), 3.23 (m, 2H), 2.99 (s, 3H), 2.61 (m, 2H), 2.41 (s, 3H). MS (ESI+) m/z 448.2 (M+H)$^+$.

Example 94

1-(5-amino-2-phenoxyphenyl)-3-methyl-2,5,6,7-tetrahydro-4H-pyrrolo[3,4-c]pyridin-4-one

Example 94a 1-(5-amino-2-phenoxyphenyl)-3-methyl-2-((2-(trimethylsilyl)ethoxy)methyl)-6,7-dihydro-2H-pyrrolo[3,4-c]pyridin-4(5H)-one Example 94a was prepared according to the procedure used for the preparation of Example 93h, substituting 4-phenoxy-3-(4,4,5,5-tetramethyl-1,3,2-dioxaborolan-2-yl)aniline for 2-fluoro-5-nitrophenylboronic acid, to provide the title compound

Example 94b 1-(5-amino-2-phenoxyphenyl)-3-methyl-6,7-dihydro-2H-pyrrolo[3,4-c]pyridin-4(5H)-one A flask with stirbar containing Example 94a was treated with 2,2,2-trifluoroacetic acid (4 mL, 52.2 mmol) and stirred at ambient temperature. After 45 minutes the reaction mixture was concentrated, chased with ether, and vacuum dried. The residues were dissolved in methanol (6 mL) and stirred with a suspension of potassium carbonate (0.484 g, 3.50 mmol) for 2 hour at ambient temperature. The reaction mixture was partitioned between dichloromethane and saturated aqueous sodium chloride. The organics were dried over anhydrous sodium sulfate. After filtration and solvent removal, the residue was purified by reverse phase HPLC (C18, 0-100% CH$_3$CN/water (0.1% TFA)) to afford the title compound as the trifluoroacetate salt. $^1$H NMR (300 MHz, DMSO-$d_6$) δ 11.01 (bds, 1H), 7.28 (m, 2H), 7.01 (t, J=7.3 Hz, 2H), 6.91-6.84 (m, 4H), 3.19 (m, 2H), 2.61 (m, 2H), 2.38 (s, 3H). MS (ESI+) m/z 334.3 (M+H)$^+$.

Example 95

N-[3-(3-methyl-4-oxo-4,5,6,7-tetrahydro-2H-pyrrolo[3,4-c]pyridin-1-yl)-4-phenoxyphenyl]methanesulfonamide A solution of Example 94b (0.060 g, 0.180 mmol) in tetrahydrofuran (2 mL) was treated sequentially with triethylamine (0.075 mL, 0.540 mmol) and methanesulfonyl chloride (0.035 mL, 0.450 mmol) and then stirred at ambient temperature for 60 minutes. Aqueous sodium hydroxide (1M, 1.5 mL, 1.500 mmol) was added and the mixture was heated at 45° C. for 1 hour. The mixture was diluted with 60 mL ethyl acetate, extracted with 1 N HCl, washed with saturated aqueous sodium chloride, and dried over anhydrous magnesium sulfate. After filtration and solvent removal, the residue was purified by reverse phase HPLC (C18, 0-100% CH$_3$CN/water (0.1% TFA)) to afford the title compound. $^1$H NMR (300 MHz, DMSO-$d_6$) δ 11.04 (bds, 1H), 9.69 (s, 1H), 7.33-7.24 (m, 3H), 7.12 (dd, J=2.7, 8.5 Hz, 2H), 7.03 (m, 1H), 6.97 (d, J=8.8 Hz, 1H), 6.93 (bds, 1H), 6.97 (m, 2H), 3.20 (m, 2H), 3.03 (s, 3H), 2.60 (m, 2H), 2.38 (s, 3H). MS (ESI+) m/z 412.2 (M+H)$^+$.

Example 96

1-[2-(cyclopropylmethoxy)-5-(methylsulfonyl)phenyl]-3-methyl-2,5,6,7-tetrahydro-4H-pyrrolo[3,4-c]pyridin-4-one

Example 96a 1-(2-fluoro-5-(methylsulfonyl)phenyl)-3-methyl-2-((2-(trimethylsilyl)ethoxy)methyl)-6,7-dihydro-2H-pyrrolo[3,4-c]pyridin-4(5H)-one A flask with stirbar was charged with Example 93f (0.136 g, 0.485 mmol), 2-bromo-1-fluoro-4-(methylsulfonyl)benzene (0.145 g, 0.573 mmol), allylpalladium(II) chloride (0.013 g, 0.036 mmol) and potassium acetate (0.149 g, 1.518 mmol), sealed and purged with nitrogen. Degassed N,N-dimethylacetamide (2.5 mL) was introduced, and the vessel was placed in an oil bath and stirred for 18 hours at 130° C. The reaction mixture was cooled and shaken in a separatory funnel with 60 mL each of ethyl acetate and saturated aqueous sodium chloride. The organics were dried over anhydrous sodium sulfate. Filtration and solvent removal followed by chromatography on a 40 g silica gel cartridge eluting with 0-100% ethyl acetate/heptane provided the title compound.

Example 96b 1-(2-(cyclopropylmethoxy)-5-(methylsulfonyl)phenyl)-3-methyl-2-((2-(trimethylsilyl)ethoxy)methyl)-6,7-dihydro-2H-pyrrolo[3,4-c]pyridine-4(5H)-one A 5 mL microwave reaction vessel equipped with stirbar was charged with sodium hydride, dry, 95% (18.8 mg, 0.744 mmol) suspended in tetrahydrofuran (0.5 mL), then cyclopropylmethanol (36 μL, 0.444 mmol) and sealed. After stirring for 10 minutes, Example 96a (67 mg, 0.148 mmol) in tetrahydrofuran (2 mL) was added. The mixture was heated at 60° C. in an oil bath for 88 hours. The mixture was cooled and partitioned between 60 mL each of ethyl acetate and aqueous ammonium chloride. The organics were dried over anhydrous sodium sulfate. Filtration and solvent removal provided the title compound.

Example 96c 1-(2-(cyclopropylmethoxy)-5-(methylsulfonyl)phenyl)-3-methyl-6,7-dihydro-2H-pyrrolo[3,4-c]pyridin-4(5H)-one Example 96c was prepared according to the procedure used for the preparation of Example 94b, substituting Example 96b for Example 94a, to provide the title compound. $^1$H NMR (300 MHz, DMSO-$d_6$) δ 11.06 (bds, 1H), 7.74 (m, 2H), 7.23 (d, J=9.5 Hz, 1H), 7.01 (bds, 1H), 3.96 (d, J=7.1 Hz 2H), 3.25 (m, 2H), 3.18 (s, 3H), 2.66 (m, 2H), 2.45 (s, 3H), 1.25 (m, 1H), 0.57 (m, 2H), 0.34 (m, 2H). MS (ESI+) m/z 375.1 (M+H)$^+$.

Example 97 methyl 3-methyl-4-oxo-1-(2-phenoxyphenyl)-4,5,6,7-tetrahydro-2H-pyrrolo[3,4-c]pyridine-6-carboxylate

Example 97a (Z and E)-ethyl 4-(3-ethoxy-2-nitro-3-oxoprop-1-enyl)-2-methyl-1-((2-(trimethylsilyl)ethoxy)methyl)-1H-pyrrole-3-carboxylate A flask equipped with stirbar was charged with 4 mL tetrahydrofuran and cooled in an ice bath. Titanium(IV) chloride, 1M solution in dichloromethane (2.1 mL, 2.100 mmol) was added by syringe, providing a suspension. After 15 minutes, a solution of Example 93c (0.322 g, 1.034 mmol) and ethyl 2-nitroacetate (0.115 mL, 1.034 mmol) in tetrahydrofuran (0.5 mL) was added. After an additional 15 minutes, a solution of 4-methylmorpholine (0.45 mL, 4.09 mmol) in tetrahydrofuran (0.3 mL) was added dropwise. The solution was allowed to warm to ambient temperature and stirred for 18 hours. The heterogeneous reaction mixture was poured into aqueous ammonium chloride and extracted twice with ether. The combined organics were washed with saturated aqueous sodium chloride then dried over anhydrous magnesium sulfate. Filtration, solvent removal, and chromatography on a 12 g silica gel cartridge eluting with 0-60% ethyl acetate/heptane provided the title compounds as a 2.5:1 mixture of olefin isomers.

Example 97b ethyl 4-(2-amino-3-ethoxy-3-oxopropyl)-2-methyl-1-((2-(trimethylsilyl)ethoxy)methyl)-1H-pyrrole-3-carboxylate Example 97b was prepared according to the procedure used for the preparation of Example 93e, substituting Example 97a for Example 93d, to provide the title compound.

Example 97c methyl 3-methyl-4-oxo-2-((2-(trimethylsilyl)ethoxy)methyl)-4,5,6,7-tetrahydro-2H-pyrrolo[3,4-c]pyridine-6-carboxylate A 5 mL microwave reaction vessel equipped with stirbar was charged with Example 97b (0.284 g, 0.713 mmol) and lithium hydroxide monohydrate (0.221 g, 5.27 mmol) in ethanol (4.75 mL)/water (0.25 mL) and sealed. The mixture was heated at 120° C. for 30 minutes in a Biotage Initiator 2 monomode microwave reactor, and then cooled to ambient temperature. The reaction mixture was treated with acetic acid (0.326 mL, 5.70 mmol), then concentrated and dried overnight. The residues were taken up in a mixture of benzene (4 mL) tetrahydrofuran (4 mL) and methanol (2 mL) then treated with a 2.0 M solution of (diazomethyl)trimethylsilane in hexanes (1 mL, 2.000 mmol). A second portion of (diazomethyl)trimethylsilane was added after 45 minutes, and a third after 2 hours. The excess (diazomethyl)trimethylsilane was quenched by addition of acetic acid. The mixture was then partitioned between ethyl acetate and saturated aqueous sodium chloride. The organics were dried over anhydrous sodium sulfate. Filtration, solvent removal and chromatography on a 12 g silica gel cartridge eluting with 0-10% methanol/dichloromethane provided the title compound.

Example 97d methyl 1-bromo-3-methyl-4-oxo-2-((2-(trimethylsilyl)ethoxy)methyl)-4,5,6,7-tetrahydro-2H-pyrrolo[3,4-c]pyridine-6-carboxylate Example 97d was prepared according to the procedure used for the preparation of Example 93g substituting Example 97c for Example 93f, to provide the title compound.

Example 97e 3-methyl-4-oxo-1-(2-phenoxyphenyl)-2-((2-(trimethylsilyl)ethoxy)methyl)-4,5,6,7-tetrahydro-2H-pyrrolo[3,4-c]pyridine-6-carboxylic acid A 5 mL microwave reaction vessel equipped with stirbar was charged with Example 97d (0.072 g, 0.173 mmol), 2-phenoxyphenylboronic acid (0.121 g, 0.565 mmol), 2 M aqueous sodium carbonate (0.86 mL, 1.720 mmol) and bis(triphenylphosphine)palladium(II) dichloride (0.0128 g, 0.018 mmol) in methanol (0.782 mL)/DME (0.782 mL) and sealed. The mixture was heated at 120° C. for 30 minutes in a Biotage Initiator 2 monomode microwave reactor, and then cooled to ambient temperature. The mixture was shaken in a separatory funnel with 75 mL ethyl acetate and 50 mL saturated aqueous sodium chloride. The aqueous phase was acidified with HCl and extracted with 75 mL ethyl acetate. The organics were dried over anhydrous sodium sulfate. Filtration and solvent removal provided the title compound.

Example 97f 3-methyl-4-oxo-1-(2-phenoxyphenyl)-4,5,6,7-tetrahydro-2H-pyrrolo[3,4-c]pyridine-6-carboxylic acid A flask with stirbar containing Example 97e (0.085 g, 0.173 mmol) was treated with 2,2,2-trifluoroacetic acid (2 mL, 26.1 mmol) and stirred at ambient temperature for 30 minutes, then stripped down and vacuum dried. The residues were taken up in methanol (4 mL) and stirred with a suspension of potassium carbonate (0.288 g, 2.084 mmol) at ambient temperature for 75 minutes. The mixture was acidified with trifluoroacetic acid, and then combined in a separatory funnel with saturated aqueous sodium chloride and extracted twice with dichloromethane. The combined organic extracts were washed with saturated aqueous sodium chloride and dried over anhydrous sodium sulfate. Filtration and solvent removal provided the title compound.

Example 97g methyl 3-methyl-4-oxo-1-(2-phenoxyphenyl)-4,5,6,7-tetrahydro-2H-pyrrolo[3,4-c]pyridine-6-carboxylate A flask with stirbar was charged with Example 97f (62.7 mg, 0.173 mmol) in a mixture of tetrahydrofuran (5.00 mL)/methanol (1 mL), then treated with a 2.0 M (diazomethyl)trimethylsilane solution in hexanes (0.260 mL, 0.519 mmol) and stirred at ambient temperature. After 2 hours the excess (diazomethyl)trimethylsilane was quenched with acetic acid. The mixture was concentrated and was purified by reverse phase HPLC (C18, 0-100% $CH_3CN$/water (0.1% TFA)) to afford the title compound. $^1$H NMR (300 MHz, DMSO-$d_6$) δ 11.12 (bds, 1H), 9.69 (s, 1H), 7.44-7.21 (m, 5H), 7.14-7.05 (m, 2H), 6.98-9.89 (m, 2H), 3.47 (s, 3H), 3.36 (m, 1H), 3.00 (d, J=5.6 Hz, 2H), 2.39 (s, 3H). MS (ESI+) m/z 377.1 (M+H)$^+$.

Example 98

1-[2-(2,4-difluorophenoxy)-5-(methylsulfonyl)phenyl]-3-methyl-2,5,6,7-tetrahydro-4H-pyrrolo[3,4-c]pyridin-4-one

Example 98a 1-(2-(2,4-difluorophenoxy)-5-(methylsulfonyl)phenyl)-3-methyl-2-((2-(trimethylsilyl)ethoxy)methyl)-6,7-dihydro-2H-pyrrolo[3,4-c]pyridin-4(5H)-one Example 98a was prepared according to the procedure used for the preparation of Example 93i, substituting Example 96a for Example 93h, to provide the title compound.

Example 98b 1-(2-(2,4-difluorophenoxy)-5-(methylsulfonyl)phenyl)-3-methyl-6,7-dihydro-2H-pyrrolo[3,4-c]pyridin-4(5H)-one Example 98b was prepared according to the procedure used for the preparation of Example 94b, substituting Example 98a for Example 94a, to provide the title compound. $^1$H NMR (500 MHz, DMSO-$d_6$) δ 11.32 (bds, 1H), 7.91 (s, 1H), 7.74 (dd, J=8.7, 2.3 Hz, 1H), 7.55 (ddd, J=11.1, 8.6, 2.9 Hz, 1H), 7.44 (td, J=9.2, 5.8 Hz, 1H), 7.21 (m, 1H), 7.06 (s, 1H), 6.91 (d, J=8.9 Hz, 1H), 3.26 (m, 2H), 3.24 (s, 3H), 2.67 (m, 2H), 2.48 (s, 3H). MS (DCI+) m/z 433.0 (M+H)$^+$.

Example 99

1-[2-fluoro-5-(methylsulfonyl)phenyl]-3-methyl-2,5,6,7-tetrahydro-4H-pyrrolo[3,4-c]pyridin-4-one Example 99 was prepared according to the procedure used for the preparation of Example 94b, substituting Example 96a for Example 94a, to provide the title compound. $^1$H NMR (300 MHz, DMSO-$d_6$) δ 11.43 (bds, 1H), 7.95 (dd, J=7.0, 2.4 Hz, 1H), 7.84 (ddd, J=6.5, 4.4, 2.3 Hz, 1H), 7.57 (dd, J=10.2, 8.7 Hz, 1H), 7.10 (s, 1H), 3.26 (m, 2H), 3.27 (s, 3H), 2.65 (m, 2H), 2.47 (s, 3H). MS (DCI+) m/z 322.9 (M+H)$^+$.

Example 100

3-methyl-1-phenyl-2,5,6,7-tetrahydro-4H-pyrrolo[3,4-c]pyridin-4-one

Example 100a

Example 100a was prepared according to the procedure used for the preparation of Example 92g, substituting phenylboronic acid for 2-phenoxyphenylboronic acid and Example 93g for Example 92f, and purified by chromatography on a 4 g silica gel cartridge eluting with 0-10% methanol/dichloromethane to provide the title compound.

Example 100b 3-methyl-1-phenyl-6,7-dihydro-2H-pyrrolo[3,4-c]pyridin-4(5H)-one Example 100b was prepared according to the procedure used for the preparation of Example 94b, substituting Example 100a for Example 94a, to provide the title compound. $^1$H NMR (500 MHz, DMSO-$d_6$) δ 11.22 (bds, 1H), 7.45 (m, 2H), 7.39 (t, J=7.8 Hz, 2H), 7.19 (t, J=7.3 Hz, 1H), 7.02 (s, 1H), 2.65 (m, 2H), 2.79 (m, 2H), 2.45 (s, 3H). MS (DCI+) m/z 227.0 (M+H)$^+$.

Example 101

1-[5-amino-2-(2,4-difluorophenoxy)phenyl]-3,6-dimethyl-2,5,6,7-tetrahydro-4H-pyrrolo[3,4-c]pyridin-4-one

Example 101a (E)-ethyl 2-methyl-4-(2-nitroprop-1-enyl)-1-((2-(trimethylsilyl)ethoxy)methyl)-1H-pyrrole-3-carboxylate Example 101a was prepared according to the procedure used for the preparation of Example 93d, substituting nitroethane for nitromethane, to provide the title compound.

Example 101b ethyl 4-(2-aminopropyl)-2-methyl-1-((2-(trimethylsilyl)ethoxy)methyl)-1H-pyrrole-3-carboxylate Example 101b was prepared according to the procedure used for the preparation of Example 93e, substituting Example 101a for Example 93d, to provide the title compound.

Example 101c 3,6-dimethyl-2-((2-(trimethylsilyl)ethoxy)methyl)-6,7-dihydro-2H-pyrrolo[3,4-c]pyridin-4(5H)-one Example 101c was prepared according to the procedure used for the preparation of Example 93f, substituting Example 101b for Example 93e, to provide the title compound.

Example 101d 3,6-dimethyl-6,7-dihydro-2H-pyrrolo[3,4-c]pyridin-4(5H)-one

Example 101d was prepared according to the procedure used for the preparation of Example 93l, substituting Example 101c for Example 93k, to provide the title compound.

Example 101e 1-bromo-3,6-dimethyl-6,7-dihydro-2H-pyrrolo[3,4-c]pyridin-4(5H)-one Example 101e was prepared according to the procedure used for the preparation of Example 93g substituting Example 101d for Example 93f, to provide the title compound.

Example 101f 1-(5-amino-2-(2,4-difluorophenoxy)phenyl)-3,6-dimethyl-6,7-dihydro-2H-pyrrolo[3,4-c]pyridin-4(5H)-one Example 101f was prepared according to the procedure used for the preparation of Example 93h, substituting 4-(2,4-difluorophenoxy)-3-(4,4,5,5-tetramethyl-1,3,2-dioxaborolan-2-yl)aniline for 2-fluoro-5-nitrophenylboronic acid and Example 101e for Example 93g, then purified by reverse phase HPLC (C18, 0-100% $CH_3CN$/water (0.1% TFA)) to afford the TFA salt of the title compound. $^1$H NMR (300 MHz, $CD_3OD$) δ 10.81 (bds, 1H), 7.31 (m, 1H), 7.17 (m, 1H), 7.10-7.01 (m, 2H), 6.96-6.88 (m, 2H), 3.69 (m, 1H), 2.86 (dd, J=15.2, 4.4 Hz, 1H), 2.53 (m, 1H), 2.49 (s, 3H), 0.08 (d, J=6.4 Hz, 3H). MS (ESI+) m/z 384.1 $(M+H)^+$.

Example 102

1-{2-(2,4-difluorophenoxy)-5-[(4-methylpiperazin-1-yl)methyl]phenyl}-3-methyl-2,5,6,7-tetrahydro-4H-pyrrolo[3,4-c]pyridin-4-one

Example 102a 4-fluoro-3-(3-methyl-4-oxo-2-((2-(trimethylsilyl)ethoxy)methyl)-4,5,6,7-tetrahydro-2H-pyrrolo[3,4-c]pyridin-1-yl)benzaldehyde Example 102a was prepared according to the procedure used for the preparation of Example 4c, substituting Example 93g for Example 4b and (2-fluoro-5-formylphenyl)boronic acid for (2-fluoro-5-nitrophenyl)boronic acid. Purification by flash chromatography (silica gel, 5-100% ethyl acetate in dichloromethane) gave 0.137 g (31%) of the title compound.

Example 102b 4-(2,4-difluorophenoxy)-3-(3-methyl-4-oxo-2-((2-(trimethylsilyl)ethoxy)methyl)-4,5,6,7-tetrahydro-2H-pyrrolo[3,4-c]pyridin-1-yl)benzaldehyde Example 102b was prepared according to the procedure used for the preparation of Example 4d, substituting Example 102a for Example 4c and heating for 5 hours at 75-80° C. Purification by flash chromatography (silica gel, 10-80% ethyl acetate in dichloromethane) gave 0.088 g (51%) of the title compound.

Example 102c 4-(2,4-difluorophenoxy)-3-(3-methyl-4-oxo-4,5,6,7-tetrahydro-2H-pyrrolo[3,4-c]pyridin-1-yl)benzaldehyde Example 102c was prepared according to the procedure used for the preparation of
Example 15b, substituting Example 102b for Example 15a. For the current example, the first stage was stirred for 1 hour instead of 35 minutes and the second stage was stirred at 60° C. overnight and then at ambient temperature for 2.5 days. Purification by reverse phase HPLC (C8, acetonitrile/water (0.1% TFA), 10-90%) gave 0.043 g (67%) of the title compound.

Example 102d 1-(2-(2,4-difluorophenoxy)-5-((4-methylpiperazin-1-yl)methyl)phenyl)-3-methyl-6,7-dihydro-2H-pyrrolo[3,4-c]pyridin-4(5H)-one Example 102c (0.0401 g, 0.105 mmol) and 1-methylpiperazine (0.016 g, 0.157 mmol were combined with 1,2-dichloroethane (1.5 mL) and acetic acid (0.1 mL) and stirred at ambient temperature for 1 hour. Sodium triacetoxyhydroborate (0.067 g, 0.315 mmol) was added in portions and stirring was continued overnight at ambient temperature. The reaction mixture was quenched with saturated aqueous ammonium chloride solution and partitioned between ethyl acetate and water. The organic layer was used for Example 103. The aqueous layer was adjusted to pH 8 with saturated sodium bicarbonate solution and extracted with ethyl acetate (2×75 mL). The combined extracts were dried over anhydrous magnesium sulfate, filtered and concentrated. The residue was purified by reverse phase HPLC (C18, acetonitrile/water (0.1% TFA), 0-80%) to provide 0.019 (31%) the TFA salt of the title compound. $^1$H NMR (400 MHz, $CD_3OD$) δ 10.74 (s, 1H), 7.43 (d, J=2.14 Hz, 1H), 7.27 (dd, J=8.24, 2.14 Hz, 1H), 7.08 (m, 1H), 6.98 (td, J=9.00, 5.49 Hz, 1H), 6.89 (m, 2H), 3.82 (s, 2H), 3.37 (t, J=6.56 Hz, 2H), 3.33 (m, 4H), 2.96 (m, 4H), 2.88 (s, 3H), 2.75 (t, J=6.56 Hz, 2H), 2.49 (s, 3H). MS (ESI+) m/z 467.0 $(M+H)^+$.

Example 103

1-[2-(2,4-difluorophenoxy)-5-(hydroxymethyl)phenyl]-3-methyl-2,5,6,7-tetrahydro-4H-pyrrolo[3,4-c]pyridin-4-one Example 103 was obtained as a side product during the preparation of Example 102d. The organic layer from partitioning the quenched reaction mixture of Example 102d between ethyl acetate and water was washed with saturated aqueous sodium chloride, dried over anhydrous magnesium sulfate, filtered and concentrated. The residue was purified by reverse phase HPLC (C18, acetonitrile/water (0.1% TFA), 20-90%) to give 0.009 g (22%) of the title compound. $^1$H NMR (400 MHz, DMSO-$d_6$) δ 11.04 (s, 1H), 7.41 (m, 1H), 7.35 (d, J=1.83 Hz, 1H), 7.19 (dd, J=8.39, 1.98 Hz, 1H), 7.06 (m, 2H), 6.94 (s, 1H), 6.78 (d, J=8.24 Hz, 1H), 4.50 (s, 2H), 3.21 (t, J=5.49 Hz, 2H), 2.60 (t, J=6.26 Hz, 2H), 2.41 (s, 3H). MS (ESI+) m/z 385.2 (M+H)$^+$.

Biological Examples

Bromodomain Domain Binding Assay

A time-resolved fluorescence resonance energy transfer (TR-FRET) assay was used to determine the affinities of compounds of the Examples listed in Table 1 for each bromodomain of BRD4. His-tagged first (BD1: amino acids K57-E168) and second (BD2: amino acids E352-E168) bromodomains of BRD4 were expressed and purified. An Alexa647-labeled BET-inhibitor was used as the fluorescent probe in the assay.

Synthesis of Alexa647-labeled bromodomain inhibitor compound 2-((6S,Z)-4-(4-chlorophenyl)-2,3,9-trimethyl-6H-thieno[3,2-f][1,2,4]triazolo[4,3-a][1,4]diazepin-6-yl)acetic acid. Methyl 2-((6S,Z)-4-(4-chlorophenyl)-2,3,9-trimethyl-6H-thieno[3,2-f][1,2,4]triazolo[4,3-a][1,4]diazepin-6-yl)acetate (see e.g., WO 2006129623)(100.95 mg, 0.243 mmol was suspended in 1 mL methanol to which was added a freshly prepared solution of lithium hydroxide monohydrate (0.973 mL, 0.5 M, 0.487 mmol) and shaken at ambient temperature for 3 hours. The methanol was evaporated and the pH adjusted with aqueous hydrochloric acid (1 M, 0.5 mL, 0.5 mmol) and extracted four times with ethyl acetate. The combined ethyl acetate layers were dried over magnesium sulfate and evaporated to afford 2-((6S,Z)-4-(4-chlorophenyl)-2,3,9-trimethyl-6H-thieno[3,2-f][1,2,4]triazolo[4,3-a][1,4]diazepin-6-yl)acetic acid (85.3 mg, 87.0%); ESI-MS m/z=401.1 [(M+H)$^+$] which was used directly in the next reaction.

N-(2-(2-(2-aminoethoxy)ethoxy)ethyl)-2-((6S,Z)-4-(4-chlorophenyl)-2,3,9-trimethyl-6H-thieno[3,2f][1,2,4]triazolo[4,3-a][1,4]diazepin-6-yl)acetamide bis(2,2,2-trifluoroacetate). 2-((6S,Z)-4-(4-chlorophenyl)-2,3,9-trimethyl-6H-thieno[3,2-f][1,2,4]triazolo[4,3-a][1,4]diazepin-6-yl)acetic acid)(85.3 mg, 0.213 mmol) was combined with 2,2'-(ethane-1,2-diylbis(oxy))diethanamine (Sigma-Aldrich, 0.315 mg, 2.13 mmol) were combined in 5 mL anhydrous dimethylformamide. (1H-benzo[d][1,2,3]triazol-1-yloxy)tripyrrolidin-1-ylphosphonium hexafluorophosphate(V) (PyBOB, CSBio, Menlo Park Calif.; 332 mg, 0.638 mmol) was added and the reaction shaken at ambient temperature for 16 hours. The reaction was diluted to 6 mL with dimethylsulfoxide:water (9:1, v:v) and purified in two injections with time collection Waters Deltapak C18 200×25 mm column eluted with a gradient of 0.1% trifluoroacetic acid (v/v) in water and acetonitrile. The fractions containing the two purified products were lyophilized to afford N-(2-(2-(2-aminoethoxy)ethoxy)ethyl)-2-((6S,Z)-4-(4-chlorophenyl)-2,3,9-trimethyl-6H-thieno[3,2-f][1,2,4]triazolo[4,3-a][1,4]diazepin-6-yl)acetamide bis(2,2,2-trifluoroacetate) (134.4 mg, 82.3%); ESI-MS m/z=531.1 [(M+H)$^+$]; 529.1 [(M−H)$^-$] and (S,Z)—N,N'-(2,2'-(ethane-1,2-diylbis(oxy))bis(ethane-2,1-diyl))bis(2-((6S,Z)-4-(4-chlorophenyl)-2,3,9-trimethyl-6H-thieno[3,2-f][1,2,4]triazolo[4,3-a][1,4]diazepin-6-yl)acetamide)bis(2,2,2-trifluoroacetate) (3.0 mg, 1.5%); ESI-MS m/z=913.2 [(M+H)$^+$]; 911.0 [(M−H)$^-$].

N-(2-(2-(2-amido-(Alexa647)-ethoxy)ethoxy)ethyl)-2-((6S,Z)-4-(4-chlorophenyl)-2,3,9-trimethyl-6H-thieno[3,2-f][1,2,4]triazolo[4,3-a][1,4]diazepin-6-yl)acetamide(2,2,2-trifluoroacetate). N-(2-(2-(2-aminoethoxy)ethoxy)ethyl)-2-((6S,Z)-4-(4-chlorophenyl)-2,3,9-trimethyl-6H-thieno[3,2-f][1,2,4]triazolo[4,3-a][1,4]diazepin-6-yl)acetamide bis(2,2,2-trifluoroacetate) (5.4 mg, 0.0071 mmol) was combined with Alexa Fluor® 647 carboxylic Acid, succinimidyl ester (Life Technologies, Grand Island, N.Y.; 3 mg, 0.0024 mmol) were combined in 1 mL anhydrous dimethylsulfoxide containing diisopropylethylamine (1% v/v) and shaken at ambient temperature for 16 hours. The reaction was diluted to 3 mL with dimethylsulfoxide:water (9:1, v:v) and purified in one injection with time collection Waters Deltapak C18 200× 25 mm column eluted with a gradient of 0.1% trifluoroacetic acid (v/v) in water and acetonitrile. The fractions containing the purified product were lyophilized to afford N-(2-(2-(2-amido-(Alexa647)-ethoxy)ethoxy)ethyl)-2-((6S,Z)-4-(4-chlorophenyl)-2,3,9-trimethyl-6H-thieno[3,2-f][1,2,4]triazolo[4,3-a][1,4]diazepin-6-yl)acetamide(2,2,2-trifluoroacetate) (1.8 mg); MALDI-MS m/z=1371.1, 1373.1 [(M+H)$^+$] as a dark blue powder.

Assay

Compound dilution series were prepared in DMSO via an approximately 3-fold serial dilution from one of the following:

Assay method A: 2.5 mM-800 nM
Assay method B: 2.5 mM-797 nM
Assay method C: 1250 µM-21 nM
Assay method D: 500 µM-8.5 nM
Assay method E: 0.47 mM to 7.8 nM
Assay method F: 250 µM-4.2 nM
Assay method G: 0.047 mM to 0.78 nM or 5-fold serial dilution from Assay Method A or Assay Method B.

For Assay methods A, C, D, and F: Compounds were then diluted 6:100 in assay buffer (20 mM Sodium Phosphate, pH 6.0, 50 mM NaCl, 1 mM Ethylenediaminetetraacetic acid, 0.01% Triton X-100, 1 mM DL-Dithiothreitol) to yield 3× working solutions. Six microliters (µL) of the working solution was then transferred to white, low-volume assay plates (Costar #3673). A 1.5× assay mixture containing His-tagged bromodomain, Europium-conjugated anti-His antibody (Invitrogen PV5596) and the Alexa-647-conjugated probe molecule was also prepared. Twelve µL of this solution were added to the assay plate to reach a final volume of 18 µL.

For Assay methods B, E, and G: Compound dilutions were added directly into white, low-volume assay plates (Perkin Elmer Proxiplate 384 Plus#6008280) using a Labcyte Echo in conjunction with Labcyte Access and Thermo Multidrop CombinL robotics. Compounds were then suspended in eight microliters (µL) of assay buffer (20 mM Sodium Phosphate, pH 6.0, 50 mM NaCl, 1 mM Ethylenediaminetetraacetic acid disodium salt dihydrate, 0.01% Triton X-100, 1 mM DL-Dithiothreitol) containing His-tagged bromodomain, Europium-conjugated anti-His antibody (Invitrogen PV5596) and Alexa-647-conjugated probe.

The final concentration of 1× assay mixture for assay methods A, B, C, D, E, F, and G contains 2% DMSO, 8 nM His-tagged bromodomain, 1 nM Europium-conjugated anti-His-tag antibody and 100 nM or 30 nM probe (for BDI or BDII, respectively) and compound concentration in the range of: 50 µM-16 nM for method A, 49.02 µM-15.63 nM for method B, 25 µM-423 pM for method C, 10 µM-169 pM for method D, 9.19 µM-150 pM for method E, 5 µM-85 pM for method F, and 0.92 µM-15 pM for method G.

After a one-hour equilibration at room temperature, TR-FRET ratios were determined using an Envision multilabel plate reader (Ex 340, Em 495/520).

TR-FRET data were normalized to the means of 24 no-compound controls ("high") and 8 controls containing 1 µM un-labeled probe ("low"). Percent inhibition was plotted as a function of compound concentration and the data were fit with the 4 parameter logistic equation to obtain IC50s Inhibition constants (Ki) were calculated from the IC50s, probe Kd and probe concentration. Typical Z' values were between 0.65 and 0.75. The minimum significant ratio was determined to evaluate assay reproducibility (Eastwood et al., (2006) J Biomol Screen, 11: 253-261). The MSR was determined to be 2.03 for BDI and 1.93 for BDII, and a moving MSR (last six run MSR overtime) for both BDI and BDII was typically <3. The $K_i$ values are reported in Table 1.

MX-1 Cell Line Proliferation Assay

The impact of compounds of the Examples on cancer cell proliferation was determined using the breast cancer cell line MX-1 (ATCC) in a 3-day proliferation assay and the data are reported in Table 1. MX-1 cells were maintained in RPMI 1640 medium (Sigma) supplemented with 10% FBS at 37 C.° and an atmosphere of 5% $CO_2$. For compound testing, MX-1 cells were plated in 96-well black bottom plates at a density of 5000 cells/well in 90 μL of culture media and incubated at 37° overnight to allow cell adhesion and spreading. Compound dilution series were prepared in DMSO via a 3-fold serial dilution from 3 mM to 0.1 μM. The DMSO dilution series were then diluted 1:100 in phosphate buffered saline, and 10 μL of the resulted solution were added to the appropriate wells of the MX-1 cell plate. The final compound concentrations in the wells were 3, 1, 0.3, 0.1, 0.03, 0.01, 0.003, 0.001, 0.0003 and 0.0001 μM. After the addition of compounds, the cells were incubated for 72 more hours and the amounts of viable cells were determined using the Cell Titer Glo assay kit (Promega) according to manufacturer suggested protocol.

Luminescence readings from the Cell Titer Glo assay were normalized to the DMSO treated cells and analyzed using the GraphPad Prism software with sigmoidal curve fitting to obtain $EC_{50}$s. The minimum significant ratio (MSR) was determined to evaluate assay reproducibility (Eastwood et al., (2006) J Biomol Screen, 11: 253-261). The overall MSR was determined to be 2.1 and a moving MSR (last six run MSR overtime) has been <2.

TABLE 1

| Example # | Enzyme assay protocol | TR-FRET Binding Ki: BRD4 (BDI_K57-E168) (μM) | TR-FRET Binding Ki: BRD4 (BDII_E352-M457) (μM) | Cellular proliferation: $EC_{50}$ (μM) |
|---|---|---|---|---|
| 1 | A | 0.00304 | 0.0246 | 0.067 |
| 2 | E | 0.00147 | 0.0215 | 0.024 |
| 3 | E | 0.00333 | 0.0198 | 0.0415 |
| 4 | E | 0.0123 | 0.0913 | 0.0776 |
| 5 | E | 0.00144 | 0.00951 | 0.0473 |
| 6 | F | 0.00123 | 0.00331 | 0.0329 |
| 7 | E | 0.00215 | 0.0159 | 0.0257 |
| 8 | E | 0.0956 | 0.615 | 0.737 |
| 9 | E | 0.00341 | 0.0293 | 0.0716 |
| 10 | F | 0.00146 | 0.00861 | 0.0574 |
| 11 | A | 0.00431 | 0.0119 | 0.0317 |
| 12 | A | 0.0826 | 0.546 | ND |
| 13 | A | 0.00438 | 0.0141 | 0.0234 |
| 14 | A | 0.0314 | 0.0676 | 0.216 |
| 15 | A | 0.105 | 0.307 | 1.12 |
| 16 | A | 0.0327 | 0.17 | 0.616 |
| 17 | D | 0.0277 | 0.00229 | 0.177 |
| 18 | E | 0.0151 | 0.0316 | 0.0901 |
| 19 | E | 0.00166 | 0.00608 | 0.27 |
| 20 | D | 0.00164 | 0.00239 | 0.146 |
| 21 | C | 0.0248 | 0.285 | 0.104 |
| 22 | C | 0.225 | 2.79 | ND |
| 23 | C | 0.00625 | 0.0451 | 0.0608 |
| 24 | C | 0.0922 | 2.75 | ND |
| 25 | C | 0.00312 | 0.0923 | 0.163 |
| 26 | C | 0.0568 | 0.118 | 0.442 |
| 27 | C | 0.00381 | 0.047 | 0.0989 |
| 28 | C | 0.0427 | 0.0168 | 0.515 |
| 29 | C | 0.0106 | 0.0467 | 0.114 |
| 30 | C | 0.0926 | 0.0488 | 1.35 |
| 31 | C | 0.0876 | 0.155 | 0.182 |
| 32 | C | 0.0228 | 0.158 | 0.102 |
| 33 | C | 0.499 | 0.759 | ND |
| 34 | C | 0.077 | 0.16 | 0.355 |
| 35 | D | 0.00521 | 0.0485 | 0.0536 |
| 36 | C | 0.00883 | 0.0209 | 0.188 |
| 37 | C | 0.0101 | 0.0139 | 0.161 |
| 38 | C | 0.0166 | 0.029 | 0.30 |
| 39 | C | 0.0121 | 0.0518 | 0.222 |
| 40 | C | 0.358 | 1.72 | ND |
| 41 | C | 0.141 | 0.944 | ND |
| 42 | C | 0.0224 | 0.0569 | >3 |
| 43 | C | 0.0159 | 0.0254 | 0.15 |
| 44 | C | 0.0667 | 0.424 | 0.233 |
| 45 | C | 0.0105 | ND | 0.18 |
| 46 | C | 1.25 | 1.22 | ND |
| 47 | C | 0.519 | 2.52 | ND |
| 48 | C | 0.00505 | 0.0964 | 0.139 |
| 49 | C | 0.00343 | 0.0702 | 0.138 |
| 50 | C | 0.0301 | 0.0113 | 0.21 |
| 51 | D | 0.00613 | 0.19 | 0.117 |
| 52 | C | 0.0369 | 0.0975 | 0.763 |
| 53 | C | 0.00825 | 0.0721 | 0.162 |
| 54 | | ND | ND | ND |
| 55 | | ND | ND | ND |
| 56 | | ND | ND | ND |
| 57 | C | 0.00178 | 0.0158 | 0.252 |
| 58 | C | 0.00202 | 0.016 | 0.329 |
| 59 | C | 0.00367 | 0.0597 | 0.223 |
| 60 | D | 0.013 | 0.116 | 0.111 |
| 61 | D | 0.01 | 0.138 | 0.159 |
| 62 | D | >2.38 | >4.08 | ND |
| 63 | D | 0.0435 | 0.257 | 0.139 |
| 64 | D | 0.00228 | 0.00711 | 0.0292 |
| 65 | D | 0.00757 | 0.0285 | 0.0711 |
| 66 | D | 0.00931 | 0.151 | 0.081 |
| 67 | D | 0.00945 | 0.078 | 0.0805 |
| 68 | D | 0.00212 | 0.0088 | 0.030 |
| 69 | D | 0.0522 | 0.416 | >3 |
| 70 | D | 0.0827 | 0.356 | >3 |
| 71 | D | 0.0385 | 0.659 | 0.204 |
| 72 | A | 0.00763 | 0.0258 | 0.178 |
| 73 | E | 0.00149 | 0.0085 | 0.0593 |
| 74 | A | 0.00188 | 0.0186 | 0.078 |
| 75 | A | 0.00366 | 0.00947 | 0.0518 |
| 76 | A | 0.00582 | 0.0162 | 0.41 |
| 77 | A | >13 | >22.2 | ND |
| 78 | A | 0.00331 | 0.0341 | 0.0605 |
| 79 | A | 0.00178 | 0.00591 | 0.0886 |
| 80 | A | 0.00326 | 0.0244 | 0.0922 |
| 81 | E | 0.0227 | 0.254 | 0.394 |
| 82 | A | 0.0367 | 0.357 | 0.167 |
| 83 | E | 0.126 | 0.627 | 1.72 |
| 84 | A | 0.0156 | 0.112 | 0.288 |
| 85 | A | 0.0924 | 0.72 | 1.24 |
| 86 | A | 1.37 | 12.3 | ND |
| 87 | A | 0.0823 | 1.18 | >3 |
| 88 | A | 0.38 | 1.62 | 0.761 |
| 89 | A | 0.212 | 0.497 | 0.963 |
| 90 | A | 0.108 | 0.791 | ND |
| 91 | A | 0.0226 | 0.117 | 0.245 |
| 92 | A | 0.0141 | 0.047 | 0.19 |
| 93 | E | 0.014 | 0.138 | 0.229 |
| 94 | E | 0.0172 | 0.0324 | 0.0919 |
| 95 | E | 0.00367 | 0.0204 | 0.0547 |
| 96 | E | 0.0343 | 0.461 | 0.407 |
| 97 | E | 0.0243 | 0.157 | >3 |
| 98 | C | 0.0349 | 0.148 | 0.721 |
| 99 | C | 1.62 | >4.44 | ND |
| 100 | C | 2.25 | 2.92 | ND |
| 101 | C | 0.00842 | 0.0115 | 0.0458 |
| 102 | D | 1.56 | 3.12 | ND |
| 103 | D | 0.122 | 0.198 | 0.239 |

ND = Not Determined

LPS (Lipopolysaccharide) Induced IL-6 Production Mouse Assay

Compounds of the Examples listed in Table 2 were assayed for their ability to inhibit LPS (lipopolysaccharide) induced IL-6 (Interleukin-6) production in mice. Fox Chase SCID® female mice (Charles Rivers Labs, 5 per group) received an intraperitoneal challenge of lipopolysaccharide (2.5 mg/kg, L2630 E. coli 0111:B4) one hour after oral administration of compounds. Mice were euthanized 2 hours after lipopolysaccharide injection, blood was removed by cardiac puncture, and then the serum harvested from the blood samples was frozen at −80° C. On the day of the assay the serum samples were brought to room temperature and then diluted 1:20 in phosphate-buffered saline containing 2% bovine serum albumin. Interleukin-6 measurements were performed using a cytokine assay from Meso Scale Discovery (Gaithersburg, Md.) for mouse serum analysis according to the manufacturer's protocol and read on a SECTOR Imager 6000 (Meso Scale Discovery, Gaithersburg, Md.) instrument. Statistical analysis was performed using Prism software (version 5.0) incorporating Dunnett's one way ANOVA. The IL-6 mean and standard deviation of the group of vehicle treated animals were compared with the IL-6 mean and standard deviation of the group treated with drug. A p value<0.05 means that there is less than a 5% probability that the mean values in the two groups are equal. The % inhibition values in Table 2 all exhibited a p value less than 0.05.

TABLE 2

Inhibition of LPS induced IL-6 production

| Compound of Example # | % inhibition at 3 mg/kg |
|---|---|
| 2 | 25 |
| 29 | 40 |
| 43 | 39 |
| 82 | 44 |
| 93 | 51 |
| 94 | 27 |
| 95 | 31 |

Vehicle for Example 2: 2% ethanol, 5% Tween-80, 20% PEG 400, 73% (0.2% HMPC). Vehicle for Examples 29, 43, 82, 93, 94, and 95: 10% ethanol, 30% PEG 400, 60% Phosal 53 MCT.

Xenograft Tumor Growth Inhibition Assay

The effect of compounds of the examples to inhibit the growth of OPM-2 xenograft tumors implanted in mice was evaluated. A suspension of cancer cells ($5 \times 10^6$ per 0.1 mL) prepared in RPMI culture medium (Invitrogen, Carlsbad, Calif.) was diluted 1:1 with a solution of Matrigel™ (BD Biosciences, Franklin Lakes, N.J.) and inoculated subcutaneously into the right hind flank of female SCID-beige (Charles River Labs) mice. Randomization into treatment and vehicle control groups (10/group) occurred when the mean tumor volume reached approximately 250 mm³. Compounds were formulated in 2.5% DMSO, 10% EtOH, 27.5% PEG 400, 60% Phosol 53 MCT. Administration of compound or vehicle was initiated on the day following randomization and continued for 21 days. Tumors were measured twice a week throughout the treatment period using a pair of calipers and tumor volumes were calculated according to the formula $V = L \times W^2/2$ (V: volume, mm³; L: length, mm. W: width, mm) Tumor growth inhibition was calculated based on the mean tumor volume measured on the first day that the mean volume of the vehicle group exceeded 2000 mm³ according to the formula % TGI=100-mean tumor volume of treatment group/mean tumor volume of control group x 100. Results are given in Table 3.

TABLE 3

OPM-2 human multiple myeloma cancer xenograft model.

| Compound of example # | Dose mg/kg | route, regimen | % TGI[a] | % TGD[b] | % removed from study[c] |
|---|---|---|---|---|---|
| 98 | 45 | PO, QDx21 | 45** | 53** | 0 |
| 98 | 150 | PO, QDx21 | 68*** | 123** | 20 |

[a]The p values (as indicated by asterisks) are derived from Student's T test comparison of treatment group vs. control group. *p < 0.05, p < 0.01, *p < 0.001.
[b]Tumor growth delay, % TGD = (T − C)/C x 100, where T = median time to endpoint of treatment group and C = median time to endpoint of control group. The p values (as indicated by asterisks) derived from Kaplan Meier log-rank comparison of treatment group vs. treatment control group based on an endpoint of 1000 mm³. *p < 0.05, p < 0.01, *p < 0.001.
[c]Percentage of treatment group that were removed from study due to morbidity or weight loss in excess of 20%.

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, formulations and/or methods of use of the invention, may be made without departing from the spirit and scope thereof. All publications, patents, and patent applications cited herein are hereby incorporated by reference in their entirety for all purposes.

The invention claimed is:

1. A compound of formula (I) or a pharmaceutically acceptable salt thereof,

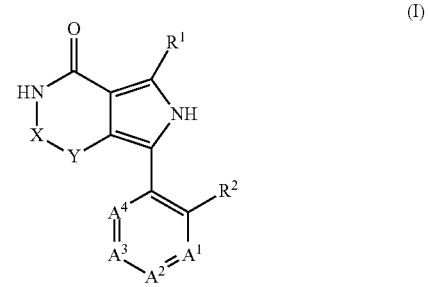

(I)

wherein
$R^1$ is $C_1$-$C_3$ alkyl or $C_1$-$C_3$ haloalkyl;
X—Y is —$CR^3$=CH—, or —$CR^6R^7$—$CR^8R^9$—; wherein the left ends of the moieties are attached to the NH group in the ring;
$A^1$, $A^2$, $A^3$, and $A^4$ are $CR^x$; or
one or two of $A^1$, $A^2$, $A^3$, and $A^4$ are N, and the others are $CR^x$;
$R^2$ is $R^{xa}$;
$R^x$ and $R^{xa}$, at each occurrence, are each independently hydrogen, $C_1$-$C_6$ alkyl, $C_2$-$C_6$ alkenyl, $C_2$-$C_6$ alkynyl, halogen, $C_1$-$C_6$ haloalkyl, —CN, $NO_2$, G, —$OR^{x1}$, —$OC(O)R^{x2}$, —$OC(O)NR^{x3}R^{x4}$, —$SR^{x1}$, —$S(O)_2R^{x1}$, —$S(O)_2NR^{x3}R^{x4}$, —$C(O)R^{x1}$, —$C(O)OR^{x1}$, —$C(O)NR^{x3}R^{x4}$, —$NR^{x3}R^{x4}$, —$N(R^{x5})C(O)R^{x2}$, —$N(R^{x5})S(O)_2R^{x2}$, —$N(R^{x5})C(O)O(R^{x2})$, —$N(R^{x5})C(O)NR^{x3}R^{x4}$, —$N(R^{x5})S(O)_2NR^{x3}R^{x4}$, —$(C_1$-$C_6$ alkylenyl)-G, —$(C_1$-$C_6$ alkylenyl)-$OR^{x1}$, —$(C_1$-$C_6$ alkylenyl)-OC(O)$R^{x2}$, —$(C_1$-$C_6$ alkylenyl)-OC(O) $NR^{x3}R^{x4}$, —$(C_1$-$C_6$ alkylenyl)-$S(O)_2R^{x1}$, —$(C_1$-$C_6$ alkylenyl)-$S(O)_2NR^{x3}R^{x4}$, —$(C_1$-$C_6$ alkylenyl)-C(O) $R^{x1}$, —$(C_1$-$C_6$ alkylenyl)-C(O)$OR^{x1}$, —$(C_1$-$C_6$ alkylenyl)-C(O)NR$^{x3}$R$^{x4}$, —(C$_1$-C$_6$ alkylenyl)-NR$^{x3}$R$^{x4}$, —(C$_1$-C$_6$ alkylenyl)-N(R$^{x5}$)C(O)R$^{x2}$, —(C$_1$-C$_6$ alkylenyl)-N(R$^{x5}$)S(O)$_2$R$^{x2}$, —(C$_1$-C$_6$ alkylenyl)-N(R$^{x5}$)C(O)O(R$^{x2}$), —(C$_1$-C$_6$ alkylenyl)-N(R$^{x5}$)C(O)NR$^{x3}$R$^{x4}$, —(C$_1$-C$_6$ alkylenyl)-N(R$^{x5}$)S(O)$_2$NR$^{x3}$R$^{x4}$, and —(C$_1$-C$_6$ alkylenyl)-CN;

R$^{x1}$, R$^{x3}$, R$^{x4}$, and R$^{x5}$, at each occurrence, are each independently H, C$_1$-C$_6$ alkyl, C$_2$-C$_6$ alkenyl, C$_2$-C$_6$ alkynyl, C$_1$-C$_6$ haloalkyl, G, or —C$_1$-C$_6$ alkylenyl-G;

R$^{x2}$, at each occurrence, is independently C$_1$-C$_6$ alkyl, C$_2$-C$_6$ alkenyl, C$_2$-C$_6$ alkynyl, C$_1$-C$_6$ haloalkyl, G, or —C$_1$-C$_6$ alkylenyl-G;

G, at each occurrence, are each independently aryl, heteroaryl, C$_3$-C$_7$ heterocycle, C$_3$-C$_8$ cycloalkyl, or C$_5$-C$_8$ cycloalkenyl; and each G group is optionally substituted with 1, 2, 3, 4, or 5 R$^g$ groups;

R$^3$ is H, —CN, C$_1$-C$_6$ alkyl, C$_2$-C$_6$ alkenyl, C$_2$-C$_6$ alkynyl, halogen, C$_1$-C$_6$ haloalkyl, —C(O)R$^{3a}$, —C(O)OR$^{3a}$, —C(O)NR$^{3b}$R$^{3c}$, —C(O)N(R$^{3b}$)NR$^{3b}$R$^{3c}$, —S(O)R$^{3d}$, —S(O)$_2$R$^{3a}$, —S(O)$_2$NR$^{3b}$R$^{3c}$ or G$^1$; wherein the C$_1$-C$_6$ alkyl, C$_2$-C$_6$ alkenyl, and C$_2$-C$_6$ alkynyl are each independently unsubstituted or substituted with 1 or 2 substituents independently selected from the group consisting of G$^1$, —C(O)R$^{3a}$, —C(O)OR$^{3a}$, —C(O)NR$^{3b}$R$^{3c}$, —C(O)N(R$^{3b}$)NR$^{3b}$R$^{3c}$, —S(O)R$^{3d}$, —S(O)$_2$R$^{3a}$, —S(O)$_2$NR$^{3b}$R$^{3c}$, —OR$^{3a}$, —OC(O)R$^{3d}$, —NR$^{3b}$R$^{3c}$, N(R$^{3b}$)C(O)R$^{3d}$, N(R$^{3b}$)SO$_2$R$^{3d}$, N(R$^{3b}$)C(O)OR$^{3d}$, N(R$^{3b}$)C(O)NR$^{3b}$R$^{3c}$, and N(R$^{3b}$)SO$_2$NR$^{3b}$R$^{3c}$;

R$^6$ is H, —CN, C$_1$-C$_6$ alkyl, C$_2$-C$_6$ alkenyl, C$_2$-C$_6$ alkynyl, halogen, or C$_1$-C$_6$ haloalkyl;

R$^8$ and R$^9$, are each independently H, C$_1$-C$_6$ alkyl, C$_2$-C$_6$ alkenyl, C$_2$-C$_6$ alkynyl, halogen, or C$_1$-C$_6$ haloalkyl;

R$^7$ is H, C$_1$-C$_6$ alkyl, C$_2$-C$_6$ alkenyl, C$_2$-C$_6$ alkynyl, halogen, C$_1$-C$_6$ haloalkyl, —C(O)R$^{7a}$, —C(O)OR$^{7a}$, —C(O)NR$^{7b}$R$^{7c}$, —S(O)R$^{7d}$, —S(O)$_2$R$^{7a}$, —S(O)$_2$NR$^{7b}$R$^{7c}$, or G$^1$; wherein the C$_1$-C$_6$ alkyl, C$_2$-C$_6$ alkenyl, and C$_2$-C$_6$ alkynyl are each independently unsubstituted or substituted with 1 or 2 substituents independently selected from the group consisting of G$^1$, —C(O)R$^{7a}$, —C(O)OR$^{7a}$, —C(O)NR$^{7b}$R$^{7c}$, —C(O)N(R$^{7b}$)NR$^{7b}$R$^{7c}$, —S(O)R$^{7d}$, —S(O)$_2$R$^{7a}$, —S(O)$_2$NR$^{7b}$R$^{7c}$, —OR$^{7a}$, —OC(O)R$^{7d}$, —NR$^{7b}$R$^{7c}$, N(R$^{7b}$)C(O)R$^{7d}$, N(R$^{7b}$)SO$_2$R$^{7d}$, N(R$^{7b}$)C(O)OR$^{7d}$, N(R$^{7b}$)C(O)NR$^{7b}$R$^{7C}$, and N(R$^{7b}$)SO$_2$NR$^{7b}$R$^{7C}$;

R$^{3a}$, R$^{3b}$, R$^{3c}$, R$^{7a}$, R$^{7b}$, and R$^{7c}$, at each occurrence, are each independently H, C$_1$-C$_6$ alkyl, C$_1$-C$_6$ haloalkyl, G$^1$, —(C$_1$-C$_6$ alkylenyl)-G$^1$, —(C$_1$-C$_6$ alkylenyl)-OR$^a$, or —(C$_1$-C$_6$ alkylenyl)-CN;

R$^{3d}$ and R$^{7d}$, at each occurrence, are each independently C$_1$-C$_6$ alkyl, C$_1$-C$_6$ haloalkyl, G$^1$, —(C$_1$-C$_6$ alkylenyl)-G$^1$, —(C$_1$-C$_6$ alkylenyl)-OR$^a$, or —(C$_1$-C$_6$ alkylenyl)-CN;

G$^1$, at each occurrence, is independently aryl, heteroaryl, C$_3$-C$_7$ heterocycle, C$_3$-C$_8$ cycloalkyl, or C$_5$-C$_8$ cycloalkenyl; and each G$^1$ is optionally substituted with 1, 2, 3, 4, or 5 R$^{1g}$ groups;

R$^g$ and R$^{1g}$, at each occurrence, are each independently selected from the group consisting of oxo, C$_1$-C$_6$ alkyl, C$_2$-C$_6$ alkenyl, C$_2$-C$_6$ alkynyl, halogen, C$_1$-C$_6$ haloalkyl, —CN, NO$_2$, G$^{1a}$, —OR$^a$, —OC(O)R$^b$, —OC(O)NR$^c$R$^d$, —SR$^a$, —S(O)$_2$R$^a$, —S(O)$_2$NR$^c$R$^d$, —C(O)R$^a$, —C(O)OR$^a$, —C(O)NR$^c$R$^d$, —NR$^c$R$^d$, —N(R$^e$)C(O)R$^b$, —N(R$^e$)S(O)$_2$R$^b$, —N(R$^e$)C(O)O(R$^b$), —N(R$^e$)C(O)NR$^c$R$^d$, —N(R$^e$)S(O)$_2$NR$^c$R$^d$, —(C$_1$-C$_6$ alkylenyl)-CN, —(C$_1$-C$_6$ alkylenyl)-G$^{2a}$, —(C$_1$-C$_6$ alkylenyl)-OR$^a$, —(C$_1$-C$_6$ alkylenyl)-OC(O)R$^b$, —(C$_1$-C$_6$ alkylenyl)-OC(O)NR$^c$R$^d$, —(C$_1$-C$_6$ alkylenyl)-S(O)$_2$R$^a$, —(C$_1$-C$_6$ alkylenyl)-S(O)$_2$NR$^c$R$^d$, —(C$_1$-C$_6$ alkylenyl)-C(O)R$^a$, —(C$_1$-C$_6$ alkylenyl)-C(O)OR$^a$, —(C$_1$-C$_6$ alkylenyl)-C(O)NR$^c$R$^d$, —(C$_1$-C$_6$ alkylenyl)-NR$^c$R$^d$, —(C$_1$-C$_6$ alkylenyl)-N(R$^e$)C(O)R$^b$, —(C$_1$-C$_6$ alkylenyl)-N(R$^e$)S(O)$_2$R$^b$, —(C$_1$-C$_6$ alkylenyl)-N(R$^e$)C(O)O(R$^b$), —(C$_1$-C$_6$ alkylenyl)-N(R$^e$)C(O)NR$^c$R$^d$, —(C$_1$-C$_6$ alkylenyl)-N(R$^e$)S(O)$_2$NR$^c$R$^d$, or —(C$_1$-C$_6$ alkylenyl)-CN;

R$^a$, R$^c$, R$^d$, and R$^e$, at each occurrence, are each independently H, C$_1$-C$_6$ alkyl, C$_2$-C$_6$ alkenyl, C$_2$-C$_6$ alkynyl, C$_1$-C$_6$ haloalkyl, G$^{2a}$, or —(C$_1$-C$_6$ alkylenyl)-G$^{2a}$;

R$^b$, at each occurrence, is independently C$_1$-C$_6$ alkyl, C$_2$-C$_6$ alkenyl, C$_2$-C$_6$ alkynyl, C$_1$-C$_6$ haloalkyl, G$^{2a}$, or —(C$_1$-C$_6$ alkylenyl)-G$^{2a}$;

G$^{2a}$, at each occurrence, are each independently aryl, heteroaryl, C$_3$-C$_7$ heterocycle, C$_3$-C$_8$ cycloalkyl, or C$_5$-C$_8$ cycloalkenyl; and each G$^{2a}$ group is optionally substituted with 1, 2, 3, 4, or 5 R$^{2g}$ groups;

R$^{2g}$, at each occurrence, is independently oxo, C$_1$-C$_6$ alkyl, C$_2$-C$_6$ alkenyl, C$_2$-C$_6$ alkynyl, halogen, C$_1$-C$_6$ haloalkyl, —CN, NO$_2$, —OR$^{z1}$, —OC(O)R$^{z2}$, —OC(O)NR$^{z3}$R$^{z4}$, —SR$^{z1}$, —S(O)$_2$R$^{z1}$, —S(O)$_2$NR$^{z3}$R$^{z4}$, —C(O)R$^{z1}$, —C(O)OR$^{z1}$, —C(O)NR$^{z3}$R$^{z4}$, —NR$^{z3}$R$^{z4}$, —N(R$^{z3}$)C(O)R$^{z2}$, —N(R$^{z3)S(O)}$$_2$R$^{z2}$, —N(R$^{z3}$)C(O)O(R$^{z2}$), —N(R$^{z3}$)C(O)NR$^{z3}$R$^{z4}$, —N(R$^{z3}$)S(O)$_2$NR$^{z3}$R$^{z4}$, —(C$_1$-C$_6$ alkylenyl)-OR$^{z1}$, —(C$_1$-C$_6$ alkylenyl)-OC(O)R$^{z2}$, —(C$_1$-C$_6$ alkylenyl)-OC(O)NR$^{z3}$R$^{z4}$, —(C$_1$-C$_6$ alkylenyl)-S(O)$_2$R$^{z1}$, —(C$_1$-C$_6$ alkylenyl)-S(O)$_2$NR$^{z3}$R$^{z4}$, —(C$_1$-C$_6$ alkylenyl)-C(O)R$^{z1}$, —(C$_1$-C$_6$ alkylenyl)-C(O)OR$^{z1}$, —(C$_1$-C$_6$ alkylenyl)-C(O)NR$^{z3}$R$^{z4}$, —(C$_1$-C$_6$ alkylenyl)-NR$^{z3}$R$^{z4}$, —(C$_1$-C$_6$ alkylenyl)-N(R$^{z3}$)C(O)R$^{z2}$, —(C$_1$-C$_6$ alkylenyl)-N(R$^{z3}$)S(O)$_2$R$^{z2}$, —(C$_1$-C$_6$ alkylenyl)-N(R$^{z3}$)C(O)O(R$^{z2}$), —(C$_1$-C$_6$ alkylenyl)-N(R$^{z3}$)C(O)NR$^{z3}$R$^{z4}$—, (C$_1$-C$_6$ alkylenyl)-N(R$^{z3}$)S(O)$_2$NR$^{z3}$R$^{z4}$, or —(C$_1$-C$_6$ alkylenyl)-CN;

R$^{z1}$, R$^{z3}$, and R$^{z4}$, at each occurrence, are each independently H, C$_1$-C$_6$ alkyl, C$_2$-C$_6$ alkenyl, C$_2$-C$_6$ alkynyl, or C$_1$-C$_6$ haloalkyl; and R$^{z2}$, at each occurrence, is independently C$_1$-C$_6$ alkyl, C$_2$-C$_6$ alkenyl, C$_2$-C$_6$ alkynyl, or C$_1$-C$_6$ haloalkyl.

2. The compound of claim 1, or a pharmaceutically acceptable salt thereof, wherein
R$^1$ is C$_1$-C$_3$ alkyl.

3. The compound of claim 1, or a pharmaceutically acceptable salt thereof, wherein
A$^1$, A$^2$, A$^3$, and A$^4$ are CR$^x$.

4. The compound of claim 1, or a pharmaceutically acceptable salt thereof, wherein
R$^3$ is H, —C(O)R$^{3a}$, —C(O)OR$^{3a}$, —C(O)NR$^{3b}$R$^{3c}$ G$^1$, or C$_1$-C$_6$ alkyl substituted with one —OR$^{3a}$ group.

5. The compound of claim 1, or a pharmaceutically acceptable salt thereof, wherein
R$^6$, R$^8$, and R$^9$ are H;
R$^7$ is H, C$_1$-C$_6$ alkyl, or —C(O)OR$^{7a}$.

6. The compound of claim 1, or a pharmaceutically acceptable salt thereof, wherein
R$^1$ is C$_1$-C$_3$ alkyl; and
A$^1$, A$^2$, A$^3$, and A$^4$ are CR$^x$.

7. The compound of claim 1, or a pharmaceutically acceptable salt, wherein
R$^1$ is C$_1$-C$_3$ alkyl;
R$^2$ is R$^{xa}$; and
R$^{xa}$ is hydrogen, C$_1$-C$_6$ alkyl, C$_2$-C$_6$ alkenyl, C$_2$-C$_6$ alkynyl, halogen, C$_1$-C$_6$ haloalkyl, —CN, —OR$^{x1}$, —SR$^{x1}$, —S(O)$_2$R$^{x1}$, —S(O)$_2$NR$^{x3}$R$^{x4}$, —C(O)R$^{x1}$, —C(O)

$NR^{x3}R^{x4}$, $-NR^{x3}R^{x4}$, $-N(R^{x5})C(O)R^{x2}$, $-N(R^{x5})S(O)_2R^{x2}$, $-(C_1-C_6$ alkylenyl)-G, or $-(C_1-C_6$ alkylenyl)-S(O)$_2R^{x1}$.

8. The compound of claim 1, or a pharmaceutically acceptable salt thereof, wherein
$R^1$ is $C_1-C_3$ alkyl;
$R^2$ is $R^{xa}$;
$R^{xa}$ is hydrogen, $C_1-C_6$ alkyl, $C_2-C_6$ alkenyl, $C_2-C_6$ alkynyl, halogen, $C_1-C_6$ haloalkyl, —CN, —OR$^{x1}$, —SR$^{x1}$, —S(O)$_2R^{x1}$, —S(O)$_2NR^{x3}R^{x4}$, —C(O)R$^{x1}$, —C(O)NR$^{x3}R^{x4}$, —NR$^{x3}R^{x4}$, —N(R$^{x5}$)C(O)R$^{x2}$, —N(R$^{x5}$)S(O)$_2R^{x2}$, —(C$_1$-C$_6$ alkylenyl)-G, or —(C$_1$-C$_6$ alkylenyl)-S(O)$_2R^{x1}$; and
$A^1, A^2, A^3$, and $A^4$ are CR$^x$.

9. The compound of claim 1, or a pharmaceutically acceptable salt thereof, wherein
$R^1$ is $C_1-C_3$ alkyl;
$R^2$ is $R^{xa}$;
$R^{xa}$ is hydrogen, $C_1-C_6$ alkyl, halogen, $C_1-C_6$ haloalkyl, —CN, —OR$^{x1}$, or —NR$^{x3}R^{x4}$;
$A^1, A^2, A^3$, and $A^4$ are CR$^x$; and
$R^x$, at each occurrence, is independently hydrogen, $C_1-C_6$ alkyl, $C_2-C_6$ alkenyl, $C_2-C_6$ alkynyl, halogen, $C_1-C_6$ haloalkyl, —CN, NO$_2$, G, —S(O)$_2R^{x1}$, —NR$^{x3}R^{x4}$, —N(R$^{x5}$)S(O)$_2R^{x2}$, —(C$_1$-C$_6$ alkylenyl) G, —(C$_1$-C$_6$ alkylenyl)-OR$^{x1}$, or —(C$_1$-C$_6$ alkylenyl)-S(O)$_2R^{x1}$.

10. The compound of claim 1, or a pharmaceutically acceptable salt thereof, wherein
$R^1$ is $C_1-C_3$ alkyl;
$A^1, A^2, A^3$, and $A^4$ are CR$^x$; and
$R^x$ is hydrogen, $C_1-C_6$ alkyl, $C_2-C_6$ alkenyl, $C_2-C_6$ alkynyl, halogen, $C_1-C_6$ haloalkyl, —CN, NO$_2$, G, —S(O)$_2R^{x1}$, —NR$^{x3}R^{x4}$, —N(R$^{x5}$)S(O)$_2R^{x2}$, —(C$_1$-C$_6$ alkylenyl)-G, —(C$_1$-C$_6$ alkylenyl)-OR$^{x1}$, or —(C$_1$-C$_6$ alkylenyl)-S(O)$_2R^{x1}$.

11. The compound of claim 1 of formula (Ia), or a pharmaceutically acceptable salt thereof, (Ia)

wherein
$R^1$ is CH$_3$,
$R^2$ is $R^{xa}$;
$R^{xa}$ is —OR$^{x1}$ or —NR$^{x3}R^{x4}$;
$R^{x1}$ and $R^{x3}$ are each independently G or —C$_1$-C$_6$ alkylenyl-G; and
$R^{x4}$ is H or C$_1$-C$_6$ alkyl.

12. The compound of claim 11, or a pharmaceutically acceptable salt thereof, wherein
$R^{xa}$ is —OR$^{x1}$;
$R^{x1}$ is G or —C$_1$-C$_3$ alkylenyl-G;
G is optionally substituted phenyl or optionally substituted C$_3$-C$_6$ cycloalkyl; and
$A^1, A^2, A^3$, and $A^4$ are CR$^x$.

13. The compound of claim 12, or a pharmaceutically acceptable salt thereof, wherein
$A^1, A^2$, and $A^4$ are CH,
$A^3$ is CR$^x$; and
$R^x$, at each occurrence, is independently hydrogen, halogen, $C_1-C_6$ haloalkyl, —CN, NO$_2$, —S(O)$_2R^{x1}$, —NR$^{x3}R^{x4}$, —N(R$^{x5}$)S(O)$_2R^{x2}$, or —(C$_1$-C$_6$ alkylenyl)-S(O)$_2R^{x1}$.

14. The compound of claim 13, or a pharmaceutically acceptable salt thereof, wherein
$R^3$ is H, —C(O)R$^{3a}$, —C(O)OR$^{3a}$, —C(O)NR$^{3b}R^{3c}$ G$^1$, or C$_1$-C$_6$ alkyl substituted with one —OR$^{3a}$ group.

15. The compound of claim 1 of formula (Id), or a pharmaceutically acceptable salt thereof, (Id)

wherein
$R^1$ is CH$_3$;
$R^2$ is $R^{xa}$;
$R^{xa}$ is —OR$^{x1}$ or —NR$^{x3}R^{x4}$;
$R^{x1}$ and $R^{x3}$ are each independently G or —C$_1$-C$_6$ alkylenyl-G; and
$R^{x4}$ is H or C$_1$-C$_6$ alkyl.

16. The compound of claim 15, or a pharmaceutically acceptable salt thereof, wherein
$R^{xa}$ is —OR$^{x1}$;
$R^{x1}$ is G or —C$_1$-C$_3$ alkylenyl-G;
G is optionally substituted phenyl or optionally substituted C$_3$-C$_6$ cycloalkyl; and
$A^1, A^2, A^3$, and $A^4$, are CR$^x$.

17. The compound of claim 16, or a pharmaceutically acceptable salt thereof, wherein
$A^1, A^2$, and $A^4$ are CH;
$A^3$ is CR$^x$; and
$R^x$ is hydrogen, halogen, $C_1-C_6$ haloalkyl, —CN, NO$_2$, —S(O)$_2R^{x1}$, —NR$^{x3}R^{x4}$, —N(R$^{x5}$)S(O)$_2R^{x2}$, or —(C$_1$-C$_6$ alkylenyl)-S(O)$_2R^{x1}$.

18. The compound of claim 17, or a pharmaceutically acceptable salt thereof, wherein
$R^6, R^8$, and $R^9$ are H; and
$R^7$ is H, C$_1$-C$_6$ alkyl, or —C(O)OR$^{7a}$.

19. The compound of claim 1 or a pharmaceutically acceptable salt thereof, wherein the compound is selected from the group consisting of
methyl 3-methyl-4-oxo-1-(2-phenoxyphenyl)-4,5-dihydro-2H-pyrrolo[3,4-c]pyridine-6-carboxylate;
methyl 1-(5-amino-2-phenoxyphenyl)-3-methyl-4-oxo-4,5-dihydro-2H-pyrrolo[3,4-c]pyridine-6-carboxylate;

methyl 3-methyl-1-{5-[(methylsulfonyl)amino]-2-phenoxyphenyl}-4-oxo-4,5-dihydro-2H-pyrrolo[3,4-c]pyridine-6-carboxylate;
ethyl 1-[5-amino-2-(2,4-difluorophenoxy)phenyl]-3-methyl-4-oxo-4,5-dihydro-2H-pyrrolo[3,4-c]pyridine-6-carboxylate;
ethyl 3-methyl-1-{5-[(methylsulfonyl)amino]-2-phenoxyphenyl}-4-oxo-4,5-dihydro-2H-pyrrolo[3,4-c]pyridine-6-carboxylate;
ethyl 1-{5-[(ethylsulfonyl)amino]-2-phenoxyphenyl}-3-methyl-4-oxo-4,5-dihydro-2H-pyrrolo[3,4-c]pyridine-6-carboxylate;
methyl 1-{5-[(ethylsulfonyl)amino]-2-phenoxyphenyl}-3-methyl-4-oxo-4,5-dihydro-2H-pyrrolo[3,4-c]pyridine-6-carboxylate;
ethyl 3-methyl-1-[4-(3-methyl-1H-pyrazol-5-yl)phenyl]-4-oxo-4,5-dihydro-2H-pyrrolo[3,4-c]pyridine-6-carboxylate;
ethyl 1-{2-(2,4-difluorophenoxy)-5-[(methylsulfonyl)amino]phenyl}-3-methyl-4-oxo-4,5-dihydro-2H-pyrrolo[3,4-c]pyridine-6-carboxylate;
ethyl 1-{2-(2,4-difluorophenoxy)-5-[(ethylsulfonyl)amino]phenyl}-3-methyl-4-oxo-4,5-dihydro-2H-pyrrolo[3,4-c]pyridine-6-carboxylate;
3-methyl-4-oxo-1-(2-phenoxyphenyl)-4,5-dihydro-2H-pyrrolo[3,4-c]pyridine-6-carboxamide;
3-methyl-4-oxo-1-(2-phenoxyphenyl)-4,5-dihydro-2H-pyrrolo[3,4-c]pyridine-6-carboxylic acid;
N,3-dimethyl-4-oxo-1-(2-phenoxyphenyl)-4,5-dihydro-2H-pyrrolo[3,4-c]pyridine-6-carboxamide;
3-methyl-1-(2-phenoxyphenyl)-2,5-dihydro-4H-pyrrolo[3,4-c]pyridin-4-one;
3-methyl-6-(morpholin-4-ylcarbonyl)-1-(2-phenoxyphenyl)-2,5-dihydro-4H-pyrrolo[3,4-c]pyridin-4-one;
3-methyl-6-[(4-methylpiperazin-1-yl)carbonyl]-1-(2-phenoxyphenyl)-2,5-dihydro-4H-pyrrolo[3,4-c]pyridin-4-one;
3-methyl-N-{4-[(4-methylpiperazin-1-yl)methyl]phenyl}-4-oxo-1-(2-phenoxyphenyl)-4,5-dihydro-2H-pyrrolo[3,4-c]pyridine-6-carboxamide;
6-(hydroxymethyl)-3-methyl-1-(2-phenoxyphenyl)-2,5-dihydro-4H-pyrrolo[3,4-c]pyridin-4-one;
1-{2-(2,4-difluorophenoxy)-5-[(methylsulfonyl)amino]phenyl}-3-methyl-4-oxo-4,5-dihydro-2H-pyrrolo[3,4-c]pyridine-6-carboxamide;
3-methyl-1-{5-[(methylsulfonyl)amino]-2-phenoxyphenyl}-4-oxo-4,5-dihydro-2H-pyrrolo[3,4-c]pyridine-6-carboxamide;
ethyl 1-[2-(2,4-difluorophenoxy)phenyl]-3-methyl-4-oxo-4,5-dihydro-2H-pyrrolo[3,4-c]pyridine-6-carboxylate;
1-[2-(2,4-difluorophenoxy)phenyl]-3-methyl-4-oxo-4,5-dihydro-2H-pyrrolo[3,4-c]pyridine-6-carboxylic acid;
1-[2-(2,4-difluorophenoxy)phenyl]-3-methyl-4-oxo-4,5-dihydro-2H-pyrrolo[3,4-c]pyridine-6-carboxamide;
ethyl 1-[5-chloro-2-(2,4-difluorophenoxy)phenyl]-3-methyl-4-oxo-4,5-dihydro-2H-pyrrolo[3,4-c]pyridine-6-carboxylate;
3-methyl-4-oxo-1-(2-phenoxyphenyl)-N-[2-(pyrrolidin-1-yl)ethyl]-4,5-dihydro-2H-pyrrolo[3,4-c]pyridine-6-carboxamide;
3-methyl-4-oxo-1-(2-phenoxyphenyl)-N-(1,3-thiazol-2-yl)-4,5-dihydro-2H-pyrrolo[3,4-c]pyridine-6-carboxamide;
3-methyl-N-[2-(morpholin-4-yl)ethyl]-4-oxo-1-(2-phenoxyphenyl)-4,5-dihydro-2H-pyrrolo[3,4-c]pyridine-6-carboxamide;
3-methyl-4-oxo-1-(2-phenoxyphenyl)-N-(pyridin-4-yl)-4,5-dihydro-2H-pyrrolo[3,4-c]pyridine-6-carboxamide;
N-(2-methoxyethyl)-3-methyl-4-oxo-1-(2-phenoxyphenyl)-4,5-dihydro-2H-pyrrolo[3,4-c]pyridine-6-carboxamide;
6-[(4-hydroxypiperidin-1-yl)carbonyl]-3-methyl-1-(2-phenoxyphenyl)-2,5-dihydro-4H-pyrrolo[3,4-c]pyridin-4-one;
N-(furan-2-ylmethyl)-3-methyl-4-oxo-1-(2-phenoxyphenyl)-4,5-dihydro-2H-pyrrolo[3,4-c]pyridine-6-carboxamide;
1-[5-chloro-2-(2,4-difluorophenoxy)phenyl]-3-methyl-4-oxo-4,5-dihydro-2H-pyrrolo[3,4-c]pyridine-6-carboxamide;
ethyl 1-[2-(2,4-difluorophenoxy)-5-nitrophenyl]-3-methyl-4-oxo-4,5-dihydro-2H-pyrrolo[3,4-c]pyridine-6-carboxylate;
1-[2-(2,4-difluorophenoxy)-5-(trifluoromethyl)phenyl]-N,3-dimethyl-4-oxo-4,5-dihydro-2H-pyrrolo[3,4-c]pyridine-6-carboxamide;
3-methyl-N-(1-methylpiperidin-4-yl)-4-oxo-1-(2-phenoxyphenyl)-4,5-dihydro-2H-pyrrolo[3,4-c]pyridine-6-carboxamide;
3-methyl-4-oxo-1-(2-phenoxyphenyl)-N-(tetrahydrofuran-3-ylmethyl)-4,5-dihydro-2H-pyrrolo[3,4-c]pyridine-6-carboxamide;
3-methyl-4-oxo-1-(2-phenoxyphenyl)-N-(tetrahydrofuran-3-yl)-4,5-dihydro-2H-pyrrolo[3,4-c]pyridine-6-carboxamide;
3-methyl-4-oxo-1-(2-phenoxyphenyl)-N-(tetrahydro-2H-pyran-4-yl)-4,5-dihydro-2H-pyrrolo[3,4-c]pyridine-6-carboxamide;
ethyl 1-[2-(2,4-difluorophenoxy)-5-(methylsulfonyl)phenyl]-3-methyl-4-oxo-4,5-dihydro-2H-pyrrolo[3,4-c]pyridine-6-carboxylate;
1-[2-(2,4-difluorophenoxy)-5-(methylsulfonyl)phenyl]-3-methyl-4-oxo-4,5-dihydro-2H-pyrrolo[3,4-c]pyridine-6-carboxylic acid;
N,N,3-trimethyl-4-oxo-1-(2-phenoxyphenyl)-4,5-dihydro-2H-pyrrolo[3,4-c]pyridine-6-carboxamide;
1-[2-(2,4-difluorophenoxy)-5-(methylsulfonyl)phenyl]-3-methyl-4-oxo-4,5-dihydro-2H-pyrrolo[3,4-c]pyridine-6-carboxamide;
1-[5-amino-2-(2,4-difluorophenoxy)phenyl]-3-methyl-4-oxo-N-propyl-4,5-dihydro-2H-pyrrolo[3,4-c]pyridine-6-carboxamide;
6-(methoxymethyl)-3-methyl-1-(2-phenoxyphenyl)-2,5-dihydro-4H-pyrrolo[3,4-c]pyridin-4-one;
3-methyl-1-(2-phenoxyphenyl)-6-[3-(pyridin-4-yl)-1,2,4-oxadiazol-5-yl]-2,5-dihydro-4H-pyrrolo[3,4-c]pyridin-4-one;
3-methyl-1-(2-phenoxyphenyl)-6-(3-phenyl-1,2,4-oxadiazol-5-yl)-2,5-dihydro-4H-pyrrolo[3,4-c]pyridin-4-one;
3-methyl-1-(2-phenoxyphenyl)-6-(3-propyl-1,2,4-oxadiazol-5-yl)-2,5-dihydro-4H-pyrrolo[3,4-c]pyridin-4-one;
ethyl 1-[2-(cyclohexyloxy)-5-fluorophenyl]-3-methyl-4-oxo-4,5-dihydro-2H-pyrrolo[3,4-c]pyridine-6-carboxylate;
3-methyl-N-(1-methylazetidin-3-yl)-4-oxo-1-(2-phenoxyphenyl)-4,5-dihydro-2H-pyrrolo[3,4-c]pyridine-6-carboxamide;
N-(trans-3-methoxycyclobutyl)-3-methyl-4-oxo-1-(2-phenoxyphenyl)-4,5-dihydro-2H-pyrrolo[3,4-c]pyridine-6-carboxamide;

3-methyl-N-[(3R)-1-methylpyrrolidin-3-yl]-4-oxo-1-(2-phenoxyphenyl)-4,5-dihydro-2H-pyrrolo[3,4-c]pyridine-6-carboxamide;

N-(2-cyanopropan-2-yl)-3-methyl-4-oxo-1-(2-phenoxyphenyl)-4,5-dihydro-2H-pyrrolo[3,4-c]pyridine-6-carboxamide;

N',N',3-trimethyl-4-oxo-1-(2-phenoxyphenyl)-4,5-dihydro-2H-pyrrolo[3,4-c]pyridine-6-carbohydrazide;

tert-butyl 4-({[3-methyl-4-oxo-1-(2-phenoxyphenyl)-4,5-dihydro-2H-pyrrolo[3,4-c]pyridin-6-yl]carbonyl}amino)piperidine-1-carboxylate;

tert-butyl (3R)-3-[({[3-methyl-4-oxo-1-(2-phenoxyphenyl)-4,5-dihydro-2H-pyrrolo[3,4-c]pyridin-6-yl]carbonyl}amino)methyl]pyrrolidine-1-carboxylate;

tert-butyl 3,3-difluoro-4-[({[3-methyl-4-oxo-1-(2-phenoxyphenyl)-4,5-dihydro-2H-pyrrolo[3,4-c]pyridin-6-yl]carbonyl}amino)methyl]pyrrolidine-1-carboxylate;

3-methyl-4-oxo-1-(2-phenoxyphenyl)-N-(piperidin-4-yl)-4,5-dihydro-2H-pyrrolo[3,4-c]pyridine-6-carboxamide;

3-methyl-4-oxo-1-(2-phenoxyphenyl)-N-[(3S)-pyrrolidin-3-ylmethyl]-4,5-dihydro-2H-pyrrolo[3,4-c]pyridine-6-carboxamide;

N-[(4,4-difluoropyrrolidin-3-yl)methyl]-3-methyl-4-oxo-1-(2-phenoxyphenyl)-4,5-dihydro-2H-pyrrolo[3,4-c]pyridine-6-carboxamide;

3-methyl-1-(2-phenoxyphenyl)-6-[3-(pyridin-3-yl)-1,2,4-oxadiazol-5-yl]-2,5-dihydro-4H-pyrrolo[3,4-c]pyridin-4-one;

3-methyl-6-(3-methyl-1,2,4-oxadiazol-5-yl)-1-(2-phenoxyphenyl)-2,5-dihydro-4H-pyrrolo[3,4-c]pyridin-4-one;

6-{3-[4-(dimethylamino)phenyl]-1,2,4-oxadiazol-5-yl}-3-methyl-1-(2-phenoxyphenyl)-2,5-dihydro-4H-pyrrolo[3,4-c]pyridin-4-one;

6-(3-cyclopropyl-1,2,4-oxadiazol-5-yl)-3-methyl-1-(2-phenoxyphenyl)-2,5-dihydro-4H-pyrrolo[3,4-c]pyridin-4-one;

3-methyl-1-(2-phenoxyphenyl)-6-[3-(1H-1,2,4-triazol-1-ylmethyl)-1,2,4-oxadiazol-5-yl]-2,5-dihydro-4H-pyrrolo[3,4-c]pyridin-4-one;

3-methyl-1-(2-phenoxyphenyl)-6-[3-(pyrazin-2-yl)-1,2,4-oxadiazol-5-yl]-2,5-dihydro-4H-pyrrolo[3,4-c]pyridin-4-one;

3-methyl-1-(2-phenoxyphenyl)-6-[3-(pyridin-3-ylmethyl)-1,2,4-oxadiazol-5-yl]-2,5-dihydro-4H-pyrrolo[3,4-c]pyridin-4-one;

3-methyl-1-(2-phenoxyphenyl)-6-[3-(pyridin-2-yl)-1,2,4-oxadiazol-5-yl]-2,5-dihydro-4H-pyrrolo[3,4-c]pyridin-4-one;

ethyl 1-{2-(2,4-difluorophenoxy)-5-[(methylsulfonyl)methyl]phenyl}-3-methyl-4-oxo-4,5-dihydro-2H-pyrrolo[3,4-c]pyridine-6-carboxylate;

ethyl 1-[2-(cyclopropylmethoxy)-5-fluorophenyl]-3-methyl-4-oxo-4,5-dihydro-2H-pyrrolo[3,4-c]pyridine-6-carboxylate;

1-[2-(cyclopropylmethoxy)-5-fluorophenyl]-3-methyl-4-oxo-4,5-dihydro-2H-pyrrolo[3,4-c]pyridine-6-carboxamide;

1-[2-(cyclopropylmethoxy)-5-fluorophenyl]-3-methyl-6-[3-(pyrazin-2-yl)-1,2,4-oxadiazol-5-yl]-2,5-dihydro-4H-pyrrolo[3,4-c]pyridin-4-one;

3-methyl-1-(2-phenoxyphenyl)-2,5,6,7-tetrahydro-4H-pyrrolo[3,4-c]pyridin-4-one;

N-[4-(2,4-difluorophenoxy)-3-(3-methyl-4-oxo-4,5,6,7-tetrahydro-2H-pyrrolo[3,4-c]pyridin-1-yl)phenyl]methanesulfonamide;

1-(5-amino-2-phenoxyphenyl)-3-methyl-2,5,6,7-tetrahydro-4H-pyrrolo[3,4-c]pyridin-4-one;

N-[3-(3-methyl-4-oxo-4,5,6,7-tetrahydro-2H-pyrrolo[3,4-c]pyridin-1-yl)-4-phenoxyphenyl]methanesulfonamide;

1-[2-(cyclopropylmethoxy)-5-(methylsulfonyl)phenyl]-3-methyl-2,5,6,7-tetrahydro-4H-pyrrolo[3,4-c]pyridin-4-one;

methyl 3-methyl-4-oxo-1-(2-phenoxyphenyl)-4,5,6,7-tetrahydro-2H-pyrrolo[3,4-c]pyridine-6-carboxylate;

1-[2-(2,4-difluorophenoxy)-5-(methylsulfonyl)phenyl]-3-methyl-2,5,6,7-tetrahydro-4H-pyrrolo[3,4-c]pyridin-4-one;

1-[2-fluoro-5-(methylsulfonyl)phenyl]-3-methyl-2,5,6,7-tetrahydro-4H-pyrrolo[3,4-c]pyridin-4-one;

3-methyl-1-phenyl-2,5,6,7-tetrahydro-4H-pyrrolo[3,4-c]pyridin-4-one;

1-[5-amino-2-(2,4-difluorophenoxy)phenyl]-3,6-dimethyl-2,5,6,7-tetrahydro-4H-pyrrolo[3,4-c]pyridin-4-one;

1-{2-(2,4-difluorophenoxy)-5[(4-methylpiperazin-1-yl)methyl]phenyl}-3-methyl-2,5,6,7-tetrahydro-4H-pyrrolo[3,4-c]pyridin-4-one; and 1-[2-(2,4-difluorophenoxy)-5-(hydroxymethyl)phenyl]-3-methyl-2,5,6,7-tetrahydro-4H-pyrrolo[3,4-c]pyridin-4-one.

20. A pharmaceutical composition comprising a therapeutically effective amount of a compound of formula (I) according to claim 1, or a pharmaceutically acceptable salt thereof, and a pharmaceutically acceptable carrier.

\* \* \* \* \*